(12) United States Patent
Mundt et al.

(10) Patent No.: US 11,596,681 B2
(45) Date of Patent: Mar. 7, 2023

(54) EHV INSERTION SITE UL43

(71) Applicant: Boehringer Ingelheim Vetmedica GmbH, Ingelheim am Rhein (DE)

(72) Inventors: Alice Mundt, Isernhagen (DE); Andreas Gallei, Wedemark (DE); Kristina Rehmet, Hannover (DE)

( * ) Notice: Subject to any disclaimer, the term of this patent is extended or adjusted under 35 U.S.C. 154(b) by 0 days.

(21) Appl. No.: 16/980,723

(22) PCT Filed: Mar. 19, 2019

(86) PCT No.: PCT/EP2019/056749
§ 371 (c)(1),
(2) Date: Sep. 14, 2020

(87) PCT Pub. No.: WO2019/179966
PCT Pub. Date: Sep. 26, 2019

(65) Prior Publication Data
US 2021/0100890 A1 Apr. 8, 2021

(30) Foreign Application Priority Data
Mar. 19, 2018 (EP) .................... 18162636

(51) Int. Cl.
*A61K 39/12* (2006.01)
*C12N 15/86* (2006.01)
*A61K 39/00* (2006.01)

(52) U.S. Cl.
CPC ............ *A61K 39/12* (2013.01); *C12N 15/86* (2013.01); *A61K 2039/53* (2013.01); *A61K 2039/552* (2013.01); *C12N 2710/16734* (2013.01); *C12N 2710/16743* (2013.01); *C12N 2760/16122* (2013.01); *C12N 2760/16134* (2013.01)

(58) Field of Classification Search
None
See application file for complete search history.

(56) References Cited

U.S. PATENT DOCUMENTS

| 6,187,320 | B1 | 2/2001 | Darai et al. |
| 10,626,414 | B2 * | 4/2020 | Gallei ................... A61P 37/04 |
| 2007/0280960 | A1 | 12/2007 | Audonnet et al. |
| 2021/0100890 | A1 * | 4/2021 | Mundt .................. A61K 39/12 |

FOREIGN PATENT DOCUMENTS

| WO | 2000008191 | 2/2000 |
| WO | 2000061736 | 10/2000 |
| WO | 2003087382 | 10/2003 |

OTHER PUBLICATIONS

Von Einem et al. (Virology. 2007; 362: 151-162).*
Sequence alignments of SEQ ID Nos. 19 and 20 with GenEmbl db acc KU206478c Mar. 5, 2018.*
(Continued)

*Primary Examiner* — Shanon A. Foley
(74) *Attorney, Agent, or Firm* — Steffan Finnegan

(57) ABSTRACT

The present invention relates to the field of (vector) vaccines, and especially to the novel EHV insertion site UL43. The present invention further concerns related expression cassettes and vectors, which are suitable to express genes of interest, especially antigen encoding sequences. The viral vectors of the present invention are useful for producing an immunogenic composition or vaccine.

13 Claims, 22 Drawing Sheets

Specification includes a Sequence Listing.

(56) References Cited

OTHER PUBLICATIONS

Said et al. (Virus Research. 2013; 173: 371-376).*
Alignment of SEQ 44 with Genseq db acc AZG98675 Aug. 2011.*
Teng Huang et al.: "Equine Herpesvirus 1 Multiply Inserted Transmembrane Protein pUL43 Cooperates with pUL56 in Downregulation of Cell Surface Major Histocompatibility Complex Class I", Journal of Virology, Jun. 1, 2015, vol. 89, pp. 6251-6263.

* cited by examiner

Figure 3

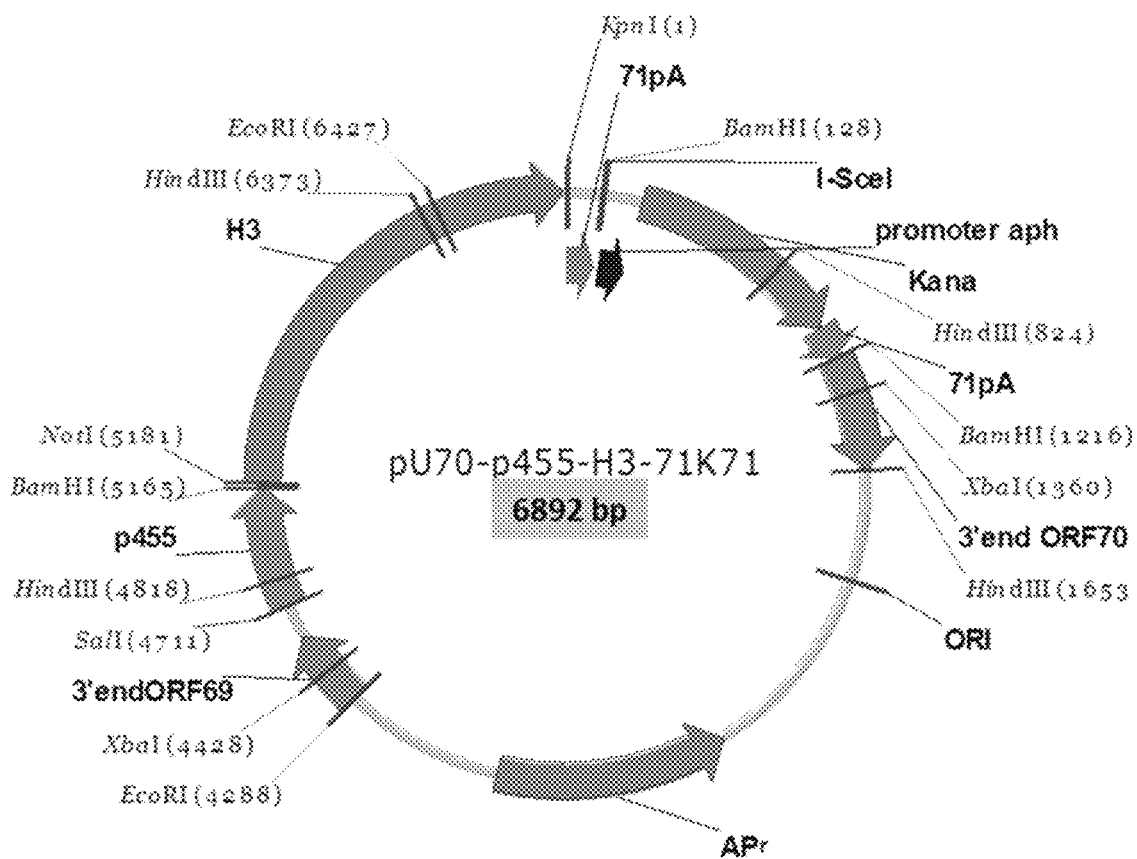

| | |
|---|---|
| 3'end ORF69 | viral genomic DNA sequence flanking the insertion site upstream |
| 3'end ORF70 | viral genomic DNA sequence flanking the insertion site downstream |
| p455 | promoter driving expression of transgene |
| H3 | transgene (IAV hemagglutinin) |
| 71pA | polyadenylation sequence |
| I-Sce1 | cleavage site for I-Sce1 |
| promoter aph | prokaryotic promoter driving expression of Kanamycin-resistance gene |
| Kana | Kanamycine resistance orf |
| ORI | origin of replication of plasmid vector |
| Apr | Ampicillin-resistance gene |

EcoRI, SalI, NotI, HindIII, KpnI, BamHI, XbaI indicate restriction endonuclease cleavage sites

Figure 4

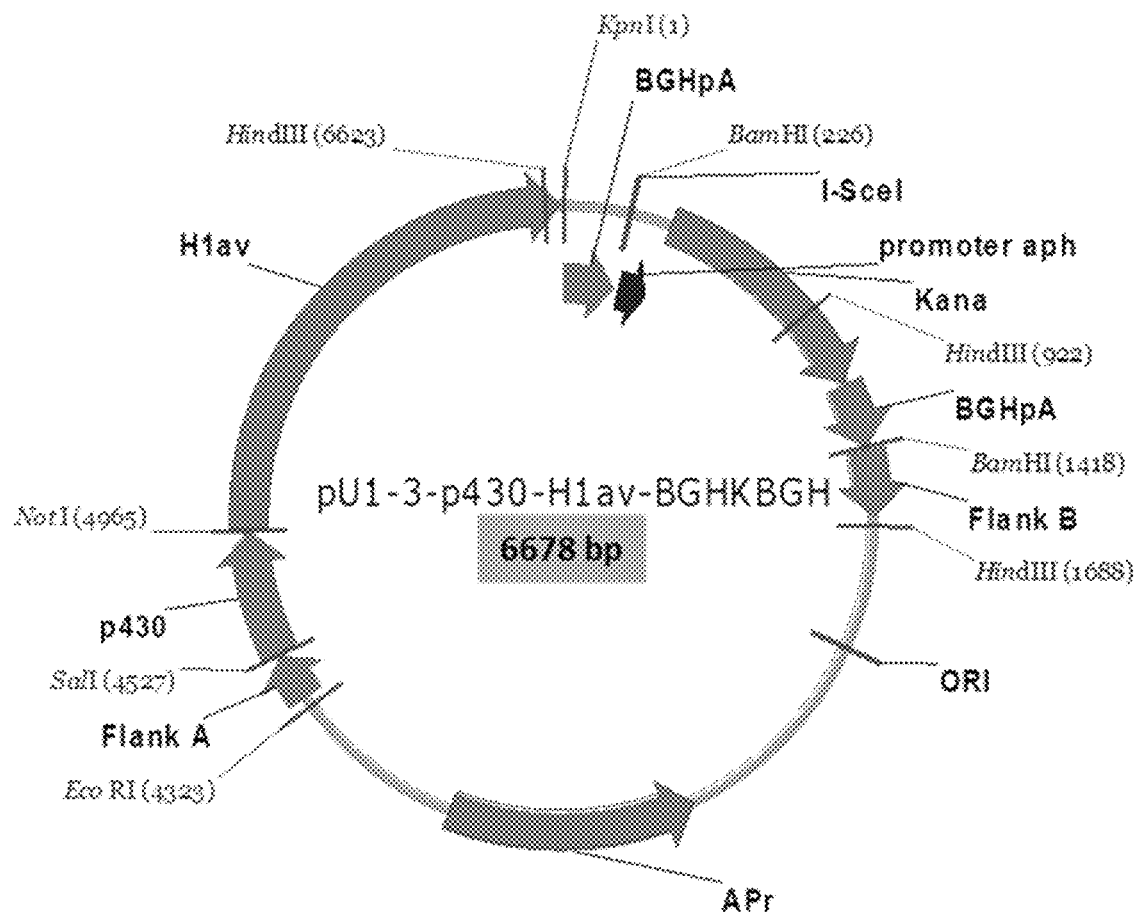

Flank A viral genomic DNA sequence flanking the insertion site upstream
Flank B viral genomic DNA sequence flanking the insertion site downstream
p430 promoter driving expression of the transgene
H1av transgene (IAV hemagglutinin)
BGHpA polyadenylation sequence
I-Sce1 cleavage site for I-Sce1
promoter aph prokaryotic promoter driving expression of Kanamycin-resistence gene
Kana Kanamycine resistance orf
ORI origin of replication of plasmid vector
Apr Ampicillin-resistance gene
EcoRI, SalI, NotI, HindIII, KpnI, BamHI indicate restriction endonuclease cleavage sites

Flank A      viral genomic DNA sequence flanking the insertion site upstream
Flank B      viral genomic DNA sequence flanking the insertion site downstream
p430         promoter driving expression of the transgene
H1hu         transgene (IAV hemagglutinin)
BGHpA        polyadenylation sequence
I-Sce1       cleavage site for I-Sce1
I-Ceu 1 cleavage site for I-Ceu1
promoter aph prokaryotic promoter driving expression of Kanamycin-resistence gene
Kana Kanamycine resistance orf
ScaI, EcoRI, SalI, NotI, HindIII, KpnI, BamHI indicate restriction endonuclease cleavage sites

Figure 9

*[Plasmid map: pU70-p455-H1pdm 71K71, 6892 bp, with the following labeled features:]*

- Kpn I(1)
- 71pA (2-226)
- Eco RI(6894)
- Bam HI(128)
- promoter aph (151-273)
- Kana (274-1089)
- H1pdm (5187-6887)
- Eco RI(5771)
- Hin dIII(824)
- 71pA (1080-1214)
- Bam HI(1216)
- Xba I(1220)
- Sca I(5180)
- 3'end orf70 (1221-165)
- Bam HI(5166)
- Hin dIII(1653)
- p455 (4714-5168)
- Hin dIII(4868)
- Sal I(4711)
- upstream orf70 (4293-4709)
- Xba I(4288)
- Eco RI(4288)
- Sca I(3586)

| | |
|---|---|
| 3'end ORF69 | viral genomic DNA sequence flanking the insertion site upstream |
| 3'end ORF70 | viral genomic DNA sequence flanking the insertion site downstream |
| p455 | promoter driving expression of transgene |
| H1pdm | transgene (IAV hemagglutinin) |
| 71pA | polyadenylation sequence |
| I-Sce1 | cleavage site for I-Sce1 |
| promoter aph | prokaryotic promoter driving expression of Kanamycin-resistance gene |
| Kana | Kanamycine resistance orf |

ScaI, EcoRI, SalI, NotI, HindIII, KpnI, BamHI, XbaI indicate restriction endonuclease cleavage sites

Figure 14

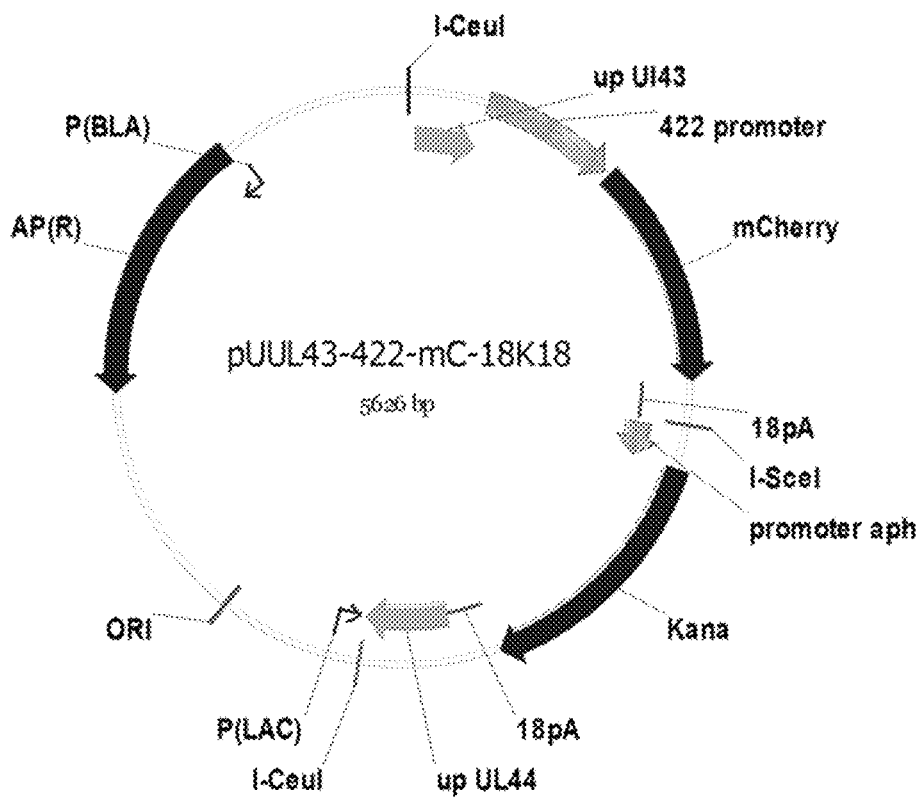

| | |
|---|---|
| UpUL43 | viral genomic DNA sequence flanking the insertion site upstream |
| UpUL44 | viral genomic DNA sequence flanking the insertion site downstream |
| 422promoter | promoter driving expression of transgene |
| mCherry | transgene (red autofluorescent protein) |
| 18pA | polyadenylation sequence |
| I-Sce1 | cleavage site for I-Sce1 |
| promoter aph | prokaryotic promoter driving expression of Kanamycin-resistence gene |
| Kana | Kanamycine resistance orf |
| P(BLA) | prokaryotic promoter driving expression of Ampicillin-resistence gene |
| AP(R) | Ampicillin-resistance gene |
| ORI | plasmid origin of replication |
| P(LAC) | prokaryotic promoter of lacZ encoding Betagalactosidase |
| I-Ceu | recognition site of the homing endocuclease I-Ceu |

Figure 16

```
                        I-Ceu I
     P(BLA)                        up UL43
                                       422 promoter
  AP(R)

pUUL43-422-H1pdm-18K18        H1pdm
                          6a6 bp

ORI
   P(LAC)                              18pA
     I-Ceu I                           I-Sce I
        up UL44                     promoter aph
            18pA       Kana
```

| | |
|---|---|
| UpUL43 | viral genomic DNA sequence flanking the insertion site upstream |
| UpUL44 | viral genomic DNA sequence flanking the insertion site downstream |
| 422promoter | promoter driving expression of transgene |
| H1pdm | transgene (Influenza A hemagglutinin) |
| 18pA | polyadenylation sequence |
| I-Sce1 | cleavage site for I-Sce1 |
| promoter aph | prokaryotic promoter driving expression of Kanamycin-resistence gene |
| Kana | Kanamycine resistance orf |
| P(BLA) | prokaryotic promoter driving expression of Ampicillin-resistence gene |
| AP(R) | Ampicillin-resistance gene |
| ORI | plasmid origin of replication |
| P(LAC) | prokaryotic promoter of lacZ encoding Betagalactosidase |
| I-Ceu | recognition site of the homing endocuclease I-Ceu |

Figure 19 a : Blot incubated with a proprietary monoclonal antibody against Influenza HA H1av
b : Blot incubated with a commercial rabbit antiserum specific for Influenza HA H3
c : Blot incubated with a proprietary monoclonal antibody against Influenza HA H1pdm
d : Blot incubated with a proprietary monoclonal antibody against EHV-1 gpII M = molecular weight marker   (kDa= kilodalton, 250, 150, 100, 75, 50, 37, 25, 20)
B = UL56-H1av-US4-H3
D =UL56-H1hu-US4-H1pdm
E = UL56-H1av-UL43-H1pdmUS4-H3
SE = empty vector
co = uninfected cells
av = only H1av  (in UL56 site)
H3 = only H3  (in US4 site)
hu = only H1hu (in UL56 site)
4p = only H1pdm in US4 site
43p = only H1pdm in UL43 site

Figure 20

Neutralizing capacities of mice sera to 100 TCID50 of IAV

| | RacH-SE B-1 | RacH-SE B-2 | RacH-SE B-3 | RacH-SE B-4 | RacH-SE B-5 | RacH-SE empty 1 | RacH-SE empty 2 | RacH-SE empty 3 | RacH-SE B-1 | RacH-SE B-2 | RacH-SE B-3 | RacH-SE B-4 | RacH-SE B-5 | RacH-SE empty 1 | RacH-SE empty 2 | RacH-SE empty 3 | RacH-SE empty 4 | RacH-SE empty 5 |
|---|---|---|---|---|---|---|---|---|---|---|---|---|---|---|---|---|---|---|
| | H3N2 | | | | | | | | H1avN1 | | | | | | | | | |
| Series1 | 403 | 102 | 108 | 37 | 27 | 0 | 0 | 0 | 49 | 22 | 39 | 156 | 53 | 0 | 0 | 0 | 0 | 0 |

Figure 21

SEQUENCE LISTING

```
<160> NUMBER OF SEQ ID NOS: 47

<210> SEQ ID NO 1
<211> LENGTH: 600
<212> TYPE: DNA
<213> ORGANISM: Equine herpesvirus 4

<400> SEQUENCE: 1
gcagactttg gagcagcaca atttccggtt gtggacccca tggaccttgg tttggctggt      60
accgtggaaa ctaacgctcc ggaagttttg gccagagcaa aatacaattc gaaggtagac     120
atatggagcg ccggaatagt tctgtttgaa atgctcgcat atccatcaac tctatttgag     180
gacccgccga gtaccccaca agagtatgta aaaagctgtc attctcaact actgagaata     240
atatcaaagc taaagataaa ccctgaggag tttccacggg aaccagagtc taggctcgtg     300
cgcggataca tcgaatacgc cagcctagag cgtaagccac atacgcgcta tccttgcttc     360
cagcgcgtga acctacacat tgacggggaa tttttgatcc ataaaatgct agcgttcaat     420
gctgcgatgc gcccatccgc agaagagttg ttgtcctacc caatgtttat gaatctgtag     480
gatgactaac agatttgggg tggagacggc gtgggcgata ctgtataaag ttgtactact     540
taccagccca gtcagtgtgc tgtagtgcca ccacctgtaa agctgtgata agctgcagtt     600

<210> SEQ ID NO 2
<211> LENGTH: 600
<212> TYPE: DNA
<213> ORGANISM: Equine herpesvirus 4

<400> SEQUENCE: 2
agctggggga gtttgtacta tagtgtatta catgcggctt gcaataactg cctggtttat      60
gtttcgcaac attcaagcag acatgctacc gctaaacact ttgcaacaat tttttattgg     120
gtgtttggcc tttggtagaa ctgtcgcgtt tttggtggta gcatatacta ccttatttat     180
acgctccgag ctgtttttca gcatgctagc acccaacgcc gagcgagagt atataactcc     240
```

| | |
|---|---|
| catcattgcc cacaagctta tgccacttat tagcgtccgc tctgccgttt gcttagtcat | 300 |
| aatatctacc gccgtttacg cagcagacgc tatctgcgac acaattggat ttgcgatacc | 360 |
| gcgcatgtgg atgtgtattt taatgagatc aacctccatg aagcgtaact aggggggcctc | 420 |
| ccactgaggc actaccggct tagcagctga ctaacacagt ataaaacgtg agaagaaatc | 480 |
| agtctcatgc gccattagcg ctaggctagt tagcgtggag gaccggagcg ctaccgccag | 540 |
| cagtttcatc cgcctggtta cgggtttgtt aacacctacc ggtgttttac cgctaccata | 600 |

```
<210> SEQ ID NO 3
<211> LENGTH: 430
<212> TYPE: DNA
<213> ORGANISM: Equine herpesvirus 4

<400> SEQUENCE: 3
```

| | |
|---|---|
| tctatttgag gacccgccga gtaccccaca agagtatgta aaaagctgtc attctcaact | 60 |
| actgagaata atatcaaagc taaagataaa ccctgaggag tttccacggg aaccagagtc | 120 |
| taggctcgtg cgcggataca tcgaatacgc cagcctagag cgtaagccac atacgcgcta | 180 |
| tccttgcttc cagcgcgtga acctacacat tgacggggaa ttttttgatcc ataaaatgct | 240 |
| agcgttcaat gctgcgatgc gcccatccgc agaaagagttg ttgtcctacc caatgtttat | 300 |
| gaatctgtag gatgactaac agatttgggg tggagacggc gtgggcgata ctgtataaag | 360 |
| ttgtactact taccagccca gtcagtgtgc tgtagtgcca ccacctgtaa agctgtgata | 420 |
| agctgcagtt | 430 |

```
<210> SEQ ID NO 4
<211> LENGTH: 449
<212> TYPE: DNA
<213> ORGANISM: Equine herpesvirus 4

<400> SEQUENCE: 4
```

| | |
|---|---|
| ttggtggtag catatactac cttatttata cgctccgagc tgtttttcag catgctagca | 60 |
| cccaacgccg agcgagagta tataactccc atcattgccc acaagcttat gccacttatt | 120 |
| agcgtccgct ctgccgtttg cttagtcata atatctaccg ccgtttacgc agcagacgct | 180 |
| atctgcgaca caattggatt tgcgataccg cgcatgtgga tgtgtatttt aatgagatca | 240 |
| acctccatga agcgtaacta ggggggcctcc cactgaggca ctaccggctt agcagctgac | 300 |
| taacacagta taaaacgtga agagaaatca gtctcatgcg ccattagcgc taggctagtt | 360 |
| agcgtggagg accggagcgc taccgccagc agtttcatcc gcctggttac gggtttgtta | 420 |
| acacctaccg gtgttttacc gctaccata | 449 |

```
<210> SEQ ID NO 5
<211> LENGTH: 422
<212> TYPE: DNA
<213> ORGANISM: Equine herpesvirus 4

<400> SEQUENCE: 5
```

| | |
|---|---|
| ccatggatcg tcagacttgg tggaagaccc atgttcgttg tttcaagaag cgtatcctct | 60 |
| actcagctcc actgatacag cattgctacg cacgcctcac gttggcgaaa ttggcgcaga | 120 |
| tgaaggacat tttgcccagt acctaattcg cgacgaatcc cccctgaaag ctgtttttcc | 180 |
| acgaatttag gttgtgcccg cctacaactt tcacttgca aactcaataa aacgcacagt | 240 |
| ttgtatattc agttgtcagt ttgctctact cgagcgtcgg cgctttgtct agccctctta | 300 |
| gtgggtattg ttaccggctg gggttttatt ggcgttgtta ttggggagat tttagttgat | 360 | agaaagcata ccgaggtttt gggggtgtcg cttaatttcg gtgtctgtaa acgtaaaaag 420 ag 422

<210> SEQ ID NO 6
<211> LENGTH: 125
<212> TYPE: DNA
<213> ORGANISM: Artificial Sequence
<220> FEATURE:
<223> OTHER INFORMATION: Sequence of the 71pA polyadenylation sequence

<400> SEQUENCE: 6
aataaacgcg gtatgtctac cttcaagcct atgatgaacg gatgtttggt gtttgcggct 60
attataacgc tcttgagttt tatgctatct ctgggaacat gcgaaaatta caggcgtgtg 120
gttcg 125

<210> SEQ ID NO 7
<211> LENGTH: 123
<212> TYPE: DNA
<213> ORGANISM: Artificial Sequence
<220> FEATURE:
<223> OTHER INFORMATION: Sequence of the 18pA polyadenylation sequence

<400> SEQUENCE: 7
ataaaaactg agactgttat attcatttca gtgtgtttaa taagaattgt gaacataact 60
tattctatat ctcattgcgt ggaaagactg gaaaacgcat tggtggtagg tggaaggctc 120
gcc 123

<210> SEQ ID NO 8
<211> LENGTH: 1235
<212> TYPE: DNA
<213> ORGANISM: Equine herpesvirus 1

<400> SEQUENCE: 8
atgttgactg tcttagcagc tctgagtctg ctcagcttgc ttacgagcgc aaccggacgg 60
ctcgccccag atgaactctg ttatgccgaa ccccgcagaa ctggcagccc accaaacacc 120
cagcccgaac gcccacccgt aatatttgag cccccaacaa ttgcgattaa agctgaatcc 180
aagggttgtg agctaatttt attagatcca cccatagatg taagctatcg cagagaagat 240
aaggtgaatg cgtccattgc ttggtttttt gactttggcg cttgccggat gcccatcgca 300
tacagagagt attacggttg tattggcaat gctgttccct ccccagagac ttgtgatgcg 360
tactcattta cccttattag gaccgagggt atcgtggagt ttaccatcgt aaacatgagc 420
ctcctgtttc agcctggaat atacgatagt ggcaatttta tctacagcgt tctcctggac 480
taccacatat ttacaggacg tgtaacgttg gaagtggaaa aggacacaaa ctatccctgt 540
ggcatgattc atggactcac tgcttacgga aacatcaacg tagatgaaac catggacaac 600
gccagcccac acccgcgtgc cgtggggtgc tttcccgagc ccatcgacaa cgaagcgtgg 660
gcaaacgtta catttactga attggggata ccagacccaa actcatttct cgatgacgag 720
ggtgattacc cgaatatatc agactgtcac tcgtgggagt catacaccta cccaaatacg 780
ctgaggcagg ccacaggacc ccagaccctg ttggtgggtg cggttggact cagaatcttg 840
gcgcaggcat ggaagtttgt cggtgacgaa acatacgaca ccatccgcgc agaagcaaag 900
aatttagaga cccacgtacc ctcaagtgct gcagagtcgt ctctagaaaa ccaatcgaca 960
caggaggagt ctaacagccc cgaagttgcc cacctgcgaa gcgtcaacag cgatgacagt 1020

-continued

```
acacacacgg gggtgcgtcg aacggcatcc aggactgtga cagtcagctc aaaactgtgt   1080
atgcctgctt ggctctaatt ggactcggca catgtgccat gatagggttg atagtttaca   1140
tttgtgtatt aaggtcaaaa ctgtcctctc ggaatttttc gcgcgcgcaa aatgtaaaac   1200
atagaaatta ccagcgactt gagtacgttg cttaa                              1235
```

```
<210> SEQ ID NO 9
<211> LENGTH: 417
<212> TYPE: DNA
<213> ORGANISM: Equine herpesvirus 1

<400> SEQUENCE: 9
ctccgagtac cccagaggag tatgtgaaaa gctgccactc gcaactactg aagataattt     60
caacgctcaa gataaatccg gaggagtttc ctcgagaccc cgggtcgagg ctcgtgcgcg    120
gatacatcga gtattctaga ctcgagcgca agccctacac gcgctacccc tgctttcaac    180
gcgtcaacct gcacattgac ggggagtttc tggttcacaa gatgctagcg ttcaatgccg    240
cgatgcgccc atcggccgag gagctgctgt catacccaat gtttgctcaa ctttaggatg    300
actaacctgt ttctgggagg agacagcgtg ggcgacggtg tataaagttg gtctgctttc    360
aagccctgcc actgcgctac agtgccacca actgtaaagc ggtagtaagc tgcagtg       417
```

```
<210> SEQ ID NO 10
<211> LENGTH: 431
<212> TYPE: DNA
<213> ORGANISM: Equine herpesvirus 1

<400> SEQUENCE: 10
gaccctgttg gtgggtgcgg ttggactcag aatcttggcg caggcatgga agtttgtcgg     60
tgacgaaaca tacgacacca tccgcgcaga agcaaagaat ttagagaccc acgtaccctc    120
aagtgctgca gagtcgtctc tagaaaacca atcgacacag gaggagtcta acagccccga    180
agttgcccac ctgcgaagcg tcaacagcga tgacagtaca cacacggggg gtgcgtcgaa    240
cggcatccag gactgtgaca gtcagctcaa aactgtgtat gcctgcttgg ctctaattgg    300
actcggcaca tgtgccatga tagggttgat agtttacatt tgtgtattaa ggtcaaaact    360
gtcctctcgg aatttttcgc gcgcgcaaaa tgtaaaacat agaaattacc agcgacttga    420
gtacgttgct t                                                         431
```

```
<210> SEQ ID NO 11
<211> LENGTH: 417
<212> TYPE: DNA
<213> ORGANISM: Equine herpesvirus 1

<400> SEQUENCE: 11
ctccgagtac cccagaggag tatgtgaaaa gctgccactc gcaactactg aagataattt     60
caacgctcaa gataaatccg gaggagtttc ctcgagaccc cgggtcgagg ctcgtgcgcg    120
gatacatcga gtattctaga ctcgagcgca agccctacac gcgctacccc tgctttcaac    180
gcgtcaacct gcacattgac ggggagtttc tggttcacaa gatgctagcg ttcaatgccg    240
cgatgcgccc atcggccgag gagctgctgt catacccaat gtttgcacaa ctttaggatg    300
actaacctgt ttctgggagg agacagcgtg ggcgacggtg tataaagttg gtctgctttc    360
aagccctgcc actgcgctac agtgccacca actgtaaagc ggtagtaagc tgcagtg       417
```

```
<210> SEQ ID NO 12
<211> LENGTH: 530
```

```
<212> TYPE: DNA
<213> ORGANISM: Equine herpesvirus 1

<400> SEQUENCE: 12
gaccctgttg gtgggtgcgg ttggactcag aatcttggcg caggcatgga agtttgtcgg     60
tgacgaaaca tacgcacacca tccgcgcaga agcaaagaat ttagagaccc acgtaccctc   120
aagtgctgca gagtcgtctc tagaaaacca atcgacacag gaggagtcta acagccccga   180
agttgcccac ctgcgaagcg tcaacagcga tgacagtaca cacacggggg gtgcgtcgaa   240
cggcatccag gactgtgaca gtcagctcaa aactgtgtat gcctgcttgg ctctaattgg   300
actcggcaca tgtgccatga tagggttgat agtttacatt tgtgtattaa ggtcaaaact   360
gtcctctcgg aattttttcgc gcgcgcaaaa tgtaaaacat agaaattacc agcgacttga   420
gtacgttgct taacacctgt caaataaaag tttcaaatca aaaacattgt tgtctgtaat   480
aactgagtgt ggttttaaaa atactaaatc gcggcaattc cggaaatagc              530

<210> SEQ ID NO 13
<211> LENGTH: 283
<212> TYPE: DNA
<213> ORGANISM: Equine herpesvirus 1

<400> SEQUENCE: 13
tctagactcg agcgcaagcc ctacacgcgc taccctgct ttcaacgcgt caacctgcac     60
attgacgggg agtttctggt tcacaagatg ctagcgttca atgccgcgat gcgcccatcg   120
gccgaggagc tgctgtcata cccaatgttt gctcaacttt aggatgacta acctgttcct   180
gggaggagac agcgtgggcg acggtgtata aagttggtct gctttcaagc cctgccactg   240
cgctacagtg ccaccaactg taaagcggta gtaagctgca gtg                      283

<210> SEQ ID NO 14
<211> LENGTH: 144
<212> TYPE: DNA
<213> ORGANISM: Equine herpesvirus 1

<400> SEQUENCE: 14
gaccctgttg gtgggtgcgg ttggactcag aatcttggcg caggcatgga agtttgtcgg     60
tgacgaaaca tacgcacacca tccgcgcaga agcaaagaat ttagagaccc acgtaccctc   120
aagtgctgca gagtcgtctc taga                                            144

<210> SEQ ID NO 15
<211> LENGTH: 1236
<212> TYPE: DNA
<213> ORGANISM: Equine herpesvirus 1

<400> SEQUENCE: 15
atgttgactg tcttagcagc cctgagtctg ctcagcttgc ttacgagcgc aaccggacgg     60
ctcgccccag atgaactctg ttatgccgaa ccccgcagaa ctggcagccc accaaacacc   120
cagcccgaac gcccacccgt aatatttgag cccccaacaa ttgcgattaa agctgaatcc   180 aagggtgtg agctaatttt attagatcca cccatagatg taagctatcg cagagaagat   240
aaggtgaatg cgtccattgc ttggtttttt gactttggcg cttgccggat gcccatcgca   300
tacagagagt attacggttg tattggcaat gctgttccct ccccagagac ttgtgatgcg   360
tactcattta cccttattag gaccgagggt atcgtggagt ttaccatcgt aaacatgagc   420
ctcctgtttc agcctggaat atacgatagt ggcaatttta tctacagcgt tctcctggac   480
```

| | |
|---|---|
| taccacatat ttacaggacg tgtaacgttg gaagtggaaa aggacacaaa ctatccctgt | 540 |
| ggcatgattc atggactcac tgcttacgga aacatcaacg tagatgaaac catggacaac | 600 |
| gccagcccac acccgcgtgc cgtggggtgc tttcccgagc ccatcgacaa cgaagcgtgg | 660 |
| gcaaacgtta catttactga attggggata ccagacccaa actcatttct cgatgacgag | 720 |
| ggtgattacc cgaatatatc agactgtcac tcgtgggagt catacaccta cccaaatacg | 780 |
| ctgaggcagg ccacaggacc ccagaccctg ttggtgggtg cggttggact cagaatcttg | 840 |
| gcgcaggcat ggaagtttgt cggtgacgaa acatacgaca ccatccgcgc agaagcaaag | 900 |
| aatttagaga cccacgtacc ctcaagtgct gcagagtcgt ctctagaaaa ccaatcgaca | 960 |
| caggaggagt ctaacagccc cgaagttgcc cacctgcgaa gcgtcaacag cgatgacagt | 1020 |
| acacacacgg ggggtgcgtc gaacggcatc caggactgtg acagtcagct caaaactgtg | 1080 |
| tatgcctgct tggctctaat tggactcggc acatgtgcca tgatagggtt gatagtttac | 1140 |
| atttgtgtat taaggtcaaa actgtcctct cggaattttt cgcgcgcgca aaatgtaaaa | 1200 |
| catagaaaatt accagcgact tgagtacgtt gcttaa | 1236 |

<210> SEQ ID NO 16
<211> LENGTH: 801
<212> TYPE: DNA
<213> ORGANISM: Equine herpesvirus 1

<400> SEQUENCE: 16

| | |
|---|---|
| atgttgactg tcttagcagc cctgagtctg ctcagcttgc ttacgagcgc aaccggacgg | 60 |
| ctcgccccag atgaactctg ttatgccgaa ccccgcagaa ctggcagccc accaaacacc | 120 |
| cagcccgaac gcccacccgt aatatttgag cccccaacaa ttgcgattaa agctgaatcc | 180 |
| aagggttgtg agctaatttt attagatcca cccatagatg taagctatcg cagagaagat | 240 |
| aaggtgaatg cgtccattgc ttggtttttt gactttggcg cttgccggat gcccatcgca | 300 |
| tacagagagt attacggttg tattggcaat gctgttccct ccccagagac ttgtgatgcg | 360 |
| tactcattta ccccttattag gaccgagggt atcgtggagt ttaccatcgt aaacatgagc | 420 |
| ctcctgtttc agcctggaat atacgatagt ggcaatttta tctacagcgt tctcctggac | 480 |
| taccacatat ttacaggacg tgtaacgttg gaagtggaaa aggacacaaa ctatccctgt | 540 |
| ggcatgattc atggactcac tgcttacgga aacatcaacg tagatgaaac catggacaac | 600 |
| gccagcccac acccgcgtgc cgtggggtgc tttcccgagc ccatcgacaa cgaagcgtgg | 660 |
| gcaaacgtta catttactga attggggata ccagacccaa actcatttct cgatgacgag | 720 |
| ggtgattacc cgaatatatc agactgtcac tcgtgggagt catacaccta cccaaatacg | 780 |
| ctgaggcagg ccacaggacc c | 801 |

<210> SEQ ID NO 17
<211> LENGTH: 803
<212> TYPE: DNA
<213> ORGANISM: Equine herpesvirus 1

<400> SEQUENCE: 17

| | |
|---|---|
| atgttgactg tcttagcagc tctgagtctg ctcagcttgc ttacgagcgc aaccggacgg | 60 |
| ctcgcccc

```
tacagagagt attacggttg tattggcaat gctgttccct ccccagagac ttgtgatgcg      360
tactcattta cccttattag gaccgagggt atcgtggagt ttaccatcgt aaacatgagc      420
ctcctgtttc agcctggaat atacgatagt ggcaatttta tctacagcgt tctcctggac      480
taccacatat ttacaggacg tgtaacgttg aagtgaaaa aggacacaaa ctatccctgt       540
ggcatgattc atggactcac tgcttacgga aacatcaacg tagatgaaac catggacaac      600
gccagcccac acccgcgtgc cgtggggtgc tttcccgagc ccatcgacaa cgaagcgtgg      660
gcaaacgtta catttactga attggggata ccagacccaa actcatttct cgatgacgag      720
ggtgattacc cgaatatatc agactgtcac tcgtgggagt catacaccta cccaaatacg      780
ctgaggcagg ccacaggacc cca                                              803

<210> SEQ ID NO 18
<211> LENGTH: 1206
<212> TYPE: DNA
<213> ORGANISM: Equine herpesvirus 1

<400> SEQUENCE: 18
atgatgtacc agccagatag agagcccggt gaagactcgt gtctggtgct aagctcatct       60
tcggtccaac gctgcaccgg ctcccagagg ggctgcatgc catgtacctg gcggcctcc      120 aaagctttcg ttggaatcgg actacaagct tgcgtcctca cttcatcgat cttacacatt      180
gacctgctaa cccggaactc aacatgtctg attctgatga tcatctcgat gtatgtgttg      240
agcctgatcc gcgtacccat atctaagatg gaaactatag taaccgtatg tcgatcgata      300
caggcgctgg ccactctagt ggcagccagt gtctgggtcg cgggatctgc agtcaaaaag      360
gaacatttac ttatagttgt taccgtttgc attttgtttg tgtttatagc cggaactcaa      420
atttccctat tttacgtcat atgctcagcc aatggaacgg ggactcactt tagagcgagc      480
ctattggcta ttatcggtgg atgtgtgcta ggggtttccg taaagctcgt tgagctgaaa      540
gatgtaccca tagggatagg gatagctatc gctattatag cttcctgtca agactttggg      600
cttgctcttc gagacacatg ccactatcga atcggacggt atgcgtgcat gcgcaccttt      660
acggaccttg gccggggtat taactacaga tgggtgacga cgttgaagc cgtccccaag      720 atcgaagaag tcgcggaaga aaaggttttcg ctgttcaagt ttttcaagga gatgccgggg      780
gtgatttcct ccccagcggt cggaactcac gcaaccccca taatatggat cgtcctacgc      840
ttggtctacg gaatttccaa cgtgtggcaa accccggcgt atgttgtctt ctgtctgact      900
gttggacacg tctctgcgat gctgctggag cagcttgtca tcagagtaaa ctacacggca      960
gaggcgagtt ccggcatcca ctccacggcc cacgctgtct gcatggtgct tgccgccttt     1020
gggtacggcg tggccggtcc cctctcgctc gcatttactg tatccggggg tatactgggg     1080
gcgctatacc ttcgcaagcg cgcaacgggc gcgcgccgcc tggcggcaac tcacatttcg     1140
aggtggctta tgtttgtgt atatgttgcc gccggttgtt gttatgcaac tataatcaca     1200
cattaa                                                              1206

<210> SEQ ID NO 19
<211> LENGTH: 226
<212> TYPE: DNA
<213> ORGANISM: Equine herpesvirus 1

<400> SEQUENCE: 19
gtataccatg cttgctatac tgaaaataaa aacgcatatt g

```
tgtttattgc ttagtttcac tatttggtta aaactattta cacttgtaga aacacgccca    120
ctaagtattt gttttatgac taatacctgg tgcataaaac catcctcttg ggtccctgta    180
cctcaaactc tccaaaggtt ggcttgctac atcaaggtta tcaatc                  226

<210> SEQ ID NO 20
<211> LENGTH: 305
<212> TYPE: DNA
<213> ORGANISM: Equine herpesvirus 1

<400> SEQUENCE: 20
accccggcgt atgttgtctt ctgtctgact gttggacacg tctctgcgat gctgctggag    60
cagcttgtca tcagagtaaa ctacacggca gaggcgagtt ccggcatcca ctccacggcc   120
cacgctgtct gcatggtgct tgccgccttt gggtacggcg tggccggtcc cctctcgctc   180
gcatttactg tatccggggg tatactgggg gcgctatacc ttcgcaagcg cgcaacgggc   240
gcgcgccgcc tggcggcaac tcacatttcg aggtggctta ttgtttgtgt atatgttgcc   300
gccgg                                                               305

<210> SEQ ID NO 21
<211> LENGTH: 870
<212> TYPE: DNA
<213> ORGANISM: Equine herpesvirus 1

<400> SEQUENCE: 21
atgatgtacc ag gcgcgccgcc tggcggcaac tcacatttcg aggtggctta ttgtttgtgt atatgttgcc 300
gccggtttgt gttatgcaac tataatcaca cattaa 336

<210> SEQ ID NO 23
<211> LENGTH: 1206
<212> TYPE: DNA
<213> ORGANISM: Equine herpesvirus 1

<400> SEQUENCE: 23
atgatgtacc agccagatag agagcccggt gaagactcgt gtctggtgct aagctcatct 60
tcggtccaac gctgcaccgg ctcccagagg ggctgcatgc catgtacctg ggcggcctcc 120
aaagctttcg ttggaatcgg actacaagct tgcgtcctca cttcatcgat cttacacatt 180
gacctgctaa cccggaactc aacatgtctg attctgatga tcatctcgat gtatgtgttg 240
agcctgatcc gcgtacccat atctaagatg gaaactatag taaccgtatg tcgatcgata 300
caggcgctgg ccactctagt ggcagccagt gtctgggtcg cgggatctgc agtcaaaaag 360
gaacatttac ttatagttgt taccgtttgc attttgtttg tgtttatagc cggaactcaa 420
atttccctat tttacgtcat atgctcagcc aatggaacgg ggactcactt tagagcgagc 480
ctattggcta ttatcggtgg atgtgtgcta ggggtttccg taaagctcgt tgagctgaaa 540
gatgtaccca tagggatagg gatagctatc gctattatag cttcctgtca agactttggg 600
cttgctcttc gagacacatg ccactatcga atcggacggt atgcgtgcat gcgcaccttt 660
acggaccttg gccggggtat taactacaga tgggtgacgg acgttgaagc cgtccccaag 720
atcgaagaag tcgcggaaga aaaggtttcg ctgttcaagt ttttcaagga gatgccgggg 780
gtgattttct ccccagcggt cggaactcac gcaaccccca taatatggat cgtcctacgc 840
ttggtctacg gaatttccaa cgtgtggcaa accccggcgt atgttgtctt ctgtctgact 900
gttggacacg tctctgcgat gctgctggag cagcttgtca tcagagtaaa ctacacggca 960
gaggcgagtt ccggcattca ctccacggcc cacgctgtct gcatggtgct tgccgccttt 1020
gggtacggcg tggccgctcc cctctcgctc gcatttactg tatccggggg tatactgggg 1080
gcgctatacc ttcgcaagcg cgcaacgggc gcgcgccgcc tggcggcaac tcacatttcg 1140
aggtggctta ttgtttgtgt atatgttgcc gccggtttgt gttatgcaac tataatcaca 1200
cattaa 1206

<210> SEQ ID NO 24
<211> LENGTH: 870
<212> TYPE: DNA
<213> ORGANISM: Equine herpesvirus 1

<400> SEQUENCE: 24
atgatgtacc agccagatag agagcccggt gaagactcgt gtctggtgct aagctcatct 60
tcggtccaac gctgcaccgg ctcccagagg ggctgcatgc catgtacctg ggcggcctcc 120
aaagctttcg ttggaatcgg actacaagct tgcgtcctca cttcatcgat cttacacatt 180
gacctgctaa cccggaactc aacatgtctg attctgatga tcatctcgat gtatgtgttg 240
agcctgatcc gcgtacccat atctaagatg gaaactatag taaccgtatg tcgatcgata 300
caggcgctgg ccactctagt ggcagccagt gtctgggtcg cgggatctgc agtcaaaaag 360
gaacatttac ttatagttgt taccgtttgc attttgtttg tgtttatagc cggaactcaa 420
atttccctat tttacgtcat atgctcagcc aatggaacgg ggactcactt tagagcgagc 480

```
ctattggcta ttatcggtgg atgtgtgcta ggggtttccg taaagctcgt tgagctgaaa      540
gatgtaccca tagggatagg gatagctatc gctattatag cttcctgtca agactttggg      600
cttgctcttc gagacacatg ccactatcga atcggacggt atgcgtgcat gcgcaccttt      660
acggaccttg gccggggtat taactacaga tgggtgacgg acgttgaagc cgtccccaag      720
atcgaagaag tcgcggaaga aaaggtttcg ctgttcaagt ttttcaagga gatgccgggg      780
gtgattttct ccccagcggt cggaactcac gcaaccccca taatatggat cgtcctacgc      840
ttggtctacg gaatttccaa cgtgtggcaa                                        870

<210> SEQ ID NO 25
<211> LENGTH: 336
<212> TYPE: DNA
<213> ORGANISM: Equine herpesvirus 1

<400> SEQUENCE: 25
accccggcgt atgttgtctt ctgtctgact gttggacacg tctctgcgat gctgctggag       60
cagcttgtca tcagagtaaa ctacacggca gaggcgagtt ccggcattca ctccacggcc      120
cacgctgtct gcatggtgct tgccgccttt gggtacggcg tggccgctcc cctctcgctc      180
gcatttactg tatccggggg tatactgggg gcgctatacc ttcgcaagcg cgcaacgggc      240
gcgcgccgcc tgcggcaac tcacatttcg aggtggctta ttgtttgtgt atatgttgcc      300
gccggtttgt gttatgcaac tataatcaca cattaa                                336

<210> SEQ ID NO 26
<211> LENGTH: 226
<212> TYPE: DNA
<213> ORGANISM: Equine herpesvirus 1

<400> SEQUENCE: 26
gtataccatg cttgctatac tgaaaataaa aacgcatatt gtaaacgaca gacgcggaaa       60
tgtttattgc ttagtttcac tatttggtta aaactattta cacttgtaga aacacgccca      120
ctaagtattt gttttatgac taataccctgg tgcataaaac catcctcttg ggtccctgta     180
cctcaaactc tccaaaggtt ggcttgctac atcaaggtta tcaatc                     226

<210> SEQ ID NO 27
<211> LENGTH: 305
<212> TYPE: DNA
<213> ORGANISM: Equine herpesvirus 1

<400> SEQUENCE: 27
accccggcgt atgttgtctt ctgtctgact gttggacacg tctctgcgat gctgctggag       60
cagcttgtca tcagagtaaa ctacacggca gaggcgagtt ccggcattca ctccacggcc      120
cacgctgtct gcatggtgct tgccgccttt gggtacggcg tggccgctcc cctctcgctc      180
gcatttactg tatccggggg tatactgggg gcgctatacc ttcgcaagcg cgcaacgggc      240
gcgcgccgcc tgcggcaac tcacatttcg aggtggctta ttgtttgtgt atatgttgcc      300
gccgg                                                                  305

<210> SEQ ID NO 28
<211> LENGTH: 5191
<212> TYPE: DNA
<213> ORGANISM: Artificial Sequence
<220> FEATURE:
<223> OTHER INFORMATION: (Nucleotide sequence of transfer vector
      pU70-p455-71K71
```

<400> SEQUENCE: 28

```
caataaacgc ggtatgtcta ccttcaagcc tatgatgaac ggatgtttgg tgtttgcggc     60
tattataacg ctcttgagtt ttatgctatc tctgggaaca tgcgaaaatt acaggcgtgt    120
ggttcgggat cctagggata cagggtaat cgatttattc aacaaagcca cgttgtgtct    180
caaaatctct gatgttacat tgcacaagat aaaaatatat catcatgaac aataaaactg    240
tctgcttaca taaacagtaa tacaagggg gttatgagcc atattcaacg ggaaacgtct    300
tgctcgaggc cgcgattaaa ttccaacatg gatgctgatt tatatgggta taaatgggct    360
cgcgataatg tcgggcaatc aggtgcgaca atctatcgat tgtatgggaa gcccgatgcg    420
ccagagttgt ttctgaaaca tggcaaaggt agcgttgcca atgatgttac agatgagatg    480
gtcagactaa actggctgac ggaatttatg cctcttccga ccatcaagca ttttatccgt    540
actcctgatg atgcatggtt actcaccact gcgatccccg ggaaaacagc attccaggta    600
ttagaagaat atcctgattc aggtgaaaat attgttgatg cgctggcagt gttcctgcgc    660
cggttgcatt cgattcctgt ttgtaattgt cctttaaca gcgatcgcgt atttcgtctc    720
gctcaggcgc aatcacgaat gaataacggt ttggttgatg cgagtgattt tgatgacgag    780
cgtaatggct ggcctgttga acaagtctgg aaagaaatgc ataagctttt gccattctca    840
ccggattcag tcgtcactca tggtgatttc tcacttgata accttatttt tgacgagggg    900
aaattaatag gttgtattga tgttggacga gtcggaatcg cagaccgata ccaggatctt    960
gccatcctat ggaactgcct cggtgagttt tctccttcat tacagaaacg ctttttcaa   1020
aaatatggta ttgataatcc tgatatgaat aaattgcagt ttcatttgat gctcgatgag   1080
ttttctaaa ataaacgcgg tatgtctacc ttcaagccta tgatgaacgg atgtttggtg   1140
tttgcggcta ttataacgct cttgagtttt atgctatctc tgggaacatg cgaaaattac   1200
aggcgtgtgg ttcgggatcc gaccctgttg gtgggtgcgg ttggactcag aatcttggcg   1260
caggcatgga agtttgtcgg tgacgaaaca tacgacacca tccgcgcaga agcaaagaat   1320
ttagagaccc acgtaccctc aagtgctgca gagtcgtctc tagaaaacca atcgacacag   1380
gaggagtcta acagcccga agttgcccac ctgcgaagcg tcaacagcga tgacagtaca   1440
cacacggggg gtgcgtcgaa cggcatccag gactgtgaca gtcagctcaa aactgtgtat   1500
gcctgcttgg ctctaattgg actcggcaca tgtgccatga tagggttgat agtttacatt   1560
tgtgtattaa ggtcaaaact gtcctctcgg aattttttcgc gcgcgcaaaa tgtaaaacat   1620
agaaattacc agcgacttga gtacgttgct taagcttggc gtaatcatgg tcatagctgt   1680
ttcctgtgtg aaattgttat ccgctcacaa ttccacacaa catacgagcc ggaagcataa   1740
agtgtaaagc ctggggtgcc taatgagtga gctaactcac attaattgcg ttgcgctcac   1800
tgcccgcttt ccagtcggga aacctgtcgt gccagctgca ttaatgaatc ggccaacgcg   1860
cggggagagg cggtttgcgt attgggcgct cttccgcttc ctcgctcact gactcgctgc   1920
gctcggtcgt tcgctgcgg cgagcggtat cagctcactc aaaggcggta atacggttat   1980
ccacagaatc aggggataac gcaggaaaga acatgtgagc aaaaggccag caaaaggcca   2040
ggaaccgtaa aaaggccgcg ttgctggcgt ttttccatag gctccgcccc cctgacgagc   2100
atcacaaaaa tcgacgctca agtcagaggt ggcgaaaccc gacaggacta taaagatacc   2160
aggcgtttcc ccctggaagc tccctcgtgc gctctcctgt tccgaccctg ccgcttaccg   2220
gatacctgtc cgcctttctc ccttcgggaa gcgtggcgct ttctcatagc tcacgctgta   2280
ggtatctcag ttcggtgtag tcgttcgct ccaagctggg ctgtgtgcac gaaccccccg   2340
```

```
ttcagcccga ccgctgcgcc ttatccggta actatcgtct tgagtccaac ccggtaagac    2400
acgacttatc gccactggca gcagccactg gtaacaggat tagcagagcg aggtatgtag    2460
gcggtgctac agagttcttg aagtggtggc ctaactacgg ctacactaga aggacagtat    2520
ttggtatctg cgctctgctg aagccagtta ccttcggaaa aagagttggt agctcttgat    2580
ccggcaaaca aaccaccgct ggtagcggtg ttttttttgt ttgcaagcag cagattacgc    2640
gcagaaaaaa aggatctcaa gaagatcctt tgatcttttc tacggggtct gacgctcagt    2700
ggaacgaaaa ctcacgttaa gggattttgg tcatgagatt atcaaaaagg atcttcacct    2760
agatcctttt aaattaaaaa tgaagtttta aatcaatcta agtatatat gagtaaactt     2820 ggtctgacag ttaccaatgc ttaatcagtg aggcacctat ctcagcgatc tgtctatttc    2880
gttcatccat agttgcctga ctccccgtcg tgtagataac tacgatacgg gagggcttac    2940
catctggccc cagtgctgca atgataccgc gagacccacg ctcaccggct ccagatttat    3000
cagcaataaa ccagccagcc ggaagggccg agcgcagaag tggtcctgca actttatccg    3060
cctccatcca gtctattaat tgttgccggg aagctagagt aagtagttcg ccagttaata    3120
gtttgcgcaa cgttgttgcc attgctacag gcatcgtggt gtcacgctcg tcgtttggta    3180
tggcttcatt cagctccggt tcccaacgat caaggcgagt tacatgatcc cccatgttgt    3240
gcaaaaaagc ggttagctcc ttcggtcctc cgatcgttgt cagaagtaag ttggccgcag    3300
tgttatcact catggttatg gcagcactgc ataattctct tactgtcatg ccatccgtaa    3360
gatgcttttc tgtgactggt gagtactcaa ccaagtcatt ctgagaatag tgtatgcggc    3420
gaccgagttg ctcttgcccg gcgtcaatac gggataatac cgcgccacat agcagaactt    3480
taaaagtgct catcattgga aaacgttctt cggggcgaaa actctcaagg atcttaccgc    3540
tgttgagatc cagttcgatg taacccactc gtgcacccaa ctgatcttca gcatctttta    3600
ctttcaccag cgtttctggg tgagcaaaaa caggaaggca aaatgccgca aaaagggaa     3660 taagggcgac acggaaatgt tgaatactca tactcttcct ttttcaatat tattgaagca    3720
tttatcaggg ttattgtctc atgagcggat acatatttga atgtatttag aaaaataaac    3780 aaatagggt tccgcgcaca tttccccgaa aagtgccacc tgacgtctaa gaaaccatta    3840
ttatcatgac attaacctat aaaaataggc gtatcacgag gccctttcgt ctcgcgcgtt    3900
tcggtgatga cggtgaaaac ctctgacaca tgcagctccc ggagacggtc acagcttgtc    3960
tgtaagcgga tgccgggagc agacaagccc gtcagggcgc gtcagcgggt gttggcgggt    4020 gtcgggctg gcttaactat gcggcatcag agcagattgt actgagagtg caccatatgc     4080
ggtgtgaaat accgcacaga tgcgtaagga gaaaataccg catcaggcgc cattcgccat    4140
tcaggctgcg caactgttgg gaagggcgat cggtgcgggc ctcttcgcta ttacgccagc    4200
tggcgaaagg gggatgtgct gcaaggcgat taagttgggt aacgccaggg ttttcccagt    4260
cacgacgttg taaaacgacg gccagtgaat tcctccgagt accccagagg agtatgtgaa    4320
aagctgccac tcgcaactac tgaagataat ttcaacgctc aagataaatc cggaggagtt    4380
tcctcgagac cccgggtcga ggctcgtgcg cggatacatc gagtattcta gactcgagcg    4440
caagccctac acgcgctacc cctgctttca acgcgtcaac ctgcacattg acggggagtt    4500
tctggttcac aagatgctag cgttcaatgc cgcgatgcgc ccatcggccg aggagctgct    4560 gtcatacccca atgtttgctc aactttagga tgactaacct gtttctggga ggagacagcg    4620
tgggcgacgg tgtataaagt tggtctgctt tcaagccctg ccactgcgct acagtgccac    4680
```

| | |
|---|---:|
| caactgtaaa gcggtagtaa gctgcagtgg tcgactggtg gtagcatata ctaccttatt | 4740 |
| tatacgctcc gagctgtttt tcagcatgct agcacccaac gccgagcgag agtatataac | 4800 |
| tcccatcatt gcccacaagc ttatgccact tattagcgtc cgctctgccg tttgcttagt | 4860 |
| cataatatct accgccgttt acgcagcaga cgctatctgc gacacaattg gatttgcgat | 4920 |
| accgcgcatg tggatgtgta ttttaatgag atcaacctcc atgaagcgta actaggggc | 4980 |
| ctcccactga ggcactaccg gcttagcagc tgactaacac agtataaaac gtgagaagaa | 5040 |
| atcagtctca tgcgccatta gcgctaggct agttagcgtg gaggaccgga gcgctaccgc | 5100 |
| cagcagtttc atccgcctgg ttacgggttt gttaacacct accggtgttt taccgctacc | 5160 |
| ataggatccg atccatgggc ggccgcggta c | 5191 |

<210> SEQ ID NO 29
<211> LENGTH: 6892
<212> TYPE: DNA
<213> ORGANISM: Artificial Sequence
<220> FEATURE:
<223> OTHER INFORMATION: Nucleotide sequence of transfer plasmid pU70-p455-H3-71K71

<400> SEQUENCE: 29

| | |
|---|---:|
| caataaacgc ggtatgtcta ccttcaagcc tatgatgaac ggatgtttgg tgtttgcggc | 60 |
| tattataacg ctcttgagtt ttatgctatc tctgggaaca tgcgaaaatt acaggcgtgt | 120 |
| ggttcgggat cctagggata acagggtaat cgatttattc aacaaagcca cgttgtgtct | 180 |
| caaaatctct gatgttacat tgcacaagat aaaaatatat catcatgaac aataaaactg | 240 |
| tctgcttaca taaacagtaa tacaagdggt gttatgagcc atattcaacg ggaaacgtct | 300 |
| tgctcgaggc cgcgattaaa ttccaacatg gatgctgatt tatatgggta taaatgggct | 360 |
| cgcgataatg tcgggcaatc aggtgcgaca atctatcgat tgtatgggaa gcccgatgcg | 420 |
| ccagagttgt ttctgaaaca tggcaaaggt agcgttgcca atgatgttac agatgagatg | 480 |
| gtcagactaa actggctgac ggaatttatg cctcttccga ccatcaagca ttttatccgt | 540 |
| actcctgatg atgcatggtt actcaccact gcgatccccg ggaaaacagc attccaggta | 600 |
| ttagaagaat atcctgattc aggtgaaaat attgttgatg cgctggcagt gttcctgcgc | 660 |
| cggttgcatt cgattcctgt ttgtaattgt ccttttaaca gcgatcgcgt atttcgtctc | 720 |
| gctcaggcgc aatcacgaat gaataacggt ttggttgatg cgagtgattt tgatgacgag | 780 |
| cgtaatggct ggcctgttga acaagtctgg aaagaaatgc ataagctttt gccattctca | 840 |
| ccggattcag tcgtcactca tggtgatttc tcacttgata accttatttt tgacgagggg | 900 |
| aaattaatag gttgtattga tgttggacga gtcggaatcg cagaccgata ccaggatctt | 960 |
| gccatcctat ggaactgcct cggtgagttt tctccttcat tacagaaacg gcttttcaa | 1020 |
| aaatatggta ttgataatcc tgatatgaat aaattgcagt ttcatttgat gctcgatgag | 1080 |
| tttttctaaa ataaacgcgg tatgtctacc ttcaagccta tgatgaacgg atgtttggtg | 1140 |
| tttgcggcta ttataacgct cttgagtttt atgctatctc tgggaacatg cgaaaattac | 1200 |
| aggcgtgtgg ttcgggatcc gaccctgttg gtgggtgcgg ttggactcag aatcttggcg | 1260 |
| caggcatgga agtttgtcgg tgacgaaaca tacgacacca tccgcgcaga agcaaagaat | 1320 |
| ttagagaccc acgtaccctc aagtgctgca gagtcgtctc tagaaaacca atcgacacag | 1380 |
| gaggagtcta acagcccga agttgcccac ctgcgaagcg tcaacagcga tgacagtaca | 1440 |
| cacacggggg gtgcgtcgaa cggcatccag gactgtgaca gtcagctcaa aactgtgtat | 1500 |

-continued

```
gcctgcttgg ctctaattgg actcggcaca tgtgccatga tagggttgat agtttacatt    1560
tgtgtattaa ggtcaaaact gtcctctcgg aattttttcgc gcgcgcaaaa tgtaaaacat   1620
agaaattacc agcgacttga gtacgttgct taagcttggc gtaatcatgg tcatagctgt    1680
ttcctgtgtg aaattgttat ccgctcacaa ttccacacaa catacgagcc ggaagcataa    1740
agtgtaaagc ctggggtgcc taatgagtga gctaactcac attaattgcg ttgcgctcac    1800
tgcccgcttt ccagtcggga aacctgtcgt gccagctgca ttaatgaatc ggccaacgcg    1860
cggggagagg cggtttgcgt attgggcgct cttccgcttc ctcgctcact gactcgctgc    1920
gctcggtcgt tcggctgcgg cgagcggtat cagctcactc aaaggcggta atacggttat    1980
ccacagaatc aggggataac gcaggaaaga acatgtgagc aaaaggccag caaaaggcca    2040
ggaaccgtaa aaaggccgcg ttgctggcgt ttttccatag gctccgcccc cctgacgagc    2100
atcacaaaaa tcgacgctca agtcagaggt ggcgaaaccc gacaggacta taaagatacc    2160
aggcgtttcc ccctggaagc tccctcgtgc gctctcctgt tccgaccctg ccgcttaccg    2220
gatacctgtc cgcctttctc ccttcgggaa gcgtggcgct ttctcatagc tcacgctgta    2280
ggtatctcag ttcggtgtag gtcgttcgct ccaagctggg ctgtgtgcac gaaccccccg    2340
ttcagcccga ccgctgcgcc ttatccggta actatcgtct tgagtccaac ccggtaagac    2400
acgacttatc gccactggca gcagccactg gtaacaggat tagcagagcg aggtatgtag    2460
gcggtgctac agagttcttg aagtggtggc ctaactacgg ctacactaga aggacagtat    2520
ttggtatctg cgctctgctg aagccagtta ccttcggaaa aagagttggt agctcttgat    2580
ccggcaaaca aaccaccgct ggtagcggtg gtttttttgt ttgcaagcag cagattacgc    2640
gcagaaaaaa aggatctcaa gaagatcctt tgatcttttc tacggggtct gacgctcagt    2700
ggaacgaaaa ctcacgttaa gggattttgg tcatgagatt atcaaaaagg atcttcacct    2760
agatcctttt aaattaaaaa tgaagtttta aatcaatcta agtatatat gagtaaactt     2820 ggtctgacag ttaccaatgc ttaatcagtg aggcacctat ctcagcgatc tgtctatttc    2880
gttcatccat agttgcctga ctccccgtcg tgtagataac tacgatacgg gagggcttac    2940
catctggccc cagtgctgca atgataccgc gagacccacg ctcaccggct ccagatttat    3000
cagcaataaa ccagccagcc ggaagggccg agcgcagaag tggtcctgca actttatccg    3060
cctccatcca gtctattaat tgttgccggg aagctagagt aagtagttcg ccagttaata    3120
gtttgcgcaa cgttgttgcc attgctacag gcatcgtggt gtcacgctcg tcgtttggta    3180
tggcttcatt cagctccggt tcccaacgat caaggcgagt tacatgatcc cccatgttgt    3240
gcaaaaaagc ggttagctcc ttcggtcctc cgatcgttgt cagaagtaag ttggccgcag    3300
tgttatcact catggttatg gcagcactgc ataattctct tactgtcatg ccatccgtaa    3360
gatgcttttc tgtgactggt gagtactcaa ccaagtcatt ctgagaatag tgtatgcggc    3420
gaccgagttg ctcttgcccg gcgtcaatac gggataatac cgcgccacat agcagaactt    3480
taaaagtgct catcattgga aaacgttctt cggggcgaaa actctcaagg atcttaccgc    3540
tgttgagatc cagttcgatg taacccactc gtgcacccaa ctgatcttca gcatctttta    3600
ctttcaccag cgtttctggg tgagcaaaaa caggaaggca aaatgccgca aaaagggaa     3660 taagggcgac acggaaatgt tgaatactca tactcttcct ttttcaatat tattgaagca    3720
tttatcaggg ttattgtctc atgagcggat acatatttga atgtatttag aaaaataaac    3780
aaataggggt tccgcgcaca tttccccgaa aagtgccacc tgacgtctaa gaaaccatta    3840
ttatcatgac attaacctat aaaaataggc gtatcacgag gccctttcgt ctcgcgcgtt    3900
```

```
tcggtgatga cggtgaaaac ctctgacaca tgcagctccc ggagacggtc acagcttgtc   3960
tgtaagcgga tgccgggagc agacaagccc gtcaggcgc  gtcagcgggt gttggcgggt   4020 gtcgggctg  gcttaactat gcggcatcag agcagattgt actgagagtg caccatatgc   4080
ggtgtgaaat accgcacaga tgcgtaagga gaaataccg  catcaggcgc cattcgccat   4140
tcaggctgcg caactgttgg gaagggcgat cggtgcgggc ctcttcgcta ttacgccagc   4200
tggcgaaagg gggatgtgct gcaaggcgat taagttgggt aacgccaggg ttttcccagt   4260
cacgacgttg taaaacgacg gccagtgaat tcctccgagt accccagagg agtatgtgaa   4320
aagctgccac tcgcaactac tgaagataat ttcaacgctc aagataaatc cggaggagtt   4380
tcctcgagac cccgggtcga ggctcgtgcg cggatacatc gagtattcta gactcgagcg   4440
caagccctac acgcgctacc cctgctttca acgcgtcaac ctgcacattg acggggagtt   4500
tctggttcac aagatgctag cgttcaatgc cgcgatgcgc ccatcggccg aggagctgct   4560
gtcataccca atgtttgctc aactttagga tgactaacct gtttctggga ggagacagcg   4620
tgggcgacgg tgtataaagt tggtctgctt tcaagccctg ccactgcgct acagtgccac   4680
caactgtaaa gcggtagtaa gctgcagtgg tcgactggtg gtagcatata ctaccttatt   4740
tatacgctcc gagctgtttt tcagcatgct agcacccaac gccgagcgag agtatataac   4800
tcccatcatt gcccacaagc ttatgccact tattagcgtc cgctctgccg tttgcttagt   4860
cataatatct accgccgttt acgcagcaga cgctatctgc gacacaattg gatttgcgat   4920
accgcgcatg tggatgtgta ttttaatgag atcaacctcc atgaagcgta actaggggc   4980 ctcccactga ggcactaccg gcttagcagc tgactaacac agtataaaac gtgagaagaa   5040
atcagtctca tgcgccatta gcgctaggct agttagcgtg gaggaccgga gcgctaccgc   5100
cagcagtttc atccgcctgg ttacgggttt gttaacacct accggtgttt taccgctacc   5160
ataggatccg atccatgggc ggccgcatga agaccgtgat cgccctgagt tacatcttct   5220
gcctggtgtt tgggcaggac ctccctggta aaggcaacaa cacggccacg ctgtgccttg   5280
ggcaccacgc cgtgccgaac ggcacccttg tgaaaactat taccgacgat cagatcgagg   5340
tgaccaacgc caccgaactg gttcagaatt ttagcatggg caaaatttgc aataacccgc   5400
accgcattct ggacggggcc aactgcacgc tgatcgattc attgctgggt gatccccact   5460
gcgatggctt tcaaaacgaa aagtgggact tgttcatcga acgcagcaag gcattcagca   5520
actgctaccc atacgacgtg cccgaataca ccagcctgcg aagcctgatc gcgagctctg   5580
ggaccctgga gttcaccaat gagaacttca attggaccgg agtgacccaa acggtggct   5640 ccagcgcctg taaaagggga cccaataaca gcttctttag caagttgaat tggctttaca   5700
agagcggcaa tacttacccg atgttgaatg tgaccatgcc caacagtgac gactttgata   5760
aactgtacat atggggcgtg caccatccca gcacggaccg cgaacagata aacctgtacg   5820
tgcaggccag cgggaagata atcgtgagca ccaagcgcag ccagcagacc atcattccca   5880
acattggcag ccgaccgtgg gtgcgcggtc tgagctcccg catcagcata tactggacca   5940
ttgtcaagcc gggagacatc ctgatcatca actctaatgg caatcttatc gccccacgcg   6000
gctacttcaa gatgcagacc ggcaaaagca gtgtgatgag gagcgacgcc cccatcgaca   6060
cctgcaatag cgaatgcatc accccccaatg gcagcatccc caacgacaag cctttccaga   6120
acgtgaataa gatcacctac ggcgcgtgcc ccaagtacat caagcagaac accctgaagc   6180
tggccaccgg catgcgcaac atccccgagc gacagacacg gggcattttt ggcgcaatcg   6240
```

| | | |
|---|---|---|
| cagggttcat tgagaatggc tgggagggaa tggttaacgg ctggtacggc ttccgccatc | 6300 | |
| agaactctga aggaatcggc caagctgcgg atctgaagtc cacgcaagca gccatcaacc | 6360 | |
| agatcaacgg caagcttaac cgcgtgattg aaaagacgaa cgagaaattc caccaaatag | 6420 | |
| agaaagaatt cagcgaggtg gagggccgca tccaagacct cgagcgctac gtggaggaca | 6480 | |
| ccaagatcga cctgtggagc tacaatgccg agctcctggt cgccttggaa aaccaacaca | 6540 | |
| ccattgacct gaccgacagc gagatgaata aactcttcga gaagacccgg aagcaactcc | 6600 | |
| gagagaacgc cgaagacatg ggtaatgggt gttttaagat ctaccacaag tgcgacaata | 6660 | |
| gctgcatgga gagcatccga aacggaacct acgaccacaa cgagtaccgc gatgaggcag | 6720 | |
| ttaataaccg cttccaaatc aaaagcgtgg aactgaagag tggctataag gactggatac | 6780 | |
| tgtggatcag ctttgccata agctgcttcc tgctgtgcgc cgtttggttg ggtttcatca | 6840 | |
| tgtgggcctg tcaaaagggc aatattcgct gtaacatctg catttgaggt ac | 6892 | |

<210> SEQ ID NO 30
<211> LENGTH: 4977
<212> TYPE: DNA
<213> ORGANISM: Artificial Sequence
<220> FEATURE:
<223> OTHER INFORMATION: Nucleotide sequence of transfer vector
      pU-1-3-p430-BGHKBGH

<400> SEQUENCE: 30

| | | |
|---|---|---|
| cctgtgcctt ctagttgcca gccatctgtt gtttgcccct cccccgtgcc ttccttgacc | 60 | |
| ctggaaggtg ccactcccac tgtcctttcc taataaaatg aggaaattgc atcgcattgt | 120 | |
| ctgagtaggt gtcattctat tctggggggt ggggtggggc aggacagcaa gggggaggat | 180 | |
| tgggaagaca atagcaggca tgctggggat gcggtgggct ctatggatcc tagggataac | 240 | |
| agggtaatcg atttattcaa caaagccacg ttgtgtctca aaatctctga tgttacattg | 300 | |
| cacaagataa aaatatatca tcatgaacaa taaaactgtc tgcttacata acagtaata | 360 | |
| caaggggtgt tatgagccat attcaacggg aaacgtcttg ctcgaggccg cgattaaatt | 420 | |
| ccaacatgga tgctgattta tatgggtata atgggctcg cgataatgtc gggcaatcag | 480 | |
| gtgcgacaat ctatcgattg tatgggaagc ccgatgcgcc agagttgttt ctgaaacatg | 540 | |
| gcaaaggtag cgttgccaat gatgttacag atgagatggt cagactaaac tggctgacgg | 600 | |
| aatttatgcc tcttccgacc atcaagcatt ttatccgtac tcctgatgat gcatggttac | 660 | |
| tcaccactgc gatccccggg aaaacagcat tccaggtatt agaagaatat cctgattcag | 720 | |
| gtgaaaatat tgttgatgcg ctggcagtgt tcctgcgccg gttgcattcg attcctgttt | 780 | |
| gtaattgtcc ttttaacagc gatcgcgtat ttcgtctcgc tcaggcgcaa tcacgaatga | 840 | |
| ataacggttt ggttgatgcg agtgattttg atgacgagcg taatggctgg cctgttgaac | 900 | |
| aagtctggaa agaaatgcat aagcttttgc cattctcacc ggattcagtc gtcactcatg | 960 | |
| gtgatttctc acttgataac cttatttttg acgaggggaa attaataggt tgtattgatg | 1020 | |
| ttggacgagt cggaatcgca gaccgatacc aggatcttgc catcctatgg aactgcctcg | 1080 | |
| gtgagttttc tccttcatta cagaaacggc ttttttcaaaa atatggtatt gataatcctg | 1140 | |
| atatgaataa attgcagttt catttgatgc tcgatgagtt tttctaacca tggctgtgcc | 1200 | |
| ttctagttgc cagccatctg ttgtttgccc ctcccccgtg ccttccttga ccctggaagg | 1260 | |
| tgccactccc actgtccttt cctaataaaa tgaggaaatt gcatcgcatt gtctgagtag | 1320 | |
| gtgtcattct attctggggg gtggggtggg gcaggacagc aagggggagg attgggaaga | 1380 | |

```
caatagcagg catgctgggg atgcggtggg ctctatggat ccgaccctcc ccggggctaa    1440
aaagctgcgt cttcacgccc gaggcgctta ttgcccactg ggtacggggc gcgcttttat    1500
atgtgtaacg tcccaccggt gtgacgcacg tactacggtt gttctaaata gctgtccccg    1560
tgattgcctc ggctgcacac atcgctaggt tttccgccgt gcctggtgtc gagggcccac    1620
ccctgtaacc aacatcgatg ggggcctgct gctccttcgc taccttagga ccgttatagt    1680
tacgtcaagc ttggcgtaat catggtcata gctgtttcct gtgtgaaatt gttatccgct    1740
cacaattcca cacaacatac gagccggaag cataaagtgt aaagcctggg gtgcctaatg    1800
agtgagctaa ctcacattaa ttgcgttgcg ctcactgccc gctttccagt cgggaaacct    1860
gtcgtgccag ctgcattaat gaatcggcca acgcgcgggg agaggcggtt tgcgtattgg    1920
gcgctcttcc gcttcctcgc tcactgactc gctgcgctcg tcgttcggc tgcggcgagc     1980 ggtatcagct cactcaaagg cggtaatacg gttatccaca gaatcagggg ataacgcagg    2040
aaagaacatg tgagcaaaag gccagcaaaa ggccaggaac cgtaaaaagg ccgcgttgct    2100
ggcgtttttc cataggctcc gcccccctga cgagcatcac aaaaatcgac gctcaagtca    2160
gaggtggcga aacccgacag gactataaag ataccaggcg tttccccctg gaagctccct    2220
cgtgcgctct cctgttccga ccctgccgct taccggatac ctgtccgcct ttctcccttc    2280
gggaagcgtg gcgctttctc atagctcacg ctgtaggtat ctcagttcgg tgtaggtcgt    2340
tcgctccaag ctgggctgtg tgcacgaacc ccccgttcag cccgaccgct gcgccttatc    2400
cggtaactat cgtcttgagt ccaacccggt aagacacgac ttatcgccac tggcagcagc    2460
cactggtaac aggattagca gagcgaggta tgtaggcggt gctacagagt tcttgaagtg    2520
gtggcctaac tacggctaca ctagaaggac agtatttggt atctgcgctc tgctgaagcc    2580
agttaccttc ggaaaaagag ttggtagctc ttgatccggc aaacaaacca ccgctggtag    2640
cggtggtttt tttgtttgca agcagcagat tacgcgcaga aaaaaggat ctcaagaaga    2700 tcctttgatc ttttctacgg ggtctgacgc tcagtggaac gaaaactcac gttaagggat    2760
tttggtcatg agattatcaa aaaggatctt cacctagatc cttttaaatt aaaaatgaag    2820
ttttaaatca atctaaagta tatatgagta aacttggtct gacagttacc aatgcttaat    2880
cagtgaggca cctatctcag cgatctgtct atttcgttca tccatagttg cctgactccc    2940
cgtcgtgtag ataactacga tacgggaggg cttaccatct ggccccagtg ctgcaatgat    3000
accgcgagac ccacgctcac cggctccaga tttatcagca ataaaccagc cagccggaag    3060
ggccgagcgc agaagtggtc ctgcaacttt atccgcctcc atccagtcta ttaattgttg    3120
ccgggaagct agagtaagta gttcgccagt taatagtttg cgcaacgttg ttgccattgc    3180
tacaggcatc gtggtgtcac gctcgtcgtt ggtatggct tcattcagct ccggttccca    3240
acgatcaagg cgagttacat gatccccat gttgtgcaaa aaagcggtta gctccttcgg    3300
tcctccgatc gttgtcagaa gtaagttggc cgcagtgtta tcactcatgg ttatggcagc    3360
actgcataat tctcttactg tcatgccatc cgtaagatgc ttttctgtga ctggtgagta    3420
ctcaaccaag tcattctgag aatagtgtat gcggcgaccg agttgctctt gcccggcgtc    3480
aatacgggat aataccgcgc cacatagcag aactttaaaa gtgctcatca ttggaaaacg    3540
ttcttcgggg cgaaaactct caaggatctt accgctgttg agatccagtt cgatgtaacc    3600
cactcgtgca cccaactgat cttcagcatc ttttactttc accagcgttt ctgggtgagc    3660
aaaaacagga aggcaaaatg ccgcaaaaaa gggaataagg gcgacacgga aatgttgaat    3720
actcatactc ttcctttttc aatattattg aagcatttat cagggttatt gtctcatgag    3780
```

```
cggatacata tttgaatgta tttagaaaaa taaacaaata ggggttccgc gcacatttcc    3840
ccgaaaagtg ccacctgacg tctaagaaac cattattatc atgacattaa cctataaaaa    3900
taggcgtatc acgaggccct ttcgtctcgc gcgtttcggt gatgacggtg aaaacctctg    3960
acacatgcag ctcccggaga cggtcacagc ttgtctgtaa gcggatgccg ggagcagaca    4020
agcccgtcag ggcgcgtcag cgggtgttgg cgggtgtcgg gctggctta actatgcggc    4080 atcagagcag attgtactga gagtgcacca tatgcggtgt gaaataccgc acagatgcgt    4140
aaggagaaaa taccgcatca ggcgccattc gccattcagg ctgcgcaact gttgggaagg    4200
gcgatcggtg cgggcctctt cgctattacg ccagctggcg aaagggggat gtgctgcaag    4260
gcgattaagt tgggtaacgc cagggttttc ccagtcacga cgttgtaaaa cgacggccag    4320
tgaattcgac gtaactataa cggtcctaag gtagcgaatt tttccattgg gcccctccct    4380
tttggctctg gtatttagc ttccctccca cttctcattc cactttctcc acctgcacct    4440
tttccatctc ctctccaact cgccgccatg agacccgagg gagtttcgcg gggccgcgcc    4500
tcctctgtct ccatctccaa ctagtgtcga cctctatttg aggacccgcc gagtacccca    4560
caagagtatg taaaaagctg tcattctcaa ctactgagaa taatatcaaa gctaaagata    4620
aaccctgagg agtttccacg ggaaccagag tctaggctcg tgcgcggata catcgaatac    4680
gccagcctag agcgtaagcc acatacgcgc tatccttgct tccagcgcgt gaacctacac    4740
attgacgggg aattttttgat ccataaaatg ctagcgttca atgctgcgat gcgcccatcc    4800
gcagaagagt tgttgtccta cccaatgttt atgaatctgt aggatgacta acagatttgg    4860
ggtggagacg gcgtgggcga tactgtataa agttgtacta cttaccagcc cagtcagtgt    4920
gctgtagtgc caccacctgt aaagctgtga taagctgcag ttgcggccgc cgggtac     4977
```

<210> SEQ ID NO 31
<211> LENGTH: 6678
<212> TYPE: DNA
<213> ORGANISM: Artificial Sequence
<220> FEATURE:
<223> OTHER INFORMATION: Nucleotide sequence of transfer plasmid
      pU1-3-p430-H1av-BGHKBGH

<400> SEQUENCE: 31

```
cctgtgcctt ctagttgcca gccatctgtt gtttgcccct cccccgtgcc ttccttgacc      60
ctggaaggtg ccactcccac tgtccttttcc taataaaatg aggaaattgc atcgcattgt    120
ctgagtaggt gtcattctat tctgggggggt ggggtggggc aggacagcaa ggggaggat    180 tgggaagaca atagcaggca tgctggggat gcggtgggct ctatggatcc tagggataac    240
agggtaatcg atttattcaa caaagccacg ttgtgtctca aaatctctga tgttacattg    300
cacaagataa aaatatatca tcatgaacaa taaaactgtc tgcttacata aacagtaata    360
caaggggtgt tatgagccat attcaacggg aaacgtcttg ctcgaggccg cgattaaatt    420
ccaacatgga tgctgattta tatgggtata atgggctcg cgataatgtc gggcaatcag    480
gtgcgacaat ctatcgattg tatgggaagc ccgatgcgcc agagttgttt ctgaaacatg    540
gcaaaggtag cgttgccaat gatgttacag atgagatggt cagactaaac tggctgacgg    600
aatttatgcc tcttccgacc atcaagcatt ttatccgtac tcctgatgat gcatggttac    660
tcaccactgc gatccccggg aaaacagcat tccaggtatt agaagaatat cctgattcag    720
gtgaaaatat tgttgatgcg ctggcagtgt tcctgcgccg gttgcattcg attcctgttt    780
gtaattgtcc ttttaacagc gatcgcgtat ttcgtctcgc tcaggcgcaa tcacgaatga    840
```

```
ataacggttt ggttgatgcg agtgattttg atgacgagcg taatggctgg cctgttgaac      900
aagtctggaa agaaatgcat aagcttttgc cattctcacc ggattcagtc gtcactcatg      960
gtgatttctc acttgataac cttattttg acgagggaa attaataggt tgtattgatg      1020
ttggacgagt cggaatcgca gaccgatacc aggatcttgc catcctatgg aactgcctcg     1080
gtgagttttc tccttcatta cagaaacggc ttttcaaaa atatggtatt gataatcctg      1140
atatgaataa attgcagttt catttgatgc tcgatgagtt tttctaacca tggctgtgcc     1200
ttctagttgc cagccatctg ttgtttgccc ctccccgtg ccttccttga ccctggaagg      1260
tgccactccc actgtccttt cctaataaaa tgaggaaatt gcatcgcatt gtctgagtag     1320
gtgtcattct attctggggg gtggggtggg gcaggacagc aaggggagg attgggaaga     1380 caatagcagg catgctgggg atgcggtggg ctctatggat ccgaccctcc ccggggctaa     1440
aaagctgcgt cttcacgccc gaggcgctta ttgcccactg ggtacggggc gcgcttttat     1500
atgtgtaacg tcccaccggt gtgacgcacg tactacggtt gttctaaata gctgtccccg     1560
tgattgcctc ggctgcacac atcgcctagg tttccgccgt gcctggtgtc gagggcccac     1620
ccctgtaacc aacatcgatg ggggcctgct gctccttcgc taccttagga ccgttatagt     1680
tacgtcaagc ttggcgtaat catggtcata gctgtttcct gtgtgaaatt gttatccgct     1740
cacaattcca cacaacatac gagccggaag cataaagtgt aaagcctggg gtgcctaatg     1800
agtgagctaa ctcacattaa ttgcgttgcg ctcactgccc gctttccagt cgggaaacct     1860
gtcgtgccag ctgcattaat gaatcggcca acgcgcgggg agaggcggtt tgcgtattgg     1920
gcgctcttcc gcttcctcgc tcactgactc gctgcgctcg gtcgttcggc tgcggcgagc     1980
ggtatcagct cactcaaagg cggtaatacg gttatccaca gaatcagggg ataacgcagg     2040
aaagaacatg tgagcaaaag gccagcaaaa ggccaggaac cgtaaaaagg ccgcgttgct     2100
ggcgtttttc cataggctcc gcccccctga cgagcatcac aaaaatcgac gctcaagtca     2160
gaggtggcga aacccgacag gactataaag ataccaggcg tttccccctg gaagctccct     2220
cgtgcgctct cctgttccga ccctgccgct taccggatac ctgtccgcct ttctcccttc     2280
gggaagcgtg gcgctttctc atagctcacg ctgtaggtat ctcagttcgg tgtaggtcgt     2340
tcgctccaag ctgggctgtg tgcacgaacc ccccgttcag cccgaccgct gcgccttatc     2400
cggtaactat cgtcttgagt ccaacccggt aagacacgac ttatcgccac tggcagcagc     2460
cactggtaac aggattagca gagcgaggta tgtaggcggt gctacagagt tcttgaagtg     2520
gtggcctaac tacggctaca ctagaaggac agtatttggt atctgcgctc tgctgaagcc     2580
agttaccttc ggaaaaagag ttggtagctc ttgatccggc aaacaaacca ccgctggtag     2640
cggtggtttt tttgtttgca agcagcagat tacgcgcaga aaaaaggat ctcaagaaga     2700 tcctttgatc ttttctacgg ggtctgacgc tcagtggaac gaaaactcac gttaagggat     2760
tttggtcatg agattatcaa aaaggatctt cacctagatc cttttaaatt aaaaatgaag     2820
ttttaaatca atctaaagta tatatgagta aacttggtct gacagttacc aatgcttaat     2880
cagtgaggca cctatctcag cgatctgtct atttcgttca tccatagttg cctgactccc     2940
cgtcgtgtag ataactacga tacgggaggg cttaccatct ggccccagtg ctgcaatgat     3000
accgcgagac ccacgctcac cggctccaga tttatcagca ataaaccagc cagccggaag     3060
ggccgagcgc agaagtggtc ctgcaacttt atccgcctcc atccagtcta ttaattgttg     3120
ccgggaagct agagtaagta gttcgccagt taatagtttg cgcaacgttg ttgccattgc     3180
```

```
tacaggcatc gtggtgtcac gctcgtcgtt tggtatggct tcattcagct ccggttccca    3240
acgatcaagg cgagttacat gatcccccat gttgtgcaaa aaagcggtta gctccttcgg    3300
tcctccgatc gttgtcagaa gtaagttggc cgcagtgtta tcactcatgg ttatggcagc    3360
actgcataat tctcttactg tcatgccatc cgtaagatgc ttttctgtga ctggtgagta    3420
ctcaaccaag tcattctgag aatagtgtat gcggcgaccg agttgctctt gcccggcgtc    3480
aatacgggat aataccgcgc cacatagcag aactttaaaa gtgctcatca ttggaaaacg    3540
ttcttcgggg cgaaaactct caaggatctt accgctgttg agatccagtt cgatgtaacc    3600
cactcgtgca cccaactgat cttcagcatc ttttactttc accagcgttt ctgggtgagc    3660
aaaaacagga aggcaaaatg ccgcaaaaaa gggaataagg gcgacacgga aatgttgaat    3720
actcatactc ttccttttc aatattattg aagcatttat cagggttatt gtctcatgag    3780
cggatacata tttgaatgta tttagaaaaa taaacaaata ggggttccgc gcacatttcc    3840
ccgaaaagtg ccacctgacg tctaagaaac cattattatc atgacattaa cctataaaaa    3900
taggcgtatc acgaggccct ttcgtctcgc gcgtttcggt gatgacggtg aaaacctctg    3960
acacatgcag ctcccggaga cggtcacagc ttgtctgtaa gcggatgccg ggagcagaca    4020
agcccgtcag ggcgcgtcag cgggtgttgg cgggtgtcgg gctggcttta actatgcggc    4080
atcagagcag attgtactga gagtgcacca tatgcggtgt gaaataccgc acagatgcgt    4140
aaggagaaaa taccgcatca ggcgccattc gccattcagg ctgcgcaact gttgggaagg    4200
gcgatcggtg cgggcctctt cgctattacg ccagctggcg aaagggggat gtgctgcaag    4260
gcgattaagt tgggtaacgc cagggttttc ccagtcacga cgttgtaaaa cgacggccag    4320
tgaattcgac gtaactataa cggtcctaag gtagcgaatt tttccattgg gccctccct     4380
tttggctctg gtatttagc ttccctccca cttctcattc cactttctcc acctgcacct     4440
tttccatctc ctctccaact cgccgccatg agacccgagg gagtttcgcg gggccgcgcc    4500
tcctctgtct ccatctccaa ctagtgtcga cctctatttg aggacccgcc gagtacccca    4560
caagagtatg taaaaagctg tcattctcaa ctactgagaa taatatcaaa gctaaagata    4620
aaccctgagg agtttccacg ggaaccagag tctaggctcg tgcgcggata catcgaatac    4680
gccagcctag agcgtaagcc acatacgcgc tatccttgct tccagcgcgt gaacctacac    4740
attgacgggg aatttttgat ccataaaatg ctagcgttca atgctgcgat gcgcccatcc    4800
gcagaagagt tgttgtccta cccaatgttt atgaatctgt aggatgacta acagatttgg    4860
ggtggagacg gcgtgggcga tactgtataa agttgtacta cttaccagcc cagtcagtgt    4920
gctgtagtgc caccacctgt aaagctgtga taagctgcag ttgcggccgc cgatggaggc    4980
aaaattgttc gtgctgttct gcgccttcac tgctctgaag gcagacacca tctgcgtggg    5040
ttaccacgcc aataattcca ccgacacggt ggataccatc ctggagaaga acgtgaccgt    5100
gactcattcc gtgaacctct tggagaactc acacaatggt aaaattgtgca gccttaacgg    5160
caaagccccg ctgcaattgg ggaattgtaa cgtggccgga tggatactgg gaaccccga    5220
gtgcgacctt ctcctgaccg ccaacagttg gtcctacatc attgagacga gcaacagcaa    5280
gaatggcgcc tgctatcctg gggagttcgc tgactacgag gagctgcgcg agcagttgtc    5340
tacagtcagc agcttcgaaa gattcgagat cttcccaaag gccactagct ggcccaacca    5400
cgatactacc aagggcacta cagtgagttg cagccacagc ggtgccaata gcttctaccg    5460
caacctgctg tggatcgtga agaagggtaa cagctacccc aagctgagca aatcttacac    5520
aaacaacaaa ggcaaagagg tgttggttat ctggggcgtg catcatcccc caaccgactc    5580
```

```
cgatcagcaa accctgtacc agaacaacca cacctacgtg agcgtcggta gctctaagta    5640
ttaccagcgc ttcaccccg aaatcgtcgc acgaccgaag gtgagagggc aggccgggag    5700
aatgaactac tactggaccc tgctggatca aggcgacact attaccttcg aggctaccgg    5760
caacttgatc gccccgtggc acgcgttcgc cctcaataaa ggatctaata gcggcataat    5820
gatgagtgat gcccacgtgc ataactgcac cacgaagtgc cagacccctc acggcgcact    5880
gaaaagcaat ctgcccttc agaatgtgca ccccatcacc atcggcgagt gcccaagta    5940 tgttaaaagc actcagctcc gcatggccac cggactgcgc aacatcccga gcatccaatc    6000
ccgcggactg ttcggcgcaa tcgcgggctt tatagagggc ggctggaccg gcatgatcga    6060
cggctggtac ggctaccacc atcaaaatga gcaaggttcc ggctacgccg cagaccagaa    6120
gagcacccaa atagcaatcg atggcatctc caacaaggtg aacagcgtga tcgaaaagat    6180
gaacatccag ttcacaagcg tggggaagga gttcaataac ctggaaaagc gcatcgagaa    6240
tctgaacaag aaggttgacg atgggttcct cgatgtctgg acctataacg ccgagctcct    6300
gatactgctt gagaacgagc gcacccctgga cttccacgac ttcaacgtga aaaacctgta    6360
cgaaaaggtc aagtcacagt gcgaaacaa tgcgaaggag ataggcaacg gctgcttcga    6420
gttctatcac aagtgtgaca acgagtgcat ggagagcgtc aagaacggca cttacaacta    6480
cccgcgctac tctgaggaga gtaagctcaa ccgcgaagag attgacgcg tgaaactgga    6540 aagcgttggt gtccatcaga tcctggccat ctacagcacc gtggctagct ctctggttct    6600
gttggtgagc ctgggcgcta taagcttttg gatgtgttct aatgggagcc tgcagtgccg    6660
catctgcatc tgaggtac                                                  6678
```

<210> SEQ ID NO 32
<211> LENGTH: 6892
<212> TYPE: DNA
<213> ORGANISM: Artificial Sequence
<220> FEATURE:
<223> OTHER INFORMATION: Nucleotide sequence of transfer plasmid
      pU70-p455-H1pdm-71K71

<400> SEQUENCE: 32

```
caataaacgc ggtatgtcta ccttcaagcc tatgatgaac ggatgtttgg tgtttgcggc      60
tattataacg ctcttgagtt ttatgctatc tctgggaaca tgcgaaaatt acaggcgtgt     120
ggttcgggat cctagggata acagggtaat cgatttattc aacaaagcca cgttgtgtct     180
caaaatctct gatgttacat tgcacaagat aaaaatatat catcatgaac aataaaactg     240
tctgcttaca taaacagtaa tacaagggt gttatgagcc atattcaacg ggaaacgtct     300
tgctcgaggc cgcgattaaa ttccaacatg gatgctgatt tatatgggta taaatgggct     360
cgcgataatg tcgggcaatc aggtgcgaca atctatcgat tgtatgggaa gcccgatgcg     420
ccagagttgt ttctgaaaca tggcaaaggt agcgttgcca atgatgttac agatgagatg     480
gtcagactaa actggctgac ggaatttatg cctcttccga ccatcaagca tttatccgt      540 actcctgatg atgcatggtt actcaccact gcgatccccg gaaaacagc attccaggta     600 ttagaagaat atcctgattc aggtgaaaat attgttgatg cgctggcagt gttcctgcgc     660
cggttgcatt cgattcctgt ttgtaattgt ccttttaaca gcgatcgcgt atttcgtctc     720
gctcaggcgc aatcacgaat gaataacggt ttggttgatg cgagtgattt tgatgacgag     780
cgtaatggct ggcctgttga acaagtctgg aaagaaatgc ataagctttt gccattctca     840
ccggattcag tcgtcactca tggtgatttc tcacttgata accttatttt tgacgagggg     900
```

```
aaattaatag gttgtattga tgttggacga gtcggaatcg cagaccgata ccaggatctt    960
gccatcctat ggaactgcct cggtgagttt tctccttcat tacagaaacg ctttttcaa   1020
aaatatggta ttgataatcc tgatatgaat aaattgcagt ttcatttgat gctcgatgag   1080
ttttctaaa ataaacgcgg tatgtctacc ttcaagccta tgatgaacgg atgtttggtg   1140
tttgcggcta ttataacgct cttgagtttt atgctatctc tgggaacatg cgaaaattac   1200
aggcgtgtgg ttcgggatcc gaccctgttg gtgggtgcgg ttggactcag aatcttggcg   1260
caggcatgga agtttgtcgg tgacgaaaca tacgacacca tccgcgcaga agcaaagaat   1320
ttagagaccc acgtacccctc aagtgctgca gagtcgtctc tagaaaacca atcgacacag   1380
gaggagtcta acagccccga agttgcccac ctgcgaagcg tcaacagcga tgacagtaca   1440
cacacggggg gtgcgtcgaa cggcatccag gactgtgaca gtcagctcaa aactgtgtat   1500
gcctgcttgg ctctaattgg actcggcaca tgtgccatga tagggttgat agtttacatt   1560
tgtgtattaa ggtcaaaact gtcctctcgg aattttttcgc gcgcgcaaaa tgtaaaacat   1620
agaaattacc agcgacttga gtacgttgct taagcttggc gtaatcatgg tcatagctgt   1680
ttcctgtgtg aaattgttat ccgctcacaa ttccacacaa catacgagcc ggaagcataa   1740
agtgtaaagc ctggggtgcc taatgagtga gctaactcac attaattgcg ttgcgctcac   1800
tgcccgcttt ccagtcggga aacctgtcgt gccagctgca ttaatgaatc ggccaacgcg   1860
cggggagagg cggtttgcgt attgggcgct cttccgcttc ctcgctcact gactcgctgc   1920
gctcggtcgt tcggctgcgg cgagcggtat cagctcactc aaaggcggta atacggttat   1980
ccacagaatc agggggataac gcaggaaaga acatgtgagc aaaaggccag caaaaggcca   2040
ggaaccgtaa aaaggccgcg ttgctggcgt ttttccatag gctccgcccc cctgacgagc   2100
atcacaaaaa tcgacgctca gtcagaggt ggcgaaaccc gacaggacta taaagatacc   2160
aggcgtttcc ccctggaagc tccctcgtgc gctctcctgt tccgaccctg ccgcttaccg   2220
gatacctgtc cgcctttctc ccttcgggaa gcgtggcgct ttctcatagc tcacgctgta   2280
ggtatctcag ttcggtgtag tcgttcgct ccaagctggg ctgtgtgcac gaaccccccg   2340
ttcagcccga ccgctgcgcc ttatccggta actatcgtct tgagtccaac ccggtaagac   2400
acgacttatc gccactggca gcagccactg gtaacaggat tagcagagcg aggtatgtag   2460
gcggtgctac agagttcttg aagtggtggc ctaactacgg ctacactaga aggacagtat   2520
ttggtatctg cgctctgctg aagccagtta ccttcggaaa aagagttggt agctcttgat   2580
ccggcaaaca aaccaccgct ggtagcggtg gttttttgt ttgcaagcag cagattacgc   2640
gcagaaaaaa aggatctcaa gaagatcctt tgatcttttc tacggggtct gacgctcagt   2700
ggaacgaaaa ctcacgttaa gggattttgg tcatgagatt atcaaaaagg atcttcacct   2760
agatcctttt aaattaaaaa tgaagtttta aatcaatcta agtatatat gagtaaactt   2820
ggtctgacag ttaccaatgc ttaatcagtg aggcacctat ctcagcgatc tgtctatttc   2880
gttcatccat agttgcctga ctccccgtcg tgtagataac tacgatacgg gagggcttac   2940
catctggccc cagtgctgca atgataccgc gagacccacg ctcaccggct ccagatttat   3000
cagcaataaa ccagccagcc ggaagggccg agcgcagaag tggtcctgca actttatccg   3060
cctccatcca gtctattaat tgttgccggg aagctagagt aagtagttcg ccagttaata   3120
gtttgcgcaa cgttgttgcc attgctacag gcatcgtggt gtcacgctcg tcgtttggta   3180
tggcttcatt cagctccggt tcccaacgat caaggcgagt tacatgatcc cccatgttgt   3240
```

```
gcaaaaaagc ggttagctcc ttcggtcctc cgatcgttgt cagaagtaag ttggccgcag    3300
tgttatcact catggttatg gcagcactgc ataattctct tactgtcatg ccatccgtaa    3360
gatgcttttc tgtgactggt gagtactcaa ccaagtcatt ctgagaatag tgtatgcggc    3420
gaccgagttg ctcttgcccg gcgtcaatac gggataatac cgcgccacat agcagaactt    3480
taaaagtgct catcattgga aaacgttctt cggggcgaaa actctcaagg atcttaccgc    3540
tgttgagatc cagttcgatg taacccactc gtgcacccaa ctgatcttca gcatctttta    3600
ctttcaccag cgtttctggg tgagcaaaaa caggaaggca aaatgccgca aaaagggaa     3660 taagggcgac acggaaatgt tgaatactca tactcttcct ttttcaatat tattgaagca    3720
tttatcaggg ttattgtctc atgagcggat acatatttga atgtatttag aaaaataaac    3780
aaataggggt tccgcgcaca tttccccgaa aagtgccacc tgacgtctaa gaaaccatta    3840
ttatcatgac attaacctat aaaaataggc gtatcacgag gccctttcgt ctcgcgcgtt    3900
tcggtgatga cggtgaaaac ctctgacaca tgcagctccc ggagacggtc acagcttgtc    3960
tgtaagcgga tgccgggagc agacaagccc gtcagggcgc gtcagcgggt gttggcgggt    4020
gtcggggctg gcttaactat gcggcatcag agcagattgt actgagagtg caccatatgc    4080
ggtgtgaaat accgcacaga tgcgtaagga gaaaataccg catcaggcgc cattcgccat    4140
tcaggctgcg caactgttgg aagggcgat cggtgcgggc ctcttcgcta ttacgccagc    4200
tggcgaaagg gggatgtgct gcaaggcgat taagttgggg aacgccaggg ttttcccagt    4260
cacgacgttg taaaacgacg gccagtgaat tcctccgagt accccagagg agtatgtgaa    4320
aagctgccac tcgcaactac tgaagataat ttcaacgctc aagataaatc cggaggagtt    4380
tcctcgagac cccgggtcga ggctcgtgcg cggatacatc gagtattcta gactcgagcg    4440
caagccctac acgcgctacc cctgctttca acgcgtcaac ctgcacattg acggggagtt    4500
tctggttcac aagatgctag cgttcaatgc cgcgatgcgc ccatcggccg aggagctgct    4560 gtcatacccca atgtttgctc aactttagga tgactaacct gtttctggga ggagacagcg    4620
tgggcgacgg tgtataaagt tggtctgctt tcaagccctg ccactgcgct acagtgccac    4680
caactgtaaa gcggtagtaa gctgcagtgg tcgactggtg gtagcatata ctaccttatt    4740
tatacgctcc gagctgtttt tcagcatgct agcacccaac gccgagcgag agtatataac    4800
tcccatcatt gcccacaagc ttatgccact tattagcgtc cgctctgccg tttgcttagt    4860
cataatatct accgccgttt acgcagcaga cgctatctgc gacacaattg gatttgcgat    4920
accgcgcatg tggatgtgta ttttaatgag atcaacctcc atgaagcgta actaggggc     4980 ctcccactga ggcactaccg gcttagcagc tgactaacac agtataaaac gtgagaagaa    5040
atcagtctca tgcgccatta gcgctaggct agttagcgtg gaggaccgga gcgctaccgc    5100
cagcagtttc atccgcctgg ttacgggttt gttaacacct accggtgttt taccgctacc    5160
ataggatccg atccatgggc ggccgcatga aggcgatcct ggttgtgctg ctgtacacct    5220
ttgccaccgc caacgccgat acgctgtgca tcggctatca cgccaacaac agcaccgaca    5280
cagtggatac cgttttggag aaaaatgtga cggtgacgca cagtgtgaat ctgttggagg    5340
acaaacataa cggcaagctg tgtaagctga gaggtgtggc tcccttcac ctgggcaagt      5400 gtaacatcgc cggctggatt cttggaaacc ccgagtgcga gagcctgagc accgcaagct    5460
cctggagcta catcgttgaa accagttcat ccgacaatgg cacctgctac cccgagact     5520 tcatcgacta cgaggagctg cgcgaacaac ttagcagcgt ctcctcattc gagcgcttcg    5580
agatcttccc gaagaccagc agctggccca accacgacag caataaggga gtgacagccg    5640
```

```
cctgtcccca cgccggtgcc aagagcttct ataagaatct gatttggctg gtgaaaaagg    5700
ggaactccta tccaaagctg tccaagtctt atatcaatga taagggcaag gaggtgctgg    5760
tgttgtgggg aattcaccac ccaagcacca gcgccgatca gcagagcctc taccagaacg    5820
cggatgctta tgtgttcgtc ggtacgtcac gctacagcaa gaagttcaag cccgagattg    5880
ccatccgccc gaaagtgcgg gaccaagaag gccgcatgaa ctactactgg accctggtgg    5940
aacctggcga caagatcacg tttgaggcta ccggcaacct ggtcgttccc cgctacgcct    6000
tcgccatgga gcgcaaagcg ggctctggca tcataatcag cgacacacct gtgcacgact    6060
gcaacactac ctgccagacc cccaagggcg ccattaacac tagcctccct ttccagaaca    6120
ttcaccccat caccataggc aaatgcccca gtatgttaa gagcactaag ctgcggctcg    6180
ccactggcct gagaaacatc ccgagcatcc agtctcgcgg tctgttcgga gccattgccg    6240
gatttatcga aggaggctgg accggtatgg tggacggctg gtatggctac caccatcaaa    6300
atgagcaggg cagcggctat gccgctgatc ttaaaagtac caaaatgca atcgacgaaa    6360 tcactaacaa ggttaacagc gtgattgaaa agatgaatac ccagtttact gcggtgggca    6420
aagagtttaa ccacctggaa aaacgcatcg aaaacctgaa caaaaagtg gacgacggct    6480 tcctggatat ctggacatac aatgcagaac tgcttgtgtt gcttgagaac gagcgcactc    6540
tggactacca cgatagcaac gtcaaaaatc tctatgaaaa ggtgcgcagc cagctcaaaa    6600
acaatgcgaa agaaatcggg aatggctgct tcgaattcta ccacaagtgc gacaacacgt    6660
gcatggagag cgttaagaac gggacgtatg attatcctaa gtatagcgaa gaagccaagc    6720
tgaatcgcga agagatcgac ggagtgaaac tggaatccac ccgcatatat cagatactgg    6780
ccatttacag cacagttgcg agcagcctgg tcctgatcgt gagcctgggt gctatatcat    6840
tctggatgtg cagcaacggc tctctccagt gccgcatctg tatctgaggt ac           6892
```

<210> SEQ ID NO 33
<211> LENGTH: 6670
<212> TYPE: DNA
<213> ORGANISM: Artificial Sequence
<220> FEATURE:
<223> OTHER INFORMATION: Nucleotide sequence of transfer plasmid pU1-3-p430-H1hu-BGHKBGH

<400> SEQUENCE: 33

```
cctgtgcctt ctagttgcca gccatctgtt gtttgcccct cccccgtgcc ttccttgacc      60
ctggaaggtg ccactcccac tgtcctttcc taataaaatg aggaaattgc atcgcattgt     120
ctgagtaggt gtcattctat tctggggggt ggggtggggc aggacagcaa gggggaggat     180
tgggaagaca atagcaggca tgctgggat gcggtgggct ctatggatcc tagggataac     240
agggtaatcg atttattcaa caaagccacg ttgtgtctca aaatctctga tgttacattg     300
cacaagataa aaatatatca tcatgaacaa taaaactgtc tgcttacata aacagtaata     360 caagggggtgt tatgagccat attcaacggg aaacgtcttg ctcgaggccg cgattaaatt     420
ccaacatgga tgctgattta tgggtata atgggctcg cgataatgtc gggcaatcag        480
gtgcgacaat ctatcgattg tatgggaagc ccgatgcgcc agagttgttt ctgaaacatg     540
gcaaaggtag cgttgccaat gatgttacag atgagatggt cagactaaac tggctgacgg     600
aatttatgcc tcttccgacc atcaagcatt ttatccgtac tcctgatgat gcatggttac     660
tcaccactgc gatccccggg aaaacagcat tccaggtatt agaagaatat cctgattcag     720
gtgaaaatat tgttgatgcg ctggcagtgt tcctgcgccg gttgcattcg attcctgttt     780
```

```
gtaattgtcc ttttaacagc gatcgcgtat ttcgtctcgc tcaggcgcaa tcacgaatga    840
ataacggttt ggttgatgcg agtgattttg atgacgagcg taatggctgg cctgttgaac    900
aagtctggaa agaaatgcat aagcttttgc cattctcacc ggattcagtc gtcactcatg    960
gtgatttctc acttgataac cttatttttg acgaggggaa attaataggt tgtattgatg   1020
ttggacgagt cggaatcgca gaccgatacc aggatcttgc catcctatgg aactgcctcg   1080
gtgagttttc tccttcatta cagaaacggc ttttttcaaaa atatggtatt gataatcctg   1140
atatgaataa attgcagttt catttgatgc tcgatgagtt tttctaacca tggctgtgcc   1200
ttctagttgc cagccatctg ttgtttgccc ctcccccgtg ccttccttga ccctggaagg   1260
tgccactccc actgtccttt cctaataaaa tgaggaaatt gcatcgcatt gtctgagtag   1320
gtgtcattct attctggggg gtggggtggg gcaggacagc aaggggagg attgggaaga   1380 caatagcagg catgctgggg atgcggtggg ctctatggat ccgaccctcc ccggggctaa   1440
aaagctgcgt cttcacgccc gaggcgctta ttgcccactg gtacggggc gcgcttttat   1500 atgtgtaacg tcccaccggt gtgacgcacg tactacggtt gttctaaata gctgtccccg   1560
tgattgcctc ggctgcacac atcgcctagg tttccgccgt gcctggtgtc gagggcccac   1620
ccctgtaacc aacatcgatg ggggcctgct gctccttcgc taccttagga ccgttatagt   1680
tacgtcaagc ttggcgtaat catggtcata gctgtttcct gtgtgaaatt gttatccgct   1740
cacaattcca cacaacatac gagccggaag cataaagtgt aaagcctggg gtgcctaatg   1800
agtgagctaa ctcacattaa ttgcgttgcg ctcactgccc gctttccagt cgggaaacct   1860
gtcgtgccag ctgcattaat gaatcggcca acgcgcgggg agaggcggtt tgcgtattgg   1920
gcgctcttcc gcttcctcgc tcactgactc gctgcgctcg tcgttcggc tgcggcgagc   1980 ggtatcagct cactcaaagg cggtaatacg gttatccaca gaatcagggg ataacgcagg   2040
aaagaacatg tgagcaaaag gccagcaaaa ggccaggaac cgtaaaaagg ccgcgttgct   2100
ggcgtttttc cataggctcc gcccccctga cgagcatcac aaaaatcgac gctcaagtca   2160
gaggtggcga aacccgacag gactataaag ataccaggcg tttccccctg gaagctccct   2220
cgtgcgctct cctgttccga ccctgccgct taccggatac ctgtccgcct ttctcccttc   2280
gggaagcgtg cgctttctc atagctcacg ctgtaggtat ctcagttcgg tgtaggtcgt   2340
tcgctccaag ctgggctgtg tgcacgaacc ccccgttcag cccgaccgct gcgccttatc   2400
cggtaactat cgtcttgagt ccaacccggt aagacacgac ttatcgccac tggcagcagc   2460
cactggtaac aggattagca gagcgaggta tgtaggcggt gctacagagt tcttgaagtg   2520
gtggcctaac tacggctaca ctagaaggac agtatttggt atctgcgctc tgctgaagcc   2580
agttaccttc ggaaaaagag ttggtagctc ttgatccggc aaacaaacca ccgctggtag   2640
cggtggtttt tttgtttgca agcagcagat tacgcgcaga aaaaaggat ctcaagaaga   2700 tcctttgatc ttttctacgg ggtctgacgc tcagtggaac gaaaactcac gttaagggat   2760
tttggtcatg agattatcaa aaaggatctt cacctagatc cttttaaatt aaaaatgaag   2820
ttttaaatca atctaaagta tatatgagta aacttggtct gacagttacc aatgcttaat   2880
cagtgaggca cctatctcag cgatctgtct atttcgttca tccatagttg cctgactccc   2940
cgtcgtgtag ataactacga tacgggaggg cttaccatct ggccccagtg ctgcaatgat   3000
accgcgagac ccacgctcac cggctccaga tttatcagca ataaaccagc cagccggaag   3060
ggccgagcgc agaagtggtc ctgcaacttt atccgcctcc atccagtcta ttaattgttg   3120
```

```
ccgggaagct agagtaagta gttcgccagt taatagtttg cgcaacgttg ttgccattgc   3180
tacaggcatc gtggtgtcac gctcgtcgtt tggtatggct tcattcagct ccggttccca   3240
acgatcaagg cgagttacat gatccccat gttgtgcaaa aaagcggtta gctccttcgg    3300
tcctccgatc gttgtcagaa gtaagttggc cgcagtgtta tcactcatgg ttatggcagc   3360
actgcataat tctcttactg tcatgccatc cgtaagatgc ttttctgtga ctggtgagta   3420
ctcaaccaag tcattctgag aatagtgtat gcggcgaccg agttgctctt gcccggcgtc   3480
aatacgggat aataccgcgc cacatagcag aactttaaaa gtgctcatca ttggaaaacg   3540
ttcttcgggg cgaaaactct caaggatctt accgctgttg agatccagtt cgatgtaacc   3600
cactcgtgca cccaactgat cttcagcatc ttttactttc accagcgttt ctgggtgagc   3660
aaaaacagga aggcaaaatg ccgcaaaaaa gggaataagg gcgacacgga aatgttgaat   3720
actcatactc ttcctttttc aatattattg aagcatttat cagggttatt gtctcatgag   3780
cggatacata tttgaatgta tttagaaaaa taaacaaata ggggttccgc gcacatttcc   3840
ccgaaaagtg ccacctgacg tctaagaaac cattattatc atgacattaa cctataaaaa   3900
taggcgtatc acgaggccct ttcgtctcgc gcgtttcggt gatgacggtg aaaacctctg   3960
acacatgcag ctcccggaga cggtcacagc ttgtctgtaa gcggatgccg ggagcagaca   4020
agcccgtcag ggcgcgtcag cgggtgttgg cgggtgtcgg gctggctta actatgcggc    4080
atcagagcag attgtactga gagtgcacca tatgcggtgt gaaataccgc acagatgcgt   4140
aaggagaaaa taccgcatca ggcgccattc gccattcagg ctgcgcaact gttgggaagg   4200
gcgatcggtg cgggcctctt cgctattacg ccagctggcg aaagggggat gtgctgcaag   4260
gcgattaagt tgggtaacgc cagggttttc ccagtcacga cgttgtaaaa cgacggccag   4320
tgaattcgac gtaactataa cggtcctaag gtagcgaatt tttccattgg cccctccct    4380
tttggctctg ggtatttagc ttccctccca cttctcattc cactttctcc acctgcacct   4440
tttccatctc ctctccaact cgccgccatg agacccgagg gagtttcgcg gggccgcgcc   4500
tcctctgtct ccatctccaa ctagtgtcga cctctatttg aggacccgcc gagtacccca   4560
caagagtatg taaaaagctg tcattctcaa ctactgagaa taatatcaaa gctaaagata   4620
aaccctgagg agtttccacg ggaaccagag tctaggctcg tgcgcggata catcgaatac   4680
gccagcctag agcgtaagcc acatacgcgc tatccttgct tccagcgcgt gaacctacac   4740
attgacgggg aattttgat ccataaaatg ctagcgttca atgctgcgat gcgcccatcc    4800
gcagaagagt tgttgtccta cccaatgttt atgaatctgt aggatgacta acagatttgg   4860
ggtggagacg gcgtgggcga tactgtataa agttgtacta cttaccagcc cagtcagtgt   4920
gctgtagtgc caccacctgt aaagctgtga taagctgcag ttgcggccgc atgaaggcca   4980
agcttcttat actgtggtgc gccctcagcg ctaccgacgc tgacaccatt tgcatcggtt   5040
accacgccaa caacagcacc gataccgttg acaccgtgct ggaaaagaac gtgaccgtta   5100
cccacagtgt taatctgctg gaggacaacc acaacggaaa gttgtgtaag ttgaagggcg   5160
tcgcaccct gcagctggga aagtgcagca tagcaggctg gattctcggt aaccccggagt   5220
gcgagagcct gttagcaaa aagtcttggt catacatcgc ggaaacccca aacgccgaaa    5280
atggtatttg ctaccccggc tacttcagcg actacgaaga gctccgcgag cagttgagca   5340
gcgttagtag ctttgaacgc ttcgagatct tccccaaaga aagctcctgg ccaaagcact   5400
ccatcggagc caccgccagc tgttccaagc agggccgcag cagcttctac cgcaacctcc   5460
tgtggctcac cgaaaaaaac ggttcttacc ccaaccttag caagagctac gtcaacgaca   5520
```

```
aggagagaga ggtgcttgtt ctgtggggcg ttcatcaccc ctctaacatc gaggaccaaa    5580
gagccatata tcgaaaggag accgcctacg tgagcgttat gagtagtctg tacaacaggc    5640
gcttcacccc cgagatcgcc aagcgcccca agatcaggaa ccaggagggc aggatcaact    5700
attattggac ccttctggaa cccaaggaca ctatcatctt cgaggccaac gggaacctca    5760
tcgccccgtg gtacgccttc gccctgtcac gcggctttga gagcgggatc atcgtgagca    5820
acgcctctat ggatgagtgt gacgccaagt gccaaacccc gcagggcgcg atcaatagca    5880
gtcttccatt tcagaatgtg cacccggtga ccattgggga gtgcccgaag tatgtgaaga    5940
gtaccaagct gaagatggcc acgggcctgc gcaacatccc cagcattcag acacggggtc    6000
tgttcggcgc tatcgccggc ttcattgaag gcggttggac tggcatgatt gatggctggt    6060
atggctatca ccatcagaac gaacaaggaa gcggctacgc ggcagatcag aagtcaaccc    6120
agaacgctat aaacggcata actaacaagg tgaacagcgt cattgacaaa atgaataccc    6180
agtttaccgc cgtgggcaaa gagttcaata agcttgaaaa acgcatggaa aaccttaaca    6240
aaaaggtgga cgacggcttc ctggacatct ggacctacaa tgccgaactg ttggtgctcc    6300
ttgagaatga gcggacgctt gatttccacg acagcaacgt gaagtcactc tacgagaagg    6360
ttaagggaca gcttaaaaac aacgctaaag aaatcggcaa cggctgtttc gagttctacc    6420
acaagtgcaa caacgagtgc atggatagcg tgaaaaatgg gacctatgac tacccccgct    6480
actcagagga gagcaagctc aaccgcgaga agatcgacgg cgtggagctg aaaagcatgg    6540
gcgtgtacca gatactggcc atatacagca ctgtcgccag cagccttgtg ttgcttgtga    6600
gccttggagc gaccagtttt tggatgtgct ccaatggcag cttgcagtgc cgcatctgca    6660
tctgaggtac                                                            6670

<210> SEQ ID NO 34
<211> LENGTH: 4916
<212> TYPE: DNA
<213> ORGANISM: Artificial Sequence
<220> FEATURE:
<223> OTHER INFORMATION: Nucleotide sequence of transfer vector
      pUUL43-p422-18K18

<400> SEQUENCE: 34
aattctaact ataacggtcc taaggtagcg aagtatacca tgcttgctat actgaaaata      60
aaaacgcata ttgtaaacga cagacgcgga aatgtttatt gcttagtttc actatttggt     120
taaaactatt tacacttgta gaaacacgcc cactaagtat ttgttttatg actaatacct     180
ggtgcataaa accatcctct tgggtccctg tacctcaaac tctccaaagg ttggcttgct     240
acatcaaggt tatcaatccc atggatcgtc agacttggtg gaagacccat gttcgttgtt     300
tcaagaagcg tatcctctac tcagctccac tgatacagca ttgctacgca cgcctcacgt     360
tggcgaaatt ggcgcagatg aaggacattt tgcccagtac ctaattcgcg acgaatcccc     420
cctgaaaggc tgttttccac gaatttaggt tgtgcccgcc tacaactttt cacttgcaaa     480
ctcaataaaa cgcacagttt gtatattcag ttgtcagttt gctctactcg agcgtcggcg     540 cttttgtctag ccctcttagt gggtattgtt accggctggg gttttattgg cgttgttatt     600
ggggagattt tagttgatag aaagcatacc gaggttttgg gggtgtcgct taatttcggt     660
gtctgtaaac gtaaaagag ggcgcgcctc agcggccgca ggtaccaata aaaactgaga     720
ctgttatatt catttcagtg tgtttaataa gaattgtgaa cataacttat tctatatctc     780
attgcgtgga aagactggaa aacgcattgg tggtaggtgg aaggctcgcc ggatcctagg     840
```

-continued

```
gataacaggg taatcgattt attcaacaaa gccacgttgt gtctcaaaat ctctgatgtt     900
acattgcaca agataaaaat atatcatcat gaacaataaa actgtctgct tacataaaca     960
gtaatacaag gggtgttatg agccatattc aacgggaaac gtcttgctcg aggccgcgat    1020
taaattccaa catggatgct gatttatatg ggtataaatg ggctcgcgat aatgtcgggc    1080
aatcaggtgc gacaatctat cgattgtatg ggaagcccga tgcgccagag ttgtttctga    1140
aacatggcaa aggtagcgtt gccaatgatg ttacagatga gatggtcaga ctaaactggc    1200
tgacggaatt tatgcctctt ccgaccatca agcattttat ccgtactcct gatgatgcat    1260
ggttactcac cactgcgatc cccgggaaaa cagcattcca ggtattagaa gaatatcctg    1320
attcaggtga aaatattgtt gatgcgctgg cagtgttcct gcgccggttg cattcgattc    1380
ctgtttgtaa ttgtcctttt aacagcgatc gcgtatttcg tctcgctcag gcgcaatcac    1440
gaatgaataa cggtttggtt gatgcgagtg attttgatga cgagcgtaat ggctggcctg    1500
ttgaacaagt ctggaaagaa atgcataagc ttttgccatt ctcaccggat tcagtcgtca    1560
ctcatggtga tttctcactt gataaccta ttttttgacga ggggaaatta ataggttgta    1620
ttgatgttgg acgagtcgga atcgcagacc gataccagga tcttgccatc ctatggaact    1680
gcctcggtga gttttctcct tcattacaga aacggctttt tcaaaaatat ggtattgata    1740
atcctgatat gaataaattg cagtttcatt tgatgctcga tgagttttc taaaataaac    1800 gtcgacaata aaaactgaga ctgttatatt catttcagtg tgtttaataa gaattgtgaa    1860
cataacttat tctatatctc attgcgtgga aagactggaa aacgcattgg tggtaggtgg    1920
aaggctcgcc tctagaaccc cggcgtatgt tgtcttctgt ctgactgttg gacacgtctc    1980
tgcgatgctg ctggagcagc ttgtcatcag agtaaactac acggcagagg cgagttccgg    2040
catccactcc acggcccacg ctgtctgcat ggtgcttgcc gcctttgggt acggcgtggc    2100
cggtcccctc tcgctcgcat ttactgtatc cgggggtata ctgggggcgc tataccttcg    2160
caagcgcgca acgggcgcgc gccgcctggc ggcaactcac atttcgaggt ggcttattgt    2220
ttgtgtatat gttgccgccg gttcgctacc ttaggaccgt tatagttact gcaggcatgc    2280
aagcttggcg taatcatggt catagctgtt tcctgtgtga attgttatc cgctcacaat    2340 tccacacaac atacgagccg gaagcataaa gtgtaaagcc tggggtgcct aatgagtgag    2400
ctaactcaca ttaattgcgt tgcgctcact gcccgctttc cagtcgggaa acctgtcgtg    2460
ccagctgcat taatgaatcg gccaacgcgc ggggagaggc ggtttgcgta ttgggcgctc    2520
ttccgcttcc tcgctcactg actcgctgcg ctcggtcgtt cggctgcggc gagcggtatc    2580
agctcactca aaggcggtaa tacggttatc cacagaatca ggggataacg caggaaagaa    2640
catgtgagca aaaggccagc aaaaggccag gaaccgtaaa aaggccgcgt tgctggcgtt    2700
tttccatagg ctccgccccc ctgacgagca tcacaaaaat cgacgctcaa gtcagaggtg    2760
gcgaaacccg acaggactat aaagatacca ggcgtttccc cctggaagct ccctcgtgcg    2820
ctctcctgtt ccgaccctgc cgcttaccgg atacctgtcc gcctttctcc cttcgggaag    2880
cgtggcgctt tctcatagct cacgctgtag gtatctcagt tcggtgtagg tcgttcgctc    2940
caagctgggc tgtgtgcacg aaccccccgt tcagcccgac cgctgcgcct tatccggtaa    3000
ctatcgtctt gagtccaacc cggtaagaca cgacttatcg ccactggcag cagccactgg    3060
taacaggatt agcagagcga ggtatgtagg cggtgctaca gagttcttga agtggtggcc    3120
taactacggc tacactagaa ggacagtatt tggtatctgc gctctgctga agccagttac    3180
```

```
cttcggaaaa agagttggta gctcttgatc cggcaaacaa accaccgctg gtagcggtgg      3240 ttttttttgtt tgcaagcagc agattacgcg cagaaaaaaa ggatctcaag aagatccttt      3300
gatcttttct acggggtctg acgctcagtg aacgaaaac tcacgttaag ggattttggt      3360
catgagatta tcaaaaagga tcttcaccta gatcctttta aattaaaaat gaagttttaa      3420
atcaatctaa agtatatatg agtaaacttg gtctgacagt taccaatgct taatcagtga      3480
ggcacctatc tcagcgatct gtctatttcg ttcatccata gttgcctgac tccccgtcgt      3540
gtagataact acgatacggg agggcttacc atctggcccc agtgctgcaa tgataccgcg      3600
agacccacgc tcaccggctc cagatttatc agcaataaac cagccagccg aagggccga      3660 gcgcagaagt ggtcctgcaa ctttatccgc ctccatccag tctattaatt gttgccggga      3720
agctagagta agtagttcgc cagttaatag tttgcgcaac gttgttgcca ttgctacagg      3780
catcgtggtg tcacgctcgt cgtttggtat ggcttcattc agctccggtt cccaacgatc      3840
aaggcgagtt acatgatccc ccatgttgtg caaaaaagcg gttagctcct tcggtcctcc      3900
gatcgttgtc agaagtaagt tggccgcagt gttatcactc atggttatgg cagcactgca      3960
taattctctt actgtcatgc catccgtaag atgcttttct gtgactggtg agtactcaac      4020
caagtcattc tgagaatagt gtatgcggcg accgagttgc tcttgcccgg cgtcaatacg      4080
ggataatacc gcgccacata gcagaacttt aaaagtgctc atcattggaa aacgttcttc      4140
ggggcgaaaa ctctcaagga tcttaccgct gttgagatcc agttcgatgt aacccactcg      4200
tgcacccaac tgatcttcag catcttttac tttcaccagc gtttctgggt gagcaaaaac      4260
aggaaggcaa aatgccgcaa aaaagggaat aagggcgaca cggaaatgtt gaatactcat      4320
actcttcctt tttcaatatt attgaagcat ttatcagggt tattgtctca tgagcggata      4380
catatttgaa tgtatttaga aaaataaaca aataggggtt ccgcgcacat ttccccgaaa      4440
agtgccacct gacgtctaag aaaccattat tatcatgaca ttaacctata aaaataggcg      4500
tatcacgagg ccctttcgtc tcgcgcgttt cggtgatgac ggtgaaaacc tctgacacat      4560
gcagctcccg gagacggtca cagcttgtct gtaagcggat gccgggagca gacaagcccg      4620
tcagggcgcg tcagcgggtg ttggcgggtg tcggggctgg cttaactatg cggcatcaga      4680
gcagattgta ctgagagtgc accatatgcg gtgtgaaata ccgcacagat gcgtaaggag      4740
aaaataccgc atcaggcgcc attcgccatt caggctgcgc aactgttggg aagggcgatc      4800
ggtgcgggcc tcttcgctat tacgccagct ggcgaaaggg ggatgtgctg caaggcgatt      4860
aagttgggta acgccagggt tttcccagtc acgacgttgt aaaacgacgg ccagtg        4916
```

<210> SEQ ID NO 35
<211> LENGTH: 5626
<212> TYPE: DNA
<213> ORGANISM: Artificial Sequence
<220> FEATURE:
<223> OTHER INFORMATION: Nucleotide sequence of transfer plasmid pUUL43-p422-mC-18K18

<400> SEQUENCE: 35

```
aattctaact ataacggtcc taaggtagcg aagtatacca tgcttgctat actgaaaata        60
aaaacgcata ttgtaaacga cagacgcgga atgtttatt gcttagtttc actatttggt       120
taaaactatt tacacttgta gaaacacgcc cactaagtat ttgttttatg actaatacct       180
ggtgcataaa accatcctct tgggtccctg tacctcaaac tctccaaagg ttggcttgct       240
acatcaaggt tatcaatccc atggatcgtc agacttggtg gaagacccat gttcgttgtt       300
```

```
tcaagaagcg tatcctctac tcagctccac tgatacagca ttgctacgca cgcctcacgt    360
tggcgaaatt ggcgcagatg aaggacattt tgcccagtac ctaattcgcg acgaatcccc    420
cctgaaaggc tgttttccac gaatttaggt tgtgcccgcc tacaactttt cacttgcaaa    480
ctcaataaaa cgcacagttt gtatattcag ttgtcagttt gctctactcg agcgtcggcg    540
ctttgtctag ccctcttagt gggtattgtt accggctggg gttttattgg cgttgttatt    600
ggggagattt tagttgatag aaagcatacc gaggttttgg gggtgtcgct taatttcggt    660
gtctgtaaac gtaaaagag ggcgcgcctc agcggccgca tggtgagcaa gggcgaggag    720
gataacatgg ccatcatcaa ggagttcatg cgcttcaagg tgcacatgga gggctccgtg    780
aacggccacg agttcgagat cgagggcgag ggcgagggcc gcccctacga gggcacccag    840
accgccaagc tgaaggtgac caaggtggc cccctgccct cgcctggga catcctgtcc    900 cctcagttca tgtacggctc caaggcctac gtgaagcacc ccgccgacat ccccgactac    960
ttgaagctgt ccttccccga gggcttcaag tgggagcgcg tgatgaactt cgaggacggc   1020
ggcgtggtga ccgtgaccca ggactcctcc ctgcaggacg gcgagttcat ctacaaggtg   1080
aagctgcgcg gcaccaactt cccctccgac ggccccgtaa tgcagaagaa gaccatgggc   1140
tgggaggcct cctccgagcg gatgtacccc gaggacggcg ccctgaaggg cgagatcaag   1200
cagaggctga agctgaagga cggcggccac tacgacgctg aggtcaagac cacctacaag   1260
gccaagaagc ccgtgcagct gcccggcgcc tacaacgtca acatcaagtt ggacatcacc   1320
tcccacaacg aggactacac catcgtggaa cagtacgaac gcgccgaggg ccgccactcc   1380
accggcggca tggacgagct gtacaagtaa ggtaccaata aaaactgaga ctgttatatt   1440
catttcagtg tgtttaataa gaattgtgaa cataacttat tctatatctc attgcgtgga   1500
aagactggaa aacgcattgg tggtaggtgg aaggctcgcc ggatcctagg gataacaggg   1560
taatcgattt attcaacaaa gccacgttgt gtctcaaaat ctctgatgtt acattgcaca   1620
agataaaaat atatcatcat gaacaataaa actgtctgct tacataaaca gtaatacaag   1680
gggtgttatg agccatattc aacgggaaac gtcttgctcg aggccgcgat taaattccaa   1740
catggatgct gatttatatg ggtataaatg gctcgcgcat aatgtcgggc aatcaggtgc   1800
gacaatctat cgattgtatg ggaagcccga tgcgccagag ttgtttctga acatggcaa   1860 aggtagcgtt gccaatgatg ttacagatga atggtcaga ctaaactggc tgacggaatt   1920
tatgcctctt ccgaccatca agcattttat ccgtactcct gatgatgcat ggttactcac   1980
cactgcgatc cccgggaaaa cagcattcca ggtattagaa gaatatcctg attcaggtga   2040
aaatattgtt gatgcgctgg cagtgttcct gcgccggttg cattcgattc ctgtttgtaa   2100
ttgtcctttt aacagcgatc gcgtatttcg tctcgctcag gcgcaatcac gaatgaataa   2160
cggtttggtt gatgcgagtg attttgatga cgagcgtaat ggctggcctg ttgaacaagt   2220
ctggaaagaa atgcataagc ttttgccatt ctcaccggat tcagtcgtca ctcatggtga   2280
tttctcactt gataacctta ttttgacga ggggaaatta ataggttgta ttgatgttgg   2340
acgagtcgga atcgcagacc gataccagga tcttgccatc ctatggaact gcctcggtga   2400
gttttctcct tcattacaga aacggctttt caaaaatat ggtattgata atcctgtatat   2460 gaataaattg cagtttcatt tgatgctcga tgagtttttc taaaataaac gtcgacaata   2520
aaaactgaga ctgttatatt catttcagtg tgtttaataa gaattgtgaa cataacttat   2580
tctatatctc attgcgtgga aagactggaa aacgcattgg tggtaggtgg aaggctcgcc   2640
tctagaaccc cggcgtatgt tgtcttctgt ctgactgttg gacacgtctc tgcgatgctg   2700
```

```
ctggagcagc ttgtcatcag agtaaactac acggcagagg cgagttccgg catccactcc    2760
acggcccacg ctgtctgcat ggtgcttgcc gcctttgggt acggcgtggc cggtcccctc    2820
tcgctcgcat ttactgtatc cgggggtata ctggggcgc tataccttcg caagcgcgca    2880
acgggcgcgc gccgcctggc ggcaactcac atttcgaggt ggcttattgt ttgtgtatat    2940
gttgccgccg gttcgctacc ttaggaccgt tatagttact gcaggcatgc aagcttggcg    3000
taatcatggt catagctgtt tcctgtgtga aattgttatc cgctcacaat tccacacaac    3060
atacgagccg gaagcataaa gtgtaaagcc tggggtgcct aatgagtgag ctaactcaca    3120
ttaattgcgt tgcgctcact gcccgctttc cagtcgggaa acctgtcgtg ccagctgcat    3180
taatgaatcg gccaacgcgc ggggagaggc ggtttgcgta ttgggcgctc ttccgcttcc    3240
tcgctcactg actcgctgcg ctcggtcgtt cggctgcggc gagcggtatc agctcactca    3300
aaggcggtaa tacggttatc cacagaatca ggggataacg caggaaagaa catgtgagca    3360
aaaggccagc aaaaggccag gaaccgtaaa aaggccgcgt tgctggcgtt tttccatagg    3420
ctccgccccc ctgacgagca tcacaaaaat cgacgctcaa gtcagaggtg gcgaaacccg    3480
acaggactat aaagatacca ggcgtttccc cctggaagct ccctcgtgcg ctctcctgtt    3540
ccgaccctgc cgcttaccgg atacctgtcc gcctttctcc cttcgggaag cgtggcgctt    3600
tctcatagct cacgctgtag gtatctcagt tcggtgtagg tcgttcgctc caagctgggc    3660
tgtgtgcacg aaccccccgt tcagcccgac cgctgcgcct tatccggtaa ctatcgtctt    3720
gagtccaacc cggtaagaca cgacttatcg ccactggcag cagccactgg taacaggatt    3780
agcagagcga ggtatgtagg cggtgctaca gagttcttga agtggtggcc taactacggc    3840
tacactagaa ggacagtatt tggtatctgc gctctgctga agccagttac cttcggaaaa    3900
agagttggta gctcttgatc cggcaaacaa accaccgctg gtagcggtgg ttttttttgtt    3960 tgcaagcagc agattacgcg cagaaaaaaa ggatctcaag aagatccttt gatcttttct    4020
acggggtctg acgctcagtg gaacgaaaac tcacgttaag ggattttggt catgagatta    4080
tcaaaaagga tcttcaccta gatcctttta aattaaaaat gaagttttaa atcaatctaa    4140
agtatatatg agtaaacttg gtctgacagt taccaatgct taatcagtga ggcacctatc    4200
tcagcgatct gtctatttcg ttcatccata gttgcctgac tccccgtcgt gtagataact    4260
acgatacggg agggcttacc atctggcccc agtgctgcaa tgataccgcg agacccacgc    4320
tcaccggctc cagatttatc agcaataaac cagccagccg aagggccga gcgcagaagt    4380 ggtcctgcaa ctttatccgc ctccatccag tctattaatt gttgccggga agctagagta    4440
agtagttcgc cagttaatag tttgcgcaac gttgttgcca ttgctacagg catcgtggtg    4500
tcacgctcgt cgtttggtat ggcttcattc agctccggtt cccaacgatc aaggcgagtt    4560
acatgatccc ccatgttgtg caaaaaagcg gttagctcct tcggtcctcc gatcgttgtc    4620
agaagtaagt tggccgcagt gttatcactc atggttatgg cagcactgca taattctctt    4680
actgtcatgc catccgtaag atgcttttct gtgactggtg agtactcaac caagtcattc    4740
tgagaatagt gtatgcggcg accgagttgc tcttgcccgg cgtcaatacg ggataatacc    4800
gcgccacata gcagaacttt aaaagtgctc atcattggaa aacgttcttc ggggcgaaaa    4860
ctctcaagga tcttaccgct gttgagatcc agttcgatgt aacccactcg tgcacccaac    4920
tgatcttcag catcttttac tttcaccagc gtttctgggt gagcaaaaac aggaaggcaa    4980
aatgccgcaa aaaagggaat aagggcgaca cggaaatgtt gaatactcat actcttcctt    5040
```

| | |
|---|---|
| tttcaatatt attgaagcat ttatcagggt tattgtctca tgagcggata catatttgaa | 5100 |
| tgtatttaga aaaataaaca aatagggdtt ccgcgcacat ttccccgaaa agtgccacct | 5160 |
| gacgtctaag aaaccattat tatcatgaca ttaacctata aaaataggcg tatcacgagg | 5220 |
| ccctttcgtc tcgcgcgttt cggtgatgac ggtgaaaacc tctgacacat gcagctcccg | 5280 |
| gagacggtca cagcttgtct gtaagcggat gccgggagca gacaagcccg tcagggcgcg | 5340 |
| tcagcgggtg ttggcgggtg tcggggctgg cttaactatg cggcatcaga gcagattgta | 5400 |
| ctgagagtgc accatatgcg gtgtgaaata ccgcacagat gcgtaaggag aaaataccgc | 5460 |
| atcaggcgcc attcgccatt caggctgcgc aactgttggg aagggcgatc ggtgcgggcc | 5520 |
| tcttcgctat tacgccagct ggcgaaaggg ggatgtgctg caaggcgatt aagttgggta | 5580 |
| acgccagggt tttcccagtc acgacgttgt aaaacgacgg ccagtg | 5626 |

<210> SEQ ID NO 36
<211> LENGTH: 6616
<212> TYPE: DNA
<213> ORGANISM: Artificial Sequence
<220> FEATURE:
<223> OTHER INFORMATION: Nucleotide sequence of transfer plasmid
      pUUL43-p422-H1pdm-18K18

<400> SEQUENCE: 36

| | |
|---|---|
| aattctaact ataacggtcc taaggtagcg aagtatacca tgcttgctat actgaaaata | 60 |
| aaaacgcata ttgtaaacga cagacgcgga aatgtttatt gcttagtttc actatttggt | 120 |
| taaaactatt tacacttgta gaaacacgcc cactaagtat ttgttttatg actaataccct | 180 |
| ggtgcataaa accatcctct tgggtccctg tacctcaaac tctccaaagg ttggcttgct | 240 |
| acatcaaggt tatcaatccc atggatcgtc agacttggtg gaagacccat gttcgttgtt | 300 |
| tcaagaagcg tatcctctac tcagctccac tgatacagca ttgctacgca cgcctcacgt | 360 |
| tggcgaaatt ggcgcagatg aaggacattt tgcccagtac ctaattcgcg acgaatcccc | 420 |
| cctgaaaggc tgttttccac gaatttaggt tgtgcccgcc tacaactttt cacttgcaaa | 480 |
| ctcaataaaa cgcacagttt gtatattcag ttgtcagttt gctctactcg agcgtcggcg | 540 |
| cttttgtctag ccctcttagt gggtattgtt accggctggg gttttattgg cgttgttatt | 600 |
| ggggagattt tagttgatag aaagcatacc gaggttttgg gggtgtcgct taatttcggt | 660 |
| gtctgtaaac gtaaaagag ggcgcgcctc agcggccgca tgaaggcgat cctggttgtg | 720 |
| ctgctgtaca cctttgccac cgccaacgcc gatacgctgt gcatcggcta tcacgccaac | 780 |
| aacagcaccg acacagtgga taccgttttg gagaaaaatg tgacggtgac gcacagtgtg | 840 |
| aatctgttgg aggacaaaca taacggcaag ctgtgtaagc tgagaggtgt ggctccctt | 900 |
| cacctgggca agtgtaacat cgccggctgg attcttggaa accccgagtg cgagagcctg | 960 |
| agcaccgcaa gctcctggag ctacatcgtt gaaaccagtt catccgacaa tggcacctgc | 1020 |
| tacccaggag acttcatcga ctacgaggag ctgcgcgaac aacttagcag cgtctcctca | 1080 |
| ttcgagcgct tcgagatctt cccgaagacc agcagctggc ccaaccacga cagcaataag | 1140 |
| ggagtgacag ccgcctgtcc ccacgccggt gccaagagct tctataagaa tctgatttgg | 1200 |
| ctggtgaaaa aggggaactc ctatccaaag ctgtccaagt cttatatcaa tgataaggc | 1260 |
| aaggaggtgc tggtgttgtg gggaattcac cacccaagca ccagcgccga tcagcagagc | 1320 |
| ctctaccaga acgcggatgc ttatgtgttc gtcggtacgt cacgctacag caagaagttc | 1380 |
| aagcccgaga ttgccatccg cccgaaagtg cgggaccaag aaggccgcat gaactactac | 1440 |

```
tggaccctgg tggaacctgg cgacaagatc acgtttgagg ctaccggcaa cctggtcgtt    1500
ccccgctacg ccttcgccat ggagcgcaaa gcgggctctg gcatcataat cagcgacaca    1560
cctgtgcacg actgcaacac tacctgccag accccaagg gcgccattaa cactagcctc     1620
cctttccaga acattcaccc catcaccata ggcaaatgcc ccaagtatgt taagagcact    1680
aagctgcggc tcgccactgg cctgagaaac atcccgagca tccagtctcg cggtctgttc    1740
ggagccattg ccggatttat cgaaggaggc tggaccggta tggtggacgg ctggtatggc    1800
taccaccatc aaaatgagca gggcagcggc tatgccgctg atcttaaaag tacccaaaat    1860
gcaatcgacg aaatcactaa caaggttaac agcgtgattg aaaagatgaa tacccagttt    1920
actgcggtgg gcaaagagtt taaccacctg gaaaaacgca tcgaaaacct gaacaaaaaa    1980
gtggacgacg gcttcctgga tatctggaca tacaatgcag aactgcttgt gttgcttgag    2040
aacgagcgca ctctggacta ccacgatagc aacgtcaaaa atctctatga aaaggtgcgc    2100
agccagctca aaaacaatgc gaaagaaatc gggaatggct gcttcgaatt ctaccacaag    2160
tgcgacaaca cgtgcatgga gagcgttaag aacgggacgt atgattatcc taagtatagc    2220
gaagaagcca agctgaatcg cgaagagatc gacggagtga aactggaatc cacccgcata    2280
tatcagatac tggccattta cagcacagtt gcgagcagcc tggtcctgat cgtgagcctg    2340
ggtgctatat cattctggat gtgcagcaac ggctctctcc agtgccgcat ctgtatctga    2400
ggtaccaata aaaactgaga ctgttatatt catttcagtg tgtttaataa gaattgtgaa    2460
cataacttat tctatatctc attgcgtgga aagactggaa aacgcattgg tggtaggtgg    2520
aaggctcgcc ggatcctagg gataacaggg taatcgattt attcaacaaa gccacgttgt    2580
gtctcaaaat ctctgatgtt acattgcaca agataaaaat atatcatcat gaacaataaa    2640
actgtctgct tacataaaca gtaatacaag gggtgttatg agccatattc aacgggaaac    2700
gtcttgctcg aggccgcgat taaattccaa catggatgct gatttatatg ggtataaatg    2760
ggctcgcgat aatgtcgggc aatcaggtgc gacaatctat cgattgtatg ggaagcccga    2820
tgcgccagag ttgtttctga acatggcaa aggtagcgtt gccaatgatg ttacagatga     2880
gatggtcaga ctaaactggc tgacggaatt tatgcctctt ccgaccatca agcattttat    2940
ccgtactcct gatgatgcat ggttactcac cactgcgatc cccgggaaaa cagcattcca    3000
ggtattagaa gaatatcctg attcaggtga aaatattgtt gatgcgctgg cagtgttcct    3060
gcgccggttg cattcgattc ctgtttgtaa ttgtccttt aacagcgatc gcgtatttcg     3120
tctcgctcag gcgcaatcac gaatgaataa cggtttggtt gatgcgagtg attttgatga    3180
cgagcgtaat ggctggcctg ttgaacaagt ctggaaagaa atgcataagc ttttgccatt    3240
ctcaccggat tcagtcgtca ctcatggtga tttctcactt gataaccta ttttgacga     3300
ggggaaatta ataggttgta ttgatgttgg acgagtcgga atcgcagacc gataccagga    3360
tcttgccatc ctatggaact gcctcggtga gttttctcct tcattacaga aacggctttt    3420
tcaaaaatat ggtattgata atcctgatat gaataaattg cagtttcatt tgatgctcga    3480
tgagttttc taaaataaac gtcgacaata aaaactgaga ctgttatatt catttcagtg    3540
tgtttaataa gaattgtgaa cataacttat tctatatctc attgcgtgga aagactggaa    3600
aacgcattgg tggtaggtgg aaggctcgcc tctagaaccc cggcgtatgt tgtcttctgt    3660
ctgactgttg gacacgtctc tgcgatgctg ctggagcagc ttgtcatcag agtaaactac    3720
acggcagagg cgagttccgg catccactcc acggcccacg ctgtctgcat ggtgcttgcc    3780
gcctttgggt acggcgtggc cggtccctc tcgctcgcat ttactgtatc cgggggtata    3840
```

```
ctgggggcgc tataccttcg caagcgcgca acgggcgcgc gccgcctggc ggcaactcac    3900
atttcgaggt ggcttattgt ttgtgtatat gttgccgccg gttcgctacc ttaggaccgt    3960
tatagttact gcaggcatgc aagcttggcg taatcatggt catagctgtt tcctgtgtga    4020
aattgttatc cgctcacaat tccacacaac atacgagccg gaagcataaa gtgtaaagcc    4080
tggggtgcct aatgagtgag ctaactcaca ttaattgcgt tgcgctcact gcccgctttc    4140
cagtcgggaa acctgtcgtg ccagctgcat taatgaatcg gccaacgcgc ggggagaggc    4200
ggtttgcgta ttgggcgctc ttccgcttcc tcgctcactg actcgctgcg ctcggtcgtt    4260
cggctgcggc gagcggtatc agctcactca aaggcggtaa tacggttatc cacagaatca    4320
ggggataacg caggaaagaa catgtgagca aaaggccagc aaaaggccag gaaccgtaaa    4380
aaggccgcgt tgctggcgtt tttccatagg ctccgccccc ctgacgagca tcacaaaaat    4440
cgacgctcaa gtcagaggtg gcgaaacccg acaggactat aaagatacca ggcgtttccc    4500
cctggaagct ccctcgtgcg ctctcctgtt ccgaccctgc cgcttaccgg atacctgtcc    4560
gcctttctcc cttcgggaag cgtggcgctt tctcatagct cacgctgtag gtatctcagt    4620
tcggtgtagg tcgttcgctc caagctgggc tgtgtgcacg aaccccccgt tcagcccgac    4680
cgctgcgcct tatccggtaa ctatcgtctt gagtccaacc cggtaagaca cgacttatcg    4740
ccactggcag cagccactgg taacaggatt agcagagcga ggtatgtagg cggtgctaca    4800
gagttcttga agtggtggcc taactacggc tacactagaa ggacagtatt tggtatctgc    4860
gctctgctga agccagttac cttcggaaaa agagttggta gctcttgatc cggcaaacaa    4920
accaccgctg gtagcggtgg tttttttgtt tgcaagcagc agattacgcg cagaaaaaaa    4980
ggatctcaag aagatccttt gatcttttct acggggtctg acgctcagtg gaacgaaaac    5040
tcacgttaag ggattttggt catgagatta tcaaaaagga tcttcaccta gatcctttta    5100
aattaaaaat gaagttttaa atcaatctaa agtatatatg agtaaacttg gtctgacagt    5160
taccaatgct taatcagtga ggcacctatc tcagcgatct gtctatttcg ttcatccata    5220
gttgcctgac tccccgtcgt gtagataact acgatacggg agggcttacc atctggcccc    5280
agtgctgcaa tgataccgcg agacccacgc tcaccggctc cagatttatc agcaataaac    5340
cagccagccg gaagggccga gcgcagaagt ggtcctgcaa ctttatccgc ctccatccag    5400
tctattaatt gttgccggga agctagagta agtagttcgc cagttaatag tttgcgcaac    5460
gttgttgcca ttgctacagg catcgtggtg tcacgctcgt cgtttggtat ggcttcattc    5520
agctccggtt cccaacgatc aaggcgagtt acatgatccc ccatgttgtg caaaaaagcg    5580
gttagctcct tcggtcctcc gatcgttgtc agaagtaagt tggccgcagt gttatcactc    5640
atggttatgg cagcactgca taattctctt actgtcatgc catccgtaag atgcttttct    5700
gtgactggtg agtactcaac caagtcattc tgagaatagt gtatgcggcg accgagttgc    5760
tcttgcccgg cgtcaatacg ggataatacc gcgccacata gcagaacttt aaaagtgctc    5820
atcattggaa aacgttcttc ggggcgaaaa ctctcaagga tcttaccgct gttgagatcc    5880
agttcgatgt aacccactcg tgcacccaac tgatcttcag catcttttac tttcaccagc    5940
gtttctgggt gagcaaaaac aggaaggcaa aatgccgcaa aaaagggaat aagggcgaca    6000
cggaaatgtt gaatactcat actcttcctt tttcaatatt attgaagcat ttatcagggt    6060
tattgtctca tgagcggata catatttgaa tgtatttaga aaaataaaca aataggggtt    6120
ccgcgcacat ttccccgaaa agtgccacct gacgtctaag aaaccattat tatcatgaca    6180
```

```
ttaacctata aaaataggcg tatcacgagg cccttccgtc tcgcgcgttt cggtgatgac    6240
ggtgaaaacc tctgacacat gcagctcccg gagacggtca cagcttgtct gtaagcggat    6300
gccgggagca gacaagcccg tcagggcgcg tcagcgggtg ttggcgggtg tcgggctgg     6360 cttaactatg cggcatcaga gcagattgta ctgagagtgc accatatgcg gtgtgaaata    6420
ccgcacagat gcgtaaggag aaaataccgc atcaggcgcc attcgccatt caggctgcgc    6480
aactgttggg aagggcgatc ggtgcgggcc tcttcgctat tacgccagct ggcgaaaggg    6540
ggatgtgctg caaggcgatt aagttgggta acgccagggt tttcccagtc acgacgttgt    6600
aaaacgacgg ccagtg                                                    6616

<210> SEQ ID NO 37
<211> LENGTH: 4435
<212> TYPE: DNA
<213> ORGANISM: Artificial Sequence
<220> FEATURE:
<223> OTHER INFORMATION: Nucleotide sequence of transfer plasmid pUmC70

<400> SEQUENCE: 37
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cctccgagta ccccagagga     420
gtatgtgaaa agctgccact cgcaactact gaagataatt caacgctca agataaatcc     480 ggaggagttt cctcgagacc ccgggtcgag gctcgtgcgc ggatacatcg agtattctag     540
actcgagcgc aagccctaca cgcgctaccc ctgctttcaa cgcgtcaacc tgcacattga     600
cggggagttt ctggttcaca agatgctagc gttcaatgcc gcgatcgcc catcggccga     660 ggagctgctg tcatacccaa tgtttgctca actttaggat gactaacctg tttctgggag     720
gagacagcgt gggcgacggt gtataaagtt ggtctgcttt caagccctgc cactgcgcta     780
cagtgccacc aactgtaaag cggtagtaag ctgcagtggt cgacatggtg agcaagggcg     840
aggaggataa catggccatc atcaaggagt tcatgcgctt caaggtgcac atggagggct     900
ccgtgaacgg ccacgagttc gagatcgagg gcgaggcga gggccgcccc tacgagggca     960
cccagaccgc caagctgaag gtgaccaagg gtggcccct gcccttcgcc tgggacatcc    1020
tgtcccctca gttcatgtac ggctccaagg cctacgtgaa gcaccccgcc gacatccccg    1080
actacttgaa gctgtccttc cccgagggct tcaagtggga gcgcgtgatg aacttcgagg    1140
acggcggcgt ggtgaccgtg acccaggact cctcccctgca ggacggcgag ttcatctaca    1200
aggtgaagct gcgcggcacc aacttcccct ccgacgccc cgtaatgcag aagaagacca    1260
tgggctggga ggcctcctcc gagcggatgt accccgagga cggcgccctg aagggcgaga    1320
tcaagcagag gctgaagctg aaggacgcg ccactacga cgctgaggtc aagaccacct    1380
acaaggccaa gaagcccgtg cagctgcccg gcgcctacaa cgtcaacatc aagttggaca    1440
tcacctccca caacgaggac tacaccatcg tggaacagta cgaacgcgcc gagggccgcc    1500
actccaccgg cggcatggac gagctgtaca agtaactgtg ccttctagtt gccagccatc    1560
tgttgtttgc ccctcccccg tgccttcctt gaccctggaa ggtgccactc ccactgtcct    1620
```

```
ttcctaataa aatgaggaaa ttgcatcgca ttgtctgagt aggtgtcatt ctattctggg    1680
gggtggggtg gggcaggaca gcaaggggga ggattgggaa gacaatagca ggcatgctgg    1740
ggatgcggtg ggctctatgg atccgaccct gttggtgggt gcggttggac tcagaatctt    1800
ggcgcaggca tggaagtttg tcggtgacga aacatacgac accatccgcg cagaagcaaa    1860
gaatttagag acccacgtac cctcaagtgc tgcagagtcg tctctagaaa accaatcgac    1920
acaggaggag tctaacagcc ccgaagttgc ccacctgcga agcgtcaaca gcgatgacag    1980
tacacacacg gggggtgcgt cgaacggcat ccaggactgt gacagtcagc tcaaaactgt    2040
gtatgcctgc ttggctctaa ttggactcgg cacatgtgcc atgatagggt tgatagttta    2100
catttgtgta ttaaggtcaa aactgtcctc tcggaatttt tcgcgcgcgc aaaatgtaaa    2160
acatagaaat taccagcgac ttgagtacgt tgcttaagct tggcgtaatc atggtcatag    2220
ctgtttcctg tgtgaaattg ttatccgctc acaattccac acaacatacg agccggaagc    2280
ataaagtgta aagcctgggg tgcctaatga gtgagctaac tcacattaat tgcgttgcgc    2340
tcactgcccg ctttccagtc gggaaacctg tcgtgccagc tgcattaatg aatcggccaa    2400
cgcgcgggga gaggcggttt gcgtattggg cgctcttccg cttcctcgct cactgactcg    2460
ctgcgctcgg tcgttcggct gcggcgagcg gtatcagctc actcaaaggc ggtaatacgg    2520
ttatccacag aatcagggga taacgcagga aagaacatgt gagcaaaagg ccagcaaaag    2580
gccaggaacc gtaaaaaggc cgcgttgctg gcgtttttcc ataggctccg ccccctgac    2640
gagcatcaca aaaatcgacg ctcaagtcag aggtggcgaa acccgacagg actataaaga    2700
taccaggcgt ttccccctgg aagctccctc gtgcgctctc ctgttccgac cctgccgctt    2760
accggatacc tgtccgcctt tctcccttcg ggaagcgtgg cgctttctca tagctcacgc    2820
tgtaggtatc tcagttcggt gtaggtcgtt cgctccaagc tgggctgtgt gcacgaaccc    2880
cccgttcagc ccgaccgctg cgccttatcc ggtaactatc gtcttgagtc aacccggta    2940
agacacgact tatcgccact ggcagcagcc actggtaaca ggattagcag agcgaggtat    3000
gtaggcggtg ctacagagtt cttgaagtgg tggcctaact acggctacac tagaaggaca    3060
gtatttggta tctgcgctct gctgaagcca gttaccttcg gaaaaagagt tggtagctct    3120
tgatccggca aacaaaccac cgctggtagc ggtggttttt ttgtttgcaa gcagcagatt    3180
acgcgcagaa aaaaggatc tcaagaagat cctttgatct tttctacggg gtctgacgct    3240
cagtggaacg aaaactcacg ttaagggatt ttggtcatga gattatcaaa aaggatcttc    3300
acctagatcc ttttaaatta aaaatgaagt tttaaatcaa tctaaagtat atatgagtaa    3360
acttggtctg acagttacca atgcttaatc agtgaggcac ctatctcagc gatctgtcta    3420
tttcgttcat ccatagttgc ctgactcccc gtcgtgtaga taactacgat acgggagggc    3480
ttaccatctg gccccagtgc tgcaatgata ccgcgagacc cacgctcacc ggctccagat    3540
ttatcagcaa taaaccagcc agccggaagg gccgagcgca gaagtggtcc tgcaacttta    3600
tccgcctcca tccagtctat taattgttgc cgggaagcta gagtaagtag ttcgccagtt    3660
aatagtttgc gcaacgttgt tgccattgct acaggcatcg tggtgtcacg ctcgtcgttt    3720
ggtatggctt cattcagctc cggttcccaa cgatcaaggc gagttacatg atcccccatg    3780
ttgtgcaaaa aagcggttag ctccttcggt cctccgatcg ttgtcagaag taagttggcc    3840
gcagtgttat cactcatggt tatggcagca ctgcataatt ctcttactgt catgccatcc    3900
gtaagatgct tttctgtgac tggtgagtac tcaaccaagt cattctgaga atagtgtatg    3960
```

-continued

```
cggcgaccga gttgctcttg cccggcgtca atacgggata ataccgcgcc acatagcaga    4020
actttaaaag tgctcatcat tggaaaacgt tcttcggggc gaaaactctc aaggatctta    4080
ccgctgttga gatccagttc gatgtaaccc actcgtgcac ccaactgatc ttcagcatct    4140
tttactttca ccagcgtttc tgggtgagca aaaacaggaa ggcaaaatgc cgcaaaaaag    4200
ggaataaggg cgacacggaa atgttgaata ctcatactct tcctttttca atattattga    4260
agcatttatc agggttattg tctcatgagc ggatacatat ttgaatgtat ttagaaaaat    4320
aaacaaatag gggttccgcg cacatttccc cgaaaagtgc cacctgacgt ctaagaaacc    4380
attattatca tgacattaac ctataaaaat aggcgtatca cgaggccctt tcgtc         4435
```

<210> SEQ ID NO 38
<211> LENGTH: 22
<212> TYPE: DNA
<213> ORGANISM: Artificial Sequence
<220> FEATURE:
<223> OTHER INFORMATION: Forward primer

<400> SEQUENCE: 38
aggctcgtgc gcggatacat cg    22

<210> SEQ ID NO 39
<211> LENGTH: 22
<212> TYPE: DNA
<213> ORGANISM: Artificial Sequence
<220> FEATURE:
<223> OTHER INFORMATION: Reverse primer

<400> SEQUENCE: 39
ttcggggctg ttagactcct cc    22

<210> SEQ ID NO 40
<211> LENGTH: 22
<212> TYPE: DNA
<213> ORGANISM: Artificial Sequence
<220> FEATURE:
<223> OTHER INFORMATION: Forward primer

<400> SEQUENCE: 40
ccaactcgcc gccatgagac cc    22

<210> SEQ ID NO 41
<211> LENGTH: 22
<212> TYPE: DNA
<213> ORGANISM: Artificial Sequence
<220> FEATURE:
<223> OTHER INFORMATION: Reverse primer

<400> SEQUENCE: 41
agcgcgcccc gtacccagtg gg    22

<210> SEQ ID NO 42
<211> LENGTH: 16
<212> TYPE: DNA
<213> ORGANISM: Artificial Sequence
<220> FEATURE:
<223> OTHER INFORMATION: Forward primer

<400> SEQUENCE: 42
cgacgcgcgt cggagg    16

<210> SEQ ID NO 43
<211> LENGTH: 21

<212> TYPE: DNA
<213> ORGANISM: Artificial Sequence
<220> FEATURE:
<223> OTHER INFORMATION: Reverse primer

<400> SEQUENCE: 43
gttataaaca taccatgcac c                                    21

<210> SEQ ID NO 44
<211> LENGTH: 566
<212> TYPE: PRT
<213> ORGANISM: swine influenza virus

<400> SEQUENCE: 44

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Thr Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Lys Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

```
Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Ile
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 45
<211> LENGTH: 566
<212> TYPE: PRT
<213> ORGANISM: swine influenza virus

<400> SEQUENCE: 45

Met Lys Thr Val Ile Ala Leu Ser Tyr Ile Phe Cys Leu Val Phe Gly
1               5                   10                  15

Gln Asp Leu Pro Gly Lys Gly Asn Asn Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Asn Phe Ser Met
    50                  55                  60

Gly Lys Ile Cys Asn Asn Pro His Arg Ile Leu Asp Gly Ala Asn Cys
65                  70                  75                  80

Thr Leu Ile Asp Ser Leu Leu Gly Asp Pro His Cys Asp Gly Phe Gln
                85                  90                  95

Asn Glu Lys Trp Asp Leu Phe Ile Glu Arg Ser Lys Ala Phe Ser Asn
            100                 105                 110

Cys Tyr Pro Tyr Asp Val Pro Glu Tyr Thr Ser Leu Arg Ser Leu Ile
        115                 120                 125

Ala Ser Ser Gly Thr Leu Glu Phe Thr Asn Glu Asn Phe Asn Trp Thr
```

```
              130                 135                 140
Gly Val Thr Gln Asn Gly Gly Ser Ser Ala Cys Lys Arg Gly Pro Asn
145                 150                 155                 160

Asn Ser Phe Phe Ser Lys Leu Asn Trp Leu Tyr Lys Ser Gly Asn Thr
                165                 170                 175

Tyr Pro Met Leu Asn Val Thr Met Pro Asn Ser Asp Asp Phe Asp Lys
            180                 185                 190

Leu Tyr Ile Trp Gly Val His His Pro Ser Thr Asp Arg Glu Gln Ile
        195                 200                 205

Asn Leu Tyr Val Gln Ala Ser Gly Lys Ile Ile Val Ser Thr Lys Arg
    210                 215                 220

Ser Gln Gln Thr Ile Ile Pro Asn Ile Gly Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Ile Leu Ile Ile Asn Ser Asn Gly Asn Leu Ile Ala Pro Arg Gly
            260                 265                 270

Tyr Phe Lys Met Gln Thr Gly Lys Ser Ser Val Met Arg Ser Asp Ala
        275                 280                 285

Pro Ile Asp Thr Cys Asn Ser Glu Cys Ile Thr Pro Asn Gly Ser Ile
    290                 295                 300

Pro Asn Asp Lys Pro Phe Gln Asn Val Asn Lys Ile Thr Tyr Gly Ala
305                 310                 315                 320

Cys Pro Lys Tyr Ile Lys Gln Asn Thr Leu Lys Leu Ala Thr Gly Met
                325                 330                 335

Arg Asn Ile Pro Glu Arg Gln Thr Arg Gly Ile Phe Gly Ala Ile Ala
            340                 345                 350

Gly Phe Ile Glu Asn Gly Trp Glu Gly Met Val Asn Gly Trp Tyr Gly
        355                 360                 365

Phe Arg His Gln Asn Ser Glu Gly Ile Gly Gln Ala Ala Asp Leu Lys
    370                 375                 380

Ser Thr Gln Ala Ala Ile Asn Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Arg Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Arg Lys Gln Leu Arg Glu Asn Ala Glu Asp Met Gly Asn
465                 470                 475                 480

Gly Cys Phe Lys Ile Tyr His Lys Cys Asp Asn Ser Cys Met Glu Ser
                485                 490                 495

Ile Arg Asn Gly Thr Tyr Asp His Asn Glu Tyr Arg Asp Glu Ala Val
            500                 505                 510

Asn Asn Arg Phe Gln Ile Lys Ser Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Ala Val Trp Leu Gly Phe Ile Met Trp Ala Cys Gln Lys Gly Asn Ile
545                 550                 555                 560
```

Arg Cys Asn Ile Cys Ile
            565

<210> SEQ ID NO 46
<211> LENGTH: 566
<212> TYPE: PRT
<213> ORGANISM: swine influenza virus

<400> SEQUENCE: 46

Met Glu Ala Lys Leu Phe Val Leu Phe Cys Ala Phe Thr Ala Leu Lys
1               5                   10                  15

Ala Asp Thr Ile Cys Val Gly Tyr His Ala Asn Asn Ser Thr Asp Thr
            20                  25                  30

Val Asp Thr Ile Leu Glu Lys Asn Val Thr Val Thr His Ser Val Asn
        35                  40                  45

Leu Leu Glu Asn Ser His Asn Gly Lys Leu Cys Ser Leu Asn Gly Lys
    50                  55                  60

Ala Pro Leu Gln Leu Gly Asn Cys Asn Val Ala Gly Trp Ile Leu Gly
65                  70                  75                  80

Asn Pro Glu Cys Asp Leu Leu Leu Thr Ala Asn Ser Trp Ser Tyr Ile
                85                  90                  95

Ile Glu Thr Ser Asn Ser Lys Asn Gly Ala Cys Tyr Pro Gly Glu Phe
            100                 105                 110

Ala Asp Tyr Glu Glu Leu Arg Glu Gln Leu Ser Thr Val Ser Ser Phe
        115                 120                 125

Glu Arg Phe Glu Ile Phe Pro Lys Ala Thr Ser Trp Pro Asn His Asp
    130                 135                 140

Thr Thr Lys Gly Thr Thr Val Ser Cys Ser His Ser Gly Ala Asn Ser
145                 150                 155                 160

Phe Tyr Arg Asn Leu Leu Trp Ile Val Lys Lys Gly Asn Ser Tyr Pro
                165                 170                 175

Lys Leu Ser Lys Ser Tyr Thr Asn Asn Lys Gly Lys Glu Val Leu Val
            180                 185                 190

Ile Trp Gly Val His His Pro Pro Thr Asp Ser Asp Gln Gln Thr Leu
        195                 200                 205

Tyr Gln Asn Asn His Thr Tyr Val Ser Val Gly Ser Ser Lys Tyr Tyr
    210                 215                 220

Gln Arg Phe Thr Pro Glu Ile Val Ala Arg Pro Lys Val Arg Gly Gln
225                 230                 235                 240

Ala Gly Arg Met Asn Tyr Tyr Trp Thr Leu Leu Asp Gln Gly Asp Thr
                245                 250                 255

Ile Thr Phe Glu Ala Thr Gly Asn Leu Ile Ala Pro Trp His Ala Phe
            260                 265                 270

Ala Leu Asn Lys Gly Ser Asn Ser Gly Ile Met Met Ser Asp Ala His
        275                 280                 285

Val His Asn Cys Thr Thr Lys Cys Gln Thr Pro His Gly Ala Leu Lys
    290                 295                 300

Ser Asn Leu Pro Phe Gln Asn Val His Pro Ile Thr Ile Gly Glu Cys
305                 310                 315                 320

Pro Lys Tyr Val Lys Ser Thr Gln Leu Arg Met Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr

```
                    355                 360                 365

His His Gln Asn Glu Gln Gly Ser Gly Tyr Ala Ala Asp Gln Lys Ser
    370                 375                 380

Thr Gln Ile Ala Ile Asp Gly Ile Ser Asn Lys Val Asn Ser Val Ile
385                 390                 395                 400

Glu Lys Met Asn Ile Gln Phe Thr Ser Val Gly Lys Glu Phe Asn Asn
                405                 410                 415

Leu Glu Lys Arg Ile Glu Asn Leu Asn Lys Lys Val Asp Asp Gly Phe
            420                 425                 430

Leu Asp Val Trp Thr Tyr Asn Ala Glu Leu Leu Ile Leu Leu Glu Asn
                435                 440                 445

Glu Arg Thr Leu Asp Phe His Asp Phe Asn Val Lys Asn Leu Tyr Glu
            450                 455                 460

Lys Val Lys Ser Gln Leu Arg Asn Asn Ala Lys Glu Ile Gly Asn Gly
465                 470                 475                 480

Cys Phe Glu Phe Tyr His Lys Cys Asp Asn Glu Cys Met Glu Ser Val
                485                 490                 495

Lys Asn Gly Thr Tyr Asn Tyr Pro Arg Tyr Ser Glu Glu Ser Lys Leu
            500                 505                 510

Asn Arg Glu Glu Ile Asp Gly Val Lys Leu Glu Ser Val Gly Val His
        515                 520                 525

Gln Ile Leu Ala Ile Tyr Ser Thr Val Ala Ser Ser Leu Val Leu Leu
            530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 47
<211> LENGTH: 564
<212> TYPE: PRT
<213> ORGANISM: swine influenza virus
<220> FEATURE:
<221> NAME/KEY: misc_feature
<222> LOCATION: (531)..(531)
<223> OTHER INFORMATION: Xaa can be any naturally occurring amino acid

<400> SEQUENCE: 47

Met Lys Ala Lys Leu Leu Ile Leu Trp Cys Ala Leu Ser Ala Thr Asp
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Asn His Asn Gly Lys Leu Cys Lys Leu Lys Gly Val
        50                  55                  60

Ala Pro Leu Gln Leu Gly Lys Cys Ser Ile Ala Gly Trp Ile Leu Gly
65                  70                  75                  80

Asn Pro Glu Cys Glu Ser Leu Phe Ser Lys Lys Ser Trp Ser Tyr Ile
                85                  90                  95

Ala Glu Thr Pro Asn Ala Glu Asn Gly Ile Cys Tyr Pro Gly Tyr Phe
                100                 105                 110

Ser Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Lys His Ser
        130                 135                 140
```

-continued

```
Ile Gly Ala Thr Ala Ser Cys Ser Lys Gln Gly Arg Ser Phe Tyr
145                 150                 155                 160

Arg Asn Leu Leu Trp Leu Thr Glu Lys Asn Gly Ser Tyr Pro Asn Leu
                165                 170                 175

Ser Lys Ser Tyr Val Asn Asp Lys Glu Arg Glu Val Leu Val Leu Trp
            180                 185                 190

Gly Val His His Pro Ser Asn Ile Glu Asp Gln Arg Ala Ile Tyr Arg
                195                 200                 205

Lys Glu Thr Ala Tyr Val Ser Val Met Ser Ser Leu Tyr Asn Arg Arg
        210                 215                 220

Phe Thr Pro Glu Ile Ala Lys Arg Pro Lys Ile Arg Asn Gln Glu Gly
225                 230                 235                 240

Arg Ile Asn Tyr Tyr Trp Thr Leu Leu Glu Pro Lys Asp Thr Ile Ile
                245                 250                 255

Phe Glu Ala Asn Gly Asn Leu Ile Ala Pro Trp Tyr Ala Phe Ala Leu
            260                 265                 270

Ser Arg Gly Phe Glu Ser Gly Ile Ile Val Ser Asn Ala Ser Met Asp
        275                 280                 285

Glu Cys Asp Ala Lys Cys Gln Thr Pro Gln Gly Ala Ile Asn Ser Ser
290                 295                 300

Leu Pro Phe Gln Asn Val His Pro Val Thr Ile Gly Glu Cys Pro Lys
305                 310                 315                 320

Tyr Val Lys Ser Thr Lys Leu Lys Met Ala Thr Gly Leu Arg Asn Ile
                325                 330                 335

Pro Ser Ile Gln Thr Arg Gly Leu Phe Gly Ala Ile Ala Gly Phe Ile
            340                 345                 350

Glu Gly Gly Trp Thr Gly Met Ile Asp Gly Trp Tyr Gly Tyr His His
        355                 360                 365

Gln Asn Glu Gln Gly Ser Gly Tyr Ala Ala Asp Gln Lys Ser Thr Gln
370                 375                 380

Asn Ala Ile Asn Gly Ile Thr Asn Lys Val Asn Ser Val Ile Asp Lys
385                 390                 395                 400

Met Asn Thr Gln Phe Thr Ala Val Gly Lys Glu Phe Asn Lys Leu Glu
                405                 410                 415

Lys Arg Met Glu Asn Leu Asn Lys Lys Val Asp Asp Gly Phe Leu Asp
            420                 425                 430

Ile Trp Thr Tyr Asn Ala Glu Leu Leu Val Leu Leu Glu Asn Glu Arg
        435                 440                 445

Thr Leu Asp Phe His Asp Ser Asn Val Lys Ser Leu Tyr Glu Lys Val
450                 455                 460

Lys Gly Gln Leu Lys Asn Asn Ala Lys Glu Ile Gly Asn Gly Cys Phe
465                 470                 475                 480

Glu Phe Tyr His Lys Cys Asn Asn Glu Cys Met Asp Ser Val Lys Asn
                485                 490                 495

Gly Thr Tyr Asp Tyr Pro Arg Tyr Ser Glu Glu Ser Lys Leu Asn Arg
            500                 505                 510

Glu Lys Ile Asp Gly Val Glu Leu Lys Ser Met Gly Val Tyr Gln Ile
        515                 520                 525

Leu Ala Xaa Tyr Ser Thr Val Ala Ser Ser Leu Val Leu Leu Val Ser
530                 535                 540
```

-continued

```
Leu Gly Ala Thr Ser Phe Trp Met Cys Ser Asn Gly Ser Leu Gln Cys
545                 550                 555                 560
Arg Ile Cys Ile
```

EHV INSERTION SITE UL43

CROSS-REFERENCE TO RELATED APPLICATIONS

This application is a U.S. national stage of International Application No. PCT/EP/2019/056749 filed on Mar. 19, 2019 and is based on European patent application EP 18162636.7 filed on Mar. 19, 2018; the disclosures of which are hereby incorporated by reference.

SEQUENCE LISTING

This application contains a sequence listing in accordance with 37 C.F.R. 1.821-1.825. The sequence listing accompanying this application is hereby incorporated by reference in its entirety.

BACKGROUND OF THE INVENTION

A. Field of the Invention

Two The present invention relates to the field of (vector) vaccines, and especially to the novel EHV insertion site UL43. The present invention further concerns related expression cassettes and vectors, which are suitable to express genes of interest, especially antigen encoding sequences. The viral vectors of the present invention are useful for producing an immunogenic composition or vaccine.

B. Background and Description of the Related Art

The horse pathogen Equid Alphaherpesvirus 1 (Equine abortion virus, EHV-1) belongs to the genus *Varicellovirus* in the subfamily Alphaherpesvirinae in the family Herpesviridae in the order Herpesvirales. It is a large, enveloped virus with a double-stranded DNA genome of approximately 150,000 base pairs. Other important members of the subgenus *Varicellovirus* are the Human Alphaherpesvirus 3 (Varicella Zoster Virus), Suid Alphaherpesvirus 1 (Pseudorabies virus), Bovine Alphaherpesvirus 1 (Infectious Bronchitis Virus), and Equid Alphaherpesvirus 4 (Equine Rhinopneumitis Virus, EHV-4) (Virus Taxonomy: 2015 Release EC 47, London, UK, July 2015; Email ratification 2016 (MSL #30)). EHV-1 and EHV-4 are endemic and affecting horses throughout the world. While EHV-4 causes a mostly mild infection of the upper respiratory tract, EHV-1 can cause systemic infection with a range of diseases from respiratory symptoms to abortion and lethal myeloencephalopathy depending on the strain and the immunological status of the host. Two licensed modified live vaccines (MLV) against EHV-1 are currently available in the USA and Europe, respectively, Rhinomune® (Boehringer Ingelheim) and Prevaccinol® (MSD). Both contain the classically attenuated EHV-1 RacH strain, which was passaged 256 times in porcine epithelial cells for attenuation (Ma et al. 2013). The mechanism of attenuation has been investigated on the molecular level. Osterrieder et al. (1996) showed that RacH lacks the two genomic copies of orf67 (IR6) and that restoration of one copy was sufficient to restore virulence. In addition, RacH carries a 1283 bp deletion removing more than 90% of the coding sequence of orf1(UL56) which encodes an immunosuppressive viral protein. Other mutations might also influence attenuation, but have not been investigated in detail, so far. All this makes RacH a very safe vaccine strain as a reversion to virulence by passaging in vaccinated animals is highly unlikely, if possible at all.

Two variants of an *E. coli* bacterial artificial chromosome (BAC) harboring the entire genome of the Equid Alphaherpes Virus 1 (EHV-1) vaccine strain RacH: pRacH and pRacH-SE are known as a platform for vector vaccine development. The BAC pRacH-SE was created on the basis of pRacH, a BAC originally cloned in the lab of Klaus Osterrieder, FU Berlin. pRacH has a deletion of orf71 (US5) encoding glycoprotein II (gpII; Wellington et al., 1996). In its place the BAC-vector sequences and a GFP-expression cassette were introduced. In order to rescue unmodified EHV-1 RacH from pRacH, it had to be co-transfected with a plasmid containing the entire orf71 (US5) plus flanking regions, so that during the course of viral replication the BAC-vector sequence portions and the GFP-expression cassette were replaced by orf71 (US5) through homologous recombination so that the original RacH genome would be restored. pRacH was modified in the present invention so that the BAC-vector sequences/GFP-expression cassette became self-excisable (SE) upon transfection in cell cultures (Tischer et al., 2007). This improved BAC was designated pRacH-SE. pRacH and pRacH-SE can both serve as platforms for vector vaccine development, with the only difference that pRacH-SE facilitates rescue of orf71 (US5)-repaired virus significantly.

It has been shown that EHV-1 RacH-based vector vaccines are able to elicit immunity in several mammalian species including pigs, cattle, and dogs (Rosas et al. 2007, Rosas et al. 2008, Trapp et al. 2005, Said et al. 2013). Genes coding for antigenic proteins of pathogens can be expressed by recombinant EHV-1 RacH. The EHV-1-RacH genome is manipulated in its BAC form in *E. coli* and tailored to express additional proteins usually by inserting transgene expression cassettes (Tischer et al., 2010). Upon transfection of pRacH-SE DNA in cultured permissive cells, EHV-1 replication is initiated by cellular transcription factors. Activity of the viral DNA polymerase leads to deletion of all BAC-vector related sequences and restoration of the EHV-1 RacH genome to its original state. Infectious virus is generated which is indistinguishable from RacH.

When pRacH-SE is manipulated in *E. coli* e.g. by insertion of transgene expression cassettes, virus reconstituted after transfection in permissive cells will carry the modification and will express the additional gene. The recombinant EHV-1 RacH can be used as a vector vaccine.

Wild-type EHV-1 strains possess three open reading frames (orf) called orf1 (UL56), orf 2 and orf3 at one end of the long unique segment of their genome (sequence coordinates 1298-3614; FIG. 1). Orf1 (UL56) and orf3 are serially arranged on one strand of the DNA while orf 2 is encoded by the complementary strand. The vaccine strain RacH has a 1283 bp deletion in that region affecting orfs 1 and 2 indicating that these genes are non-essential for viral replication. For this reason the site serves as a transgene insertion site. This insertion site is called ORF1/3 (UL56).

However, the size and number of transgenes that may be inserted into the ORF1/3 (UL56) insertion site is usually limited. Thus, in order to augment the capabilities of the EHV vector there is an unmet need for new and alternative ways to insert and express transgenes from the EHV vector, especially the recombinant EHV-1 RacH vector.

SUMMARY OF THE INVENTION

In order to augment the capabilities of the EHV vector, the present invention provides new and alternative ways to insert and express transgenes from the EHV vector backbone.

The present invention concerns a new, alternative transgene insertion site UL43 that can be used to insert transgenic sequence and express transgenic protein from an EHV vector, especially the recombinant EHV-1 RacH.

The novel "UL43 insertion site" in the EHV vector is characterized by a partial deletion, truncation, substitution, modification or the like in relation to UL43 (ORF17). A deletion of the complete UL43 would be expected to be disadvantageous for viral replication and thus vaccine manufacturing and efficacy because complete deletion of UL43 might affect the promoter of UL44 encoding for glycoprotein C. The novel UL43 insertion site and/or the insertion (of an expression cassette) into UL43 is functionally defined in such a way that UL44 remains functional or intact.

In a specific aspect, the UL43 insertion site encompasses a deletion of an approximately 870 bp portion (SEQ ID NO:21) within UL43 for RacH (SEQ ID NO:18) or a 70%, 80%, 85%, 90%, 95%, 99% homologous sequence thereof. The deleted portion in the RacH genome sequence is shown as SEQ ID NO:21 (no nucleotide numbers available because complete RacH genome sequence not known). In another specific aspect, the UL43 insertion site encompasses a theoretical 870 bp deletion within UL43 (nt 23021-24226 reverse complementary) for the wild-type EHV-1 strain V592 (Genbank accession number AY464052.1) (SEQ ID NO:23). The deleted portion is corresponding to the wild-type V592 (Genbank accession number AY464052.1 genome sequence nucleotides 23353 and 24226 reverse complementary (SEQ ID NO:24).

In the present invention "flanking regions" direct the recombination of the expression cassette comprising the sequence or gene of interest, preferably an antigen encoding sequence, into the EHV genome. These flanking regions are naturally present in EHV. The Up UL43 flanking region (226 bp, SEQ ID NO:19) and the Up UL44 flanking region (305 bp, SEQ ID NO:20) are selected for classical homologous recombination for all transfer vectors/plasmids used for the UL43 site. In the wild-type EHV-1 strain V592 (Genbank accession number AY464052.1) the corresponding sequences are located at nucleotides 24227-24452 reverse complementary (flanking region up UL43, SEQ ID NO:26) and 23049-23354 reverse complementary (flanking region up UL44, SEQ ID NO:27).

The plasmid/vector maps in FIG. 21 for the transfer plasmid pU-mC70-BGH (SEQ ID NO:37), in FIG. 22 for the transfer vector pU70-p455-71K71 (SEQ ID NO:28), and in FIG. 3 for the transfer plasmid pU70-p455-H3-71K71 (SEQ ID NO:29) are examples of vectors comprising an expression cassette including a novel ORF70 insertion site. The plasmid/vector maps in FIG. 23 for the transfer vector pU-1-3-p430-BGHKBGH (SEQ ID NO:30), and in FIG. 4 for the transfer plasmid pU1-3-p430-H1av-BGHKBGH (SEQ ID NO:31) are examples of vectors comprising an expression cassette including an ORF1/3 (UL56) insertion site.

The plasmid/vector maps in FIG. 24 for the transfer vector pUUL43-p422-18K18 (SEQ ID NO:34), in FIG. 14 for the transfer plasmid pUUL43-422-mC-18K18 (SEQ ID NO:35), and in FIG. 16 for the transfer plasmid pUUL43-422-H1pdm-18K18 (SEQ ID NO:36) are examples of vectors comprising an expression cassette including a novel UL43 insertion site.

The present invention further concerns an EHV vector expressing two different transgenes from one vector backbone without coupling two transgenes by RNA-virus-derived functions (*2a* peptides, IRES sites) under control of one promoter.

The present invention further concerns an EHV vector expressing two or three different transgenes from one vector backbone without coupling two or three transgenes by RNA-virus-derived functions (*2a* peptides, IRES sites) under control of one promoter.

The present invention further concerns an Equid alphaherpesvirus (EHV) vector, preferably EHV-1, RacH or RacH-SE, comprising a first sequence or gene of interest inserted into the new UL43 insertion site and a second sequence or gene of interest inserted into an established insertion site such as ORF1/3 (UL56) or the other insertion site ORF70 (US4). In addition, the present invention further concerns vectors based on other Herpesviruses, in particular Alphaherpesviruses, in particular Varicelloviruses including Equid alphaherpesvirus 3 (EHV-3), Equid alphaherpesvirus 4 (EHV-4), Equid alphaherpesvirus 8 (EHV-8), Equid alphaherpesvirus 9 (EHV-9), Bovine alphaherpesvirus 1 (BHV-1), Bovine alphaherpesvirus 5 (BHV-5), Canid alphaherpesvirus 1, and Felid alphaherpesvirus 1.

The present invention further concerns an Equid alphaherpesvirus (EHV) vector, preferably EHV-1, RacH or RacH-SE, comprising a first sequence or gene of interest inserted into the new UL43 insertion site and a second sequence or gene of interest inserted into the other insertion site ORF70 (US4), and a third sequence or gene of interest inserted into an established insertion site such as ORF1/3 (UL56). In addition, the present invention further concerns vectors based on other Herpesviruses, in particular Alphaherpesviruses, in particular Varicelloviruses including Equid alphaherpesvirus 3 (EHV-3), Equid alphaherpesvirus 4 (EHV-4), Equid alphaherpesvirus 8 (EHV-8), Equid alphaherpesvirus 9 (EHV-9), Bovine alphaherpesvirus 1 (BHV-1), Bovine alphaherpesvirus 5 (BHV-5), Canid alphaherpesvirus 1, and Felid alphaherpesvirus 1.

The present invention further concerns mammalian host cells comprising such vectors and methods of generating vector vaccines using such host cells, as well as immunogenic compositions and vaccines comprising the Equid alphaherpesvirus (EHV) vector of the present invention.

The present invention further concerns a promoter sequence comprising p422 (SEQ ID NO:5) or the complementary nucleotide sequences thereof or a functional fragment thereof or the complementary nucleotide sequences thereof, wherein said promoter sequence leads to expression of a nucleotide sequence of interest, preferably a gene of interest, more preferably an antigen encoding sequence. The present invention also concerns functional fragments of the promoter sequence having a sequence identity and/or homology of 70%, 80%, 85%, preferably 90%, 91%, 92%, 93%, 94%, more preferably 95%, 96%, 97%, 98%, 99%, 99.9%.

Thus, the solution to the above described technical problem is achieved by the description and the embodiments characterized in the claims and the invention in its different aspects is implemented according to the claims.

These properties allow creation of recombinant vector vaccines based on EHV, preferably EHV-1 RacH, expressing at least one antigen from the newly described UL43 insertion site or at least two different antigens in parallel with similar efficiency from the newly described UL43 insertion site and another insertion site like ORF1/3 (UL56) and/or the other insertion site ORF70 (US4). If a vaccine target consists of two different pathogens the application of the new UL43 insertion site in parallel with an established insertion site like ORF1/3 (UL56) and/or the other insertion site ORF70 (US4) can reduce cost of goods significantly and represents a clear advantage over a vector expressing only one antigenic component.

These properties allow creation of recombinant vector vaccines based on EHV, preferably EHV-1 RacH, expressing at least one antigen from the newly described UL43 insertion site or at least two different antigens in parallel with similar efficiency from the newly described UL43 insertion site and another insertion site like ORF1/3 (UL56) or the other insertion site ORF70 (US4) or at least three different antigens in parallel from the newly described UL43 insertion site and the other insertion site ORF70 (US4) and another insertion site like ORF1/3 (UL56). If a vaccine target consists of two different pathogens the application of the new UL43 insertion site in parallel with an established insertion site like ORF1/3 (UL56) or the other insertion site ORF70 (US4) can reduce cost of goods significantly and represents a clear advantage over a vector expressing only one antigenic component. If a vaccine target consists of three different pathogens the application of the new UL43 insertion site in parallel with an established insertion site like ORF1/3 (UL56) and the other insertion site ORF70 (US4) can reduce cost of goods significantly and represents a clear advantage over a vector expressing only one or two antigenic components.

DETAILED DESCRIPTION OF THE INVENTION

The present invention solves the problems inherent in the prior art and provides a distinct advance in the state of the art.

Generally, the present invention provides an expression cassette comprising
(i) at least one exogenous nucleotide sequence of interest, preferably a gene of interest, more preferably an antigen encoding sequence, whereby said nucleotide sequence of interest, preferably a gene of interest, more preferably an antigen encoding sequence, is operably linked to a promoter sequence, and
(ii) at least one upstream UL43 flanking region selected from the group consisting of: SEQ ID NO:19 and a 70%, 80%, 85%, 90%, 91%, 92%, 93%, 94%, 95%, 96%, 97%, 98%, 99% homologous and/or identical sequence thereof, SEQ ID NO:26 and a 70%, 80%, 85%, 90%, 91%, 92%, 93%, 94%, 95%, 96%, 97%, 98%, 99% homologous and/or identical sequence thereof, and
(iii) at least one upstream UL44 flanking region selected from the group consisting of: SEQ ID NO:20 and a 70%, 80%, 85%, >90%, >91%, 92%, 93%, 94%, 95%, 96%, 97%, 98%, 99% homologous and/or identical sequence thereof, SEQ ID NO:27 and a 70%, 80%, 85%, 90%, 91%, 92%, 93%, 94%, 95%, 96%, 97%, 98%, 99% homologous and/or identical sequence thereof.

The present invention further provides an Equid herpesvirus (EHV), specifically an Equid Alphaherpesvirus such as EHV-1, EHV-3, EHV-4, EHV-8 and EHV-9, more specifically an Equid Alphaherpesvirus 1 (EHV-1) vector, most specifically strain RacH, comprising the expression cassette of the present invention.

The present invention provides an Equid Alphaherpesvirus (EHV) vector, preferably EHV-1 or strain RacH, comprising the expression cassette of the present invention.

The present invention furthermore concerns an Equid herpesvirus (EHV), specifically an Equid Alphaherpesvirus such as EHV-1, EHV-3, EHV-4, EHV-8 and EHV-9, more specifically an Equid Alphaherpesvirus 1 (EHV-1) vector, most specifically strain RacH, comprising
(i) at least one exogenous nucleotide sequence of interest, preferably a gene of interest, more preferably an antigen encoding sequence, whereby said nucleotide sequence of interest, preferably a gene of interest, more preferably an antigen encoding sequence, is operably linked to a promoter sequence, and
(ii) at least one upstream UL43 flanking region selected from the group consisting of: SEQ ID NO:19 and a 70%, 80%, 85%, 90%, 91%, 92%, 93%, 94%, 95%, 96%, 97%, 98%, 99% homologous and/or identical sequence thereof, SEQ ID NO:26 and a 70%, 80%, 85%, 90%, 91%, 92%, 93%, 94%, 95%, 96%, 97%, 98%, 99% homologous and/or identical sequence thereof, and
(iii) at least one upstream UL44 flanking region selected from the group consisting of: SEQ ID NO:20 and a 70%, 80%, 85%, 90%, 91%, 92%, 93%, 94%, 95%, 96%, 97%, 98%, 99% homologous and/or identical sequence thereof, SEQ ID NO:27 and a 70%, 80%, 85%, 90%, 91%, 92%, 93%, 94%, 95%, 96%, 97%, 98%, 99% homologous and/or identical sequence thereof.

Advantageously, the experimental data provided by the present invention disclose that a new insertion site within the EHV vector has been provided that can be used for inserting and expressing antigens. Further, the provision of the new insertion site now allows the insertion and expression of antigens from different insertion sites and the expression of more than one antigen, respectively.

The present invention further concerns an Equid herpesvirus (EHV), specifically an Equid Alphaherpesvirus such as EHV-1, EHV-3, EHV-4, EHV-8 and EHV-9, more specifically an Equid Alphaherpesvirus 1 (EHV-1) vector, most specifically strain RacH, comprising a nucleotide sequence of interest, preferably a gene of interest, more preferably an antigen encoding sequence, inserted into UL43.

The present invention further concerns an Equid herpesvirus (EHV), specifically an Equid Alphaherpesvirus such as EHV-1, EHV-3, EHV-4, EHV-8 and EHV-9, more specifically an Equid Alphaherpesvirus 1 (EHV-1) vector, most specifically strain RacH, comprising a first nucleotide sequence or gene of interest, preferably an antigen encoding sequence, inserted into UL43 and a second nucleotide sequence or gene of interest, preferably another antigen encoding sequence, inserted into a second insertion site, preferably UL56 (orf1/3) or US4 (orf70). In a specific aspect of said EHV vector of the present invention the at least two genes of interest are operably linked to regulatory sequences, preferably promoter sequences.

In a specific aspect of the vector of the present invention the insertion into UL43 is characterized by a partial deletion, truncation, substitution, modification or the like in UL43, whereby UL44 remains functional.

In another specific aspect of the vector of the present invention the insertion into UL43 is characterized by the deletion of an approximately 870 bp portion within UL43 for RacH (SEQ ID NO:21) or a 70%, 80%, 85%, 90%, 91%, 92%, 93%, 94%, 95%, 96%, 97%, 98%, 99% homologous and/or identical sequence thereof.

In another specific aspect of the vector of the present invention the insertion into UL43 is characterized by the deletion of an approximately 870 bp portion within UL43 for RacH (SEQ ID NO:21) or a 70%, 80%, 85%, 90%, 91%, 92%, 93%, 94%, 95%, 96%, 97%, 98%, 99% homologous and/or identical sequence deletion thereof in any other strain.

In a further specific aspect of the vector of the present invention the insertion into UL43 is characterized by the deletion of an approximately 870 bp deletion within UL43 for the wild-type EHV-1 strain V592 (Genbank accession number AY464052.1), whereby the deleted portion in the wild-type V592 genome sequence is located between nucleotides 23353 and 24226 (SEQ ID NO:24) or a 70%, 80%, 85%, 90%, 91%, 92%, 93%, 94%, 95%, 96%, 97%, 98%, 99% homologous and/or identical sequence thereof.

In another specific aspect of the vector of the present invention the EHV vector, specifically the EHV-1 vector, comprises (i) at least one upstream UL43 flanking region selected from the group consisting of: SEQ ID NO:19, SEQ ID NO:26, and (ii) at least one upstream UL44 flanking region selected from the group consisting of: SEQ ID NO:20, SEQ ID NO:27.

In a further specific aspect of the vector or the expression cassette of the present invention said nucleotide sequence of interest, preferably a gene of interest, more preferably an antigen encoding sequence is non-naturally occurring and/or recombinant.

In another specific aspect of the vector or the expression cassette of the present invention said nucleotide sequence of interest is recombinant and/or heterologous and/or exogenous.

In a further specific aspect of the vector or the expression cassette of the present invention said antigen encoding sequence relates to a pathogen infecting an animal such as a food producing animal such as swine, poultry or cattle or companion animals such as cats, dogs or horses.

In a further specific aspect of the vector or the expression cassette of the present invention said vector or expression cassette further comprises at least one further additional regulatory sequence such as a termination signal or a polyadenylation sequence.

In another specific aspect of the vector or the expression cassette of the present invention said vector or expression cassette further comprises additional regulatory sequences such as a termination signal and/or polyadenylation sequence.

In a further specific aspect of the vector or the expression cassette of the present invention said vector or expression cassette further comprises at least one further nucleotide sequence of interest, preferably another gene of interest, more preferably an antigen encoding sequence. In one aspect at least one further nucleotide sequence of interest, preferably another gene of interest, more preferably an antigen encoding sequence, is inserted into the same insertion site UL43, e.g. via IRES/2a peptide(s). In another aspect said vector or expression cassette comprise at least one further nucleotide sequence of interest, preferably another gene of interest, more preferably an antigen encoding sequence, is inserted into another insertion site, preferably into UL56 and/or US4.

In a further aspect of the vector or the expression cassette of the present invention at least one further nucleotide sequence of interest, preferably another gene of interest, more preferably an antigen encoding sequence, is inserted into UL56. The UL56 (ORF1/3) insertion site has been described in the prior art.

In a further aspect of the vector or the expression cassette of the present invention at least one further nucleotide sequence of interest, preferably another gene of interest, more preferably an antigen encoding sequence, is inserted into US4 (ORF70).

An alternative transgene insertion site US4 (ORF70) can be used to insert transgenic sequence and express transgenic protein from an EHV vector, especially the recombinant EHV-1 or EHV-1 RacH.

The "US4 (ORF70) insertion site" in the EHV vector is characterized by a partial deletion, truncation, substitution, modification or the like in relation to US4 (ORF70). A deletion of the complete US4 (ORF70) would be expected to be disadvantageous for viral replication and thus vaccine manufacturing and efficacy because complete deletion of US4 (ORF70) would affect the promoter of US5 (ORF71) encoding for gpII. The US4 (ORF70) insertion site and/or the insertion (of an expression cassette) into US4 (ORF70) is functionally defined in such a way that US5 (ORF71) remains functional or intact.

In a specific aspect, the US4 (ORF70) insertion site encompasses a deletion of an approximately 801 bp portion within US4 (ORF70) for RacH (SEQ ID NO:17) or a 70%, 80%, 85%, 90%, 95%, 99% homologous sequence thereof. The deleted portion in the RacH genome sequence is shown as SEQ ID NO:17 (no nucleotide numbers available because complete RacH genome sequence not known). In another specific aspect, the ORF70 insertion site encompasses a theoretical 801 bp deletion within ORF70 for the wild-type EHV-1 strain ab4 (Genbank accession number AY665713.1, SEQ ID NO:16). The deleted portion is located in the wild-type ab4 (Genbank accession number AY665713.1) genome sequence between nucleotides 127681 and 128482 (SEQ ID NO:16).

In the present invention "flanking regions" direct the recombination of the expression cassette comprising the sequence or gene of interest, preferably an antigen encoding sequence, into the EHV genome. These flanking regions are naturally present in EHV. The Up70 flanking region (417 bp, SEQ ID NO:9) and the Up71 flanking region (431 bp, SEQ ID NO:10) are selected for classical homologous recombination for all transfer vectors/plasmids used for the orf70 site. In the wild-type EHV-1 strain ab4 (Genbank accession number AY665713.1) the corresponding sequences are located at nucleotides 127264-127680 (flanking region up orf70, SEQ ID NO:11) and 128483-128913 (flanking region up orf71, SEQ ID NO:12). For the RED recombination the flanking regions are truncated due to a XbaI restriction digest. These truncated flanking regions are identical to the 3' 283 bp of the 417 bp "classical" flanking region (Up70 flanking region, SEQ ID NO:9) and the 5' 144 bp of the 431 bp "classical" flanking region (Up71 flanking region, SEQ ID NO:10), which are described above. These truncated flanking regions are named Up70 flanking region (283 bp), included as SEQ ID NO:13 and Up71 flanking region (144 bp) included as SEQ ID NO:14. These various flanking regions define the same ORF70 insertion site. The flanking regions are used in pairs always one "left" flanking region such as SEQ ID NOs.: 9, 11, 13 and one "right" flanking region such as SEQ ID NOs.: 10, 12, 14.

In a further aspect of the vector of the present invention the vector further comprises
(i) at least one exogenous nucleotide sequence of interest, preferably a gene of interest, more preferably an antigen encoding sequence, whereby said nucleotide sequence of interest, preferably a gene of interest, more preferably an antigen encoding sequence, is operably linked to a promoter sequence, and
(ii) at least one left US4 (ORF70) flanking region selected from the group consisting of: SEQ ID NO:9 and a 70%, 80%, 85%, 90%, 91%, 92%, 93%, 94%, 95%, 96%, 97%, 98%, 99% homologous and/or identical sequence thereof, SEQ ID NO:11 and a 70%, 80%, 85%, 90%, 91%, 92%, 93%, 94%, 95%, 96%, 97%, 98%, 99% homologous and/or identical sequence thereof, and SEQ ID NO:13 and a 70%, 80%, 85%, 90%, 91%, 92%, 93%, 94%, 95%, 96%, 97%, 98%, 99% homologous and/or identical sequence thereof, and (iii) at least one right US4 (ORF70) flanking region selected from the group consisting of: SEQ ID NO:10 and a 70%, 80%, 85%, 90%, 91%, 92%, 93%, 94%, 95%, 96%, 97%, 98%, 99% homologous and/or identical sequence thereof, SEQ ID NO:12 and a 70%, 80%, 85%, 90%, 91%, 92%, 93%, 94%, 95%, 96%, 97%, 98%, 99% homologous and/or identical sequence thereof, and SEQ ID NO:14 and a 70%, 80%, 85%, 90%, 91%, 92%, 93%, 94%, 95%, 96%, 97%, 98%, 99% homologous and/or identical sequence thereof.

The present invention furthermore concerns an Equid herpesvirus (EHV), specifically an Equid Alphaherpesvirus 1 (EHV-1) vector, most specifically strain RacH, comprising (i) a first exogenous nucleotide sequence of interest, preferably a gene of interest, more preferably an antigen encoding sequence, whereby said nucleotide sequence of interest, preferably a gene of interest, more preferably an antigen encoding sequence, is operably linked to a promoter sequence, and at least one upstream UL43 flanking region selected from the group consisting of: SEQ ID NO:19 and a 70%, 80%, 85%, 90%, 91%, 92%, 93%, 94%, 95%, 96%, 97%, 98%, 99% homologous and/or identical sequence thereof, SEQ ID NO:26 and a 70%, 80%, 85%, 90%, 91%, 92%, 93%, 94%, 95%, 96%, 97%, 98%, 99% homologous and/or identical sequence thereof, and at least one upstream UL44 flanking region selected from the group consisting of: SEQ ID NO:20 and a 70%, 80%, 85%, 90%, 91%, 92%, 93%, 94%, 95%, 96%, 97%, 98%, 99% homologous and/or identical sequence thereof, SEQ ID NO:27 and a 70%, 80%, 85%, 90%, 91%, 92%, 93%, 94%, 95%, 96%, 97%, 98%, 99% homologous and/or identical sequence thereof; and (ii) a second exogenous nucleotide sequence of interest, preferably a gene of interest, more preferably an antigen encoding sequence, whereby said nucleotide sequence of interest, preferably a gene of interest, more preferably an antigen encoding sequence, is operably linked to a promoter sequence, and at least one left US4 (ORF70) flanking region selected from the group consisting of: SEQ ID NO:9 and a 70%, 80%, 85%, 90%, 91%, 92%, 93%, 94%, 95%, 96%, 97%, 98%, 99% homologous and/or identical sequence thereof, SEQ ID NO:11 and a 70%, 80%, 85%, 90%, 91%, 92%, 93%, 94%, 95%, 96%, 97%, 98%, 99% homologous and/or identical sequence thereof, and SEQ ID NO:13 and a 70%, 80%, 85%, 90%, 91%, 92%, 93%, 94%, 95%, 96%, 97%, 98%, 99% homologous and/or identical sequence thereof, and at least one right US4 (ORF70) flanking region selected from the group consisting of: SEQ ID NO:10 and a 70%, 80%, 85%, 90%, 91%, 92%, 93%, 94%, 95%, 96%, 97%, 98%, 99% homologous and/or identical sequence thereof, SEQ ID NO:12 and a 70%, 80%, 85%, 90%, 91%, 92%, 93%, 94%, 95%, 96%, 97%, 98%, 99% homologous and/or identical sequence thereof, and SEQ ID NO:14 and a 70%, 80%, 85%, 90%, 91%, 92%, 93%, 94%, 95%, 96%, 97%, 98%, 99% homologous and/or identical sequence thereof.

In a further aspect of the vector of the present invention the vector the insertion into US4 (ORF70) is characterized by the deletion of an approximately 801 bp portion within US4 (ORF70) for RacH (SEQ ID NO:17) or a 70%, 80%, 85%, 90%, 91%, 92%, 93%, 94%, 95%, 96%, 97%, 98%, 99% homologous and/or identical sequence thereof.

In a further aspect of the vector of the present invention the vector comprises at least one flanking region selected from the group consisting of: SEQ ID NO:9, SEQ ID NO:10, SEQ ID NO:11, SEQ ID NO:12, SEQ ID NO:13 and SEQ ID NO:14 and a 70%, 80%, 85%, 90%, 91%, 92%, 93%, 94%, 95%, 96%, 97%, 98%, 99% homologous and/or identical sequence of any one of these sequences.

In a further aspect of the vector of the present invention the vector comprises (i) at least one left US4 (ORF70) flanking region selected from the group consisting of: SEQ ID NO:9, SEQ ID NO:11, and SEQ ID NO:13, and (ii) at least one right US4 (ORF70) flanking region selected from the group consisting of: SEQ ID NO:10, SEQ ID NO:12, and SEQ ID NO:14.

In a further aspect of the vector or the expression cassette of the present invention a second further nucleotide sequence of interest, preferably another gene of interest, more preferably an antigen encoding sequence, is inserted into US4 and, whereby a third further nucleotide sequence of interest, preferably another gene of interest, more preferably an antigen encoding sequence, is inserted into UL56.

In a specific aspect of the vector of the present invention the gene of interest is operably linked to a regulatory sequence, preferably a promoter sequence.

In a further aspect of the vector or the expression cassette of the present invention the gene of interest is operably linked to a regulatory sequence, preferably a promoter sequence or the EHV vector as described herein whereby the at least two genes of interest are operably linked to regulatory sequences, preferably promoter sequences.

In a further aspect of the vector or the expression cassette of the present invention the promoter sequence(s) operably linked to the one or two or more sequences or genes of interest are selected from the group consisting of: SV40 large T, HCMV and MCMV immediate early gene 1, human elongation factor alpha promoter, baculovirus polyhedrin promoter, a functional fragment of 4pgG600 (SEQ ID NO:1), preferably said functional fragment is p430 (SEQ ID NO:3), a functional fragment of the complementary nucleotide sequence of 4pgG600 (SEQ ID NO:1), a functional fragment of 4pMCP600 (SEQ ID NO:2), preferably said functional fragment is p455 (SEQ ID NO:4), a functional fragment of the complementary nucleotide sequence of 4pMCP600 (SEQ ID NO:2) or p422 (SEQ ID NO:5) or a functional fragment thereof or the complementary nucleotide sequences thereof.

In a further aspect of the vector or the expression cassette of the present invention the promoter sequence operably linked to at least one gene of interest is p422 (SEQ ID NO:5) or a functional fragment thereof or the complementary nucleotide sequences thereof.

In a specific aspect of the vector or the expression cassette of the present invention the at least two genes of interest are operably linked to regulatory sequences, preferably promoter sequences.

In a further specific aspect of the vector or the expression cassette of the present invention the promoter sequences operably linked to the at least two genes of interest are different.

In another specific aspect of the vector or the expression cassette of the present invention the promoter sequence operably linked to at least one gene of interest is p422 (SEQ ID NO:5) or a functional fragment or derivative thereof or the complementary nucleotide sequences thereof and whereby the promoter sequence operably linked to another gene of interest is p430 (SEQ ID NO:3) or a functional fragment or derivative thereof or the complementary nucleotide sequences thereof, and whereby the promoter sequence operably linked to another gene of interest is p455 (SEQ ID NO:4) or a functional fragment or derivative thereof or the complementary nucleotide sequences thereof.

In a further specific aspect of the vector or the expression cassette of the present invention polyadenylation sequence is BGHpA, 71 pA (SEQ ID NO:6), or 18 pA (SEQ ID NO:7).

In a further specific aspect of the vector or the expression cassette of the present invention the EHV vector or expression cassette is recombinant.

In a further specific aspect of the vector or the expression cassette of the present invention said sequences or exogenous nucleotide sequence of interest or gene of interest is an antigen encoding sequence.

In a further specific aspect of the vector or the expression cassette of the present invention the antigen encoding sequence is from a pathogen selected from the list: Schmallenberg virus, Influenza A Virus, Porcine Respiratory and Reproductive Syndrome Virus, Porcine Circovirus, Classical Swine Fever Virus, African Swine Fever Virus, Hepatitis E Virus, Bovine Viral Diarrhea Virus, Rabies Virus, Feline Morbillivirus, *Clostridium tetani, Mycobacterium tuberculosis, Actinobacillus Pleuropneumoniae.*

In a further specific aspect of the vector or the expression cassette of the present invention the antigen encoding sequence is a hemagglutinin encoding sequence.

In a further specific aspect of the vector or the expression cassette of the present invention the hemagglutinin influenza antigen encoding sequence is from a Swine influenza A virus.

The four most prevalent Influenza A strains within Europe are H1N2, H3N2 and H1N1 (H1N1 avian and H1N1 pandemic) subtypes. Thus, there is a need for vaccines being highly efficacious against H1N2, H3N2 and H1N1 (H1N1 avian and H1N1 pandemic) subtypes and, thus, providing very broad protection against these Swine IAV field strains.

Further, it is advantageous to have a multivalent vaccine as multivalent vaccines in general are more cost-effective and are more time-effective than monovalent vaccines.

The EHV-vector based vaccine as described herein by not being a modified live vaccine (MLV) provides ultimate safety with regard to Swine IAV since no live IAVs are generated or given to animals, thus preventing potential reversion to virulence of the vaccine strain(s) and genetic recombination or reassortment with field strains from swine or humans. Moreover, in contrast to killed vaccines (current standard), a vector vaccine is expected to not only induce Swine IAV neutralizing antibodies but to also strongly stimulate the cellular immunity against Swine IAV by both the MHC class I and II pathways. Thus, there is a need for vector based SIAV vaccines. In addition, a vector vaccine expressing IAV hemagglutinins allows for differentiation between infected and vaccinated animals (DIVA) since other antibody-inducing proteins of Influenza virus are not part of the vector vaccine. Thus, vaccination will not induce any antibodies specific for NP (nucleoprotein) or N (neuraminidase), both of which are virus structural proteins and contained in standard killed vaccines.

In a further specific aspect of the vector or the expression cassette of the present invention the exogenous antigen encoding sequence is a hemagglutinin encoding sequence and the hemagglutinin influenza subtype is selected from the group consisting of H1, H2, H3, H4, H5, H6, H7, H8, H9, H10, H11, H12, H13, H14, H15, H16, H17 and H18.

In a further specific aspect of the vector or the expression cassette of the present invention the exogenous antigen encoding sequence is a hemagglutinin encoding sequence and the hemagglutinin influenza antigen encoding sequence is selected from a group of strains consisting of A/swine/Italy/116114/2010(H1N2), A/swine/Italy/7680/2001 (H3N2), A/swine/Gent/132/2005(H1N1), A/swine/Italy/4675/2003(H1N2), A/swine/Italy/259543/2003(H1N2), A/swine/Denmark/I3772-1/2003(H1N1), A/swine/England/MD0040352R/2009(H1N1), A/swine/Hungary/13509/2007 (H3N2), A/swine/Italy/13962/95(H3N2), A/swine/Cotes d'Armor/1121/00(H1N1), A/Swine/Colorado/1/77, A/Swine/Colorado/23619/99, A/Swine/Cote d'Armor/3633/84, A/Swine/England/195852/92, A/Swine/Finistere/2899/82, A/Swine/Hong Kong/10/98, A/Swine/Hong Kong/9/98, A/Swine/Hong Kong/81/78, A/Swine/Illinois/100084/01, A/Swine/Illinois/100085A/01, A/Swine/Illinois/21587/99, A/Swine/Indiana/1726/88, A/Swine/Indiana/9K035/99, A/Swine/Indiana/P12439/00, A/Swine/Iowa/30, A/Swine/Iowa/15/30, A/Swine/Iowa/533/99, A/Swine/Iowa/569/99, A/Swine/Iowa/3421/90, A/Swine/Iowa/8548-1/98, A/Swine/Iowa/930/01, A/Swine/Iowa/17672/88, A/Swine/Italy/1513-1/98, A/Swine/Italy/1523/98, A/Swine/Korea/CY02/02, A/Swine/Minnesota/55551/00, A/Swine/Minnesota/593/99, A/Swine/Minnesota/9088-2/98, A/Swine/Nebraska/1/92, A/Swine/Nebraska/209/98, A/Swine/Netherlands/12/85, A/Swine/North Carolina/16497/99, A/Swine/North Carolina/35922/98, A/Swine/North Carolina/93523/01, A/Swine/North Carolina/98225/01, A/Swine/Oedenrode/7C/96, A/Swine/Ohio/891/01, A/Swine/Oklahoma/18717/99, A/Swine/Oklahoma/18089/99, A/Swine/Ontario/01911-1/99, A/Swine/Ontario/01911-2/99, A/Swine/Ontario/41848/97, A/Swine/Ontario/97, A/Swine/Quebec/192/81, A/Swine/Quebec/192/91, A/Swine/Quebec/5393/91, A/Swine/Taiwan/7310/70, A/Swine/Tennessee/24/77, A/Swine/Texas/4199-2/98, A/Swine/Wisconsin/125/97, A/Swine/Wisconsin/136/97, A/Swine/Wisconsin/163/97, A/Swine/Wisconsin/164/97, A/Swine/Wisconsin/166/97, A/Swine/Wisconsin/168/97, A/Swine/Wisconsin/235/97, A/Swine/Wisconsin/238/97, A/Swine/Wisconsin/457/985 A/Swine/Wisconsin/458/98, A/Swine/Wisconsin/464/98 and A/Swine/Wisconsin/14094/99.

In a further specific aspect of the vector or the expression cassette of the present invention the exogenous antigen encoding sequence is a hemagglutinin encoding sequence and the hemagglutinin influenza antigen encoding sequence is selected from a group of strains consisting of A/swine/Italy/116114/2010(H1N2), A/swine/Italy/7680/2001 (H3N2), A/swine/Gent/132/2005(H1N1) and A/swine/Italy/4675/2003(H1N2).

In a further specific aspect of the vector or the expression cassette of the present invention the exogenous antigen encoding sequence is a hemagglutinin encoding sequence and the hemagglutinin influenza subtype is H1 and/or H3.

In a further specific aspect of the vector or the expression cassette of the present invention the antigen encoding sequence is a hemagglutinin encoding sequence and the hemagglutinin influenza antigen encoding sequence comprises a nucleic acid sequence encoding an amino acid sequence with at least 70%, at least 75%, at least 80%, at least 85%, at least 90%, least 91%, at least 92%, at least 93%, at least 94%, at least 95%, at least 96%, at least 97%, at least 98% or at least 99% identity to the amino acid sequence as set forth in SEQ ID NO:44, SEQ ID NO:45, SEQ ID NO:46 and SEQ ID NO:47.

In a further specific aspect of the vector or the expression cassette of the present invention the EHV vector or the expression cassette does not comprise NP (nucleoprotein) or N (neuraminidase) influenza antigen encoding sequences.

H1pdm in UL43 with p422:

In a further specific aspect of the vector or the expression cassette of the present invention the promoter sequence p422 (SEQ ID NO:5) or a functional fragment or a functional derivative thereof or the complementary nucleotide sequences thereof is operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO:44 (H1pdm).

In a further specific aspect of the vector or the expression cassette of the present invention the EHV vector comprises two or more hemagglutinin influenza antigen encoding sequences.

H1av in UL56 with p430:

In a further specific aspect of the vector or the expression cassette of the present invention the further hemagglutinin influenza antigen encoding sequence is a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO:46 (H1av).

In a further specific aspect of the vector or the expression cassette of the present invention said further hemagglutinin influenza antigen encoding sequence is inserted into UL56.

In a further specific aspect of the vector or the expression cassette of the present invention the hemagglutinin influenza antigen encoding sequence as described herein is operably linked to the promoter sequence p430 (SEQ ID NO:3) or a functional fragment or a functional derivative thereof or the complementary nucleotide sequences thereof.

H3 in US4 with p455:

In a further specific aspect of the vector or the expression cassette of the present invention the further hemagglutinin influenza antigen encoding sequences is a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO:45 (H3).

In a further specific aspect of the vector or the expression cassette of the present invention said further hemagglutinin influenza antigen encoding sequences is inserted into US4.

In a further specific aspect of the vector or the expression cassette of the present invention the hemagglutinin influenza antigen encoding sequence as described herein is operably linked to the promoter sequence p455 (SEQ ID NO:4) or a functional fragment or a functional derivative thereof or the complementary nucleotide sequences thereof.

Combinations

The present invention furthermore concerns an Equid herpesvirus (EHV) comprising the promoter sequence p422 (SEQ ID NO:5) or a functional fragment or a functional derivative thereof or the complementary nucleotide sequences thereof is operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO:44 (H1pdm) inserted into in UL43, and further the promoter sequence p430 (SEQ ID NO:3) or a functional fragment or a functional derivative thereof or the complementary nucleotide sequences thereof operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO:46 (H1av) inserted into in UL56.

The present invention furthermore concerns an Equid herpesvirus (EHV) comprising the promoter sequence p422 (SEQ ID NO:5) or a functional fragment or a functional derivative thereof or the complementary nucleotide sequences thereof is operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO:44 (H1pdm) inserted into in UL43, and further the promoter sequence p455 (SEQ ID NO:4) or a functional fragment or a functional derivative thereof or the complementary nucleotide sequences thereof operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO:45 (H3) inserted into in US4.

The present invention furthermore concerns an Equid herpesvirus (EHV) comprising the promoter sequence p422 (SEQ ID NO:5) or a functional fragment or a functional derivative thereof or the complementary nucleotide sequences thereof is operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO:44 (H1pdm) inserted into in UL43, and further the promoter sequence p430 (SEQ ID NO:3) or a functional fragment or a functional derivative thereof or the complementary nucleotide sequences thereof operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO:46 (H1av) inserted into in UL56, and further the promoter sequence p455 (SEQ ID NO:4) or a functional fragment or a functional derivative thereof or the complementary nucleotide sequences thereof operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO:45 (H3) inserted into in US4.

In another aspect of the vector of the present invention the EHV vector is selected from the group consisting of EHV-1, EHV-3, EHV-4, EHV-8 und EHV-9.

In another aspect of the vector of the present invention the EHV vector is EHV-1 or EHV-4.

In another aspect of the vector of the present invention the EHV vector is EHV-1, preferably RacH.

The present invention further concerns a vector or an Equid herpesvirus (EHV) comprising:
a. a first nucleotide sequence of interest, preferably a gene of interest, such as an antigen encoding sequence, into UL43,
b. said first nucleotide sequence of interest is optionally operably linked with a regulatory nucleic acid sequence/promoter sequence, preferably p455, p430 or p422.
c. said first nucleotide sequence of interest is optionally operably linked with a (further) regulatory nucleic acid, e.g. a polyadenylation sequence, preferably BGHpA, 71 pA (SEQ ID NO:6) or 18 pA (SEQ ID NO:7).

In a specific aspect the vector or EHV further comprises a. a second nucleotide sequence of interest, preferably a gene of interest, such as an antigen encoding sequence, into a second insertion site, preferably UL56 or US4,
b. said second nucleotide sequence of interest is optionally operably linked with a regulatory nucleic acid sequence/promoter sequence, preferably p455, p430 or p422.
c. said second nucleotide sequence of interest is optionally operably linked with a (further) regulatory nucleic acid, e.g. a polyadenylation sequence, preferably BGHpA, 71 pA (SEQ ID NO:6), or 18 pA (SEQ ID NO:7).

In a specific aspect the vector or EHV further comprises a. a third nucleotide sequence of interest, preferably a gene of interest, such as an antigen encoding sequence, into a third insertion site, preferably UL56 or US4,
b. said third nucleotide sequence of interest is optionally operably linked with a regulatory nucleic acid sequence/promoter sequence, preferably p455, p430 or p422.
c. said third nucleotide sequence of interest is optionally operably linked with a regulatory nucleic acid, e.g. a polyadenylation sequence, preferably 71 pA, BGHpA, or18 pA.

The present invention further concerns a plasmid comprising the flanking regions for homologous recombination or RED-mediated recombination (see both described above) into a specific target site in the viral vector genome, preferably into the orf70 (US4) site of the EHV vector, specifically the EHV-1, more specifically the RacH vector, such as transfer plasmid pU-mC70-BGH (SEQ ID NO:37) and/ortransfer vector pU70-p455-71K71 (SEQ ID NO:28), and/or transfer plasmid pU70-p455-H3-71K71 (SEQ ID NO:29) and/or transfer plasmid pU70-p455-H1pdm-71K71 (SEQ ID NO:32).

The present invention further concerns a plasmid comprising the flanking regions for homologous recombination or RED-mediated recombination (see both described above) into a specific target site in the viral vector genome, preferably into the UL43 site of the EHV vector, specifically the EHV-1, more specifically the RacH vector, such as transfer plasmid pUUL43-422-18K18 (SEQ ID NO:34) or pUUL43-422-H1pdm-18K18 (SEQ ID NO:36).

The present invention further concerns a plasmid comprising the flanking regions for homologous recombination or RED-mediated recombination (see both described above) into a specific target site in the viral vector genome, preferably into the orf1/3 (UL56) site of the EHV vector, specifically the EHV-1, more specifically the RacH vector and a regulatory nucleic acid, preferably a promoter, preferably p430, such as transfer vector pU-1-3-p430-BGHKBGH (SEQ ID NO:30), and/or transfer plasmid pU1-3-p430-H1av-BGHKBGH (SEQ ID NO:31) and/or transfer plasmid pU1-3-p430-H1hu-BGHKBGH (SEQ ID NO:33).

The present invention further concerns a plasmid comprising the flanking regions for homologous recombination or RED-mediated recombination (see both described above) into a specific target site in the viral vector genome, preferably into the UL43 site of the EHV vector, specifically the EHV-1, more specifically the RacH vector and a regulatory nucleic acid, preferably a promoter, preferably p422, such as such as transfer vector pUUL43-422-18K18 (SEQ ID: 34) or transfer plasmid pUUL43-422-mC-18K18 (SEQ ID NO:35) or pUUL43-422-H1pdm-18K18 (SEQ ID NO:36).

The present invention further concerns a plasmid comprising the flanking regions for homologous recombination or RED-mediated recombination (see both described above) into a specific target site in the viral vector genome, preferably into the orf70 (US4) site of the EHV vector, specifically the EHV-1, more specifically the RacH vector and a regulatory nucleic acid, preferably a promoter, preferably p455, such as transfer vector pU70-p455-71K71 (SEQ ID NO:28), and/or transfer plasmid pU70-p455-H3-71K71 (SEQ ID NO:29) and/or transfer plasmid pU70-p455-H1pdm-71K71 (SEQ ID NO:32).

The present invention further concerns a plasmid comprising the flanking regions for homologous recombination or RED-mediated recombination (see both described above) into a specific target site in the viral vector genome, preferably into the UL56 (orf1/3) site of the EHV vector, specifically the EHV-1, more specifically the RacH vector and a regulatory nucleic acid sequence, preferably a promoter, preferably p430, such as transfer vector pU-1-3-p430-BGHKBGH (SEQ ID NO:30), and/or transfer plasmid pU1-3-p430-H1av-BGHKBGH (SEQ ID NO:31), and/or transfer plasmid pU1-3-p430-H1hu-BGHKBGH (SEQ ID NO:33).

The present invention further concerns a plasmid comprising the flanking regions for homologous recombination or RED-mediated recombination (see both described above) into a specific target site in the viral vector genome, preferably into the UL56 (orf1/3 site) of the EHV vector, specifically the EHV-1, more specifically the RacH vector and a regulatory nucleic acid sequence, preferably a promoter, preferably p430, and a second regulatory nucleic acid, preferably a polyadenylation sequence, preferably the BGH polyadenylation sequence, such as transfer vector pU-1-3-p430-BGHKBGH (SEQ ID NO:30), and/or transfer plasmid pU1-3-p430-H1av-BGHKBGH (SEQ ID NO:31), and/or transfer plasmid pU1-3-p430-H1hu-BGHKBGH (SEQ ID NO:33).

The present invention further concerns a plasmid comprising the flanking regions for homologous recombination or RED-mediated recombination (see both described above) into a specific target site in the viral vector genome, preferably into the US4 (orf70 site) of the EHV vector, specifically the EHV-1, more specifically the RacH vector and a regulatory nucleic acid sequence, preferably a promoter, preferably p455, and a second regulatory nucleic acid, preferably a polyadenylation sequence, preferably the 71 pA polyadenylation sequence, such as transfer vector pU70-p455-71K71 (SEQ ID NO:28), and/or transfer plasmid pU70-p455-H3-71K71 (SEQ ID NO:29), and/or transfer plasmid pU70-p455-H1pdm-71K71 (SEQ ID NO:32).

The present invention further concerns a plasmid comprising the flanking regions for homologous recombination or RED-mediated recombination (see both described above) into a specific target site in the viral vector genome, preferably into the UL43 site of the EHV vector, specifically the EHV-1, more specifically the RacH vector and a regulatory nucleic acid sequence, preferably a promoter, preferably p422, and a second regulatory nucleic acid, preferably a polyadenylation sequence, preferably the 18 pA polyadenylation sequence (SEQ ID NO:7), such as transfer vector pUUL43-422-18K18 (SEQ ID NO:34), and/or transfer plasmid pUUL43-422-H1pdm-18K18 (SEQ ID NO:36), and/or transfer plasmid pUUL43-422-mC-18K18 (SEQ ID NO:35).

The present invention further concerns a method of producing the vector according to the present invention comprising:
a. Inserting a first nucleotide sequence of interest, preferably a gene of interest, such as an antigen encoding sequence, into UL43,
b. Optionally operably linking said first nucleotide sequence of interest with a regulatory nucleic acid sequence/promoter sequence, preferably p455, p430 or p422.
c. Optionally operably linking said first nucleotide sequence of interest with a (further) regulatory nucleic acid, e.g. a polyadenylation sequence, preferably BGHpA, 71 pA (SEQ ID NO:6), or 18 pA (SEQ ID NO:7).

In a specific aspect the method further comprising
a. Inserting a second nucleotide sequence of interest, preferably a gene of interest, such as an antigen encoding sequence, into a second insertion site, preferably UL56 or US4,
b. Optionally operably linking said second nucleotide sequence of interest with a regulatory nucleic acid sequence/promoter sequence, preferably p455, p430 or p422.
c. Optionally operably linking said second nucleotide sequence of interest with a regulatory nucleic acid, e.g. a polyadenylation sequence, preferably BGHpA, 71 pA (SEQ ID NO:6), or 18 pA (SEQ ID NO:7).

In a specific aspect the method further comprising
a. Inserting a third nucleotide sequence of interest, preferably a gene of interest, such as an antigen encoding sequence, into a third insertion site, preferably UL56 or US4,
b. Optionally operably linking said third nucleotide sequence of interest with a regulatory nucleic acid sequence/promoter sequence, preferably p455, p430 or p422.
c. Optionally operably linking said third nucleotide sequence of interest with a regulatory nucleic acid, e.g. a polyadenylation sequence, preferably BGHpA, 71 pA (SEQ ID NO:6), or 18 pA (SEQ ID NO:7).

The present invention further concerns a kit consisting of a vector according to the present invention, optionally transfection reagent(s), and an instruction leavelet.

The present invention also concerns a mammalian host cell characterized in that it comprises a vector according to the present invention.

The present invention further concerns a method of preparing a host cell, characterized by the following steps:
a. Infecting the mammalian host cell according to the present invention with the vector according to the present invention,
b. cultivating the infected cells under suitable conditions,
c. optionally harvesting said host cell.

The present invention further concerns the use of UL43 in an Equid herpesvirus (EHV) vector, specifically in an Equid Alphaherpesvirus such as EHV-1, EHV-3, EHV-4, EHV-8 and EHV-9, more specifically in an Equid Alphaherpesvirus 1 (EHV-1) vector, most specifically in RacH, as an insertion site in said Equid herpesvirus (EHV) vector, wherein said insertion site supports/facilitates the expression of a nucleotide sequence of interest, preferably a gene of interest, such as an antigen encoding sequence, whereby said UL43 insertion site comprising a partial deletion, truncation, substitution, modification or the like in UL43, and whereby UL44 remains functional.

The invention further concerns the use of the vector according to the present invention or the mammalian host cell according to the present invention for the manufacture of an immunogenic composition or vaccine.

The invention further concerns an immunogenic composition comprising
a. the vector according to to the present invention, and/or
b. a polypeptide expressed by the vector according to to the present invention, such as a virus, a modified live virus, a virus like particle (VLP) or the like, and
c. optionally a pharmaceutical- or veterinary-acceptable carrier or excipient, preferably said carrier is suitable for oral, intradermal, intramuscular or intranasal application,
preferably said immunogenic composition comprises a virus. In a specific aspect said virus is an infectious virus.

The invention further concerns a vaccine or pharmaceutical composition comprising
a. the vector according to the present invention, and/or
b. a polypeptide expressed by the vector according to the present invention, such as a modified live virus, a virus like particle (VLP) or the like, and
c. a pharmaceutical- or veterinary-acceptable carrier or excipient, preferably said carrier is suitable for oral, intradermal, intramuscular or intranasal application,
d. optionally said vaccine further comprises an adjuvant.

Preferably, the vaccine comprises the EHV vector as described herein. Preferably, the immunogenic composition comprises a pharmaceutical- or veterinary-acceptable carrier or excipient.

In one aspect of the present invention said pharmaceutically acceptable carrier is cell culture media or a physiological resuspension buffer.

In one aspect of the present invention said resuspension buffer is phosphate buffered saline.

In a specific aspect said immunogenic composition or vaccine or pharmaceutical composition comprises the vector or the expression cassette of the present invention, whereby said antigen encoding sequence relates to a pathogen infecting swine. In a further specific aspect said pathogen is Swine Influenza A virus (IAV). In a further specific aspect said antigen is hemagglutinin (HA) antigen, especially said hemagglutinin antigen is derived from an Influenza A virus. For example the Influenza A virus is Influenza A virus (A/swine/Italy/116114/2010(H1N2)), Influenza A virus (A/swine/Italy/7680/2001(H3N2)), Influenza A virus (A/swine/Gent/132/2005(H1N1)), and/or Influenza A virus (A/swine/Italy/4675/2003(H1N2)). In a further specific aspect said antigen comprises or consists of a sequence encoded by a SEQ ID NO selected from the group consisting of: SEQ ID NO:44, 45, 46, and 47. In another specific aspect said antigen comprises or consists of a sequence encoding an amino acid sequence with at least 70%, at least 75%, at least 80%, at least 85%, at least 90%, least 91%, at least 92%, at least 93%, at least 94%, at least 95%, at least 96%, at least 97%, at least 98% or at least 99% identity to the amino acid sequence as set forth in SEQ ID NO:44, SEQ ID NO:45, SEQ ID NO:46 and SEQ ID NO:47.

The invention further concerns a vaccine or DIVA vaccine comprising one or more EHV vectors as described herein.

The present invention further concerns a promoter sequence comprising p422 (SEQ ID NO:5) or the complementary nucleotide sequences thereof or a functional fragment thereof or the complementary nucleotide sequences thereof, wherein said promoter sequence leads to expression of a nucleotide sequence of interest, preferably a gene of interest, more preferably an antigen encoding sequence.

The present invention also concerns an expression cassette comprising the promoter sequence p422 (SEQ ID NO:5) or the complementary nucleotide sequences thereof or a functional fragment and the complementary nucleotide sequences thereof,
wherein the promoter sequence is operably linked to a sequence of interest, preferably a gene of interest such as an antigen encoding sequence, more preferably a heterologous and/or exogenous sequence of interest, gene of interest or antigen encoding sequence of interest,
wherein said promoter sequence leads to expression of a nucleotide sequence of interest, preferably a gene of interest, more preferably an antigen encoding sequence, whereby said promoter sequence is preferably a heterologous promoter sequence, more preferably an exogenous promoter sequence.

The present invention also concerns a vector comprising the promoter sequence or the expression cassette as described herein.

In a further specific aspect of the promoter or the expression cassette or the vector of the present invention the functional fragment of the promoter sequence has a sequence identity and/or homology of 70%, 80%, 85%, preferably 90%, 91%, 92%, 93%, 94%, more preferably 95%, 96%, 97%, 98%, 99%, 99.9% to the sequence of p422 (SEQ ID NO:5)

In a further specific aspect of the promoter or the expression cassette or the vector of the present invention said functional fragment of the promoter sequence has a length of 100 nucleotides, preferably 125, 150, 175, 200, 225, 250, 275, 300, 325, 350, 375, 400 nucleotides, most preferably 410 or 420 nucleotides, or wherein the functional fragment of the promoter sequence has a length of between 100 to 422 nucleotides, 200 to 422 nucleotides, 300 to 422 nucleotides or 350 to 422 nucleotides.

In a further specific aspect of the expression cassette or the vector of the present invention said expression cassette or vector comprises one or more further regulatory sequences such as a termination signal, a polyadenylation signal or a regulatory element like IRES and/or 2a peptide.

In a further specific aspect of the the expression cassette or the vector of the present invention the expression cassette or the vector further comprises a polyadenylation sequence, preferably BGHpA, 71 pA (SEQ ID NO:6), or 18 pA (SEQ ID NO:7).

In a further specific aspect of the the vector of the present invention said vector is a recombinant, and/or a heterologous and/or an exogenous vector.

In a further specific aspect of the the vector of the present invention said vector is a viral vector, preferably selected from the group consisting of herpes viridae such as Equid Alphaherpesvirus 1 (EHV-1), Equid Alphaherpesvirus 4 (EHV-4) and other Varicelloviruses like PrV (Pseudorabies virus) and BHV-1 (Bovine Herpesvirus 1), Adenoviridae (AdV) such as CAdV (Canine Adenovirus), Adeno-associated viridae, Baculoviridae, Lentiviridae such as Retroviruses, and Poxviridae.

In a further specific aspect of the the vector of the present invention said vector is a member of the family Herpesviridae, preferably of the genus Alphaherpesvirinae, more preferably of the subgenus *Varicellovirus*, most preferably said vector is Equid Alphaherpesvirus 1 (EHV-1).

Diva

A major advantage of an efficacious DIVA vaccine is that it allows the detection of food producing animals (preferably pigs) acutely infected or infected some time (at least ca. 3 weeks) before taking samples in a vaccinated animal population, and thus offers the possibility to monitor the spread or re-introduction of a pathogen (preferably swine influenza virus) in an animal population. Thus, it makes it possible to declare, with a certain level of confidence, that a vaccinated pig population is free of Swine Influenza A virus on the basis of laboratory test results.

The marker vaccine facilitates fast and effective administration and allows discrimination between animals infected with the field virus (disease-associated) and vaccinated animals.

The immunogenic composition or DIVA vaccine of the present invention does not comprise any antigen encoding sequence encoding N (neuraminidase) influenza antigen encoding sequences and/or NP (nucleoprotein) influenza antigen encoding sequences.

In contrast, after infection of animals with wild-type Swine Influenza A virus or vaccinated with a modified live vaccine or vaccinated with an inactivated whole virus vaccine or that have residual maternally derived antibodies, the infected/vaccinated animals produce/have specific antibodies against N (neuraminidase) and/or NP (nucleoprotein). However, in animals vaccinated with the immunogenic composition according to the present invention such specific antibodies against N (neuraminidase) and/or NP (nucleoprotein) cannot be detected.

By exemplary immuno tests and/or genomic analytical tests the animals only vaccinated with the immunogenic composition of the present invention can be differentiated from animals that were infected with the wildtype swine influenza virus or vaccinated with a modified live vaccine or vaccinated with an inactivated whole virus vaccine or that have residual maternally derived antibodies in that animals only vaccinated with the immunogenic composition of the present invention do not have any specific antibodies against N (neuraminidase) and/or NP (nucleoprotein) and any Swine Influenza A virus specific sequence encoding N (neuraminidase) and/or NP (nucleoprotein), respectively.

The present invention provides a method of differentiating food producing animals infected with Swine Influenza A virus from food producing animals vaccinated with the immunogenic composition or the DIVA vaccine as described herein, comprising
  a) obtaining a sample from an food producing animal, and
  b) analyzing said sample in an immuno test and/or genomic analytical test.

In one aspect of the present invention the immuno test comprises testing whether the sample comprises antibodies specifically recognizing the N (neuraminidase) protein or NP (nucleoprotein) protein of swine influenza.

In one aspect of the present invention the food producing animal is infected with Swine Influenza A virus if antibodies specifically recognizing the N (neuraminidase) protein or NP (nucleoprotein) protein of swine influenza have been detected.

In one aspect of the present invention the genomic analytical test comprises testing whether the sample comprises Swine Influenza A virus specific sequences encoding N (neuraminidase) and/or NP (nucleoprotein).

In one aspect of the present invention the food producing animal is infected with Swine Influenza A virus if Swine Influenza A virus specific sequences encoding N (neuraminidase) and/or NP (nucleoprotein) have been detected.

In one aspect of the present invention the immuno test is an EIA (enzyme immunoassay) or ELISA (enzyme linked immunosorbent assay), or, wherein the genomic analytical test is a PCR (polymerase chain reaction), RT-PCR (reverse transcriptase polymerase chain reaction) or real time PCR (polymerase chain reaction).

In one aspect of the present invention the food producing animal is swine

In one aspect of the present invention the sample is a serum sample.

Preferably, an antibody specific for the N (neuraminidase) and/or NP (nucleoprotein) of a wildtype SIAV is used to detect SIAV antigen in sections of the respiratory tract from a pig that is suspected to be infected with SIAV or that is vaccinated with a vaccine according to the invention. In such a case, only the sample of the infected pig or vaccinated with a modified live vaccine or vaccinated with an inactivated whole virus vaccine or that has residual maternally derived antibodies will show positive results by said N (neuraminidase) and/or NP (nucleoprotein) specific antibody. In contrast, the sample of a pig vaccinated with the vaccine of the present invention will show no results by said N (neuraminidase) and/or NP (nucleoprotein) specific antibody due to the absence of such antigens (only hemagglutinin) in the vaccine of the present invention.

However, epitope of N (neuraminidase) and/or NP (nucleoprotein) are evolutionarily conserved and specific for SIAV and a target for neutralizing antibodies.

Thus, a test could e.g. comprise wells with a N (neuraminidase) and/or NP (nucleoprotein) epitope of a wildtype SIAV cross-linked to micro-well assay plates. Said cross-linking preferably is performed through an anchor protein such as, for example, poly-L-lysine. Expression systems for obtaining a wildtype N (neuraminidase) and/or NP (nucleoprotein) epitopes are well known to the person skilled in the art. Alternatively, said N (neuraminidase) and/or NP (nucleoprotein) epitopes could be chemically synthesized.

Animals only vaccinated with the vaccine according to the present invention have not raised antibodies against the wild-type N (neuraminidase) and/or NP (nucleoprotein) epitope. However, such animals have raised antibodies against an HA (hemagglutinin) epitope according to the present invention. As a consequence, no antibodies bind to a well coated with the wildtype N (neuraminidase) and/or NP (nucleoprotein) epitope. In contrast, if a well has been coated with an HA epitope according to the present invention antibodies bind to said substituted HA epitope.

In one aspect of the present invention the ELISA is an indirect ELISA, Sandwich ELISA, a competitive ELISA or blocking ELISA.

However, the different ELISA techniques are well known to the person skilled in the art. ELISA's have been described exemplary by Wensvoort G. et al., 1988 (Vet. Microbiol. 17(2): 129-140), by Robiolo B. et al., 2010 (J. Virol. Methods. 166(1-2): 21-27) and by Colijn, E. O. et al., 1997 (Vet. Microbiology 59: 15-25).

Preferably, the test for differentiating an animal that is infected with field SIAV or vaccinated with a modified live vaccine or vaccinated with an inactivated whole virus vaccine or that has residual maternally derived antibodies and such that are only vaccinated with the vaccine of the present invention is provided by RNA isolation of respiratory cells and reverse transcriptase followed by amplification of the cDNA. Using specific primers for N (neuraminidase) and/or NP (nucleoprotein) a PCR can be performed. In such a case the pig is infected with the wildtype SIAV if there is a positive PCR signal. However, if no N (neuraminidase) and/or NP (nucleoprotein) specific sequence can be amplified the animal has been vaccinated with the vaccine of the present invention.

Further, real time based technique primers and/or probes may be used recognizing either the N (neuraminidase) and/or NP (nucleoprotein) and/or the specific HA (hemagglutinin). However, such methods are well known in the art.

In another aspect of the present invention the genomic analytical test is a PCR (polymerase chain reaction), RT-PCR (reverse transcriptase polymerase chain reaction) or real time PCR (polymerase chain reaction).

The invention further concerns a method for the preparation of an immunogenic composition or a vaccine for reducing the incidence or the severity of one or more clinical signs associated with or caused by an infection, comprising the following steps:

a. Infecting the mammalian host cell according to the present invention with the vector according to the present invention,
b. cultivating the infected cells under suitable conditions,
c. collecting infected cell cultures,
d. optionally purifying the collected infected cell cultures of step c)
e. optionally mixing said collected infected cell culture with a pharmaceutically acceptable carrier.

Medical Use:

The invention further concerns a method for immunizing an animal comprising administering to such animal an immunogenic composition, vaccine or DIVA vaccine as described herein.

The invention further concerns a method for reducing or preventing clinical signs caused by a pathogen in an animal of need, the method comprising administering to the animal a therapeutically effective amount of an immunogenic composition, vaccine or DIVA vaccine as described herein.

The invention further concerns a method for reducing or preventing clinical signs caused by swine influenza virus in an animal of need, the method comprising administering to the animal a therapeutically effective amount of an immunogenic composition, vaccine or DIVA vaccine as described herein.

In a further specific aspect of the medical use or method of the present invention said animal is swine, piglet or sow, poultry, cattle, horse, dog or cat.

In a further specific aspect of the medical use or method of the present invention the immunogenic composition, vaccine or DIVA vaccine is administered once.

It is understood, that a single-dose is administered only once. Preferably, the single-dose has a total volume between about 0.2 ml and 2.5 ml, more preferably between about 0.2 ml and 2.0 ml, even more preferably between about 0.2 ml and 1.75 ml, still more preferably between about 0.2 ml and 1.5 ml, even more preferably between about 0.4 ml and 1.25 ml, even more preferably between about 0.4 ml and 1.0 ml with a single 0.5 ml dose or 1.0 ml dose being the most preferred. Most preferred the single-dose has a total volume of 0.5 ml, 1 ml, 1.5 ml or 2 ml.

Preferably, the immunogenic composition or DIVA vaccine is administered to piglets before they reach three weeks of age. Preferably, the immunogenic composition or DIVA vaccine is administered to each of the piglets at 1 day of age to 21 days of age, more preferably, between 1 day of age to 10 days of age, even more preferably between 1 day of age to 9 days of age, even more preferably between 1 day of age to 8 days of age, even more preferably between 1 day of age to 7 days of age, even more preferably between 1 day of age to 6 days of age, even more preferably between 1 day of age to 5 days of age, even more preferably between 1 day of age to 4 days of age, even more preferably between 1 day of age to 3 days of age, even more preferably 1 or 2 day(s) of age, and most preferably 1 day of age.

In a further specific aspect of the medical use or method of the present invention the immunogenic composition, vaccine or DIVA vaccine is administered to the animal within the first three weeks of age, within the first two weeks of age, within the first week of age or within the first day of age.

In a further specific aspect of the medical use or method of the present invention the immunogenic composition, vaccine or DIVA vaccine is administered at two doses.

However, the immunogenic composition can be administered to the animal at two or more doses, with a first dose being administered prior to the administration of a second (booster) dose. Preferably, the first dose is administered within the first two weeks of age, more preferably within the first week of age and even more preferably within the first day of age. Preferably, the second dose is administered at least 15 days after the first dose. More preferably, the second dose is administered between 15 and 40 days after the first dose. Even more preferably, the second dose is administered at least 17 days after the first dose. Still more preferably, the second dose is administered between 17 and 30 days after the first dose. Even more preferably, the second dose is administered at least 19 days after the first dose. Still more preferably, the second dose is administered between 19 and 25 days after the first dose. Most preferably the second dose is administered at least 21 days after the first dose. In a preferred aspect of the two-time administration regimen, both the first and second doses of the immunogenic composition are administered in the same amount. Preferably, each dose is in the preferred amounts specified above, with a dose of 1 ml for the first and second dose being most preferred. In addition to the first and second dose regimen, an alternate embodiment comprises further subsequent doses. For example, a third, fourth, or fifth dose could be administered in these aspects. Preferably, subsequent third, fourth, and fifth dose regimens are administered in the same amount as the first dose, with the time frame between the doses being consistent with the timing between the first and second doses mentioned above.

In a further specific aspect of the medical use or method of the present invention the immunogenic composition, vaccine or DIVA vaccine is administered to the animal within the first week of age and a second time within the second, third or fourth week of age.

The immunogenic composition or DIVA vaccine is, preferably, administered topically or systemically. Suitable routes of administration conventionally used are oral or parenteral administration, such as intranasal, intravenous, intramuscular, intraperitoneal, subcutaneous, as well as inhalation. However, depending on the nature and mode of action of a compound, the immunogenic composition or DIVA vaccine may be administered by other routes as well. However, most preferred the immunogenic composition or DIVA vaccine is administered intramuscular or intranasal.

In a further specific aspect of the medical use or method of the present invention said immunogenic composition, vaccine or DIVA vaccine is administered intramuscular or intranasal.

In a further specific aspect of the medical use or method of the present invention said immunogenic composition or DIVA vaccine comprises $1\times10^4$ to $1\times10^9$ tissue culture infectious doses 50 ($TCID_{50}$), preferably between $1\times10^4$ to $1\times10^8$ $TCID_{50}$, even more preferably $1\times10^4$ to $1\times10^7$ $TCID_{50}$ of the EHV vector.

In a further specific aspect of the medical use or method of the present invention the immunogenic composition, vaccine or DIVA vaccine comprises $1\times10^4$ to $1\times10^7$ $TCID_{50}$ of the EHV vector.

In a further specific aspect of the medical use or method of the present invention said method results in an improvement in an efficacy parameter selected from the group consisting of: a reduction in weight loss, a reduced rectal temperature, reduced clinical symptoms, increased induction of (neutralizing) antibodies, or combinations thereof, in comparison to an animal of a non-immunized control group of the same species.

In a specific aspect of the medical use of the present invention described above or the method of immunizing an animal as described above said antigen encoding sequence relates to a pathogen infecting swine. In a further specific aspect said pathogen is Swine Influenza A virus (IAV). In a further specific aspect said antigen is hemagglutinin (HA) antigen, especially said hemagglutinin antigen is derived from an Influenza A virus. For example the Influenza A virus is Influenza A virus (A/swine/Italy/116114/2010(H1N2)), Influenza A virus (A/swine/Italy/7680/2001(H3N2)), Influenza A virus (A/swine/Gent/132/2005(H1N1)), and/or Influenza A virus (A/swine/Italy/4675/2003(H1N2)). In a further specific aspect said antigen comprises or consists of a sequence encoded by a SEQ ID NO selected from the group consisting of: SEQ ID NO:44, 45, 46, and 47. In another specific aspect said antigen comprises or consists of a sequence encoding an amino acid sequence with at least 70%, at least 75%, at least 80%, at least 85%, at least 90%, least 91%, at least 92%, at least 93%, at least 94%, at least 95%, at least 96%, at least 97%, at least 98% or at least 99% identity to the amino acid sequence as set forth in SEQ ID NO:44, SEQ ID NO:45, SEQ ID NO:46 and SEQ ID NO:47.

The invention also concerns a kit for vaccinating an animal, preferably a food producing animal such as swine, poultry or cattle or companion animals such as cats, dogs or horses, against a disease associated with and/or reducing the incidence or the severity of one or more clinical signs associated with or caused by a pathogen in an animal comprising:
a) a dispenser capable of administering a vaccine to said animal; and
b) the immunogenic composition, the vaccine or DIVA vaccine according to the present invention, and
c) optionally an instruction leaflet.

Definitions

Unless defined otherwise, all technical and scientific terms used herein have the same meaning as is commonly understood by one of skill in the art to which this invention belongs at the time of filing. The meaning and scope of terms should be clear; however, in the event of any latent ambiguity, definitions provided herein take precedent over any dictionary or extrinsic definition. Further, unless otherwise required by context, singular terms shall include pluralities and plural terms shall include the singular. Herein, the use of "or" means "and/or" unless stated otherwise. Furthermore, the use of the term "including", as well as other forms such as "includes" and "included" is not limiting. All patents and publications referred to herein are incorporated by reference herein.

The practice of the present invention will employ, unless otherwise indicated, conventional techniques of virology, molecular biology, microbiology, recombinant DNA technology, protein chemistry and immunology, which are within the skill of the art. Such techniques are explained fully in the literature. See, e.g., Sambrook, Fritsch & Maniatis, Molecular Cloning: A Laboratory Manual, Vols. I, II and III, Second Edition (1989); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (RL press, 1986); Perbal, B., A Practical Guide to Molecular Cloning (1984); the series, Methods In Enzymology (S. Colowick and N. Kaplan eds., Academic Press, Inc.); Protein purification methods—a practical approach (E. L. V. Harris and S. Angal, eds., IRL Press at Oxford University Press); and Handbook of Experimental Immunology, Vols. I-IV (D. M. Weir and C. C. Blackwell eds., 1986, Blackwell Scientific Publications).

Before describing the present invention in detail, it is to be understood that this invention is not limited to particular DNA, polypeptide sequences or process parameters as such may, of course, vary. It is also to be understood that the terminology used herein is for the purpose of describing particular embodiments of the invention only, and is not intended to be limiting. It must be noted that, as used in this specification and the appended claims, the singular forms "a", "an" and "the" include plural referents unless the content clearly dictates otherwise. Thus, for example, reference to "an antigen" includes a mixture of two or more antigens, reference to "an excipient" includes mixtures of two or more excipients, and the like.

Molecular Biology Definitions

The term "vector" as it is known in the art refers to a polynucleotide construct, typically a plasmid or a bacterial artificial chromosome, used to transmit genetic material to a host cell. Vectors can be, for example, bacteria, viruses, phages, bacterial artificial chromosomes, cosmids, or plasmids. A vector as used herein can be composed of or contain either DNA or RNA. In some embodiments, a vector is composed of DNA. In some embodiments a vector is an infectious virus. Such a viral vector contains a viral genome which was manipulated in a way that it carries a foreign gene which has no function in the replication of the viral vector neither in cell culture nor in a host animal. According to specific aspects of the present disclosure a vector may be used for various aspects such as mere transmission of genetic material, for the transfection of host cells or organisms, for use as vaccines, e.g. DNA vaccines or for gene expression purposes. Gene expression is a term describing the biosynthesis of a protein in a cell as directed by a specific polynucleotide sequence called gene. In a specific aspect a vector may be an "expression vector", which is a vector that is capable of directing the expression of a protein encoded by one or more genes carried by the vector when it is present in the appropriate environment.

Vectors and methods for making and/or using vectors (or recombinants) for expression can be by or analogous to the methods disclosed in: U.S. Pat. Nos. 4,603,112, 4,769,330, 5,174,993, 5,505,941, 5,338,683, 5,494,807, 4,722,848, 5,942,235, 5,364,773, 5,762,938, 5,770,212, 5,942,235, 382, 425, PCT publications WO 94/16716, WO 96/39491, WO 95/30018; Paoletti, "Applications of pox virus vectors to vaccination: An update," PNAS USA 93: 11349-11353, October 1996; Moss, "Genetically engineered poxviruses for recombinant gene expression, vaccination, and safety," PNAS USA 93: 11341-11348, October 1996; Smith et al., U.S. Pat. No. 4,745,051 (recombinant baculovirus); Richardson, C. D. (Editor), Methods in Molecular Biology 39, "Baculovirus Expression Protocols" (1995 Humana Press Inc.); Smith et al., "Production of Human Beta Interferon in Insect Cells Infected with a Baculovirus Expression Vector", Molecular and Cellular Biology, December, 1983, Vol. 3, No. 12, p. 2156-2165; Pennock et al., "Strong and Regulated Expression of *Escherichia coli* B-Galactosidase in Infect Cells with a Baculovirus vector," Molecular and Cellular Biology March 1984, Vol. 4, No. 3, p. 406; EPA0 370 573; U.S. application No. 920,197, filed Oct. 16, 1986; EP Patent publication No. 265785; U.S. Pat. No. 4,769,331 (recombinant herpesvirus); Roizman, "The function of herpes simplex virus genes: A primer for genetic engineering of novel vectors," PNAS USA 93:11307-11312, October 1996; Andreansky et al., "The application of genetically engineered herpes simplex viruses to the treatment of experimental brain tumors," PNAS USA 93: 11313-11318, October 1996; Robertson et al., "Epstein-Barr virus vectors for gene delivery to B lymphocytes", PNAS USA 93: 11334-11340, October 1996; Frolov et al., "Alphavirus-based expression vectors: Strategies and applications," PNAS USA 93: 11371-11377, October 1996; Kitson et al., J. Virol. 65, 3068-3075, 1991; U.S. Pat. Nos. 5,591,439, 5,552,143; WO 98/00166; allowed U.S. application Ser. Nos. 08/675, 556, and 08/675,566 both filed Jul. 3, 1996 (recombinant adenovirus); Grunhaus et al., 1992, "Adenovirus as cloning vectors," Seminars in Virology (Vol. 3) p. 237-52, 1993; Ballay et al. EMBO Journal, vol. 4, p. 3861-65, Graham, Tibtech 8, 85-87, April, 1990; Prevec et al., J. Gen Virol. 70, 42434; PCT WO 91/11525; Felgner et al. (1994), J. Biol. Chem. 269, 2550-2561, Science, 259: 1745-49, 1993; and McClements et al., "Immunization with DNA vaccines encoding glycoprotein D or glycoprotein B, alone or in combination, induces protective immunity in animal models of herpes simplex virus-2 disease", PNAS USA 93: 11414-11420, October 1996; and U.S. Pat. Nos. 5,591,639, 5,589, 466, and 5,580,859, as well as WO 90/11092, W93/19183, W94/21797, WO95/11307, WO95/20660; Tang et al., Nature, and Furth et al., Analytical Biochemistry, relating to DNA expression vectors, inter alia. See also WO 98/33510; Ju et al., Diabetologia, 41: 736-739, 1998 (lentiviral expression system); Sanford et al., U.S. Pat. No. 4,945,050; Fischbach et al. (Intracel); WO 90/01543; Robinson et al., Seminars in Immunology vol. 9, pp. 271-283 (1997), (DNA vector systems); Szoka et al., U.S. Pat. No. 4,394,448 (method of inserting DNA into living cells); McCormick et al., U.S. Pat. No. 5,677,178 (use of cytopathic viruses); and U.S. Pat. No. 5,928,913 (vectors for gene delivery); as well as other documents cited herein.

The term "viral vector" describes a genetically modified virus which was manipulated by recombinant DNA technique in a way so that its entry into a host cell results in a specific biological activity, e.g. the expression of a transgene carried by the vector. In a specific aspect the transgene is an antigen. A viral vector may or may not be replication competent in the target cell, tissue, or organism.

Generation of a viral vector can be accomplished using any suitable genetic engineering techniques well known in the art, including, without limitation, the standard techniques of restriction endonuclease digestion, ligation, transformation, plasmid purification, DNA sequencing, transfection in cell cultures, for example as described in Sambrook et al. (Molecular Cloning: A Laboratory Manual. Cold Spring Harbor Laboratory Press, N.Y. (1989)) or K. Maramorosch and H. Koprowski (Methods in Virology Volume VIII, Academic Press Inc. London, UK (2014)).

A viral vector can incorporate sequences from the genome of any known organism. The sequences can be incorporated in their native form or can be modified in any way to obtain a desired activity. For example, the sequences can comprise insertions, deletions or substitutions.

A viral vector can include coding regions for two or more proteins of interest. For example, the viral vector can include the coding region for a first protein of interest and the coding region for a second protein of interest. The first protein of interest and the second protein of interest can be the same or different. In some embodiments, the viral vector can include the coding region(s) for a third or a fourth protein of interest. The third and the fourth protein of interest can be the same or different. The total length of the two or more proteins of interest encoded by one viral vector can vary. For example, the total length of the two or more proteins can be at least about 200 amino acids. At least about 250 amino acids, at least about 300 amino acids, at least about 350 amino acids, at least about 400 amino acids, at least about 450 amino acids, at least about 500 amino acids, at least about 550 amino acids, at least about 600 amino acids, at least about 650 amino acids, at least about 700 amino acids, at least about 750 amino acids, at least about 800 amino acids, or longer.

Preferred viral vectors include herpes virus vectors such as derived from EHV-1 or EHV-4 or other varicelloviruses like PrV (Pseudorabies virus) or BHV-1 (Bovine Herpesvirus 1).

According to specific aspects of the present disclosure, the term "viral vector" or alternatively "viral construct" refers to a recombinant viral construct derived from a virus, which is selected from the families of Herpesviridae such as EHV-1, EHV-4. Preferred viral vectors include herpes virus vectors such as derived from EHV-1 or EHV-4

The terms "viral vector" and "viral construct" can be used interchangeably.

The term "construct," as used herein, refers to a recombinant nucleic acid such as a plasmid, a BAC, or a recombinant virus that has been artificially generated.

The term "plasmid" refers to cytoplasmic DNA that replicates independently of the bacterial chromosome within a bacterial host cell. In a specific aspect of the present invention the term "plasmid" and/or "transfer plasmid" refers to an element of recombinant DNA technology useful for construction of e.g. an expression cassette for insertion into a viral vector. In another specific aspect the term "plasmid" may be used to specify a plasmid useful for DNA vaccination purposes.

As used herein, the terms "nucleic acid" and "polynucleotide" are interchangeable and refer to any nucleic acid.

The term "nucleic acid", "nucleic acid sequence", "nucleotide sequence", "polynucleotide", "polynucleotide sequence", "RNA sequence" or "DNA sequence" as used herein refers to an oligonucleotide, nucleotide or polynucleotide and fragments and portions thereof and to DNA or RNA of genomic or synthetic origin, which may be single or double stranded and represent the sense or antisense strand. The sequence may be a non-coding sequence, a coding sequence or a mixture of both. The nucleic acid sequences of the present invention can be prepared using standard techniques well known to one of skill in the art.

The terms "nucleic acid" and "polynucleotide" also specifically include nucleic acids composed of bases other than the five biologically occurring bases (adenine, guanine, thymine, cytosine and uracil).

The terms "regulatory nucleic acid", "regulatory element" and "expression control element" are used interchangeably and refer to nucleic acid molecules that can influence the expression of an operably linked coding sequence in a particular host organism. These terms are used broadly to and cover all elements that promote or regulate transcription, including promoters, promoter sequences, core elements required for basic interaction of RNA polymerase and transcription factors, upstream elements, enhancers, and response elements. Exemplary regulatory elements in prokaryotes include promoters, operator sequences and ribosome binding sites. Regulatory elements that are used in eukaryotic cells can include, without limitation, transcriptional and translational control sequences, such as promoters, enhancers, splicing signals, polyadenylation signals, terminators, protein degradation signals, internal ribosome-entry sites (IRES), picornaviridal 2A sequences, and the like, that provide for and/or regulate expression of a coding sequence and/or production of an encoded polypeptide in a host cell.

An "internal ribosome entry site" or "IRES" describes a sequence which functionally promotes translation initiation independent from the gene 5' of the IRES and allows two cistrons (open reading frames) to be translated from a single transcript in an animal cell. The IRES provides an independent ribosome entry site for translation of the open reading frame immediately downstream of it. Unlike bacterial mRNA which can be polycistronic, i.e., encode several different polypeptides that are translated sequentially from the mRNAs, most mRNAs of animal cells are monocistronic and code for the synthesis of only one polypeptide. With a polycistronic transcript in a eukaryotic cell, translation would initiate from the 5' most translation initiation site, terminate at the first stop codon, and the transcript would be released from the ribosome, resulting in the translation of only the first encoded polypeptide in the mRNA. In a eukaryotic cell, a polycistronic transcript having an IRES operably linked to the second or subsequent open reading frame in the transcript allows the sequential translation of that downstream open reading frame to produce the two or more polypeptides encoded by the same transcript. The IRES can be of varying length and from various sources, e.g. Encephalomyocarditis virus (EMCV), picornaviruses (e.g. Foot-and-mouth disease virus, FMDVor Polio virus (PV), or Hepatitis C virus (HCV). Various IRES sequences and their use in vector construction have been described and are well known in the art. The downstream coding sequence is operably linked to the 3' end of the IRES at any distance that will not negatively affect the expression of the downstream gene. The optimum or permissible distance between the IRES and the start of the downstream gene can be readily determined by varying the distance and measuring expression as a function of the distance.

The term "2a" or "2a peptide" means short oligopeptide sequences, described as 2a and '2a-like', that serve as linkers which are able to mediate a co-translational cleavage between proteins by a process defined as ribosomal-skipping. Such 2a and '2a-like' sequences (from Picornaviridae and other viruses or cellular sequences) can be used to concatenate multiple gene sequences into a single gene, ensuring their co-expression within the same cell (see Luke and Ryan, 2013).

As used herein, the term "promoter" or "promoter sequence" means a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and animals such as mammals (including horses, pigs, cattle, poultry, dogs, cats and humans), birds or insects. A promoter can be inducible, repressible, and/or constitutive. Inducible promoters initiate increased levels of transcription from DNA under their control in response to some change in culture conditions, such as a change in temperature (Ptashne, 2014). Examples of promoters well known to the person skilled in the art are for example SV40 large T, HCMV and MCMV immediate early gene 1, human elongation factor alpha promoter, baculovirus polyhedrin promoter.

As used herein in the context of the present invention the term promoter refers especially to a functional fragment e.g. a truncation of 4pgG600 (SEQ ID NO:1) or the complementary nucleotide sequence thereof, preferably the sequence identity is (at least) 72% over entire length (or higher). Further, as used herein in the context of the present invention the term promoter refers especially to a functional fragment, e.g. a truncation of 4pMCP600 (SEQ ID NO:2) or the complementary nucleotide sequence thereof, preferably the sequence identity is (at least) 78% over entire length (or higher). Furthermore, as used herein in the context of the present invention the term promoter refers especially to p422 (SEQ ID NO:5) or a functional fragment thereof or the complementary nucleotide sequences thereof. Most preferably "promoter" refers to p430 (SEQ ID NO:3), p455 (SEQ ID NO:4) or p422 (SEQ ID NO:5). As further used herein in the context of the present invention the term promoter refers especially to a functional derivative of p430 (SEQ ID NO:3) or p455 (SEQ ID NO:4) or 4pgG600 (SEQ ID NO:1) or 4pMCP600 (SEQ ID NO:2) having for example a small substitution, mutation or inversion such that the sequence identity is 70%, 80%, 85%, 90%, 95%, 99% identical or homologous.

The terms "4pgG430, "p430", "gG 430" and "430" are used synonymously and interchangeably throughout the specification, figures, sequence listing etc. The terms "4pMCP455", "p455", "MCP 455" and "455" are used synonymously and interchangeably throughout the specification, figures, sequence listing etc. The terms p422 and 422 are used synonymously and interchangeably throughout the specification, figures, sequence listing etc.

The term "enhancer" denotes a polynucleotide sequence which in the cis location acts on the activity of a promoter and thus stimulates the transcription of a gene or coding sequence functionally connected to this promoter. Unlike promoters the effect of enhancers is independent of position and orientation and they can therefore be positioned in front of or behind a transcription unit, within an intron or even within the coding region. The enhancer may be located both in the immediate vicinity of the transcription unit and at a considerable distance from the promoter. It is also possible to have a physical and functional overlap with the promoter. The skilled artisan will be aware of a number of enhancers from various sources (and deposited in databanks such as GenBank, e.g. SV40 enhancers, CMV enhancers, polyoma enhancers, adenovirus enhancers) which are available as independent elements or elements cloned within polynucleotide sequences (e.g. deposited at the ATCC or from commercial and individual sources). A number of promoter sequences also contain enhancer sequences such as the frequently used CMV promoter. The human CMV enhancer is one of the strongest enhancers identified hitherto. One example of an inducible enhancer is the metallothionein enhancer, which can be stimulated by glucocorticoids or heavy metals.

The term "complementary nucleotide sequences" describes one strand of the two paired strands of polynucleotides such as DNA or RNA. The nucleotide sequence of the complementary strand mirrors the nucleotide sequence of its paired strand so that for each adenosin it contains a thymin (or uracil for RNA), for each guanine a cytosin, and vice versa. The complementary nucleotide sequence of e.g. 5'-GCATAC-3' is 3'-CGTATG-5' or for RNA 3'-CGUAUG-5'.

The terms "gene", "gene of interest", as used herein have the same meaning and refer to a polynucleotide sequence of any length that encodes a product of interest. The gene may further comprise regulatory sequences preceding (5' non-coding or untranslated sequences) and following (3' non-coding or untranslated sequences) the coding sequence. The selected sequence can be full length or truncated, a fusion or tagged gene, and can be a cDNA, a genomic DNA, or a DNA fragment. It is generally understood that genomic DNA encoding for a polypeptide or RNA may include non-coding regions (i.e. introns) that are spliced from mature messenger RNA (mRNA) and are therefore not present in cDNA encoding for the same polypeptide or RNA. It can be the native sequence, i.e. naturally occurring form(s), or can be mutated, or comprising sequences derived from different sources or otherwise modified as desired. These modifications include codon optimizations to optimize codon usage in the selected host cell or tagging. Furthermore they can include removal or additions of cis-acting sites such as (cryptic) splice donor, acceptor sites and branch points, polyadenylation signals, TATA-boxes, chi-sites, ribosomal entry sites, repeat sequences, secondary structures (e.g. stem loops), binding sites for transcription factors or other regulatory factors, restriction enzyme sites etc. to give just a few, but not limiting examples. The selected sequence can encode a secreted, cytoplasmic, nuclear, membrane bound or cell surface polypeptide.

The term "nucleotide sequence of interest" as used herein is a more general term than gene of interest as it does not necessarily comprise a gene but may comprise elements or parts of a gene or other genetic information, e.g. on (origin of replication). A nucleotide sequence of interest may be any DNA or RNA sequence independently of whether it comprises a coding sequence or not.

"Open reading frame" or "ORF" refers to a length of nucleic acid sequence, either DNA or RNA, that comprises a translation start signal or initiation codon, such as an ATG or AUG, and a termination codon and can be potentially translated into a polypeptide sequence.

The term "UL (unique long)" is an abbreviation to describe the unique long segment of the EHV, preferably EHV-1 genome.

The term "US (unique short)" is an abbreviation to describe the unique short segment of the EHV, preferably EHV-1 genome.

The term "transcription" describes the biosynthesis of mRNA in a cell.

The term "expression" as used herein refers to transcription and/or translation of a nucleic acid sequence within a host cell. According to specific aspects of the present invention the term "expression" refers to transcription and/or translation of a heterologous and/or exogenous nucleic acid sequence within a host cell. The level of expression of a desired product in a host cell may be determined on the basis of either the amount of corresponding RNA or mRNA that is present in the cell, or the amount of the desired polypeptide encoded by the selected sequence. For example, mRNA transcribed from a selected sequence can be quantitated by Northern blot hybridization, ribonuclease RNA protection, in situ hybridization to cellular RNA or by RTqPCR (reverse transcription followed by quantitative PCR). Proteins expressed from a selected sequence can be quantitated by various methods, e.g. by ELISA, by Western blotting, by radioimmunoassays, by immunoprecipitation, by assaying for the biological activity of the protein, or by immunostaining of the protein followed by FACS analysis.

The term "expression cassette" or "transcription unit" or "expression unit" defines a region within a vector, construct or polynucleotide sequence that contains one or more genes to be transcribed, wherein the nucleotide sequences encoding the transcribed gene(s) as well as the polynucleotide sequences containing the regulatory elements contained within an expression cassette are operably linked to each other. They are transcribed from a promoter and transcription is terminated by at least one polyadenylation signal. In one specific aspect, they are transcribed from one single promoter. As a result, the different genes are at least transcriptionally linked. More than one protein or product can be transcribed and expressed from each transcription unit (multicistronic transcription unit). Each transcription unit will comprise the regulatory elements necessary for the transcription and translation of any of the selected sequences that are contained within the unit. And each transcription unit may contain the same or different regulatory elements. For example, each transcription unit may contain the same terminator, IRES element or introns may be used for the functional linking of the genes within a transcription unit. A vector or polynucleotide sequence may contain more than one transcription unit.

By the term "increased expression", "increased titer or productivity" or "improved expression or productivity" is meant the increase in expression, synthesis or secretion of a heterologous and/or exogenous sequence introduced into a host cell, for example of a gene coding for a therapeutic protein, by comparison with a suitable control, for example a protein encoded by a cDNA versus a protein encoded by an intron-containing gene. There is increased titer or productivity if a cell according to the invention is cultivated according to a method according to the invention described here, and if this cell has at least a 1.2-fold, a 1.5-fold, a two-fold, a three-fold, a four-fold or a five-fold increase in specific productivity or titer. There is also increased titer or productivity if a cell according to the invention is cultivated according to a method according to the invention described here, and if this cell has at least a 1.2-fold or at least a 1.5-fold or at least a two-fold or at least a three-fold increase in specific productivity or titer. There is also in particular increased titer or productivity if a cell according to the invention is cultivated according to a method according to the invention described here, and if this cell has at least a 1.2-fold to five-fold, preferably a 1.5-fold to five-fold, more preferably—two-fold to five-fold particularly preferably a three-fold to five-fold increase in specific productivity or titer. "Increased expression" may mean as well that more cells are actually expressing the gene/sequence of interest. For example increased expression may mean that the new promoters of the present invention are active for a longer period of time during the viral replication cycle relative to other promoters.

An increased expression, titer or productivity may be obtained by using a heterologous vector according to the invention. This may be combined with other approaches such as a FACS-assisted selection of recombinant host cells which contain, as additional selectable marker, one or more fluorescent proteins (e.g. GFP) or a cell surface marker. Other methods of obtaining increased expression, and a combination of different methods may also be used, are based for example on the use of cis-active elements for manipulating the chromatin structure (e.g. LCR, UCOE, EASE, isolators, S/MARs, STAR elements), on the use of (artificial) transcription factors, treatment of the cells with natural or synthetic agents for up-regulating endogenous or heterologous and/or exogenous gene expression, improving the stability (half-life) of mRNA or the protein, improving the initiation of mRNA translation, increasing the gene dose by the use of episomal plasmids (based on the use of viral sequences as replication origins, e.g. SV40, polyoma, adenovirus, EBV or BPV), the use of amplification-promoting sequences or in vitro amplification systems based on DNA concatemers.

An assay to measure "increased expression" is LC-MS/MS-based protein measurements such as multiple reaction monitoring (MRM); antibody-based detection methods such as Western blot, dot blot, or Immunodiffusion, and flow cytometry; and measures of biological activity by hemagglutination assay.

"Promoter activity" is measured indirectly by quantification of mRNA transcribed under control of the respective promoter. mRNA is quantified by RTqPCR relative to an endogenous standard.

The term "viral titre" is a measure of infectious units per volume of a virus preparation. Viral titre is an endpoint in a biological procedure and is defined as the dilution at which a certain proportion of tests carried out in parallel show an effect (Reed and Muench, 1938). Specifically the tissue culture infectious dose fifty per milliliter (TCID50/ml) gives the dilution of a virus preparation at which 50% of a number of cell cultures inoculated in parallel with that dilution are infected.

"Transcription-regulatory elements" normally comprise a promoter upstream of the gene sequence to be expressed, transcription initiation and termination sites and a polyadenylation signal.

The term "transcription initiation site" refers to a nucleic acid in the construct corresponding to the first nucleic acid incorporated into the primary transcript, i.e. the mRNA precursor. The transcription initiation site may overlap with the promoter sequences.

The "termination signal" or "terminator" or "polyadenylation signal" or "polyA" or transcription termination site" or "transcription termination element" is a signal sequence which causes cleavage at a specific site at the 3' end of the eukaryotic mRNA and post-transcriptional incorporation of a sequence of about 100-200 adenine nucleotides (polyA tail) at the cleaved 3' end, and thus causes RNA polymerase to terminate transcription. The polyadenylation signal comprises the sequence AATAAA about 10-30 nucleotides upstream of the cleavage site and a sequence located downstream. Various polyadenylation elements are known such as tk polyA, SV40 late and early polyA, BGH polyA (described for example in U.S. Pat. No. 5,122,458) or hamster growth hormone polyA (WO2010010107).

"Translation regulatory elements" comprise a translation initiation site (AUG), a stop codon and a polyA signal for each individual polypeptide to be expressed. An internal ribosome entry site (IRES) may be included in some constructs. In order to optimize expression it may be advisable to remove, add or alter 5'- and/or 3'-untranslated regions of the nucleic acid sequence to be expressed to eliminate any potentially extra inappropriate alternative translation initiation codons or other sequences that may interfere with or reduce expression, either at the level of transcription or translation. Consensus ribosome binding sites (Kozak sequence) can be inserted immediately upstream of the start codon to enhance translation and thus expression. Increased A/U contents around this ribosome binding site further a more efficient ribosome binding.

By definition, every polynucleotide sequence or every gene inserted in a host cell and the respective protein or RNA encoded thereby is referred to as "exogenous", "exogenous sequence", "exogenous gene", "exogenous coding sequence", with respect to the host cell, when it comes from a different (virus) species. Accordingly, the EHV-4 based promoters of the present invention are exogenous in view of an EHV-1 viral vector. As used herein in respect to a sequence or gene of interest such as an antigen the term "exogenous" means that said sequence or gene of interest, specifically said antigen is expressed out of its natural species context. Accordingly, the H3, H1av or H1pdm antigens from swine IAV are examples of exogenous antigens in respect to the EHV-1 vector. Any sequence derived from a different pathogen than EHV-1 is therefore an exogenous sequence or gene of interest or antigen according to a specific aspect of the present invention.

By definition, every polynucleotide sequence or every gene inserted in a host cell and the respective protein or RNA encoded thereby is referred to as "heterologous, "heterologous sequence", "heterologous gene", "heterologous coding sequence", "transgene" or "heterologous protein" with respect to the host cell. This applies even if the sequence to be introduced or the gene to be introduced is identical to an endogenous sequence or an endogenous gene of the host cell. For example, an EHV-4 promoter sequence introduced into an EHV-4 viral vector at a different site or in modified form than in the EHV-4 wild type virus is by definition a heterologous sequence. As used herein in respect to a sequence or gene of interest such as an antigen, the term "heterologous" means that said sequence or gene of interest, specifically said antigen, is expressed out of its natural subspecies context. Accordingly, any non-EHV-1 specific sequence or gene of interest such as an antigen, for example an antigen from any Equid alphaherpesvirus except EHV-1, e.g. EHV-3, EHV-8, is therefore a heterologous sequence or gene of interest or antigen according to a specific aspect of the present invention.

The term "non-naturally occurring" means any sequence or gene of interest such as an antigen, which is not occurring in this context naturally, such as a hybrid sequence or a sequence or gene of interest such as an antigen from a different species, or sequence or gene of interest such as an antigen, which is not a product of nature due to artificial mutation, insertion, deletion or the like.

The term "recombinant" is used exchangeably with the terms "non-naturally occurring", "heterologous" and "exogenous" throughout the specification of this present invention. Thus, a "recombinant" protein is a protein expressed from a either a heterologous or an exogenous polynucleotide sequence. The term recombinant as used with respect to a virus, means a virus produced by artificial manipulation of the viral genome. A virus comprising a heterologous or an exogenous sequence such as an exogenous antigen encoding sequence is a recombinant virus. The term recombinant virus and the term non-naturally occurring virus are used interchangeably.

Thus, the term "heterologous vector" means a vector that comprises a heterologous or an exogenous polynucleotide sequence. The term "recombinant vector" means a vector that comprises a heterologous or a recombinant polynucleotide sequence.

As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element. For instance, a promoter is operably linked to a coding sequence if the promoter effects transcription or expression of the coding sequence.

Furthermore, within the scope of the present description the terms "functional linking", "functionally linked" or "operably linked" means that two or more nucleic acid sequences or sequence elements are positioned in a way that permits them to function in their intended manner. For example, a promoter/enhancer or terminator is functionally linked to a coding gene sequence if it is able to control or modulate the transcription of the linked gene sequence in the cis position. Generally, but not necessarily, the DNA sequences that are functionally linked are contiguous and, where necessary to join two polypeptide coding regions or in the case of a secretion signal peptide, contiguous and in reading frame. However, although an operably linked promoter is generally located upstream or an operably linked terminator is generally located downstream of the coding sequence, it is not necessarily contiguous with it. Enhancers do not have to be contiguous as long as they increase the transcription of the coding sequence. For this they can be located upstream or downstream of the coding sequence and even at some distance. A polyadenylation site is operably linked to a coding sequence if it is located at the 3' end of the coding sequence in a way that transcription proceeds through the coding sequence into the polyadenylation signal. Linking is accomplished by recombinant methods known in the art, e.g. by ligation at suitable restriction sites or blunt ends or by using fusion PCR methodology. Synthetic oligonucleotide linkers or adapters can be used in accord with conventional practice if suitable restriction sites are not present.

Accordingly, the term "functional fragment" or "functional derivative" of a promoter sequence means that the fragment or derivative still effects promoter activity. Functional assays of how to assess promoter activity are well known to one of ordinary skill in the art (Bustin 2000, Nolan et al. 2006). An exemplary embodiment of such a functional assay includes e.g. a promoter kinetics experiment. Cells infected with vector viruses carrying expression cassettes where a promoter or fragment thereof directs transcription of a reporter transgene are incubated for different times. Total RNA is prepared from samples collected at different times after infection. After destruction of contaminating DNA by DNAse I digestion, the RNA is reverse transcribed. One replicate sample is processed with addition of reverse transcriptase (RT), the second replicate is processed without addition of RT in order to demonstrate successful removal of contaminating DNA from the RNA preparation. The resulting cDNA is purified and used as template in a conventional PCR. Only the samples processed with the addition of RT shall produce a PCR product. These cDNAs can then be used for qPCR with primers for the reporter transgene and in parallel with primers for an essential gene of the viral vector (internal standard gene), the transcription of which provides an internal standard for the efficiency of infection and replication. qPCR values of the reporter are normalized between the different constructs and times after infection using the qPCR values of the internal standard gene. This allows an interpretation of promoter activities of different promoters and fragments thereof.

"Sequence homology", as used herein, refers to a method of determining the relatedness of two sequences. To determine sequence homology, two or more sequences are optimally aligned, and gaps are introduced if necessary. However, in contrast to "sequence identity", conservative amino acid substitutions are counted as a match when determining sequence homology.

In other words, to obtain a comparable polypeptide or polynucleotide having 95% sequence homology with a reference sequence, 85%, preferably 90%, 91%, 92%, 93%, 94%, even more preferably 95%, 96%, 97%, 98%, 99%, 99.9% of the amino acid residues or nucleotides in the reference sequence must match or comprise a conservative substitution with another amino acid or nucleotide. Alternatively, a number of amino acids or nucleotides up to 15%, preferably up to 10%, 9%, 8%, 7%, 6%, even more preferably up to 5%, 4%, 3%, 2%, 1%, 0.1% of the total amino acid residues or nucleotides, not including conservative substitutions, in the reference sequence may be inserted into the reference sequence. Preferably the homolog sequence comprises at least a stretch of 50, even more preferred of 100, even more preferred of 250, even more preferred of 500 nucleotides.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, 91%, 92%, 93%, 94%, even more preferably 95%, 96%, 97%, 98%, 99%, 99.9% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, 91%, 92%, 93%, 94%, even more preferably 95%, 96%, 97%, 98%, 99%, 99.9% identity relative to the reference nucleotide sequence, up to 15%, preferably 10%, 9%, 8%, 7%, 6%, even more preferably 5%, 4%, 3%, 2%, 1%, 0.1% of the nucleotides in the reference sequence may be deleted or substituted with another nucleotide, or a number of nucleotides up to 15%, preferably 10%, 9%, 8%, 7%, 6%, even more preferably 5%, 4%, 3%, 2%, 1%, 0.1% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, 91%, 92%, 93%, 94%, even more preferably 95%, 96%, 97%, 98%, 99% sequence identity to a reference amino acid sequence, it is intended that the given amino acid sequence of the polypeptide is identical to the reference sequence except that the given polypeptide sequence may include up to 15, preferably up to 10, 9, 8, 7, 6, even more preferably up to 5, 4, 3, 2, 1 amino acid alterations per each 100 amino acids of the reference amino acid sequence. In other words, to obtain a given polypeptide sequence having at least 85%, preferably 90%, 91%, 92%, 93%, 94%, even more preferably 95%, 96%, 97%, 98%, 99% sequence identity with a reference amino acid sequence, up to 15%, preferably up to 10%, 9%, 8%, 7%, even more preferably up to 5%, 4%, 3%, 2%, 1% of the amino acid residues in the reference sequence may be deleted or substituted with another amino acid, or a number of amino acids up to 15%, preferably up to 10%, 9%, 8%, 7%, even more preferably up to 5%, 4%, 3%, 2%, 1% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

The terms "sequence identity" or "percent identity" are used interchangeably herein. For the purpose of this invention, it is defined here that in order to determine the percent identity of two amino acid sequences or two nucleic acid sequences, the sequences are aligned for optimal comparison purposes (e.g., gaps can be introduced in the sequence of a first amino acid or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length.

A sequence comparison may be carried out over the entire lengths of the two sequences being compared or over fragment of the two sequences. Typically, the comparison will be carried out over the full length of the two sequences being compared. However, sequence identity may be carried out over a region of, for example, twenty, fifty, one hundred or more contiguous amino acid residues.

The skilled person will be aware of the fact that several different computer programs are available to determine the homology between two sequences. For instance, a comparison of sequences and determination of percent identity between two sequences can be accomplished using a mathematical algorithm. In a preferred embodiment, the percent identity between two amino acid or nucleic acid sequences is determined using the Needleman and Wunsch (J. Mol. Biol. (48): 444-453 (1970)) algorithm which has been incorporated into the GAP program in the Accelrys GCG software package, using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

The protein sequences or nucleic acid sequences of the present invention can further be used as a "query sequence" to perform a search against public databases to, for example, identify other family members or related sequences. Such searches can be performed using the BLASTN and BLASTP programs (version 2.0) of Altschul, et al. (1990) J. Mol. Biol. 215:403-10. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al. (1997) Nucleic Acids Res. 25(17): 3389-3402. When utilizing BLAST and Gapped BLAST programs, the default parameters of the respective programs (e.g., BLASTP and BLASTN) can be used. See the homepage of the National Center for Biotechnology Information.

EHV-1 and EHV-4/Recombinant Vector Technology Definitions

The term "equid" or "equine" or "equin" means of or belonging to the family Equidae, which includes the horses, asses, and zebras, preferably horses. In addition, the term "equid" or "equine" or "equin" encompasses also hybrids of members of the family Equidae (e.g. mules, hinnies, etc.).

A "Herpes virus" or "Herpes virus vector" refers to a species in the family Herpesviridae in the order Herpesvirales.

The term "Equid herpes virus vector" or "Equid herpes virus" or "EHV" means a member of the family Herpesviridae affecting horses. To date eight different species of equid herpesviruses have been identified, five belonging to the subfamily Alphaherpesvirinae (EHV-1, EHV-3, EHV-4, EHV-8 and EHV-9) and three to the Gammaherpesvirinae. Virus Taxonomy: 2015 Release EC 47, London, UK, July 2015; Email ratification 2016 (MSL #30)).

The term "EHV-1" means Equid Alphaherpesvirus 1, a member of the subgenus *Varicellovirus* in the genus Alphaherpesvirinae in the family Herpesviridae. A non-limiting reference sequence for EHV-1 would be for example the wild-type EHV-1 strain ab4 (Genbank accession number AY665713.1) or the RacH (Hbert 1996).

The term EHV-4 means Equid Alphaherpesvirus 4, a member of the subgenus *Varicellovirus* in the genus Alphaherpesvirinae in the family Herpesviridae.

The term "inserted into ORF70" means that a DNA fragment was inserted into the genomic DNA at a location encoding the Equid Alphaherpesvirus 1 open reading frame 70. In a specific aspect of the present invention the insertion referred to resulted in a deletion of the 801 5' basepairs of ORF70 leaving the remaining 423 bp of the 3' end intact but abolishing expression of the orf70 gene product glycoprotein G. The glycoprotein G of several Alphaherpesviruses including EHV-1 was shown to be secreted from infected cells and function as an immunomodulatory protein by binding pro-inflammatory cytokines. Abolishment of its expression in the viral vector should increase the immunogenicity of the viral infection as compared to a wild-type EHV-1 with intact glycoprotein G expression.

The term "inserted into UL43" means that a DNA fragment was inserted into the genomic DNA at a location encoding the Equid Alphaherpesvirus 1 open reading frame UL43 (ORF17). In a specific aspect of the present invention the insertion referred to resulted in a deletion of the 870 5' basepairs of UL43 leaving the remaining 336 bp of the 3' end intact but abolishing expression of the UL43 gene product pUL43. The pUL43 of EHV-1 was shown to function as an immunomodulatory protein together with pUL56 by interfering with MHC-I presentation.

The term "inserted into ORF1/3" means that a DNA fragment was inserted in the viral genome at a position where by accidental deletion over passaging during the attenuation procedure of the vaccine strain EHV-1 RacH a 1283 bp fragment comprising 90% of ORF1 and the entire ORF2 were lost. This insertion site was chosen because the likelyhood that expression of a transgene from this location would interfere with viral replication was expected to be extremely low.

Vaccine Definitions

An "immunogenic or immunological composition" refers to a composition of matter that comprises at least one antigen, or immunogenic portion thereof, that elicits an immunological response in the host of a cellular or antibody-mediated immune response to the composition.

The term "antigen" used herein is well understood in the art and includes substances which are immunogenic, i.e., immunogens, as well as substances which induce immunological unresponsiveness, or anergy, i.e., a lack of reactions by the body's defense mechanisms to foreign substances. As used herein, the term "antigen" is intended to mean full length proteins as well as peptide fragments thereof containing or comprising epitope.

The term "food producing animal" means animals which are used for human consumption such as swine, cattle, poultry, fish and the like, preferably food producing animal means swine and cattle, most preferably swine.

An "immunogenic composition" as used herein can refer to a polypeptide or a protein, such as for example a viral surface protein that elicits an immunological response as described herein. The term "immunogenic fragment" or "immunogenic portion" refers to a fragment or truncated and/or substituted form of a protein or polypeptide that includes one or more epitopes and thus elicits the immunological response described herein. In general, such truncated and/or substituted forms, or fragments will comprise at least six contiguous amino acids from a full-length protein. Such fragments can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by concurrently synthesizing large numbers of peptides on solid supports, the peptides corresponding to portions of the protein molecule, and reacting the peptides with antibodies while the peptides are still attached to the supports. Such techniques are known and described in the art, see e.g., U.S. Pat. No. 4,708,871; Geysen et al. (1984) Proc. Natl. Acad. Sci. USA 81:3998-4002; and Geysen et al. (1986) Molec. Immunol. 23:709-715. Similarly, conformational epitopes are readily identified by determining spatial conformation of amino acids such as by, e.g., x-ray crystallography and two-dimensional nuclear magnetic resonance. See Epitope Mapping Protocols, supra. Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; and Gardner et al., (1998) 12th World AIDS Conference, Geneva, Switzerland, Jun. 28-Jul. 3, 1998. (The teachings and content of which are all incorporated by reference herein.)

The term "immunizing" relates to an active immunization by the administration of an immunogenic composition to a food producing animal to be immunized, thereby causing an immunological response against the antigen included in such immunogenic composition.

The term "in need" or "of need", as used herein means that the administration/treatment is associated with the boosting or improvement in health or clinical signs or any other positive medicinal effect on health of the animals which receive the immunogenic composition in accordance with the present invention.

The term "vaccine" as used herein refers to a pharmaceutical composition comprising at least one immunologically active component that induces an immunological response in an animal and possibly but not necessarily one or more additional components that enhance the immunological activity of the active component. A vaccine may additionally comprise further components typical to pharmaceutical compositions. By way of distinction the immunologically active component of a vaccine may comprise complete virus particles in either their original form or as attenuated particles in a so called modified live vaccine (MLV) or particles inactivated by appropriate methods in a so called killed vaccine (KV). In another form the immunologically active component of a vaccine may comprise appropriate elements of the organisms (subunit vaccines) whereby these elements are generated either by destroying the whole particle or the growth cultures containing such particles and optionally subsequent purification steps yielding the desired structure(s), or by synthetic processes including an appropriate manipulation by use of a suitable system based on, for example, bacteria, insects, mammalian, or other species plus optionally subsequent isolation and purification procedures, or by induction of the synthetic processes in the animal needing a vaccine by direct incorporation of genetic material using suitable pharmaceutical compositions (polynucleotide vaccination). A vaccine may comprise one or simultaneously more than one of the elements described above. As used within specific aspects of the present invention "vaccine" refers to a live vaccine or live virus, also called recombinant vaccine. In another specific aspect of the present invention "vaccine" refers to an inactivated or killed virus including virus like particles (VLPs). Thus, a vaccine may be a subunit vaccine or a killed (KV) or inactivated vaccine.

The term "Multiplicity of Infection (M.O.I.)" describes how many infectious units, e.g. TCID50, of a virus preparation are used per cell to infect cultured cells. For example, a M.O.I. of 0.01 means that for every 100 cells in a culture vessel one infectious unit is inoculated.

The term "DNA vaccination" or "polynucleotide vaccination" means direct inoculation of genetic material using suitable pharmaceutical compositions.

Various physical and chemical methods of inactivation are known in the art. The term "inactivated" refers to a previously virulent or non-virulent virus or bacterium that has been irradiated (ultraviolet (UV), X-ray, electron beam or gamma radiation), heated, or chemically treated to inactivate or kill such virus or bacterium while retaining its immunogenicity. Suitable inactivating agents include beta-propiolactone, binary or beta- or acetyl-ethyleneimine, gluteraldehyde, ozone, and formalin (formaldehyde).

For inactivation by formalin or formaldehyde, formaldehyde is typically mixed with water and methyl alcohol to create formalin. The addition of methyl alcohol prevents degradation or cross reaction during the in activation process. One embodiment uses about 0.1 to 1% of a 37% solution of formaldehyde to inactivate the virus or bacterium. It is critical to adjust the amount of formalin to ensure that the material is inactivated but not so much that side effects from a high dosage occur.

More particularly, the term "inactivated" in the context of a virus means that the virus is incapable of replication in vivo or in vitro and, respectively, the term "inactivated" in the context of a bacterium means that the bacterium is incapable of reproduction in vivo or in vitro. For example, the term "inactivated" may refer to a virus that has been propagated in vitro, and has then been inactivated using chemical or physical means so that it is no longer capable of replicating. In another example, the term "inactivated" may refer to a bacterium that has been propagated, and then inactivated using chemical or physical means resulting in a suspension of the bacterium, fragments or components of the bacterium, such as resulting in a bacterin which may be used as a component of a vaccine.

As used herein, the terms "inactivated", "killed" or "KV" are used interchangeably.

The term "live vaccine" refers to a vaccine comprising either a living organism or a replication competent virus or viral vector.

A "pharmaceutical composition" essentially consists of one or more ingredients capable of modifying physiological, e.g., immunological functions, of the organism it is administered to, or of organisms living in or on the organism. The term includes, but is not restricted to, antibiotics or antiparasitics, as well as other constituents commonly used to achieve certain other objectives such as, but not limited to, processing traits, sterility, stability, feasibility to administer the composition via enteral or parenteral routes such as oral, intranasal, intravenous, intramuscular, subcutaneous, intradermal, or other suitable route, tolerance after administration, or controlled release properties. One non-limiting example of such a pharmaceutical composition, solely given for demonstration purposes, could be prepared as follows: cell culture supernatant of an infected cell culture is mixed with a stabilizer (e.g., spermidine and/or bovine serum albumin (BSA) and the mixture is subsequently lyophilized or dehydrated by other methods. Prior to vaccination, the mixture is then rehydrated in aqueous (e.g., saline, phosphate buffered saline (PBS) or non-aqueous solutions (e.g., oil emulsion, aluminum-based adjuvant).

As used herein, "pharmaceutical- or veterinary-acceptable carrier" includes any and all solvents, dispersion media, coatings, adjuvants, stabilizing agents, diluents, preservatives, antibacterial and antifungal agents, isotonic agents, adsorption delaying agents, and the like. In some preferred embodiments, and especially those that include lyophilized immunogenic compositions, stabilizing agents for use in the present invention include stabilizers for lyophilization or freeze-drying.

In some embodiments, the immunogenic composition of the present invention contains an adjuvant. "Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.), JohnWiley and Sons, NY, pp51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name CARBOPOL®; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of CARBOPOL® 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314 or muramyl dipeptide, or naturally occurring or recombinant cytokines or analogs thereof or stimulants of endogenous cytokine release, among many others.

It is expected that an adjuvant can be added in an amount of about 100 µg to about 10 mg per dose, preferably in an amount of about 100 µg to about 10 mg per dose, more preferably in an amount of about 500 µg to about 5 mg per dose, even more preferably in an amount of about 750 µg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

"Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

"Attenuation" means reducing the virulence of a pathogen. In the present invention "attenuation" is synonymous with "avirulent". In the present invention, an attenuated virus is one in which the virulence has been reduced so that it does not cause clinical signs of infection but is capable of inducing an immune response in the target animal, but may also mean that the clinical signs are reduced in incidence or severity in animals infected with the attenuated virus, especially the EHV-1 RacH viral vector as claimed, in comparison with a "control group" of animals infected with non-attenuated virus or pathogen and not receiving the attenuated virus. In this context, the term "reduce/reduced" means a reduction of at least 10%, preferably 25%, even more preferably 50%, still more preferably 60%, even more preferably 70%, still more preferably 80%, even more preferably 90% and most preferably of 100% as compared to the control group as defined above. Thus, an attenuated, avirulent pathogen such as for example an attenuated viral vector as claimed, especially the EHV-1 (preferably RacH) viral vector as claimed, is suitable for the generation of a modified live vaccine (MLV) or modified live immunogenic composition.

The term "treatment and/or prophylaxis" refers to the lessening of the incidence of the infection (in particular Swine influenza A virus infection) in a herd or the reduction in the severity of clinical signs caused by or associated with the particular infection (in particular Swine influenza A virus infection). Thus, the term "treatment and/or prophylaxis" also refers to the reduction of the number of animals in a herd that become infected with the pathogen (in particular Swine influenza A virus=lessening of the incidence of the particular Swine influenza A virus infection) or to the reduction of the severity of clinical signs normally associated with or caused by the infection (in particular Swine influenza A virus infection) in a group of animals which animals have received an effective amount of the immunogenic composition as provided herein in comparison to a group of animals which animals have not received such immunogenic composition.

The "treatment and/or prophylaxis" generally involves the administration of an effective amount of the immunogenic composition of the present invention to an animal or herd of animals in need of or that could benefit from such a treatment/prophylaxis. The term "treatment" refers to the administration of the effective amount of the immunogenic composition once the animal or at least some animals of the herd is/are already infected with such pathogen (in particular Swine influenza A virus) and wherein such animals already show some clinical signs caused by or associated with such pathogen infection (in particular Swine influenza A virus). The term "prophylaxis" refers to the administration to an animal prior to any infection of such animal with a pathogen (in particular Swine influenza A virus) or at least where such animal or none of the animals in a group of animals do not show any clinical signs caused by or associated with the infection by such pathogen (in particular Swine influenza A virus). The terms "prophylaxis" and "preventing" are used interchangeable in this application.

The term "clinical signs" as used herein refers to signs of infection of an animal from the pathogen (in particular Swine influenza A virus). The clinical signs of infection depend on the pathogen selected. Examples for such clinical signs include but are not limited to respiratory distress, otitis, roughened hair coat, slight fever, depression, and reduced appetite. However, the clinical signs also include but are not limited to clinical signs that are directly observable from a live animal. Examples for clinical signs that are directly observable from a live animal include nasal and ocular discharge, lethargy, coughing, wheezing, thumping, elevated fever, weight loss, dehydration, lameness, wasting, paleness of the skin, unthriftiness and the like.

Herein, "effective dose" means, but is not limited to, an amount of antigen that elicits, or is able to elicit, an immune response that yields a reduction of clinical symptoms in an animal to which the antigen is administered.

As used herein, the term "effective amount" means, in the context of a composition, an amount of an immunogenic composition capable of inducing an immune response that reduces the incidence of or lessens the severity of infection or incident of disease in an animal. Particularly, an effective amount refers to colony forming units (CFU) per dose. Alternatively, in the context of a therapy, the term "effective amount" refers to the amount of a therapy which is sufficient to reduce or ameliorate the severity or duration of a disease or disorder, or one or more symptoms thereof, prevent the advancement of a disease or disorder, cause the regression of a disease or disorder, prevent the recurrence, development, onset, or progression of one or more symptoms associated with a disease or disorder, or enhance or improve the prophylaxis or treatment of another therapy or therapeutic agent.

An "immune response" or "immunological response" means, but is not limited to, the development of a cellular and/or antibody-mediated immune response to the (immunogenic) composition or vaccine of interest. Usually, an immune or immunological response includes, but is not limited to, one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number of symptoms, severity of symptoms, or the lack of one or more of the symptoms associated with the infection of the pathogen, a delay in the of onset of viremia, reduced viral persistence, a reduction in the overall viral load and/or a reduction of viral excretion.

"Protection against disease", "protective immunity", "functional immunity", "reduction of clinical symptoms", "induction/production of neutralizing antibodies and/or serum conversion", and similar phrases, means a partial or complete response against a disease or condition generated by administration of one or more therapeutic compositions of the invention, or a combination thereof, that results in fewer deleterious effects than would be expected in a non-immunized subject that has been exposed to disease or infection. That is, the severity of the deleterious effects of the infection are lessened in a vaccinated subject. Infection may be reduced, slowed, or possibly fully prevented, in a vaccinated subject. Herein, where complete prevention of infection is meant, it is specifically stated. If complete prevention is not stated then the term includes partial prevention.

Herein, "reduction of the incidence and/or severity of clinical signs" or "reduction of clinical symptoms" means, but is not limited to, reducing the number of infected subjects in a group, reducing or eliminating the number of subjects exhibiting clinical signs of infection, or reducing the severity of any clinical signs that are present in one or more subjects, in comparison to wild-type infection. For example, it should refer to any reduction of pathogen load, pathogen shedding, reduction in pathogen transmission, or reduction of any clinical sign symptomatic of malaria. Preferably these clinical signs are reduced in one or more subjects receiving the therapeutic composition of the present invention by at least 10% in comparison to subjects not receiving the composition and that become infected. More preferably clinical signs are reduced in subjects receiving a composition of the present invention by at least 20%, preferably by at least 30%, more preferably by at least 40%, and even more preferably by at least 50%.

The term "increased protection" herein means, but is not limited to, a statistically significant reduction of one or more clinical symptoms which are associated with infection by an infectious agent in a vaccinated group of subjects vs. a non-vaccinated control group of subjects. The term "statistically significant reduction of clinical symptoms" means, but is not limited to, the frequency in the incidence of at least one clinical symptom in the vaccinated group of subjects is at least 10%, preferably 20%, more preferably 30%, even more preferably 50%, and even more preferably 70% lower than in the non-vaccinated control group after the challenge the infectious agent.

"Long-lasting protection" shall refer to "improved efficacy" that persists for at least 3 weeks, but more preferably at least 3 months, still more preferably at least 6 months. In the case of livestock, it is most preferred that the long lasting protection shall persist until the average age at which animals are marketed for meat.

The term "reduction of viremia" induced by a virus means, but is not limited to, the reduction of virus entering the bloodstream of an animal, wherein the viremia level, i.e. the number of virus DNA or RNA copies per mL of blood serum or the number of plaque forming colonies per deciliter of blood serum, is reduced in the blood serum of animals receiving the composition of the present invention by at least 50% in comparison to animals not receiving the composition and may become infected. More preferably, the viremia level is reduced in animals receiving the composition of the present invention by at least 90%, preferably by at least 99.9%, more preferably by at least 99.99%, and even more preferably by at least 99.999%.

The term "pathogen" is well known to the person skilled in the art. However, the term "pathogen" comprises bacteria and viruses. The term "pathogen" comprises pathogens such as Schmallenberg virus, Influenza A Virus, Porcine Respiratory and Reproductive Syndrome Virus, Porcine Circovirus, Classical Swine Fever Virus, African Swine Fever Virus, Hepatitis E Virus, Bovine Viral Diarrhea Virus, Rabies Virus, Feline Morbillivirus, *Clostridium tetani, Mycobacterium tuberculosis, Actinobacillus Pleuropneumoniae*

The term "food producing animal" means animals which are used for human consumption such as swine, cattle, poultry, fish and the like, preferably swine.

As used herein, the term "viremia" is particularly understood as a condition in which virus particles reproduce and/or circulate in the bloodstream of an animal, in particular of a mammal, a bird, or of an insect.

"Safety" refers to the absence of adverse consequences in a vaccinated animal following vaccination, including but not limited to: potential reversion of a virus-based vaccine to virulence, clinically significant side effects such as persistent, systemic illness or unacceptable inflammation at the site of vaccine administration.

The terms "vaccination" or "vaccinating" or variants thereof, as used herein means, but is not limited to, a process which includes the administration of an immunogenic composition of the invention that, when administered to an animal, elicits, or is able to elicit-directly or indirectly-, an immune response in said animal.

"Mortality", in the context of the present invention, refers to death caused by an infection, and includes the situation where the infection is so severe that an animal is euthanized to prevent suffering and provide a humane ending to its life.
Formulations The subject to which the composition is administered is preferably an animal, including but not limited to cattle, horses, sheep, pigs, poultry (e.g. chickens), goats, cats, dogs, hamsters, mice and rats, most preferably the mammal is a swine.

The formulations of the invention comprise an effective immunizing amount of one or more immunogenic compositions and a physiologically acceptable vehicle. Vaccines comprise an effective immunizing amount of one or more immunogenic compositions and a physiologically acceptable vehicle. The formulation should suit the mode of administration.

The immunogenic composition, if desired, can also contain minor amounts of wetting or emulsifying agents, or pH buffering agents. The immunogenic composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.
Methods of Treatment Preferred routes of administration include but are not limited to intranasal, oral, intradermal, and intramuscular. Administration in drinking water, most preferably in a single dose, is desirable. The skilled artisan will recognize that compositions of the invention may also be administered in one, two or more doses, as well as, by other routes of administration. For example, such other routes include subcutaneously, intracutaneously, intraperitnoeally, intracutaneously, and depending on the desired duration and effectiveness of the treatment, the compositions according to the invention may be administered once or several times, also intermittently, for instance on a daily basis for several days, weeks or months and in different dosages such as about $10^3$ to $10^8$ TCID50 (see viral titre above). In a specific aspect of the present invention the dosage is about $10^3$ to $10^8$ TCID50, especially for live virus/live vaccine.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration preferably for administration to a mammal, especially a pig. Associated with such container(s) can be a notice in the form prescribed by a governmental agency regulating the manufacture, use or sale of pharmaceuticals or biological products, which notice reflects approval by the agency of manufacture, use or sale for human administration.

Antigen Definitions

The term "swine influenza virus" is known by the person skilled in the art. The term swine influenza virus refers to a type A or type C influenza virus from the family orthomyxovirus that causes swine influenza. While orthomyxovirus has three groups: type A, type B and type C, only type A and type C influenza viruses infect pigs. Preferably, the swine influenza virus is a Swine Influenza A virus. Subtypes of swine influenza virus include H1N1, H1N2, H3N2, and H3N1. H9N2 and H5N1 can also be found in pigs. Preferably, a swine influenza virus is an influenza virus that has been isolated from swine.

The terms "HA" or "H", "NA" or "N" and "NP" are known by the person skilled in the art. However, in general, type A influenza viruses are divided into 17 H (hemagglutinin) and 10 N (Neuraminidase) subtypes which can give rise to many possible combinations (designated as H1N1, H1N2 . . . H2N1, H2N2 . . . H5N1, H5N2 . . . . and so on).

H (hemagglutinin) and N (neuraminidase) are surface glycoproteins in influenza A viruses such as SIAV. Further, N is the major antigenic target of neutralizing antibodies. Furthermore, NP (nucleoprotein) forms the nucleocapsid.

DIVA Definitions

The term "DIVA (differentiation between infected and vaccinated animals)" refers to a vaccine that can be used for differentiating a vaccinated animal from a naturally infected animal.

The term "sample" refers to a sample of a body fluid, to a sample of separated cells or to a sample from a tissue or an organ. Samples of body fluids can be obtained by well-known techniques and include, preferably, samples of blood, plasma, serum, or urine, more preferably, samples of blood, plasma or serum. Tissue or organ samples may be obtained from any tissue or organ by, e.g., biopsy. Separated cells may be obtained from the body fluids or the tissues or organs by separating techniques such as centrifugation or cell sorting.

The term "obtained" may comprise an isolation and/or purification step known to the person skilled in the art, preferably using precipitation, columns ect.

The term "immuno tests" and "genomic analytical tests" is the basis for differentiating animals vaccinated with the immunogenic composition according to the present invention and animals infected with the naturally occurring (disease-associated) swine influenza virus. Examples of immuno tests include any enzyme-immunological or immunochemical detection method such as ELISA (enzyme linked immunosorbent assay), EIA (enzyme immunoassay), RIA (radioimmunoassay), sandwich enzyme immune tests, fluorescent antibody test (FAT) electrochemiluminescence sandwich immunoassays (ECLIA), dissociation-enhanced lanthanide fluoro immuno assay (DELFIA) or solid phase immune tests, immunofluorescent test (IFT), immunohistological staining, Western blot analysis or any other suitable method available to technicians skilled in the art. Depending upon the assay used, the antigens or the antibodies can be labeled by an enzyme, a fluorophore or a radioisotope. See, e.g., Coligan et al. Current Protocols in Immunology, John Wiley & Sons Inc., New York, N.Y. (1994); and Frye et al., Oncogen 4: 1153-1157, 1987.

The term "genomic analytical test" refers to a genomic analytical method based upon the polymerase chain reaction (PCR), reverse transcription polymerase chain reaction (RT-PCR), real-time PCR (r-PCR) or real time reverse transcription PCR (rRT-PCR), Templex-PCR, nucleic-acid sequence based amplification (NASBA), and isothermal amplification methods using polymerases and specific oligonucleotides as primers. The aforementioned amplification methods are well known in the art.

CLAUSES

The The following Clauses are described herein:

The invention provides the following clauses:

1. An expression cassette comprising
   (i) at least one exogenous nucleotide sequence of interest, preferably a gene of interest, more preferably an antigen encoding sequence, whereby said nucleotide sequence of interest, preferably a gene of interest, more preferably an antigen encoding sequence is operably linked to a promoter sequence, and
   (ii) at least one upstream UL43 flanking region selected from the group consisting of: SEQ ID NO:19 and a 70%, 80%, 85%, 90%, 91%, 92%, 93%, 94%, 95%, 96%, 97%, 98%, 99% homologous and/or identical sequence thereof, SEQ ID NO:26 and a 70%, 80%, 85%, 90%, 91%, 92%, 93%, 94%, 95%, 96%, 97%, 98%, 99% homologous and/or identical sequence thereof, and
   (iii) at least one upstream UL44 flanking region selected from the group consisting of: SEQ ID NO:20 and a 70%, 80%, 85%, 90%, 91%, 92%, 93%, 94%, 95%, 96%, 97%, 98%, 99% homologous and/or identical sequence thereof, SEQ ID NO:27 and a 70%, 80%, 85%, 90%, 91%, 92%, 93%, 94%, 95%, 96%, 97%, 98%, 99% homologous and/or identical thereof.
2. An Equid Alphaherpesvirus (EHV) vector comprising the expression cassette of clause 1.
3. An Equid Alphaherpesvirus (EHV) vector comprising
   (i) at least one exogenous nucleotide sequence of interest, preferably a gene of interest, more preferably an antigen encoding sequence, whereby said nucleotide sequence of interest, preferably a gene of interest, more preferably an antigen encoding sequence, is operably linked to a promoter sequence, and
   (ii) at least one upstream UL43 flanking region selected from the group consisting of: SEQ ID NO:19 and a 70%, 80%, 85%, 90%, 91%, 92%, 93%, 94%, 95%, 96%, 97%, 98%, 99% homologous and/or identical sequence thereof, SEQ ID NO:26 and a 70%, 80%, 85%, 90%, 91%, 92%, 93%, 94%, 95%, 96%, 97%, 98%, 99% homologous and/or identical sequence thereof, and
   (iii) at least one upstream UL44 flanking region selected from the group consisting of: SEQ ID NO:20 and a 70%, 80%, 85%, 90%, 91%, 92%, 93%, 94%, 95%, 96%, 97%, 98%, 99% homologous and/or identical sequence thereof, SEQ ID NO:27 and a 70%, 80%, 85%, 90%, 91%, 92%, 93%, 94%, 95%, 96%, 97%, 98%, 99% homologous and/or identical sequence thereof.
4. An Equid Alphaherpesvirus (EHV) vector comprising a nucleotide sequence of interest, preferably a gene of interest, more preferably an antigen encoding sequence, inserted into UL43.
5. An Equid Alphaherpesvirus (EHV) vector comprising a first nucleotide sequence or gene of interest, preferably an antigen encoding sequence, inserted into UL43 and a second nucleotide sequence or gene of interest, preferably another antigen encoding sequence, inserted into a second insertion site, preferably UL56 or US4.
6. The EHV vector of any one of clauses 2 to 5, whereby the insertion into UL43 is characterized by a partial deletion, truncation, substitution, modification or the like in UL43, whereby UL44 remains functional.
7. The EHV vector of any one of clauses 2 to 6, whereby the insertion into UL43 is characterized by the deletion of an approximately 870 bp portion within UL43 for RacH (SEQ ID NO:21) or a 70%, 80%, 85%, 90%, 91%, 92%, 93%, 94%, 95%, 96%, 97%, 98%, 99% homologous and/or identical sequence thereof.
8. The EHV vector of any one of clauses 2 to 7, whereby the EHV vector comprises at least one flanking region selected from the group consisting of: SEQ ID NO:19, SEQ ID NO:20, SEQ ID NO:26, SEQ ID NO:27, and a 70%, 80%, 85%, 90%, 91%, 92%, 93%, 94%, 95%, 96%, 97%, 98%, 99% homologous and/or identical sequence of any one of these sequences.
9. The EHV vector of any one of clauses 2 to 8, whereby the EHV vector comprises (i) at least one upstream UL43 flanking region selected from the group consisting of: SEQ ID NO:19, SEQ ID NO:26, and (ii) at least one upstream UL44 flanking region selected from the group consisting of: SEQ ID NO:20, SEQ ID NO:27.
10. The EHV vector of any one of clauses 2 to 9 or the expression cassette of clause 1, whereby said nucleotide sequence of interest, preferably a gene of interest, more preferably an antigen encoding sequence is non-naturally occurring and/or recombinant.
11. The EHV vector of any one of clauses 2 to 10 or the expression cassette of clause 1 or 10, whereby said nucleotide sequence of interest is recombinant and/or heterologous and/or exogenous.
12. The EHV vector of any one of clauses 2 to 11 or the expression cassette of any one of clauses 1 or 10 to 11, whereby said antigen encoding sequence relates to a pathogen infecting an animal such as a food producing animal such as swine, poultry or cattle or companion animals such as cats, dogs or horses.
13. The EHV vector of clauses any one of 2 to 12 or the expression cassette of any one of clauses 1 or 10 to 12, further comprising additional regulatory sequences such as a termination signal or polyadenylation sequence.
14. The EHV vector of any one of clauses 2 to 13 additionally comprising at least one further nucleotide sequence of interest, preferably another gene of interest, more preferably an antigen encoding sequence, optionally inserted into another insertion site, such as UL56 and/or US4.
15. The EHV vector of any one of clauses 2 to 14, whereby the at least one further nucleotide sequence of interest, preferably another gene of interest, more preferably an antigen encoding sequence, is inserted into UL56.
16. The EHV vector of any one of clauses 2 to 15, whereby the at least one further nucleotide sequence of interest, preferably another gene of interest, more preferably an antigen encoding sequence, is inserted into US4.
17. The EHV vector of any one of clauses 2 to 14, whereby a second further nucleotide sequence of interest, preferably another gene of interest, more preferably an antigen encoding sequence, is inserted into US4 and, whereby a third further nucleotide sequence of interest, preferably another gene of interest, more preferably an antigen encoding sequence, is inserted into UL56.
18. The EHV vector of any one of clauses 2 to 17, whereby the gene of interest is operably linked to a regulatory sequence, preferably a promoter sequence or the EHV vector of clauses 5 to 17, whereby the at least two genes of interest are operably linked to regulatory sequences, preferably promoter sequences.
19. The EHV vector of any one of clauses 2 to 18 or the expression cassette of any one of clauses 1 or 10 to 13, whereby the promoter sequence(s) operably linked to the one or two or more sequences or genes of interest are selected from the group consisting of: SV40 large T, HCMV and MCMV immediate early gene 1, human elongation factor alpha promoter, baculovirus polyhedrin promoter, a functional fragment of 4pgG600 (SEQ ID NO:1), preferably said functional fragment is p430 (SEQ ID NO:3), a functional fragment of the complementary nucleotide sequence of 4pgG600 (SEQ ID NO:1), a functional fragment of 4pMCP600 (SEQ ID NO:2), preferably said functional fragment is p455 (SEQ ID NO:4), a functional fragment of the complementary nucleotide sequence of 4pMCP600 (SEQ ID NO:2) or p422 (SEQ ID NO:5) or a functional fragment thereof or the complementary nucleotide sequences thereof.
20. The EHV vector of any one of clauses 2 to 19 or the expression cassette of any one of clauses 1 or 10 to 13 or 19, whereby the promoter sequence operably linked to at least one gene of interest is p422 (SEQ ID NO:5) or a functional fragment thereof or the complementary nucleotide sequences thereof.
21. The EHV vector of any one of clauses 5 to 20, whereby the promoter sequences operably linked to the at least two genes of interest are different.
22. The EHV vector of any one of clauses 2 to 21 or the expression cassette of any one of clauses 1 or 10 to 13 or 19 to 20, whereby the EHV vector or expression cassette is recombinant.
23. The EHV vector of any one of clauses 2 to 22 or the expression cassette of any one of clauses 1 or 10 to 13 or 19 to 20 or 22, whereby said sequences or exogenous nucleotide sequence of interest or gene of interest is an antigen encoding sequence.
24. The EHV vector of any one of clauses 2 to 23 or the expression cassette of any one of clauses 1 or 10 to 13 or 19 to 20 or 22 to 23, whereby the antigen encoding sequence is from a pathogen selected from the list: Schmallenberg virus, Influenza A Virus, Porcine Respiratory and Reproductive Syndrome Virus, Porcine Circovirus, Classical Swine Fever Virus, African Swine Fever Virus, Hepatitis E Virus, Bovine Viral Diarrhea Virus, Rabies Virus, Feline Morbillivirus, *Clostridium tetani, Mycobacterium tuberculosis, Actinobacillus Pleuropneumoniae.*
25. The EHV vector of any one of clauses 2 to 24 or the expression cassette of any one of clauses 1 or 10 to 13 or 19 to 20 or 22 to 24, whereby the antigen encoding sequence is a hemagglutinin encoding sequence.
26. The EHV vector or the expression cassette of clause 25, whereby the hemagglutinin influenza antigen encoding sequence is from a Swine influenza A virus.
27. The EHV vector or the expression cassette of clause 25 or 26, whereby the exogenous antigen encoding sequence is a hemagglutinin encoding sequence and the hemagglutinin influenza subtype is selected from the group consisting of H1, H2, H3, H4, H5, H6, H7, H8, H9, H10, H11, H12, H13, H14, H15, H16, H17 and H18.
28. The EHV vector or the expression cassette of any one of clauses 25 to 27, whereby the exogenous antigen encoding sequence is a hemagglutinin encoding sequence and the hemagglutinin influenza antigen encoding sequence is selected from a group of strains consisting of A/swine/Italy/116114/2010(H1N2), A/swine/Italy/7680/2001(H3N2), A/swine/Gent/132/2005(H1N1), A/swine/Italy/4675/2003(H1N2), A/swine/Italy/259543/2003(H1N2), A/swine/Denmark/13772-1/2003(H1N1), A/swine/England/MD0040352R/2009(H1N1), A/swine/Hungary/13509/2007(H3N2), A/swine/Italy/13962/95(H3N2), A/swine/Cotes d'Armor/1121/00(H1N1), A/Swine/Colorado/1/77, A/Swine/Colorado/23619/99, A/Swine/Cote d'Armor/3633/84, A/Swine/England/195852/92, A/Swine/Finistere/2899/82, A/Swine/Hong Kong/10/98, A/Swine/Hong Kong/9/98, A/Swine/Hong Kong/81/78, A/Swine/Illinois/100084/01, A/Swine/Illinois/100085A/01, A/Swine/Illinois/21587/99, A/Swine/Indiana/1726/88, A/Swine/Indiana/9K035/99, A/Swine/Indiana/P12439/00, A/Swine/Iowa/30, A/Swine/Iowa/15/30, A/Swine/Iowa/533/99, A/Swine/Iowa/569/99, A/Swine/Iowa/3421/90, A/Swine/Iowa/8548-1/98, A/Swine/Iowa/930/01, A/Swine/Iowa/17672/88, A/Swine/Italy/1513-1/98, A/Swine/Italy/1523/98, A/Swine/Korea/CY02/02, A/Swine/Minnesota/55551/00, A/Swine/Minnesota/593/

99, A/Swine/Minnesota/9088-2/98, A/Swine/Nebraska/1/92, A/Swine/Nebraska/209/98, A/Swine/Netherlands/12/85, A/Swine/North Carolina/16497/99, A/Swine/North Carolina/35922/98, A/Swine/North Carolina/93523/01, A/Swine/North Carolina/98225/01, A/Swine/Oedenrode/7C/96, A/Swine/Ohio/891/01, A/Swine/Oklahoma/18717/99, A/Swine/Oklahoma/18089/99, A/Swine/Ontario/01911-1/99, A/Swine/Ontario/01911-2/99, A/Swine/Ontario/41848/97, A/Swine/Ontario/97, A/Swine/Quebec/192/81, A/Swine/Quebec/192/91, A/Swine/Quebec/5393/91, A/Swine/Taiwan/7310/70, A/Swine/Tennessee/24/77, A/Swine/Texas/4199-2/98, A/Swine/Wisconsin/125/97, A/Swine/Wisconsin/136/97, A/Swine/Wisconsin/163/97, A/Swine/Wisconsin/164/97, A/Swine/Wisconsin/166/97, A/Swine/Wisconsin/168/97, A/Swine/Wisconsin/235/97, A/Swine/Wisconsin/238/97, A/Swine/Wisconsin/457/985 A/Swine/Wisconsin/458/98, A/Swine/Wisconsin/464/98 and A/Swine/Wisconsin/14094/99.

29. The EHV vector or the expression cassette of any one of clauses 25 to 28, whereby the exogenous antigen encoding sequence is a hemagglutinin encoding sequence and the hemagglutinin influenza antigen encoding sequence is selected from a group of strains consisting of A/swine/Italy/116114/2010(H1N2), A/swine/Italy/7680/2001 (H3N2), A/swine/Gent/132/2005(H1N1) and A/swine/Italy/4675/2003(H1N2).

30. The EHV vector or the expression cassette of any one of clauses 25 to 29, whereby the exogenous antigen encoding sequence is a hemagglutinin encoding sequence and the hemagglutinin influenza subtype is H1 and/or H3.

31. The EHV vector or the expression cassette of any one of clauses 25 to 30, whereby the antigen encoding sequence is a hemagglutinin encoding sequence and the hemagglutinin influenza antigen encoding sequence comprises a nucleic acid sequence encoding an amino acid sequence with at least 70%, at least 75%, at least 80%, at least 85%, at least 90%, least 91%, at least 92%, at least 93%, at least 94%, at least 95%, at least 96%, at least 97%, at least 98% or at least 99% identity to the amino acid sequence as set forth in SEQ ID NO:44, SEQ ID NO:45, SEQ ID NO:46 and SEQ ID NO:47.

32. The EHV vector or the expression cassette of any one of clauses 25 to 31, whereby the EHV vector or the expression cassette does not comprise NP (nucleoprotein) or N (neuraminidase) influenza antigen encoding sequences.

33. The EHV vector or the expression cassette of any one of clauses 25 to 32 whereby the promoter sequence p422 (SEQ ID NO:5) or a functional fragment or a functional derivative thereof or the complementary nucleotide sequences thereof is operably linked to a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO:44 (H1pdm).

34. The EHV vector of clauses 2 to 33, whereby the EHV vector comprises two or more hemagglutinin influenza antigen encoding sequences.

35. The EHV vector of clause 34, whereby the further hemagglutinin influenza antigen encoding sequence is a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO:46 (H1av).

36. The EHV vector of clause 35, whereby said further hemagglutinin influenza antigen encoding sequence is inserted into UL56.

37. The EHV vector of clause 35 or 36, whereby the hemagglutinin influenza antigen encoding sequence of clause 35 is operably linked to the promoter sequence p430 (SEQ ID NO:3) or a functional fragment or a functional derivative thereof or the complementary nucleotide sequences thereof.

38. The EHV vector of clauses 34 to 37, whereby the further hemagglutinin influenza antigen encoding sequences is a nucleic acid sequence encoding an amino acid sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO:45 (H3).

39. The EHV vector of clause 38, whereby said further hemagglutinin influenza antigen encoding sequences is inserted into US4.

40. The EHV vector of clause 38 or 39, whereby the hemagglutinin influenza antigen encoding sequences of clause 38 is operably linked to the promoter sequence p455 (SEQ ID NO:4) or a functional fragment or a functional derivative thereof or the complementary nucleotide sequences thereof.

41. The EHV vector of any one of clauses 2 to 40, wherein the EHV vector is selected from the group consisting of EHV-1, EHV-3, EHV-4, EHV-8 und EHV-9.

42. The EHV vector of any one of clauses 2 to 41, wherein the EHV vector is EHV-1 or EHV-4.

43. The EHV vector of any one of clauses 2 to 42, wherein the EHV vector is EHV-1, preferably RacH.

44. A mammalian host cell characterized in that it comprises a vector according to clauses 2 to 43.

45. Use of the vector according to clauses 2 to 43 or the mammalian host cell according to clause 44 for the manufacture of an immunogenic composition or vaccine.

46. An immunogenic composition comprising
   a. the vector according to clauses 2 to 43, and/or
   b. a polypeptide expressed by the vector according to clauses 2 to 43, such as a virus, a modified live virus, a virus like particle (VLP) or the like, and
   c. optionally a pharmaceutical- or veterinary-acceptable carrier or excipient, preferably said carrier is suitable for oral, intradermal, intramuscular or intranasal application,
   preferably said immunogenic composition comprises a virus, such as an infectious virus.

47. A vaccine or pharmaceutical composition comprising
   a. the vector according to clauses 2 to 43, and/or
   b. a polypeptide expressed by the vector according to clauses 2 to 43, such as a modified live virus, a virus like particle (VLP) or the like, and
   c. a pharmaceutical- or veterinary-acceptable carrier or excipient, preferably said carrier is suitable for oral, intradermal, intramuscular or intranasal application,
   optionally said vaccine further comprises an adjuvant.

48. A vaccine or DIVA vaccine comprising one or more EHV vectors according to any one of clauses 2 to 43.

49. A method for the preparation of an immunogenic composition or a vaccine for reducing the incidence or the severity of one or more clinical signs associated with or caused by an infection, comprising the following steps:

a. Infecting the mammalian host cell according to clause 41 with the vector according to clauses 2 to 43,
b. cultivating the infected cells under suitable conditions,
c. collecting infected cell cultures,
d. optionally purifying the collected infected cell cultures of step c) optionally mixing said collected infected cell culture with a pharmaceutically acceptable carrier.

50. The immunogenic composition, vaccine or DIVA vaccine according to any one of clauses 46 to 48 for use in a method for immunizing an animal comprising administering to said animal said immunogenic composition, vaccine or DIVA vaccine.
51. The immunogenic composition, vaccine or DIVA vaccine according to any one of clauses 46 to 48 for use in a method for reducing or preventing clinical signs caused by a pathogen in an animal of need, the method comprising administering to the animal a therapeutically effective amount of said immunogenic composition, vaccine or DIVA vaccine.
52. The immunogenic composition, vaccine or DIVA vaccine according to any one of clauses 46 to 48 for use in a method for reducing or preventing clinical signs caused by swine influenza virus in an animal of need, the method comprising administering to the animal a therapeutically effective amount of said immunogenic composition, vaccine or DIVA vaccine.
53. A method for immunizing an animal comprising administering to such animal an immunogenic composition, vaccine or DIVA vaccine of any one of clauses 46 to 48.
54. A method for reducing or preventing clinical signs caused by a pathogen in an animal of need, the method comprising administering to the animal a therapeutically effective amount of an immunogenic composition, vaccine or DIVA vaccine according to any one of clauses 46 to 48.
55. A method for reducing or preventing clinical signs caused by swine influenza virus in an animal of need, the method comprising administering to the animal a therapeutically effective amount of an immunogenic composition, vaccine or DIVA vaccine according to any one of clauses 46 to 48.
56. The method or use of any one of clauses 50 to 55, wherein the animal is swine, piglet or sow, poultry, cattle, horse, dog or cat.
57. The method or use of any one of clauses 50 to 56, wherein the immunogenic composition, vaccine or DIVA vaccine is administered once.
58. The method or use of any one of clauses 50 to 57, wherein the immunogenic composition, vaccine or DIVA vaccine is administered to the animal within the first six weeks of age, within the first two weeks of age, within the first week of age or within the first day of age.
59. The method or use of any one of clauses 50 to 58, wherein the immunogenic composition, vaccine or DIVA vaccine is administered at two doses.
60. The method or use of clause 59, wherein the immunogenic composition, vaccine or DIVA vaccine is administered to the animal within the first week of age and a second time within the second, third or fourth week of age.
61. The method or use of any one of clauses 50 to 60, wherein said immunogenic composition, vaccine or DIVA vaccine is administered intramuscular or intranasal.
62. The method or use of any one of clauses 50 to 61, wherein the immunogenic composition, vaccine or DIVA vaccine comprises $1 \times 10^4$ to $1 \times 10^7$ TCID50 of the EHV vector.
63. The method or use of any one of clauses 50 to 62, wherein said method results in an improvement in an efficacy parameter selected from the group consisting of: a reduction in weight loss, a reduced rectal temperature, reduced clinical symptoms, increased induction of (neutralizing) antibodies, or combinations thereof, in comparison to an animal of a non-immunized control group of the same species.
64. A kit for vaccinating an animal, preferably a food producing animal such as swine, poultry or cattle or companion animals such as cats, dogs or horses, against a disease associated with and/or reducing the incidence or the severity of one or more clinical signs associated with or caused by a pathogen in an animal comprising:
a) a dispenser capable of administering a vaccine to said animal; and
b) the immunogenic composition according to clause 46, the vaccine according to clause 47 or the DIVA vaccine according to clause 48, and
c) optionally an instruction leaflet.
65. A promoter sequence comprising p422 (SEQ ID NO:5) or the complementary nucleotide sequences thereof or a functional fragment thereof or the complementary nucleotide sequences thereof, wherein said promoter sequence leads to expression of a nucleotide sequence of interest, preferably a gene of interest, more preferably an antigen encoding sequence.
66. An expression cassette comprising the promoter sequence p422 (SEQ ID NO:5) or the complementary nucleotide sequences thereof or a functional fragment and the complementary nucleotide sequences thereof,
wherein the promoter sequence is operably linked to a sequence of interest, preferably a gene of interest such as an antigen encoding sequence, more preferably a heterologous and/or exogenous sequence of interest, gene of interest or antigen encoding sequence of interest,
wherein said promoter sequence leads to expression of a nucleotide sequence of interest, preferably a gene of interest, more preferably an antigen encoding sequence,
whereby said promoter sequence is preferably a heterologous promoter sequence, more preferably an exogenous promoter sequence.
67. A vector comprising the promoter sequence or the expression cassette of clause 65 or 66.
68. The promoter or the expression cassette or the vector of any one of clauses 65 to 67, wherein the functional fragment of the promoter sequence has a sequence identity and/or homology of 70%, 80%, 85%, preferably 90%, 91%, 92%, 93%, 94%, more preferably 95%, 96%, 97%, 98%, 99%, 99.9% to the sequence of p422 (SEQ ID NO:5).
69. The promoter or the expression cassette or the vector of any one of clauses 65 to 68, wherein said functional fragment of the promoter sequence has a length of 100 nucleotides, preferably 125, 150, 175, 200, 225, 250, 275, 300, 325, 350, 375, 400 nucleotides, most preferably 410 or 420 nucleotides, or wherein the functional fragment of the promoter sequence has a length of between 100 to 422 nucleotides, 200 to 422 nucleotides, 300 to 422 nucleotides or 350 to 422 nucleotides.
70. The expression cassette or the vector of any one of clauses 66 to 69, wherein the expression cassette or the vector further comprises a polyadenylation sequence, preferably BGHpA, 71 pA (SEQ ID NO:6), or 18 pA (SEQ ID NO:7).

71. The expression cassette or the vector of any one of clauses 66 to 70, wherein said expression cassette or vector comprises one or more further regulatory sequences such as a termination signal, a polyadenylation signal or a regulatory element like IRES and/or 2a peptide.

72. The vector of any one of clauses 67 to 71, wherein said vector is a recombinant, and/or a heterologous and/or an exogenous vector.

73. The vector of any one of clauses 67 to 72, wherein said vector is a viral vector, preferably selected from the group consisting of herpes viridae such as Equid Alphaherpesvirus 1 (EHV-1), Equid Alphaherpesvirus 4 (EHV-4) and other Varicelloviruses like PrV (Pseudorabies virus) and BHV-1 (Bovine Herpesvirus 1), Adenoviridae (AdV) such as CAdV (Canine Adenovirus), Adeno-associated viridae, Baculoviridae, Lentiviridae such as Retroviruses, and Poxviridae.

74. The vector of any one of clauses 67 to 73, wherein said vector is a member of the family Herpesviridae, preferably of the genus Alphaherpesvirinae, more preferably of the subgenus *Varicellovirus*, most preferably said vector is Equid Alphaherpesvirus 1 (EHV-1).

Sequences Overview

The following sequences are detailed and disclosed hereby in the present invention:
Promoter and polyA sequences
  (SEQ ID NO:1) 600 bp DNA fragment 4pgG600
  (SEQ ID NO:2) 600 bp DNA fragment 4pMCP600:
  (SEQ ID NO:3) In particular the 600 bp promoters were truncated to 430 bp for 4pgG, new name: p430
  (SEQ ID NO:4) and to 449 bp for 4pMCP, new name: p455
  (SEQ ID NO:5) Sequence of the p422 promoter
  (SEQ ID NO:6) Sequence of the 71 pA polyadenylation sequence
  (SEQ ID NO:7) Sequence of the 18 pA polyadenylation sequence Insertion region sequences
  (SEQ ID NO:8) US4 (orf70) sequence of RacH
  (SEQ ID NO:9) Up70 flanking region (417 bp)
  (SEQ ID NO:10) Up71 flanking region (431 bp)
  (SEQ ID NO:11) 127264-127680 (flanking region up orf70)
  (SEQ ID NO:12) 128484-128913 (flanking region up orf71)
  (SEQ ID NO:13) Up70 flanking region (283 bp)=identical to the 3' 283 bp of the 417 bp "classical" flanking region
  (SEQ ID NO:14) Up71 flanking region (144 bp)=identical to the 5' 144 bp of the 431 bp "classical" flanking region
  (SEQ ID NO:15) Sequence of US4 (orf70) of the wt strain ab4 nt 127681-128916
  (SEQ ID NO:16) Deleted portion of orf70 (US4) in the wild-type ab4 (Genbank accession number AY665713.1) genome sequence:nt 127681-128482
  (SEQ ID NO:17) Deleted portion of orf70 (US4) in the RacH genome sequence (no nt numbers available because complete genome sequence not known)
  (SEQ ID NO:18) Sequence of UL43 of RacH
  (SEQ ID NO:19) Sequence of the upstream recombination region Up UL43
  (SEQ ID NO:20) Sequence of the downstream recombination region Up UL44
  (SEQ ID NO:21) Sequence of the deleted portion of UL43 in RacH
  (SEQ ID NO:22) Sequence of the retained 3' end of UL43 in RacH
  (SEQ ID NO:23) Sequence of UL43 in wt EHV-1 V592 (nt 23021-24226 reverse complementary)
  (SEQ ID NO:24) Deleted portion (870 bp) of UL43 in wt EHV-1 V592 (nt 23353-24226 reverse complementary)
  (SEQ ID NO:25) Retained portion of the UL43 reading frame in wt EHV-1 V592 (nt 23021-23354 reverse complementary)
  (SEQ ID NO:26) Sequence of the corresponding upstream recombination region Up UL43 in wt EHV-1 V592 (nt 24227-24452 reverse
  (SEQ ID NO:27) Sequence of the corresponding downstream recombination region Up UL44 in wt EHV-1 V592 (nt 23049-23354 reverse complementary) Plasmid sequences
  (SEQ ID NO:28) Nucleotide sequence of transfer vector pU70-p455-71K71
  (SEQ ID NO:29) Nucleotide sequence of transfer plasmid pU70-p455-H3-71K71
  (SEQ ID NO:30) Nucleotide sequence of transfer vector pU-1-3-p430-BGHKBGH
  (SEQ ID NO:31) Nucleotide sequence of transfer plasmid pU1-3-p430-H1av-BGHKBGH
  (SEQ ID NO:32) Nucleotide sequence of transfer plasmid pU70-p455-H1pdm-71K71
  (SEQ ID NO:33) Nucleotide sequence of transfer plasmid pU1-3-p430-H1hu-BGHKBGH
  (SEQ ID NO:34) Nucleotide sequence of transfer vector pUUL43-p422-18K18
  (SEQ ID NO:35) Nucleotide sequence of transfer plasmid pUUL43-p422-mC-18K18
  (SEQ ID NO:36) Nucleotide sequence of transfer plasmid pUUL43-p422-H1pdm-18K18
  (SEQ ID NO:37) Nucleotide sequence of transfer plasmid pUmC70
Primer Sequences
For the orf70/US4 insertion region

```
Forward primer
                                    (SEQ ID NO: 38)
AGGCTCGTGCGCGGATACATCG Reverse primer
                                    (SEQ ID NO: 39)
TTCGGGGCTGTTAGACTCCTCC
```

For the orf1/3/UL56 insertion region

```
Forward primer
                                    (SEQ ID NO: 40)
CCAACTCGCCGCCATGAGACCC Reverse primer
                                    (SEQ ID NO: 41)
AGCGCGCCCCGTACCCAGTGGG
```

For the UL43 insertion region

```
Forward primer
                                    (SEQ ID NO: 42)
CGACGCGCGTCGGAGG Reverse primer
                                    (SEQ ID NO: 43)
GTTATAAACATACCATGCACC
```

Amino Acid Sequences of the Influenza a Virus Hemagglutinins (SEQ ID NO:44) hemagglutinin [Influenza A virus (A/swine/Italy/116114/2010(H1N2))]; GenBank: ADR01746.1 H1pdm (SEQ ID NO:45) hemagglutinin [Influenza A virus (A/swine/Italy/7680/2001(H3N2))]; GenBank: ABS50302.2 H3

(SEQ ID NO:46) hemagglutinin [Influenza A virus virus (A/swine/Gent/132/2005(H1N1))]; GenBank: AFR76623.1 H1av (SEQ ID NO:47) hemagglutinin [Influenza A virus (A/swine/Italy/4675/2003(H1N2))]; GenBank: ADK98476.1*Hihu

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Figure 1:
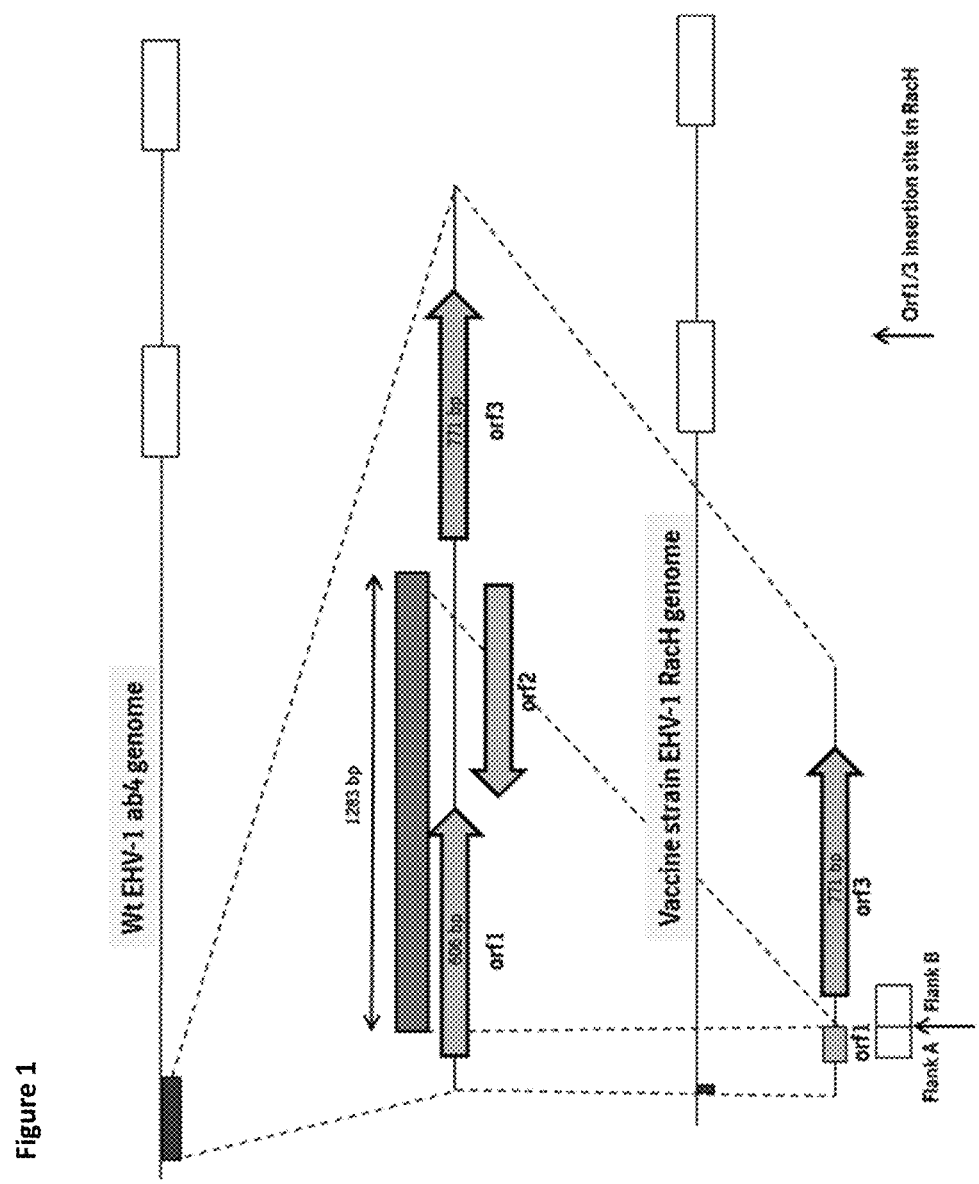
FIG. 1. Schematic illustration comparing the UL56 (orf1/3) regions of wild-type (wt) EHV-1 strain ab4 and attenuated vaccine strain EHV-1 RacH. orf1, orf2, orf3=first three open reading frames in the EHV-1 genome, orf1 has a homolog in other alphaherpesviruses designated UL56
Flank A, Flank B=recombination regions for insertion of transgene expression cassette into the orf1/3 (UL56) site (prior art)
Figure 2:
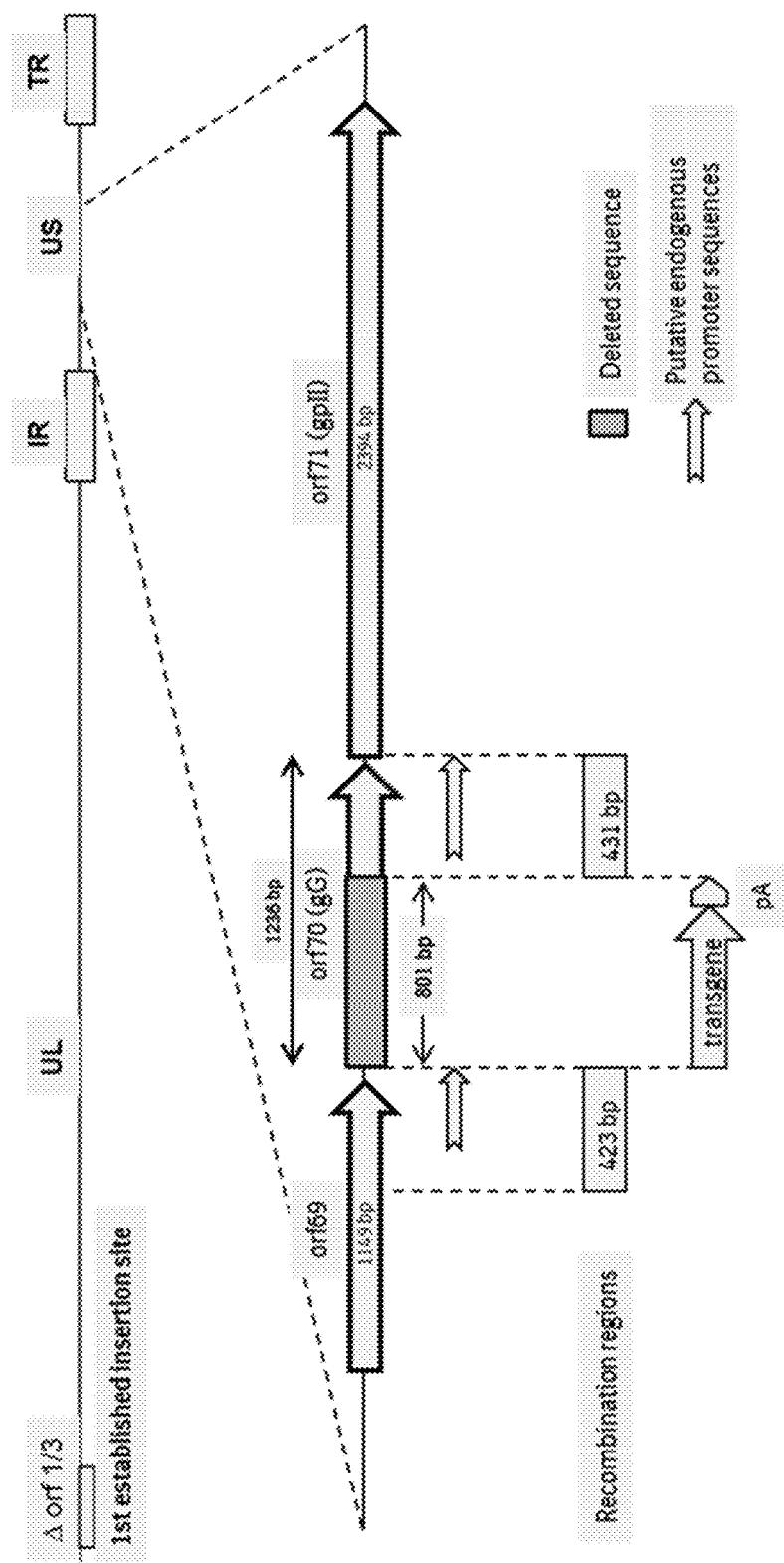
FIG. 2. Schematic drawing of the US4 (orf70) insertion site
UL=long unique segment
US=short unique segment
IR=inner inverted repeat
TR=terminal inverted repeat
gG=glycoprotein G
pA=polyadenylation sequence at the termination of a coding sequence
gpII=glycoprotein II
orf=open reading frame orf69, orf70, orf71=US3, US4, US5 (open reading frames relevant for the orf70/US4 insertion site)
Δorf1/3=orf1/3 (UL56) insertion site (prior art)
bp=base pairs FIG. 3. Plasmid map of transfer plasmid pU-p455-H3-71K71 H3=open reading frame encoding for Influenza A virus hemagglutinin H3
71 pA=new polyA sequence as described in invention disclosure EM P2016-022
I-SceI=cleavage site for the restriction endonuclease I-SceI promoter aph=prokaryotic Kanamycin resistance gene promoter
Kana=Kanamycine resistance gene
3' end ORF70=recombination region downstream of insertion site
ORI=origin of replication of the plasmid
AP$_r$=Ampicillin resistence gene of the plasmid
upstream orf70=recombination region upstream of insertion site
p455=new promoter p455
bp=base pairs FIG. 4. Plasmid map of transfer vector pU1-3-p430-H1av-BGHKBGH H1av=open reading frame encoding for Influenza A virus hemagglutinin H1av
BGHpA=polyA sequence of the bovine growth hormone gene
I-SceI=cleavage site for the restriction endonuclease I-SceI promoter aph=prokaryotic Kanamycin resistance gene promoter
Kana=Kanamycine resistance gene
Flank A=recombination region upstream of insertion site
ORI=origin of replication of the plasmid
AP$_r$=Ampicillin resistence gene of the plasmid
Flank B=recombination region downstream of insertion site
p430=new promoter p430
bp=base pairs FIG. 5. Schematic illustration of the genome of rEHV-1 RacH-SE-70-p455-H3 with the US4 (orf70) insertion region enlarged orf69/US3: open reading frame number 69(US3) upstream of the insertion site in orf70 (US4)
p455: new promoter described herein
H3: transgene Influenza Virus hemagglutinin
71 pA: new polyadenylation sequence
Δorf70 (US4): remainder of orf70 (US4) containing the promoter for orf71 (US5), which encodes the structural viral glycoprotein II (gpII)
bp=base pairs FIG. 6. Schematic illustration of the genome of rEHV-1 RacH-SE-1/3-p430-H1av with the UL56 (orf1/3) insertion region enlarged.
p430: new promoter described herein
H1av: transgene Influenza Virus hemagglutinin
BGHpA: bovine growth hormone polyadenylation sequence
Δorf1/UL56: remainder of orf1 (UL56)
Orf3: EHV-1 open reading frame orf3 (no homolog in other alphaherpesviridae)
bp=base pairs FIG. 7. Schematic illustration of the genome of rEHV-1 RacH-SE-1/3-p430-H1av-70-p455-H3 (rEHV-1-RacH-SE B) with the two insertion regions enlarged.
p430: new promoter described herein
H1av: transgene Influenza Virus hemagglutinin
BGHpA: bovine growth hormone polyadenylation sequence
Δorf1/UL56: remainder of orf1 (UL56)
Orf3: EHV-1 open reading frame orf3 (no homolog in other alphaherpesviridae)
orf69/US3: open reading frame number 69(US3) upstream of the insertion site in orf70 (US4)
p455: new promoter described herein
H3: transgene Influenza Virus hemagglutinin
71 pA: new polyadenylation sequence
Δorf70 (US4): remainder of orf70 (US4) containing the promoter for orf71 (US5), which encodes the structural viral glycoprotein II (gpII)
bp=base pairs FIG. 8. Plasmid map of transfer plasmid pU1/3-p430-H1hu-BGHKBGH p430=new promoter p430
H1hu=open reading frame encoding for Influenza A virus hemagglutinin H1hu
BGHpA=polyA sequence of the bovine growth hormone gene
I-SceI=cleavage site for the restriction endonuclease I-SceI promoter aph=prokaryotic Kanamycin resistance gene promoter
Kana=Kanamycine resistance gene
Flank A=recombination region upstream of insertion site
ORI=origin of replication of the plasmid
Flank B=recombination region downstream of insertion site
I-Ceu=homing endonuclease for release of fragment for RED recombination
bp=base pairs FIG. 9. Plasmid map of transfer plasmid pU70-p455-H1pdm-71K71 upstream orf 70=recombination sequence upstream of insertion site p455=new promoter described herein
H1pdm=transgene Influenza Virus hemagglutinin H1pdm
71 pA=new polyadenylation sequence
3' end orf70=recombination sequence downstream of insertion site
promoter aph=prokaryotic Kanamycin resistance gene promoter
Kana=Kanamycine resistance gene
bp=base pairs
ScaI, EcoRI, SalI, NotI, KpnI, BamHI, XbaI=restriction endonuclease cleavage sites FIG. 10. Schematic illustration of the genome of rEHV-1 RacH-SE-70-p455-H1pdm with the US4 (orf70) insertion region enlarged.
orf69/US3=open reading frame number 69 (US3) upstream of the insertion site in orf70 (US4)
p455=new promoter described herein
H1pdm=transgene Influenza Virus hemagglutinin H1pdm
71 pA=new polyadenylation sequence
Δorf70 (US4): remainder of orf70 (US4) containing the promoter for orf71 (US5), which encodes the structural viral glycoprotein II (gpII)
bp=base pairs FIG. 11. Schematic illustration of the genome of rEHV-1 RacH-SE-1/3-p430-H1hu with the UL56 (orf1/3) insertion region enlarged.
p430=new promoter described herein
H1hu=transgene Influenza Virus hemagglutinin H1hu
BGHpA=bovine growth hormone polyadenylation sequence
Δorf1/UL56=remainder of orf1 (UL56)
Orf3=EHV-1 open reading frame orf3 (no homolog in other alphaherpesviridae)
bp=base pairs FIG. 12. Schematic illustration of the genome of rEHV-1 RacH-SE-1/3-p430-H1hu-70-p455-H1pdm (virus D) with the insertion regions enlarged.
p430=new promoter described herein
H1hu=transgene Influenza Virus hemagglutinin H1hu
BGHpA=bovine growth hormone polyadenylation sequence
Δorf1/UL56=remainder of orf1 (UL56)
Orf3=EHV-1 open reading frame orf3 (no homolog in other alphaherpesviridae)
orf69/US3=open reading frame number 69(US3) upstream of the insertion site in orf70 (US4)
p455=new promoter described herein
H1pdm=transgene Influenza Virus hemagglutinin H1pdm
71 pA=new polyadenylation sequence
Δorf70 (US4)=remainder of orf70 (US4) containing the promoter for orf71 (US5), which encodes
the structural viral glycoprotein II (gpII)
bp=base pairs FIG. 13. Schematic illustration of the construction of the new transgene insertion site UL43
UL44, UL43, UL42 open reading frames in the insertion region
18 pA: new polyadenylation site
422 promoter: new p422 promoter
bp: basepairs FIG. 14. Plasmid map of transfer plasmid pUUL43-422-mC-18K18
UpUL43=viral genomic DNA sequence flanking the insertion site upstream
UpUL44=viral genomic DNA sequence flanking the insertion site downstream
422promoter=promoter driving expression of transgene
mC=transgene (autofluorescent protein mCherry)
18 pA=new polyadenylation sequence
I-SceI=cleavage site for I-SceI
promoter aph=prokaryotic promoter driving expression of Kanamycin-resistence gene
Kana=Kanamycine resistance orf
P(BLA)=prokaryotic promoter driving expression of Ampicillin-resistence gene
AP(R)=Ampicillin-resistance gene
ORI=plasmid origin of replication
P(LAC)=prokaryotic promoter of lacZ encoding Betagalactosidase
I-Ceu=recognition site of the homing endocuclease I-Ceu FIG. 15. Schematic illustration of the genome of rEHV-1 RacH-SE-UL43-422-mC with the UL43 insertion region enlarged
UL=Unique long segment of the EHV genome
US=Unique short segment of the EHV genome
IRS and TRS=Inner and terminal repeat regions framing the unique short segment
UL44, UL43, UL42=open reading frames in the insertion region
ΔUL43=remainder of UL43
18 pA=new polyadenylation site
p422=new p422 promoter
bp=basepairs FIG. 16. Plasmid map of transfer plasmid pUUL43-422-H1pdm-18K18
UpUL43=viral genomic DNA sequence flanking the insertion site upstream
UpUL44=viral genomic DNA sequence flanking the insertion site downstream
422promoter=promoter driving expression of transgene
H1pdm=transgene (Influenza A hemagglutinin H1pdm)
18 pA=new polyadenylation sequence
I-SceI=cleavage site for I-SceI
promoter aph=prokaryotic promoter driving expression of Kanamycin-resistence gene
Kana=Kanamycine resistance orf
P(BLA)=prokaryotic promoter driving expression of Ampicillin-resistence gene
AP(R)=Ampicillin-resistance gene
ORI=plasmid origin of replication
P(LAC)=prokaryotic promoter of lacZ encoding Betagalactosidase
I-Ceu=recognition site of the homing endocuclease I-Ceu FIG. 17. Schematic illustration of the genome of rEHV-1 RacH-SE-UL43-422-H1pdm with the UL43 insertion region enlarged
UL=Unique long segment of the EHV genome
US=Unique short segment of the EHV genome
IRS and TRS=Inner and terminal repeat regions framing the unique short segment
UL44, UL43, UL42=open reading frames in the insertion region
ΔUL43=remainder of UL43
18 pA=new polyadenylation site
H1pdm=transgene (Influenza A hemagglutinin H1pdm)
p422=new p422 promoter
bp=basepairs FIG. 18. Schematic illustration of the genome of rEHV-1 RacH-SE-1/3-p430-H1av-UL43-422-H1pdm-70-p455-H3 with insertion regions enlarged
Δorf1/UL56: remainder of UL56 at the boundary of the expression cassette
p430: new promoter p430
BGHpA: bovine growth hormone polyadenylation site
H1av, H3, H1pdm: transgenes (Influenza A hemagglutinins)

Δorf70/US4: remainder of US4 at the boundary of the expression cassette
orf69 (US3) and orf71 (US5) open reading frames in the US4 insertion region
71 pA: new polyadenylation sequence
UL44, UL43, UL42 open reading frames in the UL43 insertion region
18 pA: new polyadenylation site
p422: new p422 promoter
bp: basepairs
FIG. 19. Western blot
Quadruplicate blots incubated with four different antibodies
a: Blot incubated with a proprietary monoclonal antibody against Influenza HA H1av
b: Blot incubated with a commercial rabbit antiserum specific for Influenza HA H3
c: Blot incubated with a proprietary monoclonal antibody against Influenza HA H1pdm
d: Blot incubated with a proprietary monoclonal antibody against EHV-1 gpII M = molecular weight marker (kDa = kilodalton, 250, 150, 100, 75, 50, 37, 25, 20)

| Virus name | Abbreviation | Used insertion sites | Expressed transgenes |
|---|---|---|---|
| rEHV-1 RacH-SE-70-p455-H3 | US4-H3 | US4 | H3 |
| rEHV-1 RacH-SE-1/3-p430-H1av | UL56-H1av | UL56 | H1av |
| rEHV-1 RacH-SE-70-p455-H1pdm | US4-H1pdm | US4 | H1pdm |
| rEHV-1 RacH-SE-1/3-p430-H1hu | UL56-H1hu | UL56 | H1hu |
| rEHV-1 RacH-SE-1/3-p430-H1av-70-455-H3 | B | US4 and UL56 | H3 and H1av |
| rEHV-1 RacH-SE-1/3-p430-H1hu-70-455-H1pdm | D | US4 and UL56 | H1pdm and H1hu |
| rEHV-1 RacH-SE-UL43-H1pdm | UL43-H1pdm | UL43 | H1pdm |
| rEHV-1 RacH-SE-1/3-p430-H1av-UL43-422-H1pdm70-455-H3 | E | US4 and UL56 and UL43 | H3, H1av, and H1pdm |
| rEHV-1 RacH-SE | SE | none | none | promoter aph=prokaryotic promoter driving expression of Kanamycin-resistence gene Kana=Kanamycine resistance orf P(BLA)=prokaryotic promoter driving expression of Ampicillin-resistence gene AP(R)=Ampicillin-resistance gene ORI=plasmid origin of replication P(LAC)=prokaryotic promoter of lacZ encoding Betagalactosidase I-Ceu=recognition site of the homing endocuclease I-Ceu KpnI, NotI, XbaI=restriction endonuclease cleavage sites bp=base pairs FIG. 23: Plasmid map of transfer vector pU1/3-p430-BGHKBGH Flank A=viral genomic DNA sequence flanking the insertion site upstream Flank B=viral genomic DNA sequence flanking the insertion site downstream 4pgG430=promoter driving expression of transgene BGHpA=polyadenylation sequence of the bovine growth hormone gene FIG. 20: Results of Influenza A virus neutralization tests of mice sera. Virus neutralization tests were done in duplicate or triplicate depending on the available amounts of mouses sera. Neutralization titres were normalized to 100 TCID50 and shown as reciprocal neutralization capacities. *Error bars indicate standard deviation.

FIG. 21: Plasmid map of transfer plasmid pUmC70

3' end orf69=portion of orf69(US3) contained in the transfer vector up70=recombination sequence upstream of insertion site mCherry=transgene (autofluorescent protein mCherry)

BGHpA=bovine growth hormone polyadenylation sequence up71=recombination sequence downstream of insertion site 3' end orf70=remainder of orf70 (US4) downstream of insert bp=base pairs ScaI, EcoRI, SalI, NotI, KpnI, BamHI, XbaI=restriction endonuclease cleavage sites FIG. 22: Plasmid map of transfer vector pU70-p455-71K71

Up70=viral genomic DNA sequence flanking the insertion site upstream

Up71=viral genomic DNA sequence flanking the insertion site downstream

4pMCP455=promoter driving expression of transgene

EHV-4orf71pApA=new polyadenylation sequence 71 pA

I-Sce1=cleavage site for I-Sce1

I-Sce1=cleavage site for I-Sce1 promoter aph=prokaryotic promoter driving expression of Kanamycin-resistence gene Kana=Kanamycine resistance orf I-Ceu=recognition site of the homing endocuclease I-Ceu KpnI, NotI=restriction endonuclease cleavage sites bp=base pairs FIG. 24: Plasmid map of transfer plasmid pUUL43-422-H1pdm-18K18

UpUL43=viral genomic DNA sequence flanking the insertion site upstream

UpUL44=viral genomic DNA sequence flanking the insertion site downstream p422=promoter driving expression of transgene 18 pA=new polyadenylation sequence I-Sce1=cleavage site for I-Sce1 promoter aph=prokaryotic promoter driving expression of Kanamycin-resistence gene Kana=Kanamycine resistance orf P(BLA)=prokaryotic promoter driving expression of Ampicillin-resistence gene AP(R)=Ampicillin-resistance gene ORI=plasmid origin of replication P(LAC)=prokaryotic promoter of lacZ encoding Betagalactosidase I-Ceu=recognition site of the homing endocuclease I-Ceu bp=base pairs

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Establishment of the New Insertion Site ORF70/US4

In order to augment the capabilities of the EHV-1 vector the inventors sought to find a way to express two different transgenes from one vector backbone without coupling two transgenes by RNA-virus-derived functions under control of one promoter. The inventors hypothesized that the herpesvirus genome would tolerate the use of two independent transgene insertion sites in parallel. To determine whether the EHV-1 ORF70/US4 was a suitable transgene insertion site, 801 basepairs of the 5' end of orf70/US4 (1236 bp) were replaced with an expression cassette coding for the autofluorescent mCherry protein (Shaner et al. 2004) by classical homologous recombination. A map of the plasmid pU-mC70-BGH is in FIG. 21 (SEQUENCE ID NO:37). The DNA fragment used for homologous recombination was excised from pU-mC70-BGH with XbaI. The gel-purified fragment was co-transfected with viral genomic DNA of EHV-1 RacH into RK13 cells. Efficient rescue of recombinant vector virus and efficient replication in cultured cells were shown by live fluorescence and virus titrations (not shown). Deletion of two thirds of orf70/US4 had the additional benefit that expression of glycoprotein G encoded by orf70/US4 was abolished. Glycoprotein G of EHV-1 was shown to be a non-structural, secreted chemokine binding protein counter-acting the host's immune response (Drummer et al., 1998; Bryant et al., 2003). Since a vector vaccine is intended to stimulate the vaccinee's immune response, removal of this particular immunosuppressive function of the viral vector might additionally improve performance of the viral vector platform EHV-1 RacH-SE.

Example 2

Use of the New ORF70/US4 Insertion Site with p455 Promoter in Recombinant EHV-1 Vector Vaccines and Construction of a Recombinant Virus The p455 promoter:
For a first animal experiment an Influenza hemagglutinin subtype H3 from a swine origin Influenza A virus (A/swine/Italy/7680/2001(H3N2), GenBank accession NO:ABS50302.2) was used. Its coding sequence was synthesized and subcloned in the transfer vector pU70-p455-71K71 (SEQ ID NO:28) generating the transfer plasmid pU70-p455-H3-71K71, placing H3 under control of the new p455 promoter and the new 71 pA polyadenylation signal and framing the cassette with the recombination regions for insertion into orf70 (FIG. 3, SEQ ID NO:29).

By en-passant mutagenesis using the RED recombination system (Tischer et al. 2006) the expression cassette p455-H3-71 was inserted in orf70/US4 of pRacH-SE to generate pRacH-SE70-p455-H3.

Figure 5:
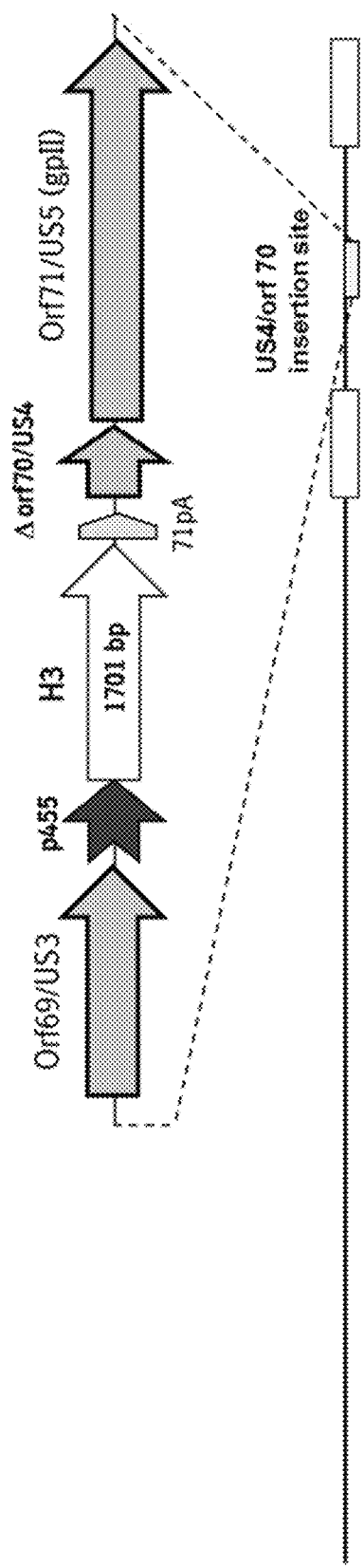

PK/WRL cells were transfected with pRacH-SE70-p455-H3, recombinant virus rEHV-1 RacH-SE70-p455-H3 (FIG. 5) was rescued and plaque-purified twice. Correct insertion of the expression cassette was verified by sequencing of a high-fidelity PCR product of the insertion region. Expression of the transgene in infected cells was analyzed by indirect immunofluorescence assay.

Restoration of orf71 encoding EHV-1 gpII was confirmed by IFA (not shown) and Western blot (FIG. 19) using a monoclonal antibody Ai2G7 (owned by BI). Appearance of trimers of H3 on the plasma membrane of infected cells was assayed by a hemadsorption test using chicken erythrozytes (not shown). Peak titers determined as $TCID_{50}$/ml in PK/WRL cells were in the same range as titers of the parental virus rEHV-1 RacH-SE which indicates that transgene expression had no detrimental effect on viral replication (not shown). This was confirmed by passaging of rEHV-1 RacH-SE70-p455-H3 in PK/WRL cells up to passage 20 (P20) after rescue. At P5, P10, P15, and P20 the virus was characterized by titration, sequencing, and Western blot, at P10 and P20 additionally by IFA, and HA expression and genetic stability of the HA encoding insert along with the promoter and polyA sequences were confirmed.

By double immunofluorescence assay (dIFA) of viral plaques in cells infected with P20 using a monoclonal anti-H3 antibody and a horse anti-EHV antiserum, it was confirmed that virtually all EHV-1 induced plaques also express H3 (not shown). All tests confirmed stability of the recombinant EHV-1 RacH-SE-70-p455-H3.

Example 3

Use of the New p430 Promoter in Recombinant EHV-1 Vector Vaccines and Construction of a Recombinant Virus The p430 promoter:
The newly identified p430 promoter was used to drive expression of another Influenza hemagglutinin from an H1N1 virus ((A/swine/Gent/132/2005(H1N1), GenBank accession NO:AFR76623.1). Since the hemagglutinin gene in this virus isolate originated from an avian IAV it will be referred to as H1av. H1av was synthesized and subcloned in a transfer vector pU1/3-p430-BGHKBGH (SEQ ID NO:30) for the orf1/3/UL56 insertion region to generate pU1/3-p430-H1av-BGH_K_BGH (FIG. 4, SEQ ID NO:31). Expression of H1av was placed under control of the p430 promoter and the bovine growth hormone (BGH) polyA signal.

By en-passant mutagenesis using the RED recombination system (Tischer et al. 2006) the expression cassette p430-H1av-BGH was inserted in orf1/3/UL56 of pRacH-SE to generate pRacH-SE1/3-p430-H1av.

Figure 6:
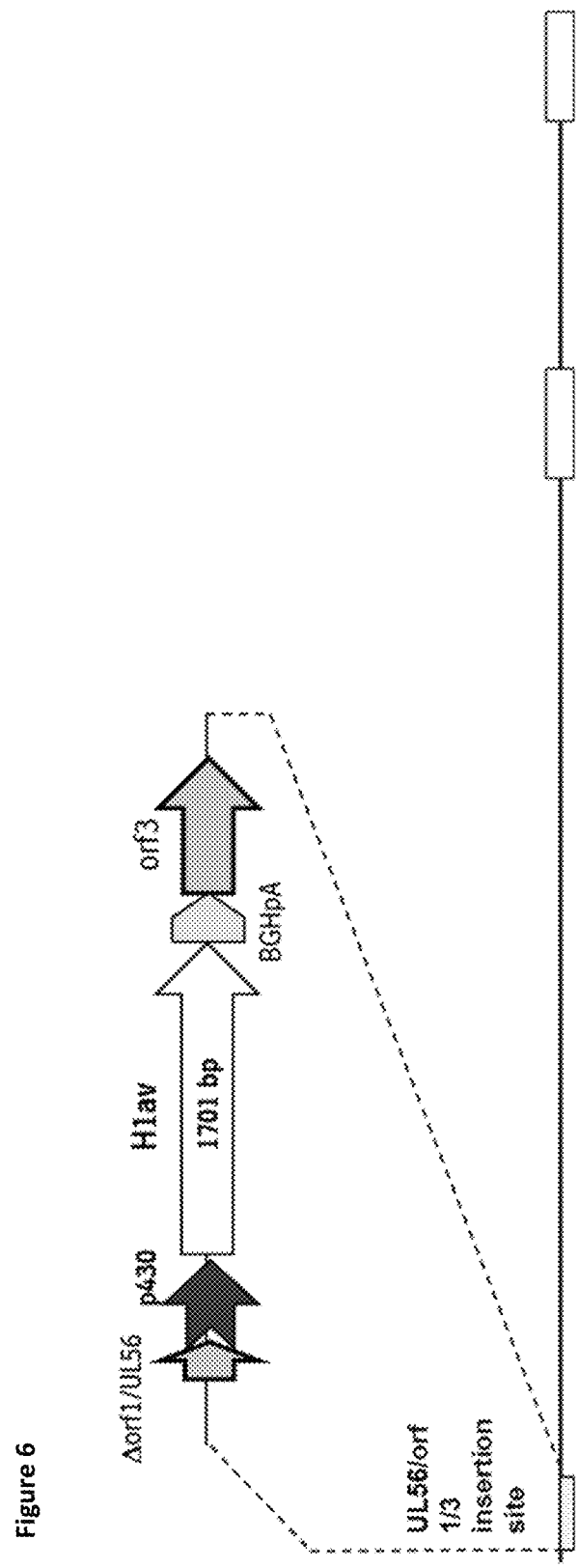

PK/WRL cells were transfected with pRacH-SE1/3-p430-H1av, recombinant virus rEHV-1 RacH-SE1/3-p430-H1av (FIG. 6) was rescued and plaque-purified twice. Correct insertion of the expression cassette was verified by sequencing of a high-fidelity PCR product of the insertion region. Expression of the transgene in infected cells was analyzed by indirect immunofluorescence assay (IFA) and Western blot using monoclonal and polyclonal antibodies (FIG. 19). Specific detection of a broad band migrating at 75 kDa by antibody PA-34929 is in concordance with the expected appearance of the recombinant HA glycoprotein as predicted from its sequence.

Restoration of orf71/US5 encoding EHV-1 gpII was confirmed by IFA and Western blot using a monoclonal antibody Ai2G7 (owned by BI), (FIG. 19). Peak titers determined as TCID50/ml in PK/WRL cells were in the same range as titers of the parental virus RacH-SE which indicates that transgene expression had no detrimental effect on viral replication (not shown).

In order to test whether the expressed recombinant hemagglutinins were processed and transported as expected, VERO-cells were infected with rEHV-1 RacH-SE-1/3-p430-H1av, rEHV-1 RacH-SE-70-p455-H3, rEHV-1 RacH-SE (parent) at an m.o.i. of 0.01, or left uninfected. 24 h p.i. live infected and uninfected cells were incubated with a suspension of chicken erythrocytes in PBS, washed with PBS and stained with the fluorescent Hoechst 33342 nuclear stain. Since erythrocytes of birds contain cell nuclei they can be stained with Hoechst33342 and appear as tiny blue specks by fluorescence microscopy, Compared with cells that were infected with rEHV-1 RacH-SE that does not express hemagglutinin, adsorption of chicken erythrocytes was significantly increased on cells infected with either rEHV-1 RacH-SE-1/3-p430-H1av or rEHV-1 RacH-SE-70-p455-H3 (not shown). From this it can be concluded that the hemagglutinins were translated, processed and transported to the plasma membrane of vector virus infected cells in a manner as if they were produced by authentic influenza virus infection.

The clear phenotype of hemadsorption of infected cells supports the findings of the Western blots and immunofluorescence assays showing efficient expression of the transgenic proteins and suggesting formation of functional HA trimers on the cell surface of EHV-1 vector infected cells.

Example 4

Use of the New ORF70 Insertion Site and the ORF1/3(UL56) Insertion Site in Recombinant EHV-1 Vector Vaccines in Parallel To show that the two new promoters can be used in parallel a recombinant EHV-1 RacH was generated expressing two different hemagglutinins of two different Influenza A virus subtypes.

Specificity and lack of cross-reactivity of the polyclonal commercial antibody to H3 (PA5-34930) and the proprietary monoclonal antibodies to H1av and H1pdm is obvious from the Western blots of infected cells as shown in FIG. 19. Identical samples were run in quadruplicate SDS-PAGE and transferred to nylon membranes before incubation with four different antibodies.

The open reading frame encoding the hemagglutinin of Influenza A virus (A/swine/Gent/132/2005(H1N1)) was synthesized and cloned into the transfer vector pU1-3-p430-BGHKBGH (SEQ ID NO:30) resulting in pU1-3-p430-H1av-BGHKBGH (FIG. 4, SEQ ID NO:31). Starting with the recombinant BAC pRacH-SE-70-p455-H3, the expression cassette p430-H1av-BGH as assembled in pU1/3-p430-H1av-BGHKBGH (FIG. 4, SEQ ID NO:31) was inserted into the orf1/3/UL56 insertion site by two-step RED recombination to generate pRacH-SE-1/3-p430-Hiav-70-p455-H3. PK/WRL cells were transfected with pRacH-SE1/3-p430-Hav-70-p455-H3, and recombinant virus rEHV-1 RacH-SE1/3-p430-H1av-70-p455-H3 (FIG. 7) was rescued and plaque-purified twice.

The short designation for this recombinant virus is rEHV-1 RacH-SE_B. Correct insertion of the expression cassette was verified by sequencing of high-fidelity PCR products of the insertion regions together with flanking sequences. Expression of the transgenes in infected cells was analyzed by indirect immunofluorescence assay (IFA, not shown) and Western blot using monoclonal and polyclonal antibodies (FIG. 19). Restoration of orf7l/US5 encoding EHV-1 gpII was confirmed by IFA (not shown) and Western blot using a monoclonal antibody Ai2G7 (owned by BI), (FIG. 19).

As shown in FIG. 19 both transgenes H3 and H1av were expressed in parallel in cell cultures infected with the dual insert recombinant rEHV-1 RacH-SE-1/3-p430-Hav-70-p455-H3 (B). Transgene expression was stable and did not impair viral titres tested until passage 11 in AI-ST A1 cells (BI proprietary swine testis cell line, Table 3).

The two new promoters p430 and p455 were shown to be functional in the context of rEHV1-RacH-SE replication in cell cultures. Activity levels during the viral replication cycle appear to be very similar as deduced from comparable intensities of signals in Western blots specific for the individual transgenes. These properties allow creation of recombinant vector vaccines based on EHV-1 RacH or other vector platforms expressing two different antigens in parallel with similar efficiency. If a vaccine target consists of two different pathogens application of the two new promoters in two insertion sites combined with two polyadenylation sequences can reduce cost of goods significantly and represents a clear advantage over a vector expressing only one antigenic component.

Example 5

Generation, In Vitro Characterization and In Vivo Testing of A Bivalent EHV-1 Vectored Influenza a Virus Vaccine As described below, in the described invention two of the four above-described Swine IAV hemagglutinin (HA) antigens derived from H3N2 and H1N1 avian Swine IAV sub-/serotypes are expressed by one recombinant EHV-1 vector virus. This new bivalent vaccine against swine IAV provides a DIVA feature, e.g. by detection of antibodies against Swine IAV proteins NP or NA in animals that were infected by Swine IAV field strains but not in animals only vaccinated with the vaccine described here since it only expresses the Swine IAV HA proteins.

The new bivalent Swine IAV vaccine was characterized in vitro and tested in vivo for its ability to induce Influenza A virus neutralizing antibodies in mice.

In order to test whether the expressed recombinant hemagglutinins were processed and transported as expected, VERO-cells were infected with rEHV-1 RacH-SE-1/3-p430-H1av, rEHV-1 RacH-SE-70-p455-H3, rEHV-1 RacH-SE (parent) at an m.o.i. of 0.01, or left uninfected. 24 h p.i. live infected and uninfected cells were incubated with a suspension of chicken erythrocytes in PBS, washed with PBS and stained with the fluorescent Hoechst 33342 nuclear stain. Since erythrocytes of birds contain cell nuclei they can be stained with Hoechst33342 and appear as tiny blue specks by fluorescence microscopy, compared with cells that were infected with rEHV-1 RacH-SE that does not express hemagglutinin, adsorption of chicken erythrocytes was significantly increased on cells infected with either rEHV-1 RacH-SE-1/3-p430-H1av or rEHV-1 RacH-SE-70-p455-H3 (not shown). From this it can be concluded that the hemagglutinins were translated, processed and transported to the plasma membrane of vector virus infected cells in a manner as if they were produced by authentic influenza virus replication. The phenotype of hemadsorption of infected cells supports the findings of the Western blots (FIG. 19) and immunofluorescence assays (not shown) showing efficient expression of the transgenic proteins and suggesting formation of functional HA trimers on the cell surface of EHV-1 vector infected cells.

The enhanced EHV-1 vector with two insertion sites and two new promoters was shown to express two Influenza virus hemagglutinins in parallel. Subcellular localization as determined by IFA and mobility in SDS-PAGE as determined by Western blot (FIG. 19) corresponded to authentic uncleaved hemagglutinins expressed in Influenza A virus infected cells known from the literature.

Genetic and phenotypic stabilities of the recombinant rEHV-1 were shown by passaging in cell culture, determining viral titres every 5 passages. Sequences of the insertion regions were confirmed every ten passages as well as transgene expression by Western blot (not shown). Expression fidelity was assessed by double IFA of plaques under methocel-overlay, counting plaques stained with anti-EHV-antibodies and transgene-specific antibodies (not shown).

Example 6

Induction of a Neutralizing Antibody Response Against Two Antigens in Mice Vaccinated with a Bivalent rEHV-1 Rach Vector Vaccine The rEHV-1 RacH SE B (rEHV-1 RacH-SE-1/3-p430-H1av-70-p455-H3 see FIG. 7) was used for immunization of Balb/c mice in order to demonstrate that the expressed transgenes are immunogenic in another species than swine and that neutralizing antibodies are induced against either one of the two antigens by intranasal application.

In detail, three groups of five Balb/c mice per group, 3-5 weeks of age, were intranasally inoculated on study days 0 and 21 either with 40 µl of rEHV-1 RacH SE B (rEHV-1 RacH-SE-1/3-430-H1av-7-455-H3, group 1), or 40 µl of empty vector (rEHV-1 RacH-SE, group 2, vector control), or 40 µl of tissue culture medium (group 3 negative control), respectively. For groups 1 and 2, infectious recombinant EHV-1 dosages were $1 \times 10^7$ TCID50/40 µl, respectively. Mice were bled on study days 0 (before $1^{st}$ inoculation), 7, 14, 21 (before $2^{nd}$ inoculation), 28, and 35. Serum was prepared from the blood samples and stored frozen at −80° C.

Immunofluorescence Assay for Detection of Antibodies Against the Vector Virus

AI-ST cells were infected at a multiplicity of infection (MOI) of 0.001 with rEHV-1 RacH-SE1212, a virus rescued from the empty vector BAC pRacH-SE1.2. 24 hours p.i. distinctive plaques were observed and cells were processed for indirect immunofluorescence assay (IFA). Sera of all three groups of the final bleeds (obtained 14 days after the second vaccination) diluted 1:50 in PBS were tested. As positive control serum from an EHV-1 vaccinated horse was used in a dilution of 1:500. Secondary antibodies were commercially available FITC-conjugated rabbit anti-mouse IgG for the mice sera and Cy5-conjugated goat-anti horse IgG for the horse serum and used at 1:200 dilution. Antibody binding was evaluated by fluorescence microscopy. All vaccinated mice had developed antibodies reactive in IFA with rEHV-1 RacH-SE-infected cells. Uninfected cells were not bound by any of the tested sera. Sera from the negative control group of mice did not show any specific binding neither to infected nor to uninfected cells. Data are summarized in the table below.

TABLE 4

Fluorescence microscopy results of IFA for anti-EHV-1 antibodies

| Treatment | Mouse number | ID in experiment | dilution | Uninfected cells | Infected cells |
|---|---|---|---|---|---|
| Group 3 (Negative control) | 1 | 1 | 1:50 | neg | neg |
| | 2 | 2 | 1:50 | neg | neg |
| | 3 | 3 | 1:50 | neg | neg |
| | 4 | 4 | 1:50 | neg | neg |
| | 5 | 5 | 1:50 | neg | neg |
| Group 2 (Empty vector) | 1 | 6 | 1:50 | neg | pos |
| | 2 | 7 | 1:50 | neg | pos |
| | 3 | 8 | 1:50 | neg | pos |
| | 4 | 9 | 1:50 | neg | pos |
| | 5 | 10 | 1:50 | neg | pos |
| Group 1 (rEHV-1 RacH SE B) | 1 | 11 | 1:50 | neg | pos |
| | 2 | 12 | 1:50 | neg | pos |
| | 3 | 13 | 1:50 | neg | pos |
| | 4 | 14 | 1:50 | neg | pos |
| | 5 | 15 | 1:50 | neg | pos |
| Control antibody | Specific for | | | | |
| Horse serum | EHV-1 | 22 | 1:500 | neg | pos |
| Secondary antibodies | Specific for | | | | |
| FITC-goat anti- | mouse | 23 | 1:200 | neg | neg |
| Cy5 goat anti- | horse | 24 | 1:200 | neg | neg |

From this it can be concluded that inoculation of the rEHV-1 into the nostrils of the mice resulted in infection and viral replication, so that the mice immune systems were stimulated to produce anti-EHV-1 antibodies.

Virus Neutralization Tests (VNT)

In order to show induction of protective immunity against the expressed transgenes originating either from Influenza A virus (IAV) (A/swine/Italy/7680/2001(H3N2)) or (A/swine/Gent/132/2005(H1N1)) the mice sera were tested for neutralizing activity against the respective viruses (Allwinn et al. 2010; Trombetta et al. 2014). IAV used for neutralization tests were isolates from pigs in Germany from 2014, specifically A/swine/Germany/AR452/2014 (H3N2) and A/swine/Germany/AR1181/2014 (H1N1). As these are heterologous from the strains the vaccine targets were derived from, any neutralization of these viruses by the mouse sera will be indicative of broad and efficient induction of protective immunity by the rEHV-1 vaccination. As a negative control serum, a serum from a pig which had been shown to be negative for Influenza virus antibodies was used.

Influenza a Virus Neutralization Tests:

MDCK cells for virus neutralization as well as backtitration in 96-well plates were incubated for two days at 37° C./5% $CO_2$ prior to use. The respective IAV stocks H3N2 and H1avN1 were thawed on ice and diluted in MEM containing Gentamycin and the double concentration of trypsin (MEM/Genta/2× trypsin).

Sera tested were from the final bleeds of group 1 (rEHV-1 RacH SE B), group 2 (empty vector), a positive control (serum from a pig vaccinated with inactivated multivalent IAV vaccine, and a negative control.

Sera were heat inactivated and in two and three independent tests, respectively, serially 1:2 diluted starting at 1:16 up to 1:4096. IAV was diluted to approximately 100 TCID50/neutralization reaction. Neutralization reactions were incubated for 2 hours at 37° C., 5% $CO_2$. Back-titration of used virus was done in quadruplicate. Growth medium was removed and MDCK-cells were washed with medium containing Gentamycin and trypsin before adding the neutralization reactions or the virus dilutions of the back-titrations. VNT and titration plates were incubated at 37° C./5% $CO_2$ for 1 h after addition of neutralization reaction or virus dilutions to the MDCK-cells, respectively. Thereafter inocula were removed and cells were overlaid with fresh medium containing Gentamycin and trypsin. Five days p.i. CPE was monitored and documented. Actually used virus titre in the test was calculated as TCID50/ml according to Reed and Münch and dilutions at which the tested sera prevented induction of Influenza virus-typical CPE were reported, see tables below.

TABLE 5

Results Influenza H1avN1 VNT

| | H1avN1 | | | | | | | |
|---|---|---|---|---|---|---|---|---|
| | VNT#1 | | VNT#2 | | VNT#3 | | | |
| | 146 TCID50/well | | 32 TCID50/well | | 181 TCID50/well | | | |
| mouse | Reciprocal neutralizing dilution | capacity | Reciprocal neutralizing dilution | capacity | Reciprocal neutralizing dilution | capacity | Average neutralizing capacity | SD (standard deviation) |
| rEHV-1 RacH SE B-1 | 32 | 4672 | 128 | 4096 | 32 | 5792 | 4853 | 862 |
| rEHV-1 RacH SE B-2 | 16 | 2336 | 64 | 2048 | neg | | 2192 | 204 |
| rEHV-1 RacH SE B-3 | 32 | 4672 | 128 | 4096 | 16 | 2896 | 3888 | 906 |
| rEHV-1 RacH SE B-4 | 128 | 18688 | 512 | 16384 | 64 | 11584 | 15552 | 3624 |
| rEHV-1 RacH SE B-5 | 32 | 4672 | 256 | 8192 | 16 | 2896 | 5253 | 2695 |
| Empty vector-1 | n.d. | n/a | neg | n/a | neg | n/a | n/a | n/a |
| Empty vector-2 | n.d. | n/a | neg | n/a | neg | n/a | n/a | n/a |
| Empty vector-3 | n.d. | n/a | neg | n/a | neg | n/a | n/a | n/a |
| Empty vector-4 | neg | n/a | neg | n/a | neg | n/a | n/a | n/a |
| Empty vector-5 | n.d. | n/a | neg | n/a | neg | n/a | n/a | n/a |
| Pos control pig serum | 32 | n/a | n.d | n/a | n.d | n/a | n/a | n/a |

TABLE 6

Results Influenza H3N2 VNT

| | H3N2 | | | | | | | |
|---|---|---|---|---|---|---|---|---|
| | VNT#1 | | VNT#2 | | VNT#3 | | | |
| | 16 TCID50/well | | 24 TCID50/well | | 15 TCID50/well | | | |
| mouse | Reciprocal neutralizing dilution | capacity | Reciprocal neutralizing dilution | capacity | Reciprocal neutralizing dilution | capacity | Average neutralizing capacity | SD (standard deviation) |
| rEHV-1 RacH SE B-1 | 4096 | 65536 | 1024 | 24576 | 2048 | 30720 | 40277 | 22089 |

TABLE 6-continued

Results Influenza H3N2 VNT

| | H3N2 | | | | | | | |
|---|---|---|---|---|---|---|---|---|
| | VNT#1 | | VNT#2 | | VNT#3 | | | |
| | 16 TCID50/ well Reciprocal neutralizing | | 24 TCID50/ well Reciprocal neutralizing | | 15 TCID50/ well Reciprocal neutralizing | | Average neutralizing | SD (standard |
| mouse | dilution | capacity | dilution | capacity | dilution | capacity | capacity | deviation) |
| rEHV-1 RacH SE B-2 | 1024 | 16384 | 512 | 12288 | 128 | 1920 | 10197 | 7455 |
| rEHV-1 RacH SE B-3 | 1024 | 16384 | 512 | 12288 | 256 | 3840 | 10837 | 6397 |
| rEHV-1 RacH SE B-4 | 256 | 4096 | 256 | 6144 | 64 | 960 | 3733 | 2611 |
| rEHV-1 RacH SE B-5 | 256 | 4096 | 128 | 3072 | 64 | 960 | 2709 | 1599 |
| Empty vector-1 | neg | n/a | neg | n/a | neg | n/a | n/a | n/a |
| Empty vector-2 | neg | n/a | neg | n/a | neg | n/a | n/a | n/a |
| Empty vector-3 | neg | n/a | neg | n/a | neg | n/a | n/a | n/a |

In order to compare results of independent tests neutralizing capacity was calculated by multiplication of the reciprocal serum dilution and the respective titre that was neutralized by it. Averages of three tests were then divided by 100 to reflect neutralization of 100 TCID50 (Tables 4, 5, and 6). Data are summarized and shown graphically in FIG. 20.

All mice vaccinated with rEHV-1 RacH SE Bhad developed neutralizing antibodies against the respective IAV, heterologous strains of subtypes H3N2 and H1avN1. Thus, twofold intranasal application of rEHV-1 RacH-SE expressing hemagglutinins of IAV from the orf70 insertion site under control of the p455 promoter (H3) and in parallel from the orf1/3 insertion site under control of the p430 promoter (H1av), successfully stimulated protective immune response in BALB/c mice.

It can be concluded that the vector rEHV-1 RacH-SE can be used for parallel expression of two different transgenes to stimulate immune response after intranasal vaccination.

Western Blot

1. Infection: Three wells each of confluent monolayers of AI-ST cells in 6-well plates were infected at an M.O.I. of approximately 1 with recombinant viruses by directly adding 10 µl of thawed virus stocks to the growth medium. Three wells were left uninfected. Infected and uninfected cells were incubated for two days and then processed for Western blot. Viruses used for infection are summarized in the table below (Table 2)

TABLE 2

Viruses tested in Western blot

| Virus name | Abbreviation | Used insertion sites | Expressed transgenes |
|---|---|---|---|
| rEHV-1 RacH-SE-70-p455-H3 | H3 | US4 | H3 |
| rEHV-1 RacH-SE-1/3-p430-H1av | av | UL56 | H1av |
| rEHV-1 RacH-SE-70-p455-H1pdm | 4p | US4 | H1pdm |
| rEHV-1 RacH-SE-1/3-p430-H1hu | hu | UL56 | H1hu |
| rEHV-1 RacH-SE-1/3-p430-H1av-70-455-H3 | B | US4 and UL56 | H3 and H1av |
| rEHV-1 RacH-SE-1/3-p430-H1hu-70-455-H1pdm | D | US4 and UL56 | H1pdm and H1hu |
| rEHV-1 RacH-SE-UL43-H1pdm | 43p | UL43 | H1pdm |
| rEHV-1 RacH-SE-1/3-p430-H1av-UL43-422-H1pdm70-455-H3 | E | US4 and UL56 and UL43 | H3, H1av, and H1pdm |
| rEHV-1 RacH-SE | SE | none | none |

2. Preparation of lysates: RIPA buffer supplemented with protease inhibitor cocktail (RIPA+PI) was prepared as follows: 0.7 ml 10×RIPA lysis buffer Millipore Cat #20-188 were added to 6.3 ml H$_2$O, Fisher Scientific Cat #BP2470-1, and 1 tablet Complete™ Mini Protease inhibitor cocktail (Roche cat #11 836 153 001) was dissolved in 7 ml 1×RIPA buffer. Uninfected controls were scraped into the medium and suspensions from the three replicate wells were pooled in 15 ml centrifuge tubes and placed on ice. Infected cells were rinsed off in the medium and the suspensions from the three replicate wells were pooled in 15 ml centrifuge tubes and placed on ice. Cells were sedimented by centrifugation at 1000×g 4° C. for 5 min. Supernatants were carefully aspirated and the cell pellets were resuspended in RIPA+PI (Uninfected cells in 300 µl, infected cells in 150 µl). Suspensions were incubated on ice for 30 min and vortexed every 10 min. Suspensions were transferred to 1.5 ml microfuge tubes and undissolved material was sedimented by centrifugation at 15000 rpm, 4° C., for 10 min in a microcentrifuge. Clear supernatants were transferred to new 1.5 ml microfuge tubes and stored at −80° C. until use.

3. SDS-PAGE and transfer on nylon membranes: Materials: BioRad Criterion TGX Stain Free Precast Gels, 4-20%, 26 well Cat #_567-8095; Bio Rad Precision Plus Dual Colour Marker, Cat #161-0374; Bio Rad Precision Plus All Blue Marker, Cat #161-0373; Bio Rad Trans Blot Turbo transfer kit, Midi format Cat #170-4159; Bio Rad 4× Laemmli Sample Buffer (Cat no. 161-0747) (Bio Rad Laboratories GmbH, Heidemannstrasse 164, D-80939 Mnchen); TGS Running buffer (Sambrook et al.), Blocking Solution 1: 5% FBS in PBST (Sambrook et al.); PBST. Samples were prepared without addition of a reducing agent. Samples were thawed on ice and mixed with 1 volume of 4× Lämmli buffer, boiled for 6 min at 96° C., and kept at RT until loading of the gel. Gel was run for 30 min at 230 mA and then assembled for electrotransfer using the BioRad Trans Blot Turbo system. Transfer was set to 2.5 A 25 V 10 min. Membrane was rinsed in sterile distilled H$_2$O and incubated with 25 mL Blocking Solution 5% FBS in PBST for 30 min at 4° C.

Antibody Incubation and Detection
Materials: Immun-Star WesternC Chemiluminecent Kit (Bio Rad Laboratories GmbH,
Heidemannstrasse 164, D-80939 München) Cat #170-5070
Primary Antibodies see figure legend 19 a to d.
Secondary Antibody: Peroxidase conjugated Goat anti-mouse, (Jackson Immune Research #115-035-146) 1:5000.
All incubations were done in sufficient volume under constant agitation. Antibodies were diluted in 5% FBS/TBST. Primary antibodies were incubated over night at 4° C. Antibody solution was removed and blots were washed three times with TBST for 5-10 min. Diluted secondary antibody was incubated with the blots for 1 h at RT, removed and blots were washed three times with TBST for 5-10 min. Blots were placed on a clear plastic sheet protector. Peroxide and Lumino/Enhancer solutions were mixed 1 ml+1 ml (2 ml total for each blot), pipetted on the blots and incubated for 3 to 5 min. Thereafter the membranes were placed in the ChemiDocXRS imaging system (Bio Rad Laboratories GmbH, Heidemannstrasse 164, D-80939 München) and signals were recorded using Image Lab software.

Virus Titrations
AI-ST cells were seeded in 96-well plates (Corning Incorporated—Life Sciences, One Becton Circle, Durham, N.C. 27712, USA; REF 353072) at 2×10$^4$ cells/well in MEM supplemented with 10% FBS one day before infection. Virus stocks were quickly thawed and placed on ice. Ten serial 1:10 dilutions were prepared in MEM in 1.2 ml volume per dilution. 100 µl/well of the virus dilutions were added to the cells, 8 wells in one vertical row per dilution. Vertical rows 11 and 12 of each plate served as medium control by addition of 100 l/well MEM. Titrations were done in triplicate and cells were incubated for 5 days at 37° C./5% CO$_2$. Cell cultures were inspected microscopically and wells where EHV-1 RacH typical CPE was observed were recorded. Titres were calculated as TCID50/ml according to the method by Reed and Muench (1938).

Example 7

Establishment of the New UL43 Insertion Site

Using the EHV-vector platform as described in the previous examples only two antigens can be expressed in parallel in their authentic forms. A blend of two vector vaccines would increase cost of goods and might also result in biased expression of transgenes, if replication efficiency varies between the different recombinant viruses, which is not unlikely. Although there are ways to couple two antigens in one insertion site either by an internal ribosome entry site (IRES) or by a picornavirus 2a peptide (2a) these techniques are not sufficient for the task. If two transgenes are coupled by a 2a peptide, which triggers a ribosomal skip which results in the synthesis of a discrete downstream translation product (Donnelly et al., 2001) the 2a peptide will structurally alter the first one of the expressed proteins, which will have 19 amino acid residues from the 2a peptide added to its C-terminus. One amino acid residue, a proline, will be added to the N-terminus of the second protein (Ryan et al., 1994). Since this one additional amino acid will be cleaved off with the signal peptide of HA, it is very likely not of any consequence. Still, the 19 amino acid tail on the first HA might interfere with trimerization and prevent sufficient efficacy. To find a solution to overcome the described hurdles the inventors established a third transgene expression site in pRacH-SE.

Use of the unified Alphaherpesvirus nomenclature
With the availability of the first genomic sequences of the various alphaherpesviruses, the in-silico identified open reading frames (orfs) were numbered for each virus individually according to their positions in the respective genomes. Later it was found that the majority of the alphaherpesvirus genes were homologs present in the different species. In order to facilitate comparison of data it is now a common practice to assign genes and gene products the designation of their homologs in the genome of human herpesvirus-1. Accordingly, we have changed the old designations of the EHV orfs according to the new nomenclature as listed in table 1.

TABLE 1

| EHV orf | Unified nomenclature | Gene product |
| --- | --- | --- |
| orf1 | UL56 | pUL56 |
| orf2 | (none) | orf2 protein |
| orf3 | (none) | orf3 protein |
| orf16 | UL44 | Glycoprotein C |
| orf17 | UL43 | pUL43 |
| orf18 | UL42 | DNA polymerase processivity factor |
| orf70 | US4 | Glycoprotein G |
| orf71 | US5 | Glycoprotein II (or glycoprotein J) |

For the construction of the insertion site though, care had to be taken not to destroy the putative promoter and poly A signals of the upstream and downstream genes UL42 encoding for a DNA polymerase processivity factor and UL44 encoding for glycoprotein C.

Figure 13:
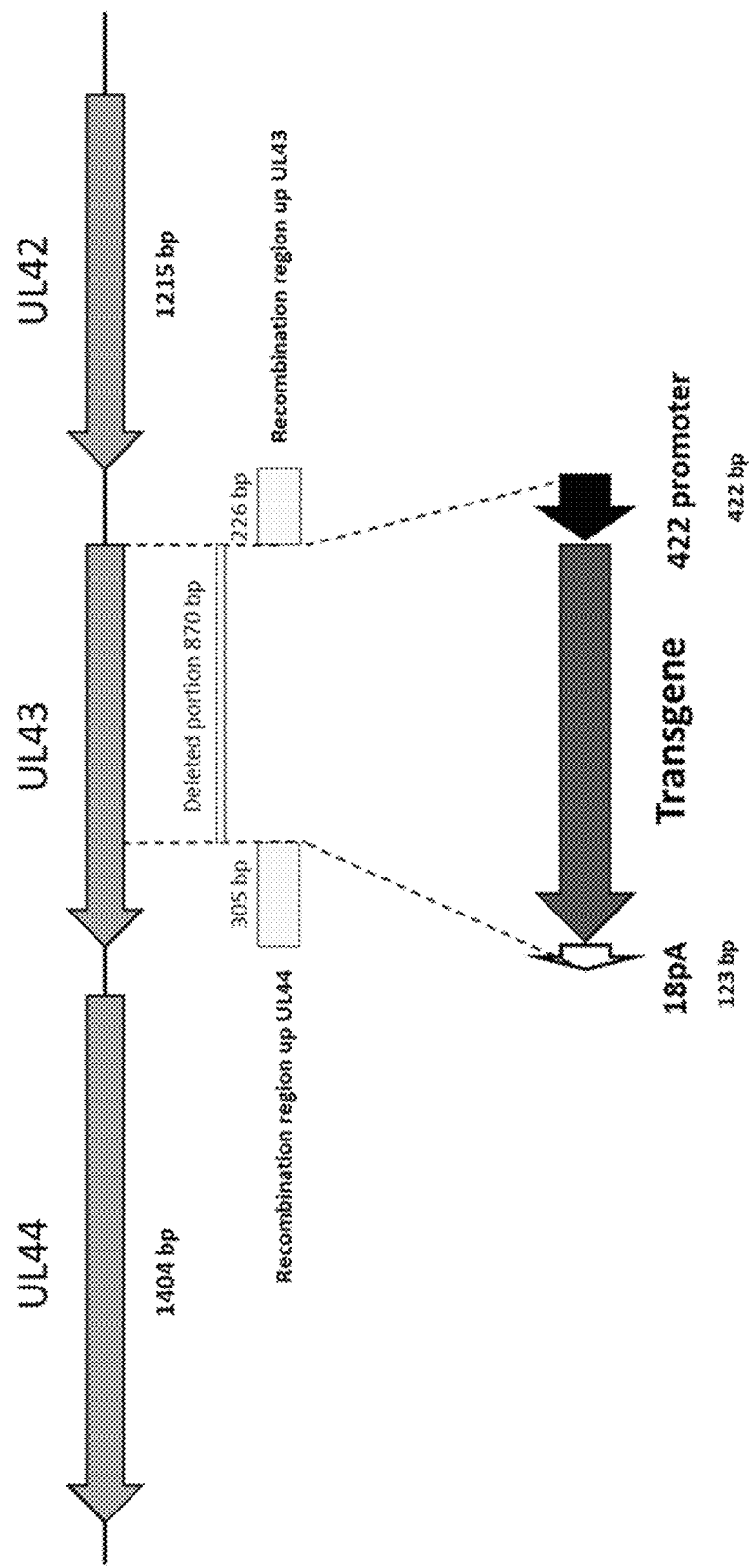

Construction of the new UL43 insertion site is illustrated in FIG. 13.

Thus, 870 basepairs (SEQ ID NO:21) of the 5' end of UL43 (SEQ ID NO:18) were replaced with an expression cassette coding for the autofluorescent mCherry protein by RED recombination of the BAC pRacH-SE. The open reading frame (orf) for mCherry was placed under control of the putative promoter (p422, SEQ ID NO:5) and polyA sequence (SEQ ID NO:7) of EHV-4 UL18 encoding for the capsid triplex subunit 2.

The 18 pA polyadenylation sequence (SEQ ID NO:7) was introduced in the transfer vector for RED recombination upstream and downstream of a Kanamycin-resistance expression cassette (Kana) to fulfill a dual function: 1. During the second step of the en-passant-mutagenesis (2nd RED) it serves as the homologous region for deletion of Kana, 2. It functions as polyadenylation signal for the transgene. For a map of the transfer vector pUUL43-422-mC-18K18 see FIG. 14.

Figure 15:
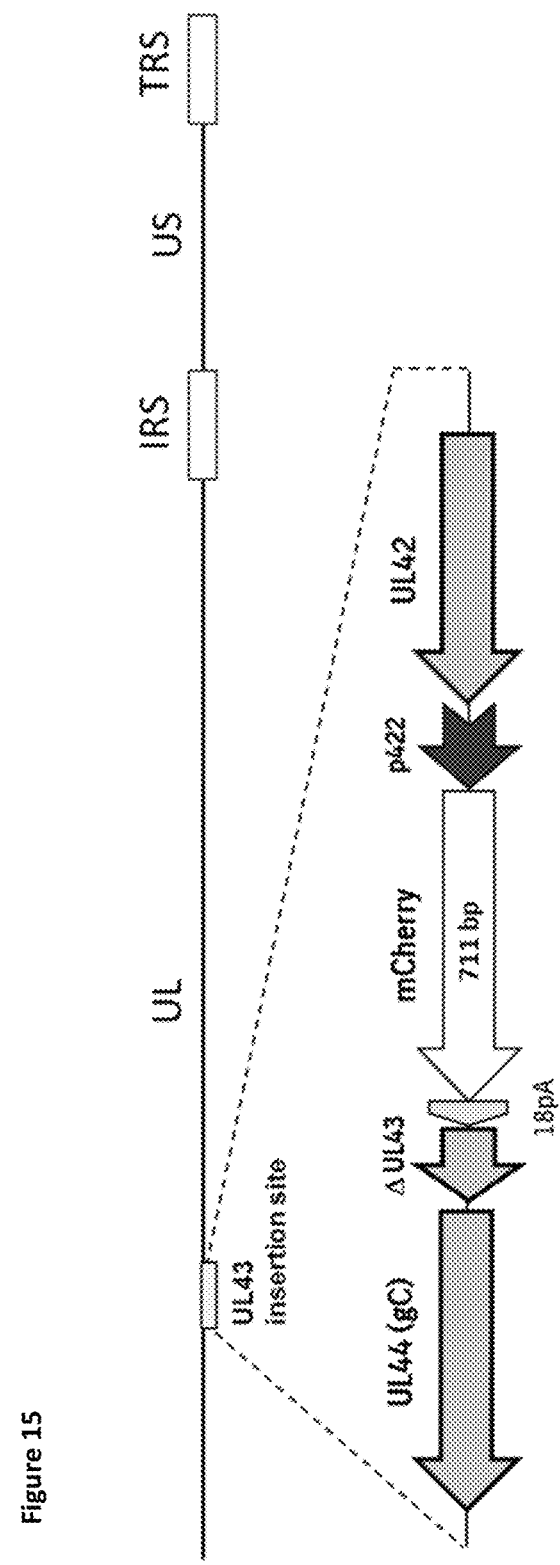

A fragment of pUUL43-422-mC-18K18 (FIG. 14; SEQ ID NO:35) encompassing the flanking regions for recombination in the viral genome, the expression cassette, and the Kanamycin-resistance cassette was cut out of the transfer vector using the homing restriction endonuclease I-CeuI and purified by agarose-gel-electrophoresis. The purified DNA fragment was then inserted in the BAC pRacH-SE by en-passant RED recombination (Tischer et al. 2006). After sequence integrity was confirmed, recombinant EHV-1 RacH-SE-UL43-422-mCherry (FIG. 15) was rescued after transfection of permissive cell cultures and plaque purified. Expression of the fluorescent mCherry protein as investigated by fluorescence microscopy showed that the new expression cassette in the new insertion site was functional (not shown).

To test performance of the third insertion site as a vector vaccine Influenza hemagglutinin subtype H1pdm (SEQ ID NO:44) from a swine origin Influenza A virus ((A/swine/Italy/116114/2010 (H1N2) GenBank accession NO:ADR01746) was inserted in the new site of pRacH-SE.

Figure 17:
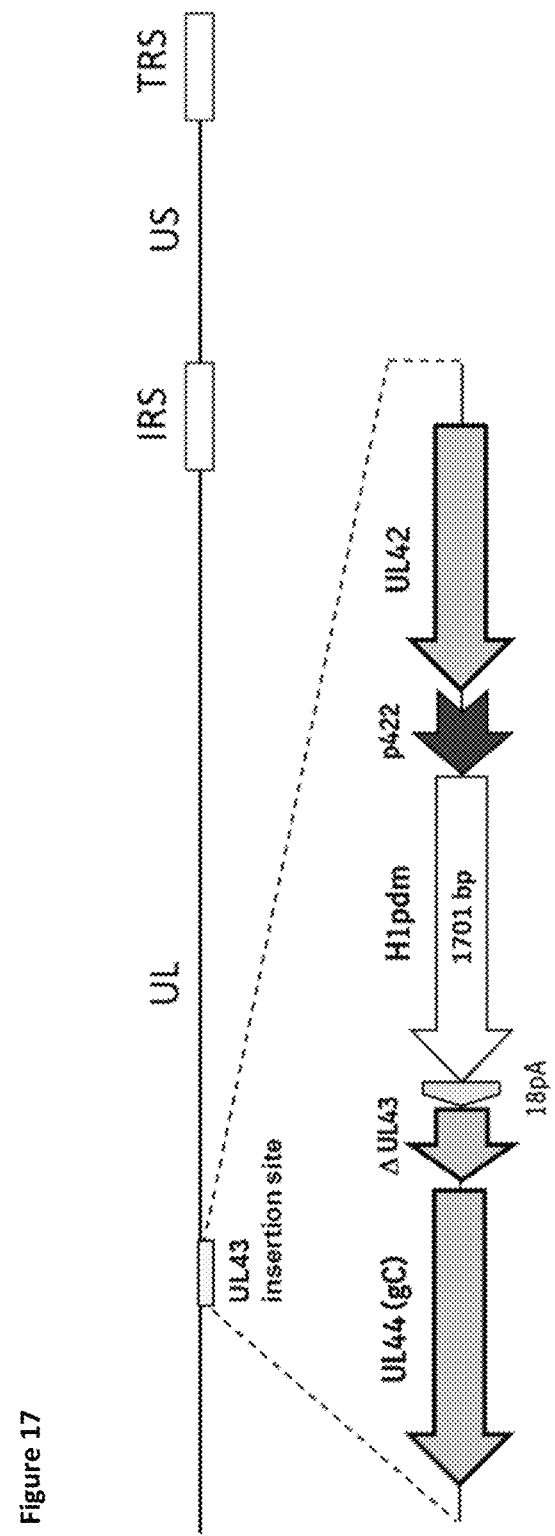

To this end, the orf encoding for mCherry was cut out of the transfer vector pUUL43-422-mC-18K18 (FIG. 14; SEQ ID NO:35) and the orf encoding H1pdm was inserted instead. The resulting transfer plasmid was named accordingly pUUL43-422-H1pdm-18K18 (FIG. 16, SEQ ID NO:36). A fragment of pUUL43-422-H1pdm-18K18 encompassing the flanking regions for recombination in the viral genome, the expression cassette, and the Kanamycin-resistance cassette was cut out of the transfer vector using the homing restriction endonuclease I-CeuI and purified by agarose-gel-electrophoresis. The purified DNA fragment was then inserted in the BAC pRacH-SE by en-passant RED recombination (Tischer et al. 2006). After sequence integrity was confirmed, recombinant EHV-1 RacH-SE-UL43-422-H1pdm (FIG. 17) was rescued after transfection of permissive cell cultures and plaque purified.

Figure 7:
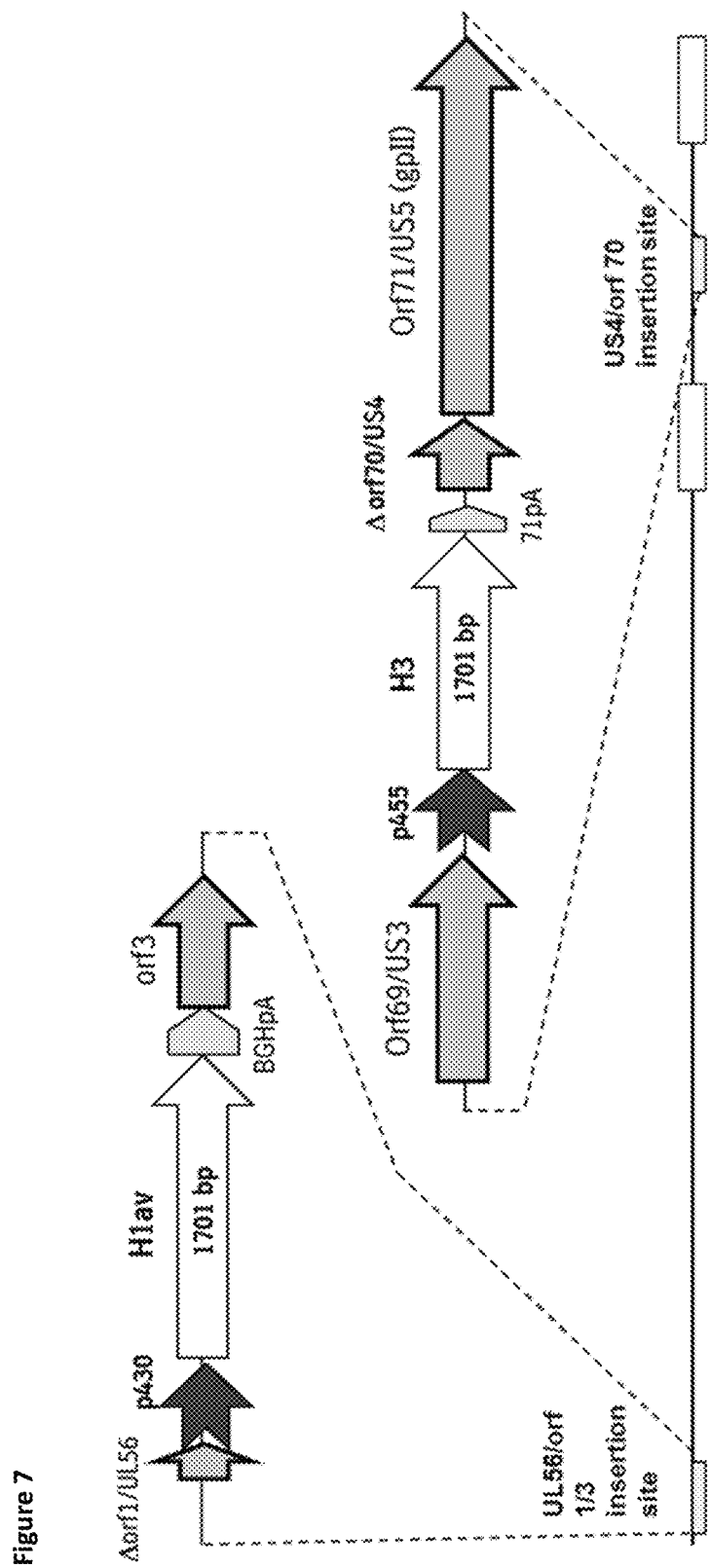
Figure 8:
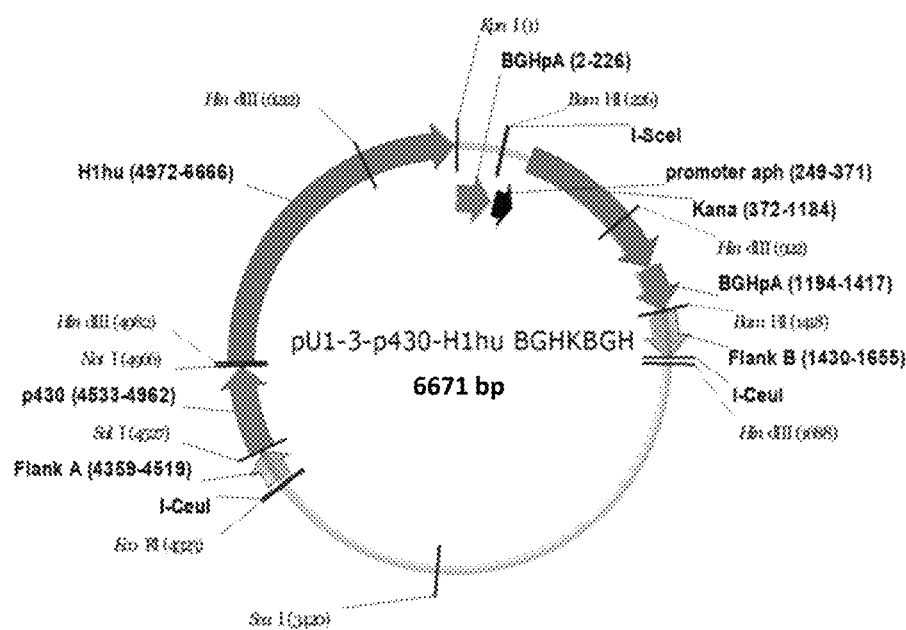

The same procedure was used to generate a recombinant EHV-1 RacH-SE based on rEHV-1 RacH-SE-B (rEHV-1 RacH-SE-orf1/3-p430-H1av-70-p455-H3, FIG. 7). The generated triple-insert recombinant was named rEHV-1 RacH-SE-UL56-430-H1av-UL43-422-H1pdm-US4-455-H3 (abbreviated rEHV-1 RacH-SE-E, FIG. 18).

Figure 18:
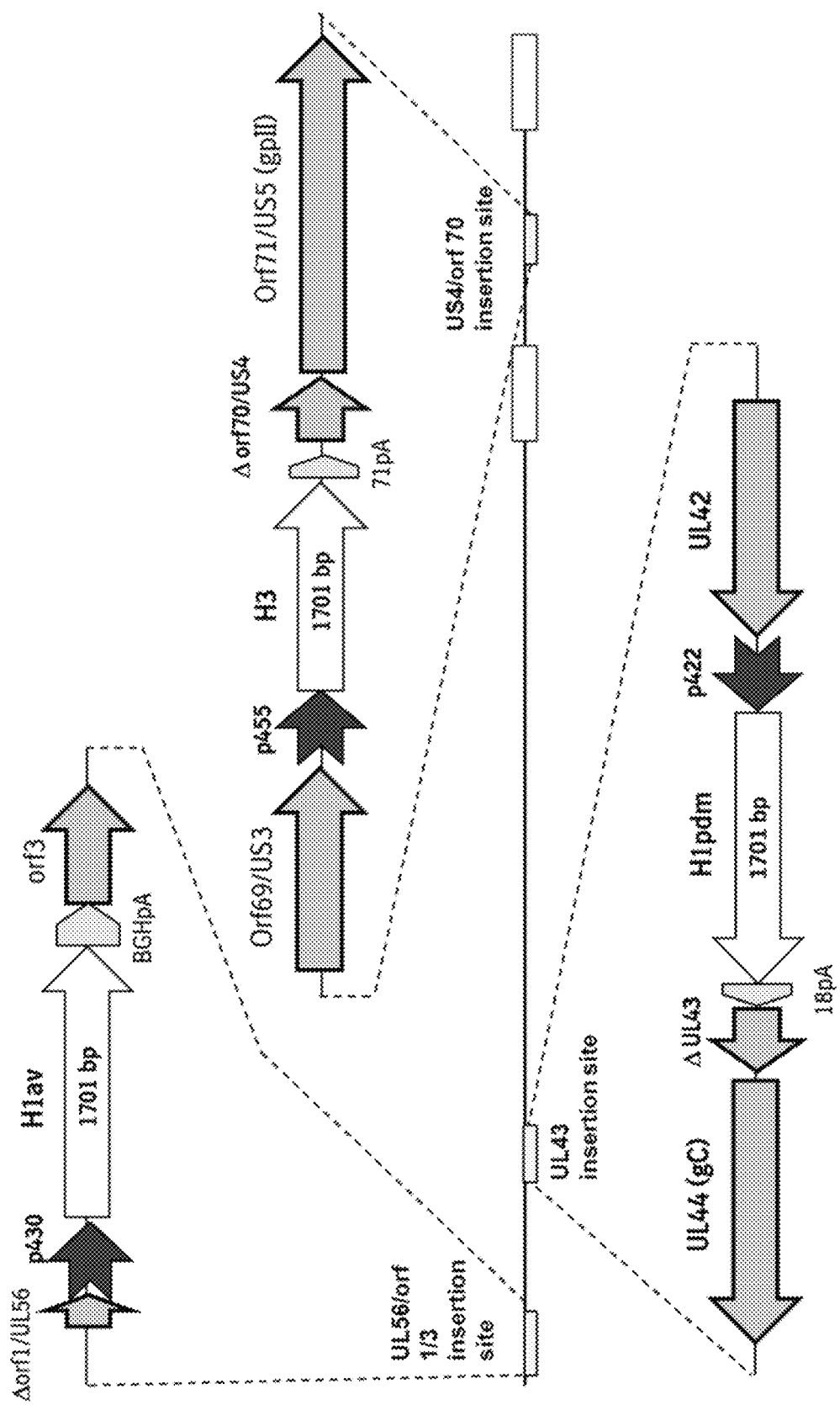
Figure 22:
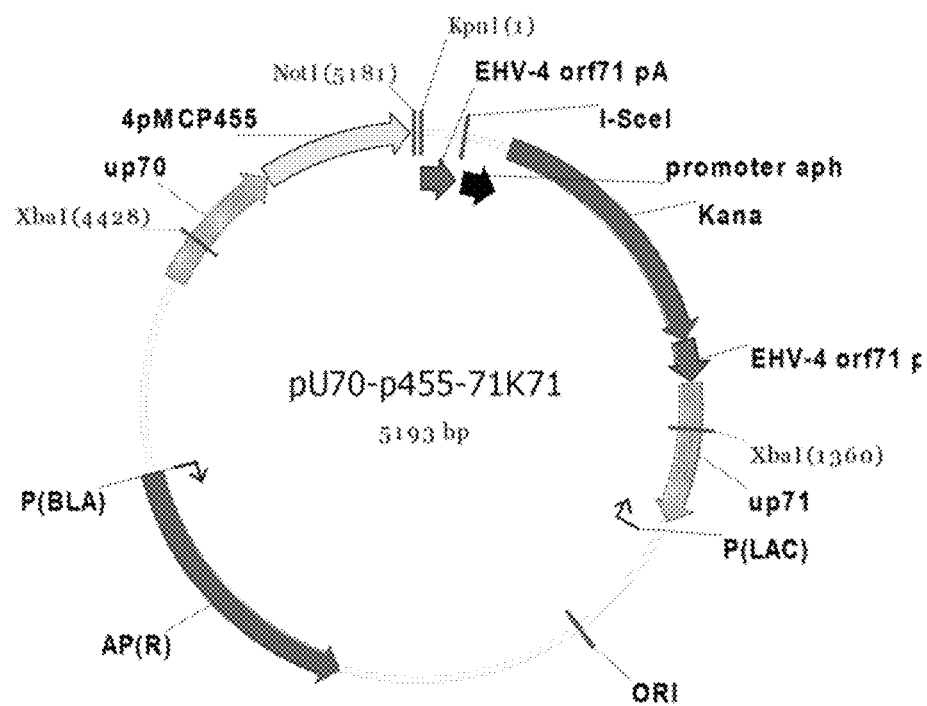
Figure 23:
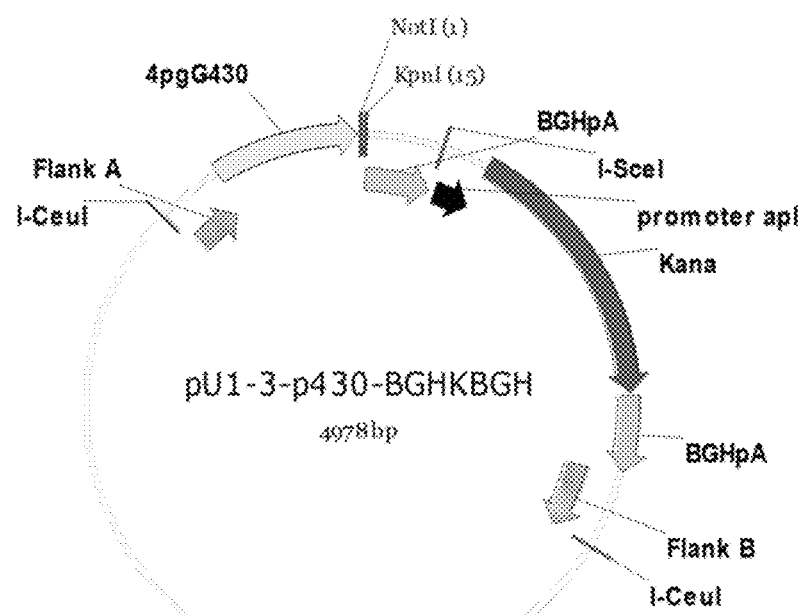
Figure 24:
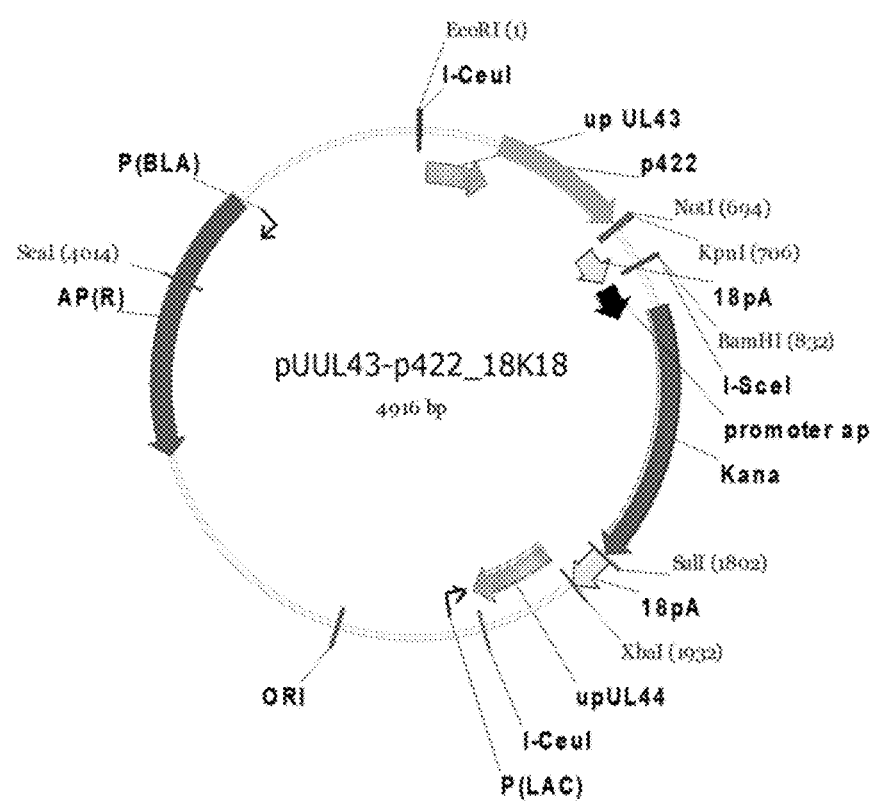

A schematic drawing of the genome of the triple-insert rEHV-1 RacH-SE-UL56-430-H1av-UL43-422-H1pdm-US4-455-H3 (abbreviated as rEHV-1-E) is depicted in FIG. 18. While the name of the predecessor construct uses the original EHV-orf nomenclature, the new triple insert virus name is based on the unified nomenclature of Alphaherpesviruses, where genes are named according to their homologs in Human Herpesvirus 1.

Recombinant plaque-purified viruses were characterized by sequencing the insertion site regions (not shown), Western blots (FIG. 19) and virus titrations (Table 3).

Figure 10:
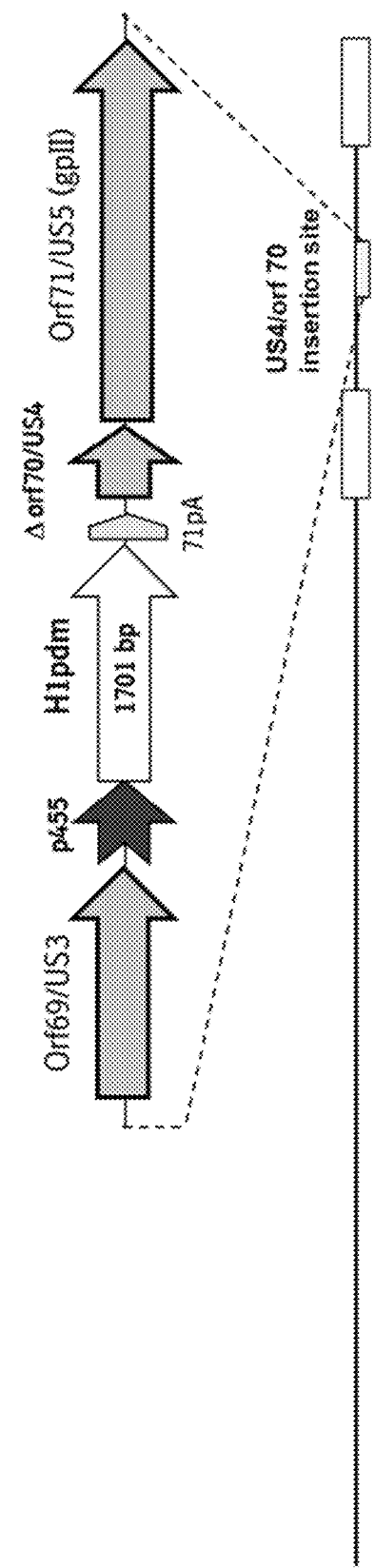
Figure 11:
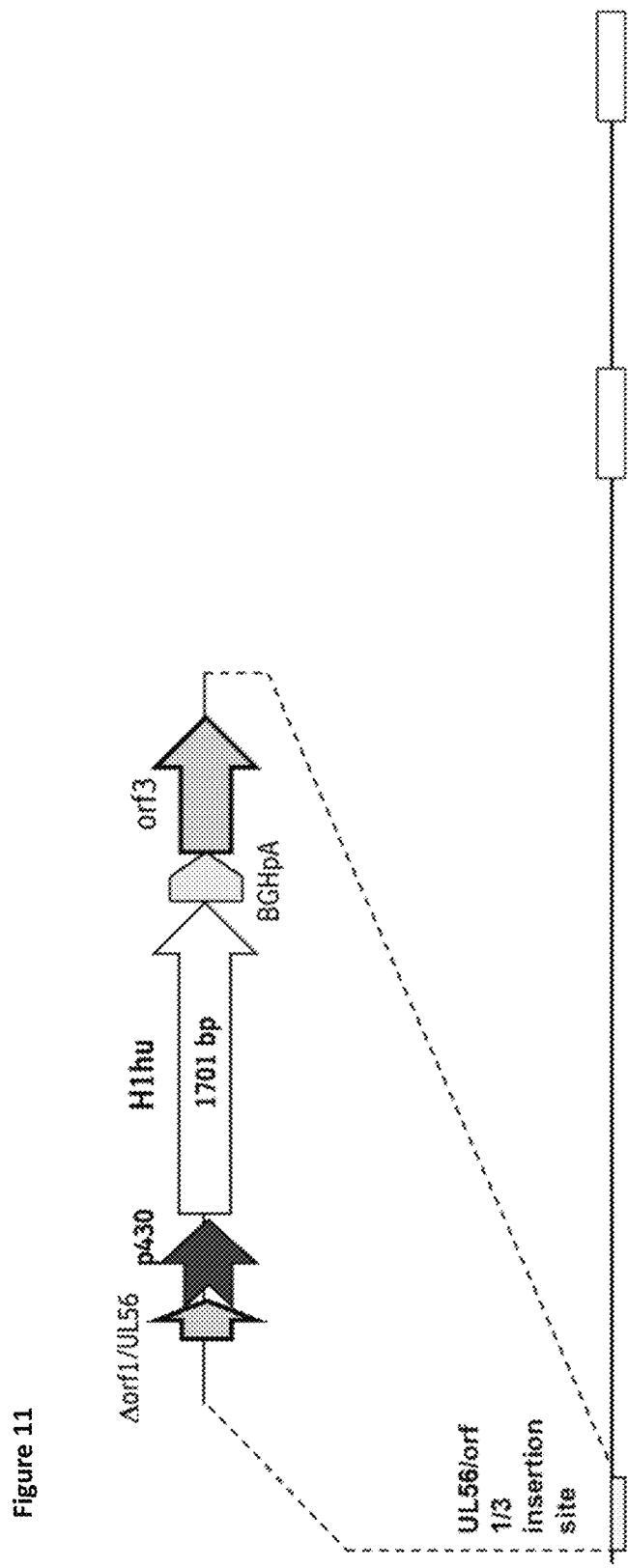
Figure 12:
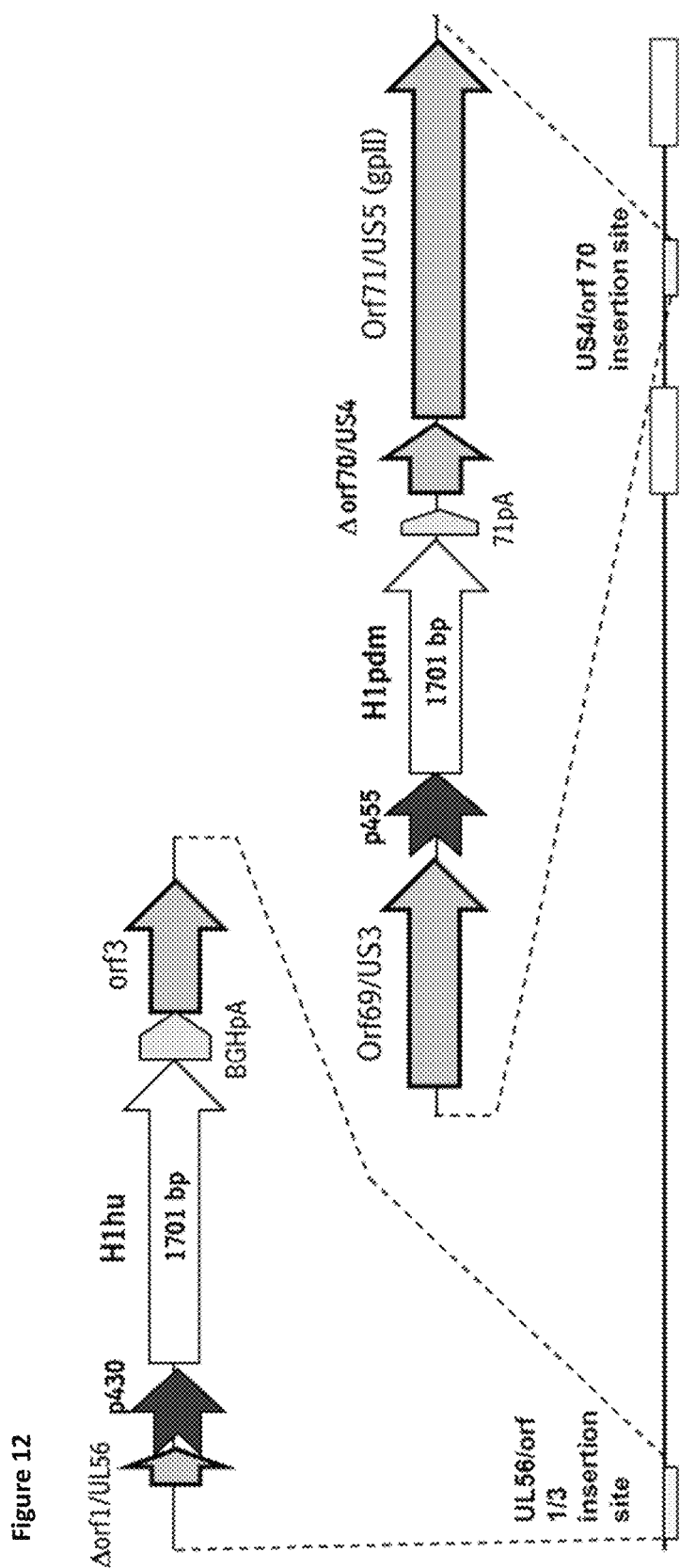

The dual-insert recombinant EHV-1, rEHV-1 RacH-SE-UL56-430-H1hu-US4-455-H1pdm (abbreviated rEHV-1 RacH-SE-D, FIG. 12) was used to compare expression strength of the transgenes. In addition a single-insert rEHV-1 RacH-SE, rEHV-1 RacH-SE-orf70-p455-H1pdm (FIG. 10), which expresses the IAV HA H1pdm from the new orf70/US4 expression site under control of the p455 promoter was included in the tests.

In order to assess expression strength of the new recombinant EHV-1 RacH-SE-UL43-422-H1pdm and EHV-1 RacH-SE-E in comparison with the two other rEHV-1 RacH-SE expressing H1pdm Western blot analysis was performed. In addition, all single-insert rEHV-1 RacH-SE expressing different IAV HA and the two dual-insert rEHV-1 RacH-SE B and D, respectively, were included. For a list of the used viruses see table 2.

TABLE 2

List of viruses analyzed by Western blot (FIG. 19)

| Long name | Abbreviation | transgenes |
|---|---|---|
| rEHV-1 RacH-SE-UL56-430-H1av-US4-455-H3 | B | H1av H3 |
| rEHV-1 RacH-SE-UL56-430-H1hu-US4-455-H1pdm | D | H1hu H1pdm |
| rEHV-1 RacH-SE-UL56-430-H1av-UL43-422-H1pdm-US4-455-H3 | E | H1av H1pdm H3 |
| rEHV-1 RacH-SE-UL56-430-H1av | av | H1av |
| rEHV-1 RacH-SE-UL56-430-H1hu | hu | H1hu |
| rEHV-1 RacH-SE-US4-455-H3 | H3 | H3 |
| rEHV-1 RacH-SE-US4-455-H1pdm | 4p | H1pdm |
| rEHV-1 RacH-SE-UL43-H1pdm | 43p | H1pdm |
| rEHV-1 RacH-SE | SE | none |

Three proprietary monospecific monoclonal antibodies directed against hemagglutinins H1av or H1pdm, or against the EHV-1 glycoprotein II and a commercial polyclonal anti-H3 antibody were used. The method allowed for a semi-quantitative assessment of the amounts of transgenes expressed in cells infected with the different tested recombinant viruses. As cell culture control cells were left uninfected and as background virus control a rEHV-1 RacH-SE was used that had been rescued and plaque purified from an "empty" vector backbone BAC (SE). AI-ST cell cultures infected with the recombinant EHV-1 B, D, E, SE, av, hu, H3, 4p, 43p (see table 2), or left uninfected were collected 30 h p.i. and processed for SDS-PAGE under reducing conditions. After electrophoresis, proteins were electrotransferred to nylon membranes and incubated with monoclonal antibodies to either HA H1av, H1pdm or the EHV-1 glycoprotein II or a commercial rabbit polyclonal antibody to HA H3. The Western blot (FIG. 19d) confirms successful infection and replication of all nine viruses. Quantities of gpII expressed in B, D, av, hu, H3, 4p, 43p and SE-infected cells appear similar, which is indicative of comparable replication efficiency. The gpII amount in E-infected cells is slightly reduced compared to the others. Western blots (FIGS. 19a and 19b) confirm expression of the hemagglutinins H1av and H3, respectively, by the new recombinant E. In comparison to B, the quantities appear comparable. In contrast, the amount of hemagglutinin H1pdm expressed by the new recombinant EHV-1 RacH-SE-E and -43p (Western blot (FIG. 19c)) appears greatly reduced when compared to D and 4p, where the identical protein is expressed in the US4 (orf70) insertion site under control of the 455 promoter.

To assess whether expression of three hemagglutinins in parallel would impair viral replication efficiency, rEHV-1 RacH-SE-B, -D, and -E were passaged in AI-ST cells until passage eleven and titres were determined in parallel as triplicates (Table 3). All titres were in a comparable range indicating that the third transgene expression cassette had no obvious negative impact on viral fitness under cell culture conditions.

TABLE 3

Comparison of viral titres at passage 11

| Virus ID | Passage no. | TCID50/ml | Standard deviation |
| --- | --- | --- | --- |
| rEHV-1RacH-SE-B | 11 | 2.01E+08 | 1.09E+07 |
| rEHV-1RacH-SE-D | 11 | 1.76E+08 | 8.59E+07 |
| rEHV-1RacH-SE-E | 11 | 1.67E+08 | 8.88E+07 |

Taken together it was shown that a recombinant EHV-1 expressed three different Influenza A hemagglutinins from three different expression sites in parallel. While expression from the UL56 (orf1/3) and the US4 (orf70) insertions sites under control of the 430 and 455 promoters, respectively, was of comparable strength, expression from the new site UL43 under control of the new 422 promoter was weaker. Also in a recombinant EHV-1 RacH-SE expressing only hemagglutinin H1pdm in from the new insertion site in UL43 under control of the p422 promoter, the amount appeared reduced as compared to the same protein expressed from the US4 (orf70) insertion site under control of the p455 promoter. Thus, the new expression system presents itself as an option if the goal demands less strong expression of a third transgene in addition to the ones being expressed from the UL56 site and the US4 site. A lower expression from the UL43 site is advantageous when expressed proteins are known to exert toxic effects in cell cultures when present in high amounts. Furthermore, combination of strong and weak expression sites can be used if a certain ratio of proteins is needed for a purpose, e.g. for the formation of virus like particles consisting of different viral structural proteins at specific ratios. In addition, a weaker transgene expression might be desirable if the expressed protein has a tendency to destabilize the recombinant vector virus.

The enhanced EHV-1 vector BAC pRacH-SE can be used as a platform for the generation of vector vaccines against diverse pathogens of mammalian species including horses, dogs, and pigs (Trapp et al. 2005, Rosas et al. 2007a, 2007b, 2008). Three different transgenes can be expressed in parallel by the enhanced vector virus in their authentic form. Three different antigens may represent three serotypes of one pathogen or originate from different pathogens of the species the vaccine is designed for. In addition, a vector vaccine generated on the basis of the enhanced EHV-1 vector pRacH-SE expressing antigens of horse pathogens has the putative potential to be tetravalent, since it would also vaccinate against EHV-1 infection.

Information on the enhanced EHV-1 vector BAC pRacH-SE has not been published or presented outside of BI.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

REFERENCES

The following references, to the extent that they provide exemplary procedural or other details supplementary to those set forth herein, are specifically incorporated herein by reference.
1. Bryant, N. A., Davis-Poynter, N., Vanderplasschen, A., and Alcami, A. 2003. Glycoprotein G isoforms from some alphaherpesviruses function as broad-spectrum chemokine binding proteins. The EMBO Journal Vol. 22 (4), 833-846.
2. Colle, C. F. 3rd, O'Callaghan, D. J. 1995. Transcriptional analyses of the unique short segment of EHV-1 strain Kentucky A. Virus Genes; 9(3):257-68.
3. Donnelly, M. L., Luke, G., Mehrotra, A., Li, X., Hughes, L. E., Gani, D., and Ryan, M. D. 2001. Analysis of the aphthovirus 2A/2B polyprotein 'cleavage' mechanism indicates not a proteolytic reaction, but a novel translational effect: a putative ribosomal 'skip'. J Gen Virol. May; 82(Pt 5):1013-25
4. Drummer, H. E., Studdert, M. J., Crabb, B. S. 1998. Equine herpesvirus-4 glycoprotein G is secreted as a disulphide-linked homodimer and is present as two homodimeric species in the virion. J. Gen. Virol. 79: 1205-1213
5. Fields, B, Knipe, D. M.; and Howley, P. M. 2013. Virology. 6$^{th}$ ed. Philadelphia; Wolters Kluwer Health/ Lippincott Williams & Wilkins
6. Jang, S. K., Pestova, T. V., Hellen, C. U., Witherell, G. W., Wimmer, E. 1990. Cap-independent translation of picornavirus RNAs: structure and function of the internal ribosomal entry site. Enzyme; 44(1-4):292-309.
7. Jöns A., and Mettenleiter T C. 1997. Green fluorescent protein expressed by recombinant pseudorabies virus as an in vivo marker for viral replication. J. Virol. Meth. 66: 283-292.
8. Lee, E. C., Yu, D., Martinez de Velasco, J., Tessarollo, L., Swing, D. A. et al. 2001. A highly efficient *Escherichia coli*-based chromosome engineering system adapted for recombinogenic targeting and subcloning of BAC DNA. Genomics 73: 56-65.
9. Ma, G., Azab, W., Osterrieder, N. 2013. Equine herpesviruses type 1 (EHV-1) and 4 (EHV-4)-masters of coevolution and a constant threat to equids and beyond. Vet Microbiol. 167(1-2):123-34.
10. Osterrieder, N., Neubauer, A., Brandmuller, C., Kaaden, O. R., and O'Callaghan, D. J. 1996. The equine herpesvirus 1 IR6 protein influences virus growth at elevated temperature and is a major determinant of virulence. Virology 226:243-251.
11. Proudfoot, N. J. 2011. Ending the message: poly(A) signals then and now. Genes & Development 25:1770-1782.

12. Rosas, C. T., Konig, P., Beer, M., Dubovi, E. J., Tischer, B. K., Osterrieder, N., 2007a. Evaluation of the vaccine potential of an equine herpesvirus type 1 vector expressing bovine viral diarrhea virus structural proteins. J. Gen. Virol. 88 (3), 748-757.
13. C. T. Rosas, B. K. Tischer, G. A. Perkins, B. Wagner, L. B. Goodman, N. Osterrieder Live-attenuated recombinant equine herpesvirus type 1 (EHV-1) induces a neutralizing antibody response against West Nile virus (WNV) Virus Research, 125 2007b, pp. 69-78
14. Rosas, C. T., Van de Walle, G. R., Metzger, S. M., Loelzer, K., Dubovi, E. J., Kim, S. G., Parrish, C. R., Osterrieder, N., 2008. Evaluation of a vectored equine herpesvirus type 1 (EHV-1) vaccine expressing H3 haemagglutinin in the protection of dogs against canine influenza. Vaccine 26 (19), 2335-3234.
15. Ryan, M. D., and Drew J. 1994. Foot-and-mouth disease virus 2A oligopeptide mediated cleavage of an artificial polyprotein. EMBO JFeb 15; 13(4):928-33.
16. Tischer, B. K, Smith, G. A., and Osterrieder, N. in: Jeff Braman (ed.), *In Vitro Mutagenesis Protocols: Third Edition*, Methods in Molecular Biology, vol. 634, DOI 10.1007/978-1-60761-652-8_30, © Springer Science+ Business Media, LLC 2010, Chapter 30: *En Passant Mutagenesis: A Two Step Markerless Red Recombination System*.
17. Tischer, B. K., von Einem, J., Kaufer, B., Osterrieder, N. 2006. Two-step red-mediated recombination for versatile high-efficiency markerless DNA manipulation in *Escherichia coli*. Biotechnol. Tech. 40, 191-197.
18. Tischer, B. K., Kaufer, B. B., Sommer, M., Wussow, F., Arvin, A., and Osterrieder, N. 2007. Self-Excisable Infectious Bacterial Artificial Chromosome Clone of Varicella-Zoster Virus Allows Analysis of the Essential Tegument Protein Encoded by *ORF9*. J. Virol. 81 (23), 13200-13208.
19. Thompson, S. R. 2012. Tricks an IRES uses to enslave ribosomes. Trends Microbiol. November; 20(11):558-66. doi: 10.1016/j.tim.2012.08.002. Epub 2012 Aug. 31.
20. Trapp, S., von Einem, J., Hofmann, H., Kostler, J., Wild, J., Wagner, R., Beer, M., Osterrieder, N., 2005. Potential of equine herpesvirus 1 as a vector for immunization. J. Virol. 79, 5445-5454.
21. Said, A., Elke Lange, E., Beer, M. Damiani, A., Osterrieder, N. 2013. Recombinant equine herpesvirus 1 (EHV-1) vaccine protects pigs against challenge with influenza A(H1N1)pmd09 Virus Research 173: 371-376
22. Wellington, J. E., Allen, G. P., Gooley, A. A., Love, D. N., Packer, N. H., Yan, J. X., Whalley, J. M. 1996. The highly O-glycosylated glycoprotein gp2 of equine herpesvirus 1 is encoded by gene 71. J Virol. 70(11):8195-8.

What is claimed is:

1. An Equid Alphaherpesvirus (EHV) RacH vector comprising an expression cassette into UL43, wherein the expression cassette comprises
   (i) at least one exogenous antigen encoding sequence operably linked to a promoter sequence, and
   (ii) at least one upstream UL43 flanking region selected from the group consisting of: sequences having at least 90% sequence identity and/or homology to SEQ ID NO:19, sequences having at least 90% sequence identity to SEQ ID NO:26, and
   (iii) at least one upstream UL44 flanking region selected from the group consisting of: sequences having at least 90% sequence identity and/or homology to SEQ ID NO:20, sequences having at least 90% sequence identity to SEQ ID NO:27.

2. The Equid Alphaherpesvirus (EHV) RacH vector of claim 1 comprising at least one further antigen encoding sequence, inserted into UL56 and/or US4.

3. The EHV RacH vector of claim 1, whereby the insertion into UL43 results in a deletion, truncation, or substitution in UL43, whereby UL44 remains functional.

4. The EHV RacH vector of claim 1, whereby the insertion into UL43 results in the deletion of an approximately 870 bp portion within UL43 for RacH (SEQ ID NO:21) or at least 90% of SEQ ID NO:21 is deleted.

5. The EHV RacH vector of claim 1, whereby the EHV vector comprises at least one flanking region selected from the group consisting of: sequences having at least 90% sequence identity and/or homology to SEQ ID NO:19, SEQ ID NO:20, SEQ ID NO:26, and SEQ ID NO:27.

6. The EHV RacH vector of claim 1, wherein said antigen encoding sequence relates to a pathogen infecting an animal selected from the group consisting of swine, poultry, cattle, cats, dogs, and horses.

7. The EHV RacH vector of claim 1, wherein the antigen encoding sequence is operably linked to a promoter sequence selected from the group consisting of: SV40 large T, HCMV and MCMV immediate early gene 1, human elongation factor alpha promoter, baculovirus polyhedrin promoter, 4pgG600 (SEQ ID No. 1), p430 (SEQ ID NO:3), the complementary nucleotide sequence of 4pgG600 (SEQ ID No. 1), 4pMCP600 (SEQ ID No. 2), p455 (SEQ ID NO:4), the complementary nucleotide sequence of 4pMCP600 (SEQ ID No. 2) or p422 (SEQ ID NO:5.

8. The EHV RacH vector of claim 1, wherein the antigen encoding sequence is from a pathogen selected from the group consisting of: Schmallenberg virus, Influenza A Virus, Porcine Respiratory and Reproductive Syndrome Virus, Porcine Circovirus, Classical Swine Fever Virus, African Swine Fever Virus, Hepatitis E Virus, Bovine Viral Diarrhea Virus, Rabies Virus, Feline Morbillivirus, *Clostridium tetani, Mycobacterium tuberculosis, Actinobacillus Pleuropneumoniae.*

9. The EHV RacH vector of claim 1, wherein the antigen encoding sequence is a hemagglutinin encoding sequence or whereby the antigen encoding sequence is a hemagglutinin influenza antigen encoding sequence from a Swine influenza A virus.

10. The EHV RacH vector of claim 9, wherein the antigen encoding sequence is a hemagglutinin encoding sequence and the hemagglutinin influenza antigen encoding sequence comprises a nucleic acid sequence encoding an amino acid sequence with at least, at least 90% identity to the amino acid sequence as set forth in SEQ ID NO:44, SEQ ID NO:45, SEQ ID NO:46 and SEQ ID NO:47.

11. An immunogenic composition comprising the EHV RacH vector of claim 1.

12. A method for immunizing a porcine animal comprising administering to such animal an immunogenic composition of claim 11, wherein the antigen encoding sequence encodes for at least one influenza antigen.

13. A method for reducing or preventing clinical signs caused by a pathogen in a porcine, the method comprising administering to the animal a therapeutically effective amount of an immunogenic composition according to claim 11, wherein the antigen encoding sequence encodes for at least one infulenza antigen.

* * * * *